US012583931B2

(12) United States Patent
Yang et al.

(10) Patent No.: US 12,583,931 B2
(45) Date of Patent: Mar. 24, 2026

(54) ANTIBODY AND CHIMERIC ANTIGEN RECEPTOR (CAR) BINDING TO CD70, AND APPLICATION THEREOF

(71) Applicant: Nanjing IASO Biotechnology Co., Ltd., Nanjing (CN)

(72) Inventors: Yongkun Yang, Nanjing (CN); Guang Hu, Nanjing (CN); Panpan Niu, Nanjing (CN); Guangrong Meng, Nanjing (CN); Jialu Mo, Nanjing (CN); Jianhua Zhang, Nanjing (CN); Qianli Hu, Nanjing (CN); Wei Cheng, Nanjing (CN); Taochao Tan, Nanjing (CN); Qiaoe Wei, Nanjing (CN); Xiangyin Jia, Nanjing (CN); Zhenyu Dai, Nanjing (CN)

(73) Assignee: Nanjing IASO Biotechnology Co., Ltd., Nanjing (CN)

( * ) Notice: Subject to any disclaimer, the term of this patent is extended or adjusted under 35 U.S.C. 154(b) by 531 days.

(21) Appl. No.: 18/248,771

(22) PCT Filed: Oct. 12, 2021

(86) PCT No.: PCT/CN2021/123347

§ 371 (c)(1),
(2) Date: Apr. 12, 2023

(87) PCT Pub. No.: WO2022/078344

PCT Pub. Date: Apr. 21, 2022

(65) Prior Publication Data

US 2023/0399412 A1 Dec. 14, 2023

(30) Foreign Application Priority Data

Oct. 12, 2020 (CN) .......................... 202011081505.7

(51) Int. Cl.
| | |
|---|---|
| *C07K 16/28* | (2006.01) |
| *A61K 40/11* | (2025.01) |
| *A61K 40/31* | (2025.01) |
| *A61K 40/42* | (2025.01) |
| *C07K 14/705* | (2006.01) |
| *C07K 14/71* | (2006.01) |
| *C07K 14/725* | (2006.01) |
| *C12N 5/0783* | (2010.01) |

(52) U.S. Cl.
CPC .......... *C07K 16/2875* (2013.01); *A61K 40/11* (2025.01); *A61K 40/31* (2025.01); *A61K 40/4224* (2025.01); *A61K 40/4232* (2025.01); *C07K 14/7051* (2013.01); *C07K 14/70517* (2013.01); *C07K 14/71* (2013.01); *C12N 5/0636* (2013.01); *A61K 2239/13* (2023.05); *C07K 2317/21* (2013.01); *C07K 2317/569* (2013.01); *C07K 2317/622* (2013.01); *C07K 2319/03* (2013.01)

(58) Field of Classification Search
CPC .................................................. C07K 16/2875
See application file for complete search history.

(56) References Cited

U.S. PATENT DOCUMENTS

2020/0255803 A1 8/2020 Zhang et al.

FOREIGN PATENT DOCUMENTS

| | | |
|---|---|---|
| AU | 2012200923 A1 | 3/2012 |
| CN | 101370830 A | 2/2009 |
| CN | 101605906 A | 12/2009 |
| CN | 109021106 A | 12/2018 |
| CN | 110592023 A | 12/2019 |
| CN | 111139223 A | 5/2020 |
| WO | 2020/113224 A2 | 6/2020 |

OTHER PUBLICATIONS

Communication Pursuant to Rule 164(1) with Supplementary Partial Search Report mailed Sep. 9, 2024, issued in related EP Application No. 21879388.3, filed Oct. 12, 2021, 14 pages.
"Magic™ Human Single Domain Antibody Production Using Transgenic Mice," © 2024 Creative Biolabs, Nov. 12, 2017 <https://web.archive.org/web/20171112172620/https://www.creative-biolabs.com/Human-Single-Domain-Antibody-Production-usingTransgenic-Mice.html> [retrieved Jul. 31, 2024], 5 pages.
International Search Report mailed Jan. 14, 2022, issued in International Application No. PCT/CN2021/123347, filed Oct. 12, 2021, 8 pages.
International Written Opinion mailed Jan. 14, 2022, issued in International Application No. PCT/CN2021/123347, filed Oct. 12, 2021, 8 pages.

*Primary Examiner* — Prema M Mertz
(74) *Attorney, Agent, or Firm* — Christensen O'Connor Johnson Kindness PLLC

(57) ABSTRACT

A CD70 antibody and a chimeric antigen receptor (CAR) that can specifically bind to a CD70 protein. The CAR comprises a CD70 binding domain, a transmembrane domain, a costimulatory domain, and an intracellular signaling domain. Further disclosed is an application of the antibody and the CAR for treating diseases or conditions related to CD70 expression.

18 Claims, 23 Drawing Sheets

Specification includes a Sequence Listing.

| CD107a% | U266 AM++ | Raji BL++ | THP-1 AM++ | REH ALL+ | RS4;11 ALL+ | Molm-13 AM+ | HL-60 AM+ | KG-1 AM+ | HEL AM- | K562 CM- | buffer - |
|---|---|---|---|---|---|---|---|---|---|---|---|
| PXL1323 | 78.65% | 77.66% | 81.29% | 58.98% | 46.95% | 72.55% | 14.98% | 11.25% | 8.25% | 10.63% | 11.80% |
| PXL1331 | 80.09% | 80.00% | 86.66% | 64.56% | 66.11% | 86.71% | 12.72% | 7.58% | 9.74% | 5.21% | 5.39% |
| PXL1332 | 70.85% | 89.42% | 70.52% | 54.12% | 43.49% | 60.97% | 14.30% | 12.29% | 10.00% | 11.03% | 11.02% |
| PXL1394 | 76.57% | 65.94% | 88.12% | 50.29% | 35.59% | 54.62% | 21.89% | 22.42% | 21.40% | 17.41% | 26.52% |
| PXL1398 | 79.55% | 77.34% | 82.66% | 68.40% | 59.44% | 71.10% | 17.50% | 16.70% | 12.53% | 14.20% | 15.28% |
| PXL1421 | 57.85% | 43.14% | 62.25% | 43.68% | 33.59% | 42.13% | 27.20% | 21.83% | 18.36% | 20.83% | 20.40% |
| PXL1422 | 77.67% | 74.37% | 78.00% | 55.65% | 46.79% | 59.63% | 27.40% | 22.38% | 28.47% | 19.09% | 21.45% |
| PXL1423 | 78.03% | 74.80% | 84.99% | 53.62% | 44.40% | 64.47% | 27.34% | 27.45% | 29.84% | 21.84% | 24.10% |
| PXL1424 | 84.96% | 80.99% | 85.19% | 70.08% | 57.56% | 71.29% | 19.62% | 15.33% | 11.55% | 12.39% | 15.21% |
| T cell | 3.35% | 2.14% | 2.45% | 1.82% | 2.03% | 2.10% | 2.10% | 1.69% | 2.08% | 1.86% | 1.49% |

| MFI | U266 AM++ | Raji BL++ | THP-1 AM++ | REH ALL+ | RS4;11 ALL+ | Molm-13 AM+ | HL-60 AM+ | KG-1 AM+ | HEL AM- | K562 CM- | buffer - |
|---|---|---|---|---|---|---|---|---|---|---|---|
| PXL1323 | 16.09 | 20.39 | 21.56 | 12.58 | 7.31 | 20.74 | 1.75 | 1.80 | 1.38 | 1.63 | 1.65 |
| PXL1331 | 22.89 | 28.63 | 28.27 | 14.78 | 17.27 | 30.98 | 2.18 | 1.89 | 2.03 | 1.87 | 2.01 |
| PXL1332 | 14.22 | 17.02 | 17.93 | 10.28 | 6.31 | 20.03 | 2.27 | 1.93 | 2.10 | 2.29 | 2.20 |
| PXL1394 | 18.66 | 18.18 | 26.14 | 10.02 | 5.68 | 12.35 | 3.92 | 3.83 | 3.81 | 3.18 | 4.17 |
| PXL1398 | 26.31 | 31.40 | 36.26 | 23.21 | 17.63 | 25.86 | 2.04 | 1.88 | 1.78 | 1.82 | 2.10 |
| PXL1421 | 8.03 | 8.29 | 13.82 | 7.81 | 4.14 | 5.79 | 3.50 | 1.70 | 2.35 | 2.55 | 2.51 |
| PXL1422 | 17.31 | 18.50 | 21.27 | 11.34 | 6.82 | 12.50 | 3.63 | 2.19 | 3.70 | 3.12 | 3.48 |
| PXL1423 | 16.17 | 18.40 | 27.05 | 10.63 | 6.98 | 13.20 | 4.18 | 3.69 | 4.00 | 3.55 | 3.52 |
| PXL1424 | 15.45 | 17.41 | 20.89 | 13.32 | 8.59 | 18.57 | 1.85 | 1.03 | 1.48 | 1.83 | 1.74 |

| CD107a% in CD8+/CAR+ | | U266 | Raji | THP-1 | MOLM-13 | RS4;11 | HL-60 | HEL | KG1 | K562 | Buffer |
|---|---|---|---|---|---|---|---|---|---|---|---|
| PXL1331 | Cusa-bbz | 70.00% | 62.50% | 54.41% | 38.41% | 15.97% | 6.46% | 2.65% | 5.11% | 3.11% | 2.42% |
| PXL1698 | vhh13+20-bbz | 62.46% | 57.66% | 51.85% | 36.48% | 19.46% | 9.86% | 4.14% | 4.87% | 5.03% | 3.97% |
| PXL1700 | vhh20+13-bbz | 48.59% | 49.22% | 45.96% | 34.17% | 22.74% | 9.08% | 6.23% | 7.08% | 6.07% | 5.20% |
| PXL1702 | vhh13+21-bbz | 58.60% | 56.14% | 48.68% | 37.39% | 15.91% | 6.74% | 2.83% | 3.52% | 2.77% | 2.36% |
| PXL1704 | vhh21+13-bbz | 58.60% | 62.27% | 54.57% | 41.89% | 19.15% | 7.29% | 1.79% | 2.61% | 2.25% | 1.57% |
| PXL1748 | vhh09+13-bbz | 49.17% | 44.08% | 42.19% | 33.79% | 18.97% | 8.73% | 4.21% | 4.51% | 5.04% | 4.17% |
| PXL1750 | vhh13+09-bbz | 50.22% | 44.89% | 42.22% | 32.05% | 15.74% | 7.68% | 2.99% | 5.05% | 4.17% | 4.46% |
| PXL1752 | vhh09+21-bbz | 58.68% | 49.08% | 39.42% | 28.78% | 14.38% | 8.40% | 2.96% | 3.45% | 3.35% | 2.61% |
| PXL1754 | vhh21+09-bbz | 55.57% | 44.98% | 43.02% | 33.40% | 11.59% | 7.84% | 3.69% | 4.66% | 4.05% | 4.42% |
| CD70 KO T | | 1.59% | 0.75% | 0.44% | 0.54% | 0.36% | 0.94% | 0.53% | 0.52% | 0.34% | 0.41% |
| CD70 WT T | | 2.52% | 1.36% | 1.31% | 1.41% | 1.81% | 1.33% | 1.55% | 1.65% | 1.79% | 1.43% |

| MFI Ratio | | U266 | Raji | THP-1 | MOLM-13 | RS4;11 | HL-60 | HEL | KG1 | K562 | Buffer |
|---|---|---|---|---|---|---|---|---|---|---|---|
| PXL1331 | Cusa-bbz | 18.2 | 20.4 | 13.3 | 6.2 | 2.1 | 1.4 | 1.2 | 1.5 | 1.3 | 1.4 |
| PXL1698 | vhh13+20-bbz | 18.4 | 22.6 | 14.8 | 5.9 | 2.8 | 1.8 | 1.4 | 1.6 | 1.6 | 1.5 |
| PXL1700 | vhh20+13-bbz | 18.4 | 20.1 | 17.4 | 7.1 | 4.6 | 3 | 2.8 | 2.8 | 2.8 | 2.9 |
| PXL1702 | vhh13+21-bbz | 17.9 | 19.2 | 10.7 | 5.5 | 2 | 1.5 | 1.2 | 1.3 | 1.3 | 1.1 |
| PXL1704 | vhh21+13-bbz | 18.4 | 24.3 | 15.9 | 7.9 | 2.5 | 1.5 | 1.3 | 1.4 | 1.4 | 1.1 |
| PXL1748 | vhh09+13-bbz | 19.6 | 20.6 | 13.5 | 6.2 | 2.8 | 1.8 | 1.5 | 1.6 | 1.7 | 1.4 |
| PXL1750 | vhh13+09-bbz | 17.8 | 19.8 | 12.7 | 5 | 2.3 | 1.7 | 1.4 | 1.6 | 1.5 | 1.5 |
| PXL1752 | vhh09+21-bbz | 19.6 | 21.6 | 9.8 | 4 | 2.3 | 1.5 | 1.4 | 1.4 | 1.4 | 1.5 |
| PXL1754 | vhh21+09-bbz | 19.2 | 20.5 | 12.5 | 5.2 | 2.3 | 1.8 | 1.5 | 1.7 | 1.8 | 1.6 |

Affinity panning is performed to enrich specific antibody clones targeting CD70 protein from the phage antibody library

828 monoclonal antibodies are used for primary screening by ELISA and FACS

344 clones that are specific and dually positive by primary screening by ELISA and FACS are sequenced

41 different monoclonal sequences are obtained after sequencing

Whether the 41 monoclonal antibodies have good specificity for multiple antigens and cell lines is verified by ELISA and FACS

40 specific monoclonal sequences are obtained after verification by ELISA and FACS

FIG. 12

SEQUENCE LISTING

<160> NUMBER OF SEQ ID NOS: 94

<210> SEQ ID NO 1
<211> LENGTH: 63
<212> TYPE: DNA
<213> ORGANISM: Artificial
<220> FEATURE:
<223> OTHER INFORMATION: CD8a signal nucleic acid sequence

<400> SEQUENCE: 1
atggccctgc ctgtgacagc tctgctcctc cctctggccc tgctgctcca tgccgccaga      60
ccc                                                                   63

<210> SEQ ID NO 2
<211> LENGTH: 63
<212> TYPE: DNA
<213> ORGANISM: Artificial
<220> FEATURE:
<223> OTHER INFORMATION: CD8a signal nucleic acid sequence

<400> SEQUENCE: 2
atggccctac ctgtgacagc cctactgtta cccctggccc tccttctgca tgctgctaga      60
cct                                                                   63

<210> SEQ ID NO 3
<211> LENGTH: 21
<212> TYPE: PRT
<213> ORGANISM: Artificial

<220> FEATURE:
<223> OTHER INFORMATION: CD8a signal protein sequence

<400> SEQUENCE: 3

Met Ala Leu Pro Val Thr Ala Leu Leu Leu Pro Leu Ala Leu Leu Leu
1               5                   10                  15

His Ala Ala Arg Pro
            20

<210> SEQ ID NO 4
<211> LENGTH: 165
<212> TYPE: DNA
<213> ORGANISM: Artificial
<220> FEATURE:
<223> OTHER INFORMATION: CD8a hinge nucleic acid sequence

<400> SEQUENCE: 4
ttcgtgcccg tgttcctgcc cgccaaacct actactaccc ctgcacctag gcctcccacc      60
ccagccccaa caatcgccag ccagcctctg tctctgcggc ccgaagcctg tagacctgct     120
gccggcggag ccgtgcacac cagaggcctg gacttcgcct gcgac                     165

<210> SEQ ID NO 5
<211> LENGTH: 165
<212> TYPE: DNA
<213> ORGANISM: Artificial
<220> FEATURE:
<223> OTHER INFORMATION: CD8a hinge nucleic acid sequence

<400> SEQUENCE: 5
tttgtgcctg tatttctgcc tgccaagccc accacaacac ctgcccctag accacccacc      60
cctgccccca ccattgcttc tcagcccctt agcttaagac ctgaagcctg tagacctgct     120
gctggggggg ctgtgcacac aagaggcctg gactttgcct gtgac                     165

<210> SEQ ID NO 6
<211> LENGTH: 55
<212> TYPE: PRT
<213> ORGANISM: Artificial
<220> FEATURE:
<223> OTHER INFORMATION: CD8a hinge protein sequence

<400> SEQUENCE: 6

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 7
<211> LENGTH: 84
<212> TYPE: DNA
<213> ORGANISM: Artificial
<220> FEATURE:
<223> OTHER INFORMATION: CD8a TM nucleic acid sequence

<400> SEQUENCE: 7
atctacatct gggcccctct ggccggcacc tgtggcgtgc tgctgctgag cctggtgatc      60
accctgtact gcaaccaccg gaac                                             84

<210> SEQ ID NO 8
<211> LENGTH: 84
<212> TYPE: DNA
<213> ORGANISM: Artificial
<220> FEATURE:
<223> OTHER INFORMATION: CD8a TM nucleic acid sequence

<400> SEQUENCE: 8
atctacatct gggcccccct ggctggcacc tgtggggtgc tgctgctgag cctggtgatc      60
accctgtact gcaaccacag aaac                                              84

<210> SEQ ID NO 9
<211> LENGTH: 28
<212> TYPE: PRT
<213> ORGANISM: Artificial
<220> FEATURE:
<223> OTHER INFORMATION: CD8a TM protein sequence

<400> SEQUENCE: 9

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25

<210> SEQ ID NO 10
<211> LENGTH: 126
<212> TYPE: DNA
<213> ORGANISM: Artificial
<220> FEATURE:
<223> OTHER INFORMATION: 4-1BB intracellular domain nucleic acid
      sequence

<400> SEQUENCE: 10
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 11
<211> LENGTH: 126
<212> TYPE: DNA
<213> ORGANISM: Artificial
<220> FEATURE:
<223> OTHER INFORMATION: 4-1BB intracellular domain nucleic acid
      sequence

<400> SEQUENCE: 11
aagagaggca gaaagaagct gctgtacatc ttcaagcagc ccttcatgag acctgtgcag      60
accacccaag aggaggatgg ctgcagctgc agattccctg aggaggagga gggggggctgt     120 gagctg                                                                126

<210> SEQ ID NO 12
<211> LENGTH: 42
<212> TYPE: PRT
<213> ORGANISM: Artificial
<220> FEATURE:
<223> OTHER INFORMATION: 4-1BB intracellular domain protein sequence

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 336
<212> TYPE: DNA
<213> ORGANISM: Artificial
<220> FEATURE:
<223> OTHER INFORMATION: CD3z intracellular signaling domain nucleic
      acid sequence

<400> SEQUENCE: 13
agagtgaagt tcagcagatc cgccgacgcc cctgcctacc agcagggaca gaaccagctg      60
tacaacgagc tgaacctggg cagacgggaa gagtacgacg tgctggacaa gcggagaggc     120
cgggaccccg agatgggcgg aaagcccaga cggaagaacc cccaggaagg cctgtataac     180
gaactgcaga aagacaagat ggccgaggcc tacagcgaga tcggcatgaa gggcgagcgg     240
aggcgcggca aggccacga tggcctgtac cagggcctga gcaccgccac caaggacacc     300
tacgacgccc tgcacatgca ggccctgccc cccaga                               336

<210> SEQ ID NO 14
<211> LENGTH: 336
<212> TYPE: DNA
<213> ORGANISM: Artificial
<220> FEATURE:
<223> OTHER INFORMATION: CD3z intracellular signaling domain nucleic
      acid sequence

<400> SEQUENCE: 14
agagtgaagt tcagcagatc tgctgatgcc cctgcctatc agcaagggca gaatcagctg      60
tacaatgagc tgaatctggg cagaagagag gagtatgatg tgctggacaa gagaagaggc     120
agagaccctg agatgggggg caagcctaga agaaagaacc cccagagggg cctgtataat     180
gagctgcaga aggacaagat ggctgaggcc tactctgaga ttggcatgaa gggggagaga     240
agaagaggca agggccatga tggcctgtac caaggcctga gcacagccac caaggacacc     300
tatgatgccc tacacatgca agctctgcct cctaga                               336

<210> SEQ ID NO 15
<211> LENGTH: 112
<212> TYPE: PRT
<213> ORGANISM: Artificial
<220> FEATURE:
<223> OTHER INFORMATION: CD3z intracellular signaling domain protein
      sequence

<400> SEQUENCE: 15

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
        100                 105                 110

<210> SEQ ID NO 16
<211> LENGTH: 54
<212> TYPE: DNA
<213> ORGANISM: Artificial
<220> FEATURE:
<223> OTHER INFORMATION: Cleaving peptide T2A nucleic acid sequence

<400> SEQUENCE: 16
gagggaaggg gcagcttatt aacatgtggc gatgtggaag agaaccccgg tccc          54

<210> SEQ ID NO 17
<211> LENGTH: 54
<212> TYPE: DNA
<213> ORGANISM: Artificial
<220> FEATURE:
<223> OTHER INFORMATION: Cleaving peptide T2A nucleic acid sequence

<400> SEQUENCE: 17
gaaggaaggg gcagcctact gacctgtggg gatgtggagg agaaccctgg cccc          54

<210> SEQ ID NO 18
<211> LENGTH: 18
<212> TYPE: PRT
<213> ORGANISM: Artificial
<220> FEATURE:
<223> OTHER INFORMATION: Cleaving peptide T2A protein sequence

<400> SEQUENCE: 18

Glu Gly Arg Gly Ser Leu Leu Thr Cys Gly Asp Val Glu Glu Asn Pro
1               5                   10                  15

Gly Pro

<210> SEQ ID NO 19
<211> LENGTH: 66
<212> TYPE: DNA
<213> ORGANISM: Artificial
<220> FEATURE:
<223> OTHER INFORMATION: CSF2RA signal nucleic acid sequence

<400> SEQUENCE: 19
atgctgctgc tcgtgacctc tttactgtta tgtgagctgc cccaccccgc tttttactg          60 atccct                                                                    66

<210> SEQ ID NO 20
<211> LENGTH: 66
<212> TYPE: DNA
<213> ORGANISM: Artificial
<220> FEATURE:
<223> OTHER INFORMATION: CSF2RA signal nucleic acid sequence

<400> SEQUENCE: 20
atgttgctat tagtaaccag cctgctgctg tgtgagctgc cccaccctgc cttcctgtta          60
atccca                                                                    66

<210> SEQ ID NO 21
<211> LENGTH: 22
<212> TYPE: PRT
<213> ORGANISM: Artificial
<220> FEATURE:
<223> OTHER INFORMATION: CSF2RA signal protein sequence

<400> SEQUENCE: 21

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 22
<211> LENGTH: 1005
<212> TYPE: DNA
<213> ORGANISM: Artificial
<220> FEATURE:
<223> OTHER INFORMATION: tEGFR nucleic acid sequence

<400> SEQUENCE: 22

```
cgtaaggtgt gtaacggaat cggcattggc gagttcaagg actctttaag catcaacgcc      60
acaaacatca agcacttcaa gaattgtacc tccatcagcg gcgatttaca cattctcccc     120 gtggctttc gtggcgattc cttcacccac accccccctc tggacccca agagctggac      180 atttttaaaa ccgtgaagga gatcaccggc tttctgctga tccaagcttg gcccgagaat     240
cgtaccgacc tccacgcctt cgagaattta gagattattc gtggaaggac caagcagcac     300
ggccagttct ctttagccgt cgtgtcttta aacattacca gcctcggttt aaggtcttta     360
aaggagatta gcgacggcga cgtgatcatc tccggcaaca gaacctctg ctacgccaac      420 accatcaact ggaagaagct gttcggaacc agcggccaaa agaccaagat catcagcaat     480
cgtggagaga actcttgtaa ggccactggt caagtttgcc acgccctctg tagccccgaa     540
ggatgttggg gccccgagcc tagggactgt gttagctgca gaaacgtgag cagaggcaga     600
gagtgtgtgg acaaatgcaa tttactggaa ggagagccta gggagttcgt ggagaacagc     660
gaatgtatcc agtgccaccc cgagtgttta cctcaagcca tgaacatcac ttgtaccgga     720
aggggccccg ataactgcat ccaatgcgcc cactacatcg acggacccca ctgcgtgaaa     780
acttgtcccg ccggagtgat gggagagaat aacactttag tgtggaagta cgccgacgct     840
ggccacgtct gccatctgtg ccaccccaac tgtacctacg gctgcactgg tcccggttta     900
gagggatgtc ctaccaacgg ccccaagatc ccctccatcg ccaccggaat ggtgggcgct     960
ctgttattac tgctggtggt ggctctgggc atcggttttat tcatg                   1005
```

<210> SEQ ID NO 23
<211> LENGTH: 1005
<212> TYPE: DNA
<213> ORGANISM: Artificial
<220> FEATURE:
<223> OTHER INFORMATION: tEGFR nucleic acid sequence

<400> SEQUENCE: 23

```
cgaaaggtat gtaatggcat tggcattggg gagtttaagg acagcctgag catcaatgcc      60
accaacatca agcacttcaa gaactgcaca agcatcagtg gggacttgca catcctgcct     120
gtggccttca gaggggacag cttcacccac accccccccc tggaccccca agagctggac     180
atcctgaaga cagtgaagga gatcactggc ttcttgctga tccaagcctg gcctgagaac     240
agaacagacc tgcatgcctt tgagaacctg gagatcatca gaggcagaac caagcagcat     300
gggcagttca gcctggctgt ggtgagcctg aacatcacaa gcctgggcct gagaagctta     360
aaggagatct ctgatgggga tgtgatcatc tctggcaaca gaacctgtg ctatgccaac      420 accatcaact ggaagaagct gtttggcacc tctgggcaga agaccaagat catcagcaac     480
agaggggaga actcctgtaa ggccactggc caagtgtgtc atgccctatg cagccctgag     540
```

```
gggtgctggg gccctgagcc tagagactgt gtgagctgca gaaatgtgag cagaggcaga    600
gagtgtgtgg acaagtgcaa cctgctggag ggggagccta gagagtttgt ggagaactct    660
gagtgtattc agtgtcatcc tgagtgcctg ccccaagcca tgaacatcac ctgcactggc    720
agaggccctg acaactgcat tcagtgtgcc cactacattg atggccccca ctgtgtgaag    780
acctgccctg ctggggtgat gggggagaac aacaccctgg tgtggaagta tgctgatgct    840
ggccatgtgt gtcacctgtg ccatcccaac tgcacctatg ctgcactggg ccctggcctg    900
gagggctgcc ccaccaatgg tcccaagatt cctagcattg ccactggcat ggtgggggcc    960
ctgctcctac ttctggtggt tgccctgggc attggcctgt tcatg               1005
```

<210> SEQ ID NO 24
<211> LENGTH: 335
<212> TYPE: PRT
<213> ORGANISM: Artificial
<220> FEATURE:
<223> OTHER INFORMATION: tEGFR protein sequence

<400> SEQUENCE: 24

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
    275                 280                 285
```

```
Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335
```

```
<210> SEQ ID NO 25
<211> LENGTH: 759
<212> TYPE: DNA
<213> ORGANISM: Artificial
<220> FEATURE:
<223> OTHER INFORMATION: Scfv 06  nucleic acid sequence

<400> SEQUENCE: 25
caggctgtgc tgactcagcc accctcagcg tctgcgaccc ccgggcagag ggtctccatc      60
tcctgttcgg ggagcagctc caacatcgga aggaatactg ttaattggta ccagcacctc     120
cctggaacgg cccccaaact cctcatttat agtaatgatc atcggccctc aggggtccct     180
gaccgattct ctggctccca gtctggcacc tcagcctccc tggccatcag tgggctccag     240
tctgaggatg aggctgatta ttactgtgca tcatgggatg acagcctgac tggatgggtg     300
ttcggcggag ggaccaaggt caccgtccta ggttctagag gtggtggtgg tagcggcggc     360
ggcggctctg gtggtggtgg atccctcgag atggcccagg tgcagctggt gcagtctggg     420
gctgaggtga agaaggctgg gtcctcgctg aaggtctcgt gcaaggctaa tggaggcagt     480
ttcaccaact atcttatcaa ctgggtgcgc caggcccctg gacaggggct tgagtggatg     540
ggagggatca tccctgtcta tggaacacca atctactcac agaaattcca gggcagagtc     600
acatttaccg cggacgagcc cacgaggaca gcctacatgg aactgagcag cctgacattt     660
gaggacacgg ccgtgtatta ttgtgtgaga gaagacgaag ctacggtga cctttatctc      720 gcctactggg gacagggac cctggtcacc gtctcctca                              759
```

```
<210> SEQ ID NO 26
<211> LENGTH: 253
<212> TYPE: PRT
<213> ORGANISM: Artificial
<220> FEATURE:
<223> OTHER INFORMATION: Scfv 06 protein sequence

<400> SEQUENCE: 26

Gln Ala Val Leu Thr Gln Pro Pro Ser Ala Ser Ala Thr Pro Gly Gln
1                 5                  10                  15

Arg Val Ser Ile Ser Cys Ser Gly Ser Ser Ser Asn Ile Gly Arg Asn
                20                  25                  30

Thr Val Asn Trp Tyr Gln His Leu Pro Gly Thr Ala Pro Lys Leu Leu
            35                  40                  45

Ile Tyr Ser Asn Asp His Arg Pro Ser Gly Val Pro Asp Arg Phe Ser
    50                  55                  60

Gly Ser Gln Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Ser Leu
                85                  90                  95

Thr Gly Trp Val Phe Gly Gly Gly Thr Lys Val Thr Val Leu Gly Ser
            100                 105                 110

Arg Gly Gly Gly Gly Ser Gly Gly Gly Ser Gly Gly Gly Gly Ser
        115                 120                 125
```

-continued

```
Leu Glu Met Ala Gln Val Gln Leu Val Gln Ser Gly Ala Glu Val Lys
    130             135             140
```

```
Lys Ala Gly Ser Ser Leu Lys Val Ser Cys Lys Ala Asn Gly Gly Ser
145             150             155             160
```

```
Phe Thr Asn Tyr Leu Ile Asn Trp Val Arg Gln Ala Pro Gly Gln Gly
            165             170             175
```

```
Leu Glu Trp Met Gly Gly Ile Ile Pro Val Tyr Gly Thr Pro Ile Tyr
                180             185             190
```

```
Ser Gln Lys Phe Gln Gly Arg Val Thr Phe Thr Ala Asp Glu Pro Thr
        195             200             205
```

```
Arg Thr Ala Tyr Met Glu Leu Ser Ser Leu Thr Phe Glu Asp Thr Ala
    210             215             220
```

```
Val Tyr Tyr Cys Val Arg Glu Asp Glu Gly Tyr Gly Asp Leu Tyr Leu
225             230             235             240
```

```
Ala Tyr Trp Gly Gln Gly Thr Leu Val Thr Val Ser Ser
            245             250
```

```
<210> SEQ ID NO 27
<211> LENGTH: 369
<212> TYPE: DNA
<213> ORGANISM: Artificial
<220> FEATURE:
<223> OTHER INFORMATION: VH06 nucleic acid sequence

<400> SEQUENCE: 27
atggcccagg tgcagctggt gcagtctggg gctgaggtga agaaggctgg gtcctcgctg      60
aaggtctcgt gcaaggctaa tggaggcagt ttcaccaact atcttatcaa ctgggtgcgc     120
caggcccctg gacagggggct tgagtggatg ggagggatca tccctgtcta tggaacacca     180
atctactcac agaaattcca gggcagagtc acatttaccg cggacgagcc cacgaggaca     240
gcctacatgg aactgagcag cctgacattt gaggacacgg ccgtgtatta ttgtgtgaga     300
gaagacgaag gctacggtga cctttatctc gcctactggg gacagggggac cctggtcacc     360 gtctcctca                                                            369
```

```
<210> SEQ ID NO 28
<211> LENGTH: 123
<212> TYPE: PRT
<213> ORGANISM: Artificial
<220> FEATURE:
<223> OTHER INFORMATION: VH06 protein sequence

<400> SEQUENCE: 28
```

```
Met Ala Gln Val Gln Leu Val Gln Ser Gly Ala Glu Val Lys Lys Ala
1               5               10              15
```

```
Gly Ser Ser Leu Lys Val Ser Cys Lys Ala Asn Gly Gly Ser Phe Thr
            20              25              30
```

```
Asn Tyr Leu Ile Asn Trp Val Arg Gln Ala Pro Gly Gln Gly Leu Glu
        35              40              45
```

```
Trp Met Gly Gly Ile Ile Pro Val Tyr Gly Thr Pro Ile Tyr Ser Gln
    50              55              60
```

```
Lys Phe Gln Gly Arg Val Thr Phe Thr Ala Asp Glu Pro Thr Arg Thr
65              70              75              80
```

```
Ala Tyr Met Glu Leu Ser Ser Leu Thr Phe Glu Asp Thr Ala Val Tyr
            85              90              95
```

```
Tyr Cys Val Arg Glu Asp Glu Gly Tyr Gly Asp Leu Tyr Leu Ala Tyr
            100             105             110
```

```
Trp Gly Gln Gly Thr Leu Val Thr Val Ser Ser
        115                 120

<210> SEQ ID NO 29
<211> LENGTH: 333
<212> TYPE: DNA
<213> ORGANISM: Artificial
<220> FEATURE:
<223> OTHER INFORMATION: VL06 nucleic acid sequence

<400> SEQUENCE: 29
caggctgtgc tgactcagcc accctcagcg tctgcgaccc ccgggcagag ggtctccatc      60
tcctgttcgg ggagcagctc caacatcgga aggaatactg ttaattggta ccagcacctc     120
cctggaacgg cccccaaact cctcatttat agtaatgatc atcggccctc aggggtccct     180
gaccgattct ctggctccca gtctggcacc tcagcctccc tggccatcag tgggctccag     240
tctgaggatg aggctgatta ttactgtgca tcatgggatg acagcctgac tggatgggtg     300
ttcggcggag ggaccaaggt caccgtccta ggt                                   333

<210> SEQ ID NO 30
<211> LENGTH: 111
<212> TYPE: PRT
<213> ORGANISM: Artificial
<220> FEATURE:
<223> OTHER INFORMATION: VL06 protein sequence

<400> SEQUENCE: 30

Gln Ala Val Leu Thr Gln Pro Pro Ser Ala Ser Ala Thr Pro Gly Gln
1               5                   10                  15

Arg Val Ser Ile Ser Cys Ser Gly Ser Ser Ser Asn Ile Gly Arg Asn
            20                  25                  30

Thr Val Asn Trp Tyr Gln His Leu Pro Gly Thr Ala Pro Lys Leu Leu
        35                  40                  45

Ile Tyr Ser Asn Asp His Arg Pro Ser Gly Val Pro Asp Arg Phe Ser
    50                  55                  60

Gly Ser Gln Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Ser Leu
                85                  90                  95

Thr Gly Trp Val Phe Gly Gly Gly Thr Lys Val Thr Val Leu Gly
            100                 105                 110

<210> SEQ ID NO 31
<211> LENGTH: 369
<212> TYPE: DNA
<213> ORGANISM: Artificial
<220> FEATURE:
<223> OTHER INFORMATION: VHH 09 nucleic acid sequence

<400> SEQUENCE: 31
gaagttcagc tgctggaaag cggtggtggt ctggttcagc ctggtggtag cctgcgtctg      60
agctgtgcag caagcggttt tacctttaac atcgatgcca tgggttgggt tcgtcaggca     120
cctggtaaag tctggaatg ggttagcagc atcagcagca gcggcggcac cacctattat      180
gcagatagcg ttaaaggtcg ttttaccatt agccgtgata cagcaaaaa taccctgtac      240 ctgcagatga atagtctgcg tgcagaggat accgcagtgt attattgtgc gcgctctcgt     300
tactctgttc cggacggtcg tggttcttac gatgtttggg gtcaaggtac tctggtgacc     360
```

```
gtctcctca                                                            369

<210> SEQ ID NO 32
<211> LENGTH: 369
<212> TYPE: DNA
<213> ORGANISM: Artificial
<220> FEATURE:
<223> OTHER INFORMATION: VHH 09 nucleic acid sequence

<400> SEQUENCE: 32
gaggtgcaac ttcttgagtc tggggggggc ttggtgcagc ctggggggcag tctgagactg    60 agctgtgctg cctctggctt taccttcaac attgatgcca tgggttgggt aagacaagcc   120
cctggcaagg gtctggagtg ggtgagcagc atcagctctt ctgggggcac tacctactat   180
gctgactctg tgaagggcag attcaccatc agcagagaca acagcaagaa caccctgtac   240
ctgcaaatga atagccttag ggctgaggac acagctgtat actactgtgc tagaagcaga   300
tactctgtgc ctgatggcag aggcagctat gatgtgtggg gccaagggac cttggtcaca   360
gtgagctct                                                            369

<210> SEQ ID NO 33
<211> LENGTH: 123
<212> TYPE: PRT
<213> ORGANISM: Artificial
<220> FEATURE:
<223> OTHER INFORMATION: VHH 09 protein sequence

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ile Asp
            20                  25                  30

Ala Met Gly Trp Val Arg Gln Ala Pro Gly Lys Gly Leu Glu Trp Val
        35                  40                  45

Ser Ser Ile Ser Ser Ser Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Tyr Ser Val Pro Asp Gly Arg Gly Ser Tyr Asp Val
            100                 105                 110

Trp Gly Gln Gly Thr Leu Val Thr Val Ser Ser
        115                 120

<210> SEQ ID NO 34
<211> LENGTH: 363
<212> TYPE: DNA
<213> ORGANISM: Artificial
<220> FEATURE:
<223> OTHER INFORMATION: VHH13 nucleic acid sequence

<400> SEQUENCE: 34
gaagttcagc tgctggaaag cggtggtggt ctggttcagc ctggtggtag cctgcgtctg    60
agctgtgcag caagcggttt taccttagc agcgaagcca tgggttgggt tcgtcaggca   120
cctggtaaag tctggaatg ggttagcagc atcaacggca gcggccgcaa cacctattat   180
gcagatagcg ttaaaggtcg ttttaccatt agccgtgata acagcaaaaa taccctgtac   240
ctgcagatga atagtctgcg tgcagaggat accgcagtgt attactgtgc cgcaaacat    300
```

```
ggtgaatact acgactctgg ttacgatgtt tggggtcaag gtactctggt gaccgtctcc        360
tca                                                                      363
```

```
<210> SEQ ID NO 35
<211> LENGTH: 363
<212> TYPE: DNA
<213> ORGANISM: Artificial
<220> FEATURE:
<223> OTHER INFORMATION: VHH13 nucleic acid sequence

<400> SEQUENCE: 35
gaggtgcagc tactggaatc tggggggggc ttagttcagc ctggtggtag ccttagatta         60
agctgtgctg catctggctt cacctttagc tctgaggcca tgggttgggt aagacaagcc        120
cctggcaagg gtctggagtg ggtgagcagc atcaatggct ctggcagaaa cacctattat        180
gctgattctg tgaagggcag attcaccatc agcagagaca acagcaagaa caccctgtac        240
ctgcagatga acagcctcag agctgaagac acagctgtgt attattgtgc tagaaaacat        300
ggggagtact atgactctgg ctatgatgtg tggggggcaag gcaccttagt gacagtgtca        360
tct                                                                      363
```

```
<210> SEQ ID NO 36
<211> LENGTH: 121
<212> TYPE: PRT
<213> ORGANISM: Artificial
<220> FEATURE:
<223> OTHER INFORMATION: VHH13 protein sequence

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Glu
            20                  25                  30

Ala Met Gly Trp Val Arg Gln Ala Pro Gly Lys Gly Leu Glu Trp Val
        35                  40                  45

Ser Ser Ile Asn Gly Ser Gly Arg Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys His Gly Glu Tyr Tyr Asp Ser Gly Tyr Asp Val Trp Gly
            100                 105                 110

Gln Gly Thr Leu Val Thr Val Ser Ser
        115                 120
```

```
<210> SEQ ID NO 37
<211> LENGTH: 360
<212> TYPE: DNA
<213> ORGANISM: Artificial
<220> FEATURE:
<223> OTHER INFORMATION: VHH 20 nucleic acid sequence

<400> SEQUENCE: 37
gaagttcagc tgctggaaag cggtggtggt ctggttcagc ctggtggtag cctgcgtctg         60
agctgtgcag caagcggttt tacctttagc agctatgcca tgggttgggt tcgtcaggca        120
cctggtaaag gtctggaatg ggttagcagc atcagcggct atggcgaaga aacctattat        180
```

```
gcagatagcg ttaaaggtcg ttttaccatt agccgtgata acagcaaaaa taccctgtac    240
ctgcagatga atagtctgcg tgcagaggat accgcagtgt attattgtgc gcgcttctac    300
taccgttact ggaaagaatt cgattactgg ggtcaaggta ctctggtgac cgtctcctca    360
```

<210> SEQ ID NO 38
<211> LENGTH: 360
<212> TYPE: DNA
<213> ORGANISM: Artificial
<220> FEATURE:
<223> OTHER INFORMATION: VHH 20 nucleic acid sequence

<400> SEQUENCE: 38

```
gaggttcagc tcctggaatc tggggggggg ctggttcaac ctggggggctc actgaggctg    60 agctgtgctg cctctggatt tacctttagc agctatgcca tgggttgggt tcgtcaggcc   120
cctggcaagg gcctggaatg ggttagcagc attagtggtt atggggagga gacctattat   180
gctgactctg tgaaaggcag atttaccatc agcagagata tagcaaaaa taccctgtac   240 ctacaaatga acagcctgag agctgaggac acagctgtgt actactgtgc tagattctac   300
taccgttact ggaaagagtt tgactactgg ggccaaggca ccctggtgac agtgtcatcc   360
```

<210> SEQ ID NO 39
<211> LENGTH: 120
<212> TYPE: PRT
<213> ORGANISM: Artificial
<220> FEATURE:
<223> OTHER INFORMATION: VHH20 protein sequence

<400> SEQUENCE: 39

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ser Ile Ser Gly Tyr Gly Glu Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Tyr Arg Tyr Trp Lys Glu Phe Asp Tyr Trp Gly Gln
            100                 105                 110

Gly Thr Leu Val Thr Val Ser Ser
        115                 120
```

<210> SEQ ID NO 40
<211> LENGTH: 378
<212> TYPE: DNA
<213> ORGANISM: Artificial
<220> FEATURE:
<223> OTHER INFORMATION: VHH21 nucleic acid sequence

<400> SEQUENCE: 40

```
gaagttcagc tgctggaaag cggtggtggt ctggttcagc ctggtggtag cctgcgtctg    60
agctgtgcag caagcggttt tacctttagc aactatgcca tgggttgggt tcgtcaggca   120
cctggtaaag tctggaatg ggttagcagc atcaccggcc tgggcggcaa catgtattat   180
gcagatagcg ttaaaggtcg ttttaccatt agccgtgata acagcaaaaa taccctgtac   240
```
ctgcagatga atagtctgcg tgcagaggat accgcagtgt attattgtgc gcgcatgtac        300
tactctcagg gtgttaacaa ctactcttac ccgtctactg atatctgggg tcaaggtact        360
ctggtgaccg tctcctca                                                       378

<210> SEQ ID NO 41
<211> LENGTH: 378
<212> TYPE: DNA
<213> ORGANISM: Artificial
<220> FEATURE:
<223> OTHER INFORMATION: VHH21 nucleic acid sequence

<400> SEQUENCE: 41
gaggtgcagc tgctggagtc tggggggggc ttggttcaac ctggggggaag cctgaggctg         60 agctgtgctg cctctggatt caccttcagc aattatgcca tggggtgggt tagacaagcc        120
cctggcaagg gcctggagtg ggtgtcaagc atcactggcc tgggggggcaa catgtattat        180 gctgactctg tgaaaggcag atttaccatc tctagagaca atagcaaaaa taccctctat        240
ctgcagatga atagcctgag agctgaggac acagctgtgt actattgtgc tagaatgtac        300
tacagccaag gggtgaacaa ctacagctac cctagtactg atatatgggg ccaaggtact        360
ctggtgaccg tctccagc                                                       378

<210> SEQ ID NO 42
<211> LENGTH: 126
<212> TYPE: PRT
<213> ORGANISM: Artificial
<220> FEATURE:
<223> OTHER INFORMATION: VHH21 protein sequence

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ser Ile Thr Gly Leu Gly Gly Asn Met Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Tyr Tyr Ser Gln Gly Val Asn Asn Tyr Ser Tyr Pro Ser
            100                 105                 110

Thr Asp Ile Trp Gly Gln Gly Thr Leu Val Thr Val Ser Ser
        115                 120                 125

<210> SEQ ID NO 43
<211> LENGTH: 48
<212> TYPE: DNA
<213> ORGANISM: Artificial
<220> FEATURE:
<223> OTHER INFORMATION: Whitlow Linker nucleic acid sequence

<400> SEQUENCE: 43
ggcagcacct ctggctctgg caagcctggc tctggggagg gctcaaca                       48

<210> SEQ ID NO 44

-continued

```
<211> LENGTH: 16
<212> TYPE: PRT
<213> ORGANISM: Artificial
<220> FEATURE:
<223> OTHER INFORMATION: Whitlow Linker protein sequence

<400> SEQUENCE: 44

Gly Ser Thr Ser Gly Ser Gly Lys Pro Gly Ser Gly Glu Gly Ser Thr
1               5                   10                  15

<210> SEQ ID NO 45
<211> LENGTH: 1533
<212> TYPE: DNA
<213> ORGANISM: Artificial
<220> FEATURE:
<223> OTHER INFORMATION: pXL1416 CAR nucleic acid sequence

<400> SEQUENCE: 45
atggccctgc ctgtgacagc tctgctcctc cctctggccc tgctgctcca tgccgccaga      60
ccccaggctg tgctgactca gccaccctca gcgtctgcga cccccgggca gagggtctcc     120
atctcctgtt cggggagcag ctccaacatc ggaaggaata ctgttaattg gtaccagcac     180
ctccctggaa cggcccccaa actcctcatt tatagtaatg atcatcggcc ctcaggggtc     240
cctgaccgat tctctggctc ccagtctggc acctcagcct ccctggccat cagtgggctc     300
cagtctgagg atgaggctga ttattactgt gcatcatggg atgacagcct gactggatgg     360
gtgttcggcg gagggaccaa ggtcaccgtc ctaggttcta gaggtggtgg tggtagcggc     420
ggcggcggct ctggtggtgg tggatccctc gagatggccc aggtgcagct ggtgcagtct     480
ggggctgagg tgaagaaggc tgggtcctcg ctgaaggtct cgtgcaaggc taatggaggc     540
agtttcacca actatcttat caactgggtg cgccaggccc ctggacaggg gcttgagtgg     600
atgggaggga tcatccctgt ctatggaaca ccaatctact cacagaaatt ccagggcaga     660
gtcacatttt ccgcggacga gcccacgagg acagcctaca tggaactgag cagcctgaca     720
tttgaggaca cggccgtgta ttattgtgtg agagaagacg aaggctacgg tgacctttat     780
ctcgcctact ggggacaggg gaccctggtc accgtctcct cattcgtgcc cgtgttcctg     840
cccgccaaac tactactac ccctgcacct aggcctccca ccccagcccc aacaatcgcc     900
agccagcctc tgtctctgcg gcccgaagcc tgtagacctg ctgccggcgg agccgtgcac     960
accagaggcc tggacttcgc ctgcgacatc tacatctggg cccctctggc cggcacctgt    1020
ggcgtgctgc tgctgagcct ggtgatcacc ctgtactgca ccaccggaa caaacggggc     1080 agaaagaaac tcctgtatat attcaaacaa ccatttatga ccagtacaa actactcaa      1140 gaggaagatg gctgtagctg ccgatttcca gaagaagaag aaggaggatg tgaactgaga    1200
gtgaagttca gcagatccgc cgacgcccct gcctaccagc agggacagaa ccagctgtac    1260
aacgagctga acctgggcag acgggaagag tacgacgtgc tggacaagcg gagaggccgg    1320
gaccccgaga tgggcggaaa gcccagacgg aagaacccc aggaaggcct gtataacgaa      1380
ctgcagaaag acaagatggc cgaggcctac agcgagatcg gcatgaaggg cgagcggagg    1440
cgcggcaagg ccacgatgg cctgtaccag ggcctgagca ccgccaccaa ggacacctac      1500
gacgccctgc acatgcaggc cctgccccc aga                                  1533

<210> SEQ ID NO 46
<211> LENGTH: 511
<212> TYPE: PRT
<213> ORGANISM: Artificial
<220> FEATURE:
```

<223> OTHER INFORMATION: pXL1416 CAR protein sequence

<400> SEQUENCE: 46

```
Met Ala Leu Pro Val Thr Ala Leu Leu Leu Pro Leu Ala Leu Leu Leu
1               5                   10                  15

His Ala Ala Arg Pro Gln Ala Val Leu Thr Gln Pro Pro Ser Ala Ser
            20                  25                  30

Ala Thr Pro Gly Gln Arg Val Ser Ile Ser Cys Ser Gly Ser Ser Ser
        35                  40                  45

Asn Ile Gly Arg Asn Thr Val Asn Trp Tyr Gln His Leu Pro Gly Thr
    50                  55                  60

Ala Pro Lys Leu Leu Ile Tyr Ser Asn Asp His Arg Pro Ser Gly Val
65                  70                  75                  80

Pro Asp Arg Phe Ser Gly Ser Gln Ser Gly Thr Ser Ala Ser Leu Ala
                85                  90                  95

Ile Ser Gly Leu Gln Ser Glu Asp Glu Ala Asp Tyr Tyr Cys Ala Ser
            100                 105                 110

Trp Asp Asp Ser Leu Thr Gly Trp Val Phe Gly Gly Gly Thr Lys Val
            115                 120                 125

Thr Val Leu Gly Ser Arg Gly Gly Gly Gly Ser Gly Gly Gly Gly Ser
    130                 135                 140

Gly Gly Gly Gly Ser Leu Glu Met Ala Gln Val Gln Leu Val Gln Ser
145                 150                 155                 160

Gly Ala Glu Val Lys Lys Ala Gly Ser Ser Leu Lys Val Ser Cys Lys
                165                 170                 175

Ala Asn Gly Gly Ser Phe Thr Asn Tyr Leu Ile Asn Trp Val Arg Gln
            180                 185                 190

Ala Pro Gly Gln Gly Leu Glu Trp Met Gly Gly Ile Ile Pro Val Tyr
            195                 200                 205

Gly Thr Pro Ile Tyr Ser Gln Lys Phe Gln Gly Arg Val Thr Phe Thr
    210                 215                 220

Ala Asp Glu Pro Thr Arg Thr Ala Tyr Met Glu Leu Ser Ser Leu Thr
225                 230                 235                 240

Phe Glu Asp Thr Ala Val Tyr Tyr Cys Val Arg Glu Asp Glu Gly Tyr
                245                 250                 255

Gly Asp Leu Tyr Leu Ala Tyr Trp Gly Gln Gly Thr Leu Val Thr Val
            260                 265                 270

Ser Ser Phe Val Pro Val Phe Leu Pro Ala Lys Pro Thr Thr Thr Pro
            275                 280                 285

Ala Pro Arg Pro Pro Thr Pro Ala Pro Thr Ile Ala Ser Gln Pro Leu
    290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
            340                 345                 350

Cys Asn His Arg Asn Lys Arg Gly Arg Lys Lys Leu Leu Tyr Ile Phe
            355                 360                 365

Lys Gln Pro Phe Met Arg Pro Val Gln Thr Thr Gln Glu Glu Asp Gly
    370                 375                 380

Cys Ser Cys Arg Phe Pro Glu Glu Glu Glu Gly Gly Cys Glu Leu Arg
385                 390                 395                 400
```

```
Val Lys Phe Ser Arg Ser Ala Asp Ala Pro Ala Tyr Gln Gln Gly Gln
                405                 410                 415

Asn Gln Leu Tyr Asn Glu Leu Asn Leu Gly Arg Arg Glu Glu Tyr Asp
            420                 425                 430

Val Leu Asp Lys Arg Arg Gly Arg Asp Pro Glu Met Gly Gly Lys Pro
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
            485                 490                 495

Lys Asp Thr Tyr Asp Ala Leu His Met Gln Ala Leu Pro Pro Arg
        500                 505                 510
```

<210> SEQ ID NO 47
<211> LENGTH: 1143
<212> TYPE: DNA
<213> ORGANISM: Artificial
<220> FEATURE:
<223> OTHER INFORMATION: pXL1394 CAR nucleic acid sequence

<400> SEQUENCE: 47

```
atggccctgc ctgtgacagc tctgctcctc cctctggccc tgctgctcca tgccgccaga      60
cccgaagttc agctgctgga aagcggtggt ggtctggttc agcctggtgg tagcctgcgt     120
ctgagctgtg cagcaagcgg tttttacctt aacatcgatg ccatgggttg ggttcgtcag     180
gcacctggta aaggtctgga atgggttagc agcatcagca gcagcggcgg caccacctat     240
tatgcagata gcgttaaagg tcgtttttacc attagccgtg ataacagcaa aaataccctg     300
tacctgcaga tgaatagtct gcgtgcagag gataccgcag tgtattattg tgcgcgctct     360
cgttactctg ttccggacgg tcgtggttct tacgatgttt ggggtcaagg tactctggtg     420
accgtctcct cattcgtgcc cgtgttcctg cccgccaaac ctactactac ccctgcacct     480
aggcctccca ccccagcccc aacaatcgcc agccagcctc tgtctctgcg gcccgaagcc     540
tgtagacctg ctgccggcgg agccgtgcac accagaggcc tggacttcgc ctgcgacatc     600
tacatctggg cccctctggc cggcacctgt ggcgtgctgc tgctgagcct ggtgatcacc     660
ctgtactgca accaccggaa caaacggggc agaaagaaac tcctgtatat attcaaacaa     720
ccatttatga ccagtaca aactactcaa gaggaagatg ctgtagctg ccgatttcca     780 gaagaagaag aaggaggatg tgaactgaga gtgaagttca gcagatccgc cgacgccct     840 gcctaccagc agggacagaa ccagctgtac aacgagctga acctgggcag acgggaagag     900
tacgacgtgc tggacaagcg gagaggccgg gaccccgaga tgggcggaaa gcccagacgg     960 aagaacccc aggaaggcct gtataacgaa ctgcagaaag acaagatggc cgaggcctac    1020
agcgagatcg gcatgaaggg cgagcggagg cgcggcaagg ccacgatgg cctgtaccag    1080 ggcctgagca ccgccaccaa ggacacctac gacgccctgc acatgcaggc cctgccccc    1140 aga                                                                 1143
```

<210> SEQ ID NO 48
<211> LENGTH: 381
<212> TYPE: PRT
<213> ORGANISM: Artificial
<220> FEATURE:
<223> OTHER INFORMATION: pXL1394 CAR protein sequence

```
<400> SEQUENCE: 48

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Asn Ile Asp Ala Met Gly Trp Val Arg Gln Ala Pro Gly Lys
    50                  55                  60

Gly Leu Glu Trp Val Ser Ser Ile Ser Ser Ser Gly Gly Thr Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ser Arg Tyr Ser Val Pro Asp Gly Arg
            115                 120                 125

Gly Ser Tyr Asp Val Trp Gly Gln Gly Thr Leu Val Thr Val Ser Ser
    130                 135                 140

Phe Val Pro Val Phe Leu Pro Ala Lys Pro Thr Thr Thr Pro Ala Pro
145                 150                 155                 160

Arg Pro Pro Thr Pro Ala Pro Thr Ile Ala Ser Gln Pro Leu Ser Leu
            165                 170                 175

Arg Pro Glu Ala Cys Arg Pro Ala Ala Gly Gly Ala Val His Thr Arg
            180                 185                 190

Gly Leu Asp Phe Ala Cys Asp Ile Tyr Ile Trp Ala Pro Leu Ala Gly
            195                 200                 205

Thr Cys Gly Val Leu Leu Leu Ser Leu Val Ile Thr Leu Tyr Cys Asn
    210                 215                 220

His Arg Asn Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys Ser
            245                 250                 255

Cys Arg Phe Pro Glu Glu Glu Glu Gly Gly Cys Glu Leu Arg Val Lys
            260                 265                 270

Phe Ser Arg Ser Ala Asp Ala Pro Ala Tyr Gln Gln Gly Gln Asn Gln
    275                 280                 285

Leu Tyr Asn Glu Leu Asn Leu Gly Arg Arg Glu Glu Tyr Asp Val Leu
    290                 295                 300

Asp Lys Arg Arg Gly Arg Asp Pro Glu Met Gly Gly Lys Pro Arg Arg
305                 310                 315                 320

Lys Asn Pro Gln Glu Gly Leu Tyr Asn Glu Leu Gln Lys Asp Lys Met
            325                 330                 335

Ala Glu Ala Tyr Ser Glu Ile Gly Met Lys Gly Glu Arg Arg Arg Gly
            340                 345                 350

Lys Gly His Asp Gly Leu Tyr Gln Gly Leu Ser Thr Ala Thr Lys Asp
            355                 360                 365

Thr Tyr Asp Ala Leu His Met Gln Ala Leu Pro Pro Arg
    370                 375                 380

<210> SEQ ID NO 49
<211> LENGTH: 1137
<212> TYPE: DNA
<213> ORGANISM: Artificial
```

<220> FEATURE:
<223> OTHER INFORMATION: pXL1398 CAR nucleic acid sequence

<400> SEQUENCE: 49
atggccctgc ctgtgacagc tctgctcctc cctctggccc tgctgctcca tgccgccaga      60
cccgaagttc agctgctgga aagcggtggt ggtctggttc agcctggtgg tagcctgcgt     120
ctgagctgtg cagcaagcgg tttttacctttt agcagcgaag ccatgggttg ggttcgtcag   180
gcacctggta aaggtctgga atgggttagc agcatcaacg gcagcggccg caacacctat     240
tatgcagata gcgttaaagg tcgtttttacc attagccgtg ataacagcaa aaatacccctg    300 tacctgcaga tgaatagtct gcgtgcagag gataccgcag tgtattactg tgcgcgcaaa     360
catggtgaat actacgactc tggttacgat gtttggggtc aaggtactct ggtgaccgtc     420
tcctcattcg tgcccgtgtt cctgcccgcc aaacctacta ctacccctgc acctaggcct     480 cccacccccag ccccaacaat cgccagccag cctctgtctc tgcggcccga agcctgtaga     540
cctgctgccg gcggagccgt gcacaccaga ggcctggact cgcctgcga catctacatc     600 tgggcccctc tggccggcac ctgtggcgtg ctgctgctga gcctggtgat caccctgtac     660
tgcaaccacc ggaacaaacg gggcagaaag aaactcctgt atatattcaa acaaccattt     720
atgagaccag tacaaactac tcaagaggaa gatggctgta gctgccgatt ccagaagaa     780 gaagaaggag gatgtgaact gagagtgaag ttcagcagat ccgccgacgc ccctgcctac     840
cagcagggac agaaccagct gtacaacgag ctgaacctgg gcagacggga agagtacgac     900
gtgctggaca gcggagagg ccgggacccc gagatgggcg gaaagcccag acggaagaac     960
ccccaggaag gcctgtataa cgaactgcag aaagacaaga tggccgaggc ctacagcgag    1020
atcggcatga gggcgagcg gaggcgcggc aagggccacg atggcctgta ccagggcctg    1080
agcaccgcca ccaaggacac ctacgacgcc ctgcacatgc aggccctgcc ccccaga      1137

<210> SEQ ID NO 50
<211> LENGTH: 379
<212> TYPE: PRT
<213> ORGANISM: Artificial
<220> FEATURE:
<223> OTHER INFORMATION: pXL1398 CAR protein sequence

<400> SEQUENCE: 50

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Glu Ala Met Gly Trp Val Arg Gln Ala Pro Gly Lys
    50                  55                  60

Gly Leu Glu Trp Val Ser Ser Ile Asn Gly Ser Gly Arg Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Lys His Gly Glu Tyr Tyr Asp Ser Gly
        115                 120                 125

Tyr Asp Val Trp Gly Gln Gly Thr Leu Val Thr Val Ser Ser Phe Val
    130                 135                 140

```
Pro Val Phe Leu Pro Ala Lys Pro Thr Thr Thr Pro Ala Pro Arg Pro
145                 150                 155                 160

Pro Thr Pro Ala Pro Thr Ile Ala Ser Gln Pro Leu Ser Leu Arg Pro
                165                 170                 175

Glu Ala Cys Arg Pro Ala Ala Gly Gly Ala Val His Thr Arg Gly Leu
            180                 185                 190

Asp Phe Ala Cys Asp Ile Tyr Ile Trp Ala Pro Leu Ala Gly Thr Cys
            195                 200                 205

Gly Val Leu Leu Leu Ser Leu Val Ile Thr Leu Tyr Cys Asn His Arg
    210                 215                 220

Asn Lys Arg Gly Arg Lys Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
                245                 250                 255

Phe Pro Glu Glu Glu Glu Gly Gly Cys Glu Leu Arg Val Lys Phe Ser
            260                 265                 270

Arg Ser Ala Asp Ala Pro Ala Tyr Gln Gln Gly Gln Asn Gln Leu Tyr
            275                 280                 285

Asn Glu Leu Asn Leu Gly Arg Arg Glu Glu Tyr Asp Val Leu Asp Lys
    290                 295                 300

Arg Arg Gly Arg Asp Pro Glu Met Gly Gly Lys Pro Arg Arg Lys Asn
305                 310                 315                 320

Pro Gln Glu Gly Leu Tyr Asn Glu Leu Gln Lys Asp Lys Met Ala Glu
                325                 330                 335

Ala Tyr Ser Glu Ile Gly Met Lys Gly Glu Arg Arg Arg Gly Lys Gly
            340                 345                 350

His Asp Gly Leu Tyr Gln Gly Leu Ser Thr Ala Thr Lys Asp Thr Tyr
            355                 360                 365

Asp Ala Leu His Met Gln Ala Leu Pro Pro Arg
    370                 375
```

```
<210> SEQ ID NO 51
<211> LENGTH: 1134
<212> TYPE: DNA
<213> ORGANISM: Artificial
<220> FEATURE:
<223> OTHER INFORMATION: pXL1423 CAR nucleic acid sequence

<400> SEQUENCE: 51
atggccctgc ctgtgacagc tctgctcctc cctctggccc tgctgctcca tgccgccaga      60
cccgaagttc agctgctgga aagcggtggt ggtctggttc agcctggtgg tagcctgcgt     120
ctgagctgtg cagcaagcgg ttttaccttt agcagctatg ccatgggttg ggttcgtcag     180
gcacctggta aaggtctgga atgggttagc agcatcagcg ctatggcga agaaacctat     240 tatgcagata cgttaaagg tcgtttacc attagccgtg ataacagcaa aaataccctg     300
tacctgcaga tgaatagtct gcgtgcagag gataccgcag tgtattattg tgcgcgcttc     360
tactaccgtt actggaaaga attcgattac tggggtcaag gtactctggt gaccgtctcc     420
tcattcgtgc ccgtgttcct gcccgccaaa cctactacta ccctgcacc taggcctccc     480 accccagccc caacaatcgc cagccagcct ctgtctctgc ggcccgaagc ctgtagacct     540
gctgccggcg gagccgtgca ccagagagc ctggacttcg cctgcgacat ctacatctgg     600
gcccctctgg ccggcacctg tggcgtgctg ctgctgagcc tggtgatcac cctgtactgc     660
aaccaccgga acaaacgggg cagaaagaaa ctcctgtata tattcaaaca accatttatg     720
```

```
agaccagtac aaactactca agaggaagat ggctgtagct gccgatttcc agaagaagaa    780
gaaggaggat gtgaactgag agtgaagttc agcagatccg ccgacgcccc tgcctaccag    840
cagggacaga accagctgta caacgagctg aacctgggca gacgggaaga gtacgacgtg    900
ctggacaagc ggagaggccg ggaccccgag atgggcggaa agcccagacg gaagaacccc    960
caggaaggcc tgtataacga actgcagaaa gacaagatgg ccgaggccta cagcgagatc   1020
ggcatgaagg gcgagcggag cgcggcaag ggccacgatg gcctgtacca gggcctgagc    1080
accgccacca aggacaccta cgacgccctg cacatgcagg ccctgccccc caga           1134
```

<210> SEQ ID NO 52
<211> LENGTH: 378
<212> TYPE: PRT
<213> ORGANISM: Artificial
<220> FEATURE:
<223> OTHER INFORMATION: pXL1423 CAR protein sequence

<400> SEQUENCE: 52

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Gly Trp Val Arg Gln Ala Pro Gly Lys
    50                  55                  60

Gly Leu Glu Trp Val Ser Ser Ile Ser Gly Tyr Gly Glu Glu Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Phe Tyr Tyr Arg Tyr Trp Lys Glu Phe
            115                 120                 125

Asp Tyr Trp Gly Gln Gly Thr Leu Val Thr Val Ser Ser Phe Val Pro
        130                 135                 140

Val Phe Leu Pro Ala Lys Pro Thr Thr Thr Pro Ala Pro Arg Pro Pro
145                 150                 155                 160

Thr Pro Ala Pro Thr Ile Ala Ser Gln Pro Leu Ser Leu Arg Pro Glu
                165                 170                 175

Ala Cys Arg Pro Ala Ala Gly Gly Ala Val His Thr Arg Gly Leu Asp
            180                 185                 190

Phe Ala Cys Asp Ile Tyr Ile Trp Ala Pro Leu Ala Gly Thr Cys Gly
            195                 200                 205

Val Leu Leu Leu Ser Leu Val Ile Thr Leu Tyr Cys Asn His Arg Asn
        210                 215                 220

Lys Arg Gly Arg Lys Lys Leu Leu Tyr Ile Phe Lys Gln Pro Phe Met
225                 230                 235                 240

Arg Pro Val Gln Thr Thr Gln Glu Glu Asp Gly Cys Ser Cys Arg Phe
                245                 250                 255

Pro Glu Glu Glu Glu Gly Gly Cys Glu Leu Arg Val Lys Phe Ser Arg
            260                 265                 270

Ser Ala Asp Ala Pro Ala Tyr Gln Gln Gly Gln Asn Gln Leu Tyr Asn
            275                 280                 285
```

```
Glu Leu Asn Leu Gly Arg Arg Glu Glu Tyr Asp Val Leu Asp Lys Arg
    290                 295                 300

Arg Gly Arg Asp Pro Glu Met Gly Gly Lys Pro Arg Arg Lys Asn Pro
305                 310                 315                 320

Gln Glu Gly Leu Tyr Asn Glu Leu Gln Lys Asp Lys Met Ala Glu Ala
                325                 330                 335

Tyr Ser Glu Ile Gly Met Lys Gly Glu Arg Arg Arg Gly Lys Gly His
                340                 345                 350

Asp Gly Leu Tyr Gln Gly Leu Ser Thr Ala Thr Lys Asp Thr Tyr Asp
            355                 360                 365

Ala Leu His Met Gln Ala Leu Pro Pro Arg
    370                 375
```

```
<210> SEQ ID NO 53
<211> LENGTH: 1152
<212> TYPE: DNA
<213> ORGANISM: Artificial
<220> FEATURE:
<223> OTHER INFORMATION: pXL1424 CAR nucleic acid sequence

<400> SEQUENCE: 53
atggccctgc ctgtgacagc tctgctcctc cctctggccc tgctgctcca tgccgccaga      60
cccgaagttc agctgctgga aagcggtggt ggtctggttc agcctggtgg tagcctgcgt     120
ctgagctgtg cagcaagcgg tttttacctt agcaactatg ccatgggttg ggttcgtcag     180
gcacctggta aaggtctgga atgggttagc agcatcaccg gcctgggcgg caacatgtat     240
tatgcagata gcgttaaagg tcgttttacc attagccgtg ataacagcaa aaataccctg     300
tacctgcaga tgaatagtct gcgtgcagag gataccgcag tgtattattg tgcgcgcatg     360
tactactctc agggtgttaa caactactct tacccgtcta ctgatatctg gggtcaaggt     420
actctggtga ccgtctcctc attcgtgccc gtgttcctgc ccgccaaacc tactactacc     480
cctgcaccta ggcctccac cccagcccca acaatcgcca gccagcctct gtctctgcgg     540
cccgaagcct gtagacctgc tgccggcgga gccgtgcaca ccagaggcct ggacttcgcc     600
tgcgacatct acatctgggc ccctctggcc ggcacctgtg gcgtgctgct gctgagcctg     660
gtgatcaccc tgtactgcaa ccaccggaac aaacggggca gaaagaaact cctgtatata     720
ttcaaacaac catttatgag accagtacaa actactcaag aggaagatgg ctgtagctgc     780
cgatttccag aagaagaaga aggaggatgt gaactgagag tgaagttcag cagatccgcc     840 gacgccctg cctaccagca gggacagaac cagctgtaca cgagctgaa cctgggcaga     900 cgggaagagt acgacgtgct ggacaagcgg agaggccggg accccgagat gggcggaaag     960
cccagacgga agaaccccca ggaaggcctg tataacgaac tgcagaaaga caagatggcc    1020
gaggcctaca gcgagatcgg catgaagggc gagcggaggc gcggcaaggg ccacgatggc    1080
ctgtaccagg gcctgagcac cgccaccaag gacacctacg acgccctgca catgcaggcc    1140 ctgccccca ga                                                        1152
```

```
<210> SEQ ID NO 54
<211> LENGTH: 384
<212> TYPE: PRT
<213> ORGANISM: Artificial
<220> FEATURE:
<223> OTHER INFORMATION: pXL1424 CAR protein sequence

<400> SEQUENCE: 54

Met Ala Leu Pro Val Thr Ala Leu Leu Leu Pro Leu Ala Leu Leu Leu
```

-continued

```
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
            35                  40                  45

Thr Phe Ser Asn Tyr Ala Met Gly Trp Val Arg Gln Ala Pro Gly Lys
            50                  55                  60

Gly Leu Glu Trp Val Ser Ser Ile Thr Gly Leu Gly Gly Asn Met Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Met Tyr Tyr Ser Gln Gly Val Asn Asn
            115                 120                 125

Tyr Ser Tyr Pro Ser Thr Asp Ile Trp Gly Gln Gly Thr Leu Val Thr
            130                 135                 140

Val Ser Ser Phe Val Pro Val Phe Leu Pro Ala Lys Pro Thr Thr Thr
145                 150                 155                 160

Pro Ala Pro Arg Pro Pro Thr Pro Ala Pro Thr Ile Ala Ser Gln Pro
                165                 170                 175

Leu Ser Leu Arg Pro Glu Ala Cys Arg Pro Ala Ala Gly Gly Ala Val
            180                 185                 190

His Thr Arg Gly Leu Asp Phe Ala Cys Asp Ile Tyr Ile Trp Ala Pro
            195                 200                 205

Leu Ala Gly Thr Cys Gly Val Leu Leu Leu Ser Leu Val Ile Thr Leu
            210                 215                 220

Tyr Cys Asn His Arg Asn Lys Arg Gly Arg Lys Lys Leu Leu Tyr Ile
225                 230                 235                 240

Phe Lys Gln Pro Phe Met Arg Pro Val Gln Thr Thr Gln Glu Glu Asp
                245                 250                 255

Gly Cys Ser Cys Arg Phe Pro Glu Glu Glu Glu Gly Gly Cys Glu Leu
                260                 265                 270

Arg Val Lys Phe Ser Arg Ser Ala Asp Ala Pro Ala Tyr Gln Gln Gly
            275                 280                 285

Gln Asn Gln Leu Tyr Asn Glu Leu Asn Leu Gly Arg Arg Glu Glu Tyr
            290                 295                 300

Asp Val Leu Asp Lys Arg Arg Gly Arg Asp Pro Glu Met Gly Gly Lys
305                 310                 315                 320

Pro Arg Arg Lys Asn Pro Gln Glu Gly Leu Tyr Asn Glu Leu Gln Lys
                325                 330                 335

Asp Lys Met Ala Glu Ala Tyr Ser Glu Ile Gly Met Lys Gly Glu Arg
            340                 345                 350

Arg Arg Gly Lys Gly His Asp Gly Leu Tyr Gln Gly Leu Ser Thr Ala
            355                 360                 365

Thr Lys Asp Thr Tyr Asp Ala Leu His Met Gln Ala Leu Pro Pro Arg
            370                 375                 380
```

<210> SEQ ID NO 55
<211> LENGTH: 1545
<212> TYPE: DNA
<213> ORGANISM: Artificial
<220> FEATURE:
<223> OTHER INFORMATION: pXL1698 CAR nucleic acid sequence

```
<400> SEQUENCE: 55
atggccctac ctgtgacagc cctactgtta cccctggccc tccttctgca tgctgctaga      60
cctgaggtgc agctactgga atctgggggg ggcttagttc agcctggtgg tagccttaga     120
ttaagctgtg ctgcatctgg cttcaccttt agctctgagg ccatgggttg ggtaagacaa     180
gcccctggca agggtctgga gtgggtgagc agcatcaatg gctctggcag aaacacctat     240
tatgctgatt ctgtgaaggg cagattcacc atcagcagag acaacagcaa gaacaccctg     300
tacctgcaga tgaacagcct cagagctgaa gacacagctg tgtattattg tgctagaaaa     360
catggggagt actatgactc tggctatgat gtgtgggggc aaggcacctt agtgacagtg     420
tcatctggca gcacctctgg ctctggcaag cctggctctg gggagggctc aacagaggtt     480
cagctcctgg aatctggggg ggggctggtt caacctgggg gctcactgag gctgagctgt     540
gctgcctctg gatttacctt tagcagctat gccatgggtt gggttcgtca ggcccctggc     600
aagggcctgg aatgggttag cagcattagt ggttatgggg aggagaccta ttatgctgac     660
tctgtgaaag gcagatttac catcagcaga gataatagca aaaataccct gtacctacaa     720
atgaacagcc tgagagctga ggacacagct gtgtactact gtgctagatt ctactaccgt     780
tactggaaag agtttgacta ctggggccaa ggcaccctgg tgacagtgtc atcctttgtg     840
cctgtatttc tgcctgccaa gcccaccaca cacctgccc ctagaccacc cacccctgcc     900
cccaccattg cttctcagcc ccttagctta agacctgaag cctgtagacc tgctgctggg     960
ggggctgtgc acacaagagg cctggacttt gcctgtgaca tctacatctg gccccccctg    1020
gctggcacct gtgggggtgct gctgctgagc ctggtgatca ccctgtactg caaccacaga    1080
aacaagagag gcagaaagaa agctgctgtac atcttcaagc agcccttcat gagacctgtg    1140
cagaccaccc aagaggagga tggctgcagc tgcagattcc ctgaggagga ggagggggc    1200 tgtgagctga gagtgaagtt cagcagatct gctgatgccc ctgcctatca gcaagggcag    1260
aatcagctgt acaatgagct gaatctgggc agaagagagg agtatgatgt gctggacaag    1320
agaagaggca gagaccctga tggggggggc aagcctagaa gaaagaaccc ccaagagggc    1380
ctgtataatg agctgcagaa ggacaagatg gctgaggcct actctgagat tggcatgaag    1440
ggggagagaa gaagaggcaa gggccatgat ggcctgtacc aaggcctgag cacagccacc    1500
aaggacacct atgatgccct acacatgcaa gctctgcctc ctaga                     1545

<210> SEQ ID NO 56
<211> LENGTH: 513
<212> TYPE: PRT
<213> ORGANISM: Artificial
<220> FEATURE:
<223> OTHER INFORMATION: pXL1698 CAR protein sequence

<400> SEQUENCE: 56

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Glu Ala Met Gly Trp Val Arg Gln Ala Pro Gly Lys Gly Leu
    50                  55                  60

Glu Trp Val Ser Ser Ile Asn Gly Ser Gly Arg Asn Thr Tyr Tyr Ala
65                  70                  75                  80
```

```
Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Lys His Gly Glu Tyr Tyr Asp Ser Gly Tyr Asp
            115                 120                 125

Val Trp Gly Gln Gly Thr Leu Val Thr Val Ser Ser Gly Ser Thr Ser
    130                 135                 140

Gly Ser Gly Lys Pro Gly Ser Gly Glu Gly Ser Thr Glu Val Gln Leu
145                 150                 155                 160

Leu Glu Ser Gly Gly Gly Leu Val Gln Pro Gly Gly Ser Leu Arg Leu
                165                 170                 175

Ser Cys Ala Ala Ser Gly Phe Thr Phe Ser Ser Tyr Ala Met Gly Trp
            180                 185                 190

Val Arg Gln Ala Pro Gly Lys Gly Leu Glu Trp Val Ser Ser Ile Ser
            195                 200                 205

Gly Tyr Gly Glu Glu Thr Tyr Tyr Ala Asp Ser Val Lys Gly Arg Phe
    210                 215                 220

Thr Ile Ser Arg Asp Asn Ser Lys Asn Thr Leu Tyr Leu Gln Met Asn
225                 230                 235                 240

Ser Leu Arg Ala Glu Asp Thr Ala Val Tyr Tyr Cys Ala Arg Phe Tyr
                245                 250                 255

Tyr Arg Tyr Trp Lys Glu Phe Asp Tyr Trp Gly Gln Gly Thr Leu Val
            260                 265                 270

Thr Val Ser Ser Phe Val Pro Val Phe Leu Pro Ala Lys Pro Thr Thr
            275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Asn His Arg Asn Lys Arg Gly Arg Lys Lys Leu Leu Tyr
            355                 360                 365

Ile Phe Lys Gln Pro Phe Met Arg Pro Val Gln Thr Thr Gln Glu Glu
    370                 375                 380

Asp Gly Cys Ser Cys Arg Phe Pro Glu Glu Glu Glu Gly Gly Cys Glu
385                 390                 395                 400

Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
            420                 425                 430

Tyr Asp Val Leu Asp Lys Arg Arg Gly Arg Asp Pro Glu Met Gly Gly
            435                 440                 445

Lys Pro Arg Arg Lys Asn Pro Gln Glu Gly Leu Tyr Asn Glu Leu Gln
    450                 455                 460

Lys Asp Lys Met Ala Glu Ala Tyr Ser Glu Ile Gly Met Lys Gly Glu
465                 470                 475                 480

Arg Arg Arg Gly Lys Gly His Asp Gly Leu Tyr Gln Gly Leu Ser Thr
                485                 490                 495

Ala Thr Lys Asp Thr Tyr Asp Ala Leu His Met Gln Ala Leu Pro Pro
```

-continued

```
              500             505             510

Arg

<210> SEQ ID NO 57
<211> LENGTH: 1545
<212> TYPE: DNA
<213> ORGANISM: Artificial
<220> FEATURE:
<223> OTHER INFORMATION: pXL1700 CAR  nucleic acid sequence

<400> SEQUENCE: 57
atggccctac ctgtgacagc cctactgtta cccctggccc tccttctgca tgctgctaga      60
cctgaggttc agctcctgga atctggggggg gggctggttc aacctggggg ctcactgagg     120
ctgagctgtg ctgcctctgg atttaccttt agcagctatg ccatgggttg ggttcgtcag      180
gcccctggca agggcctgga atgggttagc agcattagtg gttatgggga ggagacctat      240
tatgctgact ctgtgaaagg cagatttacc atcagcagag ataatagcaa aaataccctg      300
tacctacaaa tgaacagcct gagagctgag gacacagctg tgtactactg tgctagattc      360
tactaccgtt actggaaaga gtttgactac tggggccaag gcaccctggt gacagtgtca      420
tccggcagca cctctggctc tggcaagcct ggctctgggg agggctcaac agaggtgcag      480
ctactggaat ctgggggggg cttagttcag cctggtggta gccttagatt aagctgtgct      540
gcatctggct tcacctttag ctctgaggcc atgggttggg taagacaagc ccctggcaag      600
ggtctggagt gggtgagcag catcaatggc tctggcagaa acacctatta tgctgattct      660
gtgaagggca gattcaccat cagcagagac aacagcaaga cacccttgta cctgcagatg      720
aacagcctca gagctgaaga cacagctgtg tattattgtg ctagaaaaca tggggagtac      780
tatgactctg ctatgatgt gtgggggcaa ggcaccttag tgacagtgtc atctttgtg        840 cctgtatttc tgcctgccaa gcccaccaca cacctgccc ctagaccacc caccccgcc        900 cccaccattg cttctcagcc ccttagctta agacctgaag cctgtagacc tgctgctggg      960
ggggctgtgc acacaagagg cctggacttt gcctgtgaca tctacatctg gccccccctg     1020
gctggcacct gtggggtgct gctgctgagc ctggtgatca ccctgtactg caaccacaga     1080
aacaagagag gcagaaagaa gctgctgtac atcttcaagc agcccttcat gagacctgtg     1140
cagaccaccc aagaggagga tggctgcagc tgcagattcc ctgaggagga ggagggggggc    1200 tgtgagctga gagtgaagtt cagcagatct gctgatgccc ctgcctatca gcaagggcag     1260
aatcagctgt acaatgagct gaatctgggc agaagagagg agtatgatgt gctggacaag     1320
agaagaggca gagaccctga gatggggggc aagcctagaa gaaagaaccc ccaagagggc     1380
ctgtataatg agctgcagaa ggacaagatg gctgaggcct actctgagat tggcatgaag     1440
ggggagagaa gaagaggcaa gggccatgat ggcctgtacc aaggcctgag cacagccacc     1500
aaggacacct atgatgccct acacatgcaa gctctgcctc ctaga                    1545

<210> SEQ ID NO 58
<211> LENGTH: 515
<212> TYPE: PRT
<213> ORGANISM: Artificial
<220> FEATURE:
<223> OTHER INFORMATION: pXL1700 CAR protein sequence

<400> SEQUENCE: 58

Met Ala Leu Pro Val Thr Ala Leu Leu Leu Pro Leu Ala Leu Leu Leu
1               5                   10                  15
```

-continued

```
His Ala Ala Arg Pro Glu Val Gln Leu Leu Glu Ser Gly Gly Gly Leu
            20              25              30

Val Gln Pro Gly Gly Ser Leu Arg Leu Ser Cys Ala Ala Ser Gly Phe
        35              40              45

Thr Phe Ser Ser Tyr Ala Met Gly Trp Val Arg Gln Ala Pro Gly Lys
    50              55              60

Gly Leu Glu Trp Val Ser Ser Ile Ser Gly Tyr Gly Glu Glu Thr Tyr
65              70              75              80

Tyr Ala Asp Ser Val Lys Gly Arg Phe Thr Ile Ser Arg Asp Asn Ser
                85              90              95

Lys Asn Thr Leu Tyr Leu Gln Met Asn Ser Leu Arg Ala Glu Asp Thr
            100             105             110

Ala Val Tyr Tyr Cys Ala Arg Phe Tyr Tyr Arg Tyr Trp Lys Glu Phe
            115             120             125

Asp Tyr Trp Gly Gln Gly Thr Leu Val Thr Val Ser Ser Gly Ser Thr
    130             135             140

Ser Gly Ser Gly Lys Pro Gly Ser Gly Glu Gly Ser Thr Glu Val Gln
145             150             155             160

Leu Leu Glu Ser Gly Gly Gly Leu Val Gln Pro Gly Gly Ser Leu Arg
            165             170             175

Leu Ser Cys Ala Ala Ser Gly Phe Thr Phe Ser Ser Glu Ala Met Gly
            180             185             190

Trp Val Arg Gln Ala Pro Gly Lys Gly Leu Glu Trp Val Ser Ser Ile
    195             200             205

Asn Gly Ser Gly Arg Asn Thr Tyr Tyr Ala Asp Ser Val Lys Gly Arg
    210             215             220

Phe Thr Ile Ser Arg Asp Asn Ser Lys Asn Thr Leu Tyr Leu Gln Met
225             230             235             240

Asn Ser Leu Arg Ala Glu Asp Thr Ala Val Tyr Tyr Cys Ala Arg Lys
            245             250             255

His Gly Glu Tyr Tyr Asp Ser Gly Tyr Asp Val Trp Gly Gln Gly Thr
            260             265             270

Leu Val Thr Val Ser Ser Phe Val Pro Val Phe Leu Pro Ala Lys Pro
    275             280             285

Thr Thr Thr Pro Ala Pro Arg Pro Pro Thr Pro Ala Pro Thr Ile Ala
    290             295             300

Ser Gln Pro Leu Ser Leu Arg Pro Glu Ala Cys Arg Pro Ala Ala Gly
305             310             315             320

Gly Ala Val His Thr Arg Gly Leu Asp Phe Ala Cys Asp Ile Tyr Ile
            325             330             335

Trp Ala Pro Leu Ala Gly Thr Cys Gly Val Leu Leu Leu Ser Leu Val
            340             345             350

Ile Thr Leu Tyr Cys Asn His Arg Asn Lys Arg Gly Arg Lys Lys Leu
            355             360             365

Leu Tyr Ile Phe Lys Gln Pro Phe Met Arg Pro Val Gln Thr Thr Gln
    370             375             380

Glu Glu Asp Gly Cys Ser Cys Arg Phe Pro Glu Glu Glu Glu Gly Gly
385             390             395             400

Cys Glu Leu Arg Val Lys Phe Ser Arg Ser Ala Asp Ala Pro Ala Tyr
            405             410             415

Gln Gln Gly Gln Asn Gln Leu Tyr Asn Glu Leu Asn Leu Gly Arg Arg
            420             425             430

Glu Glu Tyr Asp Val Leu Asp Lys Arg Arg Gly Arg Asp Pro Glu Met
```

-continued

```
        435              440              445
Gly Gly Lys Pro Arg Arg Lys Asn Pro Gln Glu Gly Leu Tyr Asn Glu
    450              455              460

Leu Gln Lys Asp Lys Met Ala Glu Ala Tyr Ser Glu Ile Gly Met Lys
465              470              475              480

Gly Glu Arg Arg Arg Gly Lys Gly His Asp Gly Leu Tyr Gln Gly Leu
                485              490              495

Ser Thr Ala Thr Lys Asp Thr Tyr Asp Ala Leu His Met Gln Ala Leu
            500              505              510

Pro Pro Arg
        515

<210> SEQ ID NO 59
<211> LENGTH: 1563
<212> TYPE: DNA
<213> ORGANISM: Artificial
<220> FEATURE:
<223> OTHER INFORMATION: pXL1702 CAR  nucleic acid sequence

<400> SEQUENCE: 59
atggccctac ctgtgacagc cctactgtta cccctggccc tccttctgca tgctgctaga      60
cctgaggtgc agctactgga atctgggggg ggcttagttc agcctggtgg tagccttaga     120
ttaagctgtg ctgcatctgg cttcaccttt agctctgagg ccatgggttg ggtaagacaa     180
gcccctggca agggtctgga gtgggtgagc agcatcaatg gctctggcag aaacacctat     240
tatgctgatt ctgtgaaggg cagattcacc atcagcagag acaacagcaa gaacaccctg     300
tacctgcaga tgaacagcct cagagctgaa gacacagctg tgtattattg tgctagaaaa     360
catggggagt actatgactc tggctatgat gtgtgggggc aaggcacctt agtgacagtg     420
tcatctggca gcacctctgg ctctggcaag cctggctctg gggagggctc aacagaggtg     480
cagctgctgg agtctggggg gggcttggtt caacctgggg gaagcctgag gctgagctgt     540
gctgcctctg gattcacctt cagcaattat gccatggggt gggttagaca gcccctggcc     600
aagggcctgg agtgggtgtc aagcatcact ggcctggggg gcaacatgta ttatgctgac     660
tctgtgaaag gcagatttac catctctaga gacaatagca aaaatacccct ctatctgcag     720 atgaatagcc tgagagctga ggacacagct gtgtactatt gtgctagaat gtactacagc     780
caaggggtga caactacag ctaccctagt actgatatat ggggccaagg tactctggtg     840
accgtctcca gctttgtgcc tgtatttctg cctgccaagc ccaccacaac acctgcccct     900
agaccaccca cccctgcccc caccattgct tctcagcccc ttagcttaag acctgaagcc     960
tgtagacctg ctgctggggg ggctgtgcac acaagaggcc tggactttgc ctgtgacatc    1020
tacatctggg cccccctggc tggcacctgt ggggtgctgc tgctgagcct ggtgatcacc    1080
ctgtactgca accacagaaa caagagaggc agaaagaagc tgctgtacat cttcaagcag    1140
cccttcatga cctgtgca gaccacccaa gaggaggatg ctgcagctg cagattccct     1200 gaggaggagg agggggggctg tgagctgaga gtgaagttca gcagatctgc tgatgcccct    1260
gcctatcagc aagggcagaa tcagctgtac aatgagctga atctgggcag aagagaggag    1320
tatgatgtgc tggacaagag aagaggcaga gaccctgaga tgggggggcaa gcctagaaga    1380 aagaacccc aagagggcct gtataatgag ctgcagaagg acaagatggc tgaggcctac    1440
tctgagattg gcatgaaggg gggagagaaga agaggcaagg gccatgatgg cctgtaccaa    1500
ggcctgagca cagccaccaa ggacacctat gatgccctac acatgcaagc tctgcctcct    1560
```

-continued aga                                                                1563

<210> SEQ ID NO 60
<211> LENGTH: 521
<212> TYPE: PRT
<213> ORGANISM: Artificial
<220> FEATURE:
<223> OTHER INFORMATION: pXL1702 CAR protein sequence

<400> SEQUENCE: 60

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Glu Ala Met Gly Trp Val Arg Gln Ala Pro Gly Lys
    50                  55                  60

Gly Leu Glu Trp Val Ser Ser Ile Asn Gly Ser Gly Arg Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Lys His Gly Glu Tyr Tyr Asp Ser Gly
            115                 120                 125

Tyr Asp Val Trp Gly Gln Gly Thr Leu Val Thr Val Ser Ser Gly Ser
    130                 135                 140

Thr Ser Gly Ser Gly Lys Pro Gly Ser Gly Glu Gly Ser Thr Glu Val
145                 150                 155                 160

Gln Leu Leu Glu Ser Gly Gly Gly Leu Val Gln Pro Gly Gly Ser Leu
                165                 170                 175

Arg Leu Ser Cys Ala Ala Ser Gly Phe Thr Phe Ser Asn Tyr Ala Met
            180                 185                 190

Gly Trp Val Arg Gln Ala Pro Gly Lys Gly Leu Glu Trp Val Ser Ser
            195                 200                 205

Ile Thr Gly Leu Gly Gly Asn Met Tyr Tyr Ala Asp Ser Val Lys Gly
    210                 215                 220

Arg Phe Thr Ile Ser Arg Asp Asn Ser Lys Asn Thr Leu Tyr Leu Gln
225                 230                 235                 240

Met Asn Ser Leu Arg Ala Glu Asp Thr Ala Val Tyr Tyr Cys Ala Arg
                245                 250                 255

Met Tyr Tyr Ser Gln Gly Val Asn Asn Tyr Ser Tyr Pro Ser Thr Asp
            260                 265                 270

Ile Trp Gly Gln Gly Thr Leu Val Thr Val Ser Ser Phe Val Pro Val
    275                 280                 285

Phe Leu Pro Ala Lys Pro Thr Thr Thr Pro Ala Pro Arg Pro Pro Thr
    290                 295                 300

Pro Ala Pro Thr Ile Ala Ser Gln Pro Leu Ser Leu Arg Pro Glu Ala
305                 310                 315                 320

Cys Arg Pro Ala Ala Gly Gly Ala Val His Thr Arg Gly Leu Asp Phe
            325                 330                 335

Ala Cys Asp Ile Tyr Ile Trp Ala Pro Leu Ala Gly Thr Cys Gly Val
            340                 345                 350

Leu Leu Leu Ser Leu Val Ile Thr Leu Tyr Cys Asn His Arg Asn Lys

```
            355               360               365

Arg Gly Arg Lys Lys Leu Leu Tyr Ile Phe Lys Gln Pro Phe Met Arg
    370               375               380

Pro Val Gln Thr Thr Gln Glu Glu Asp Gly Cys Ser Cys Arg Phe Pro
385               390               395               400

Glu Glu Glu Glu Gly Gly Cys Glu Leu Arg Val Lys Phe Ser Arg Ser
              405               410               415

Ala Asp Ala Pro Ala Tyr Gln Gln Gly Gln Asn Gln Leu Tyr Asn Glu
          420               425               430

Leu Asn Leu Gly Arg Arg Glu Glu Tyr Asp Val Leu Asp Lys Arg Arg
          435               440               445

Gly Arg Asp Pro Glu Met Gly Gly Lys Pro Arg Arg Lys Asn Pro Gln
      450               455               460

Glu Gly Leu Tyr Asn Glu Leu Gln Lys Asp Lys Met Ala Glu Ala Tyr
465               470               475               480

Ser Glu Ile Gly Met Lys Gly Glu Arg Arg Arg Gly Lys Gly His Asp
              485               490               495

Gly Leu Tyr Gln Gly Leu Ser Thr Ala Thr Lys Asp Thr Tyr Asp Ala
          500               505               510

Leu His Met Gln Ala Leu Pro Pro Arg
          515               520

<210> SEQ ID NO 61
<211> LENGTH: 1563
<212> TYPE: DNA
<213> ORGANISM: Artificial
<220> FEATURE:
<223> OTHER INFORMATION: pXL1704 CAR  nucleic acid sequence

<400> SEQUENCE: 61
atggccctac ctgtgacagc cctactgtta cccctggccc tccttctgca tgctgctaga      60
cctgaggtgc agctgctgga gtctgggggg ggcttggttc aacctggggg aagcctgagg     120
ctgagctgtg ctgcctctgg attcaccttc agcaattatg ccatggggtg ggttagacaa     180
gcccctggca agggcctgga gtgggtgtca agcatcactg gctggggggg caacatgtat     240
tatgctgact ctgtgaaagg cagatttacc atctctagag acaatagcaa aaataccctc     300
tatctgcaga tgaatagcct gagagctgag gacacagctg tgtactattg tgctagaatg     360
tactacagcc aagggggtgaa caactacagc taccctagta ctgatatatg gggccaaggt     420
actctggtga ccgtctccag cggcagcacc tctggctctg gcaagcctgg ctctggggag     480
ggctcaacag aggtgcagct actggaatct gggggggggct tagttcagcc tggtggtagc     540
cttagattaa gctgtgctgc atctggcttc acctttagct ctgaggccat gggttgggta     600
agacaagccc ctggcaaggg tctggagtgg gtgagcagca tcaatggctc tggcagaaac     660
acctattatg ctgattctgt gaagggcaga ttcaccatca gcagagacaa cagcaagaac     720
accctgtacc tgcagatgaa cagcctcaga gctgaagaca cagctgtgta ttattgtgct     780
agaaaacatg gggagtacta tgactctggc tatgatgtgt gggggcaagg caccttagtg     840
acagtgtcat cttttgtgcc tgtatttctg cctgccaagc ccaccacaac acctgcccct     900
agaccaccca cccctgcccc caccattgct tctcagcccc ttagcttaag acctgaagcc     960
tgtagacctg ctgctggggg ggctgtgcac acaagaggcc tggactttgc ctgtgacatc    1020
tacatctggg cccccctggc tggcacctgt ggggtgctgc tgctgagcct ggtgatcacc    1080
ctgtactgca accacagaaa caagagaggc agaaagaagc tgctgtacat cttcaagcag    1140
```

```
cccttcatga gacctgtgca gaccacccaa gaggaggatg gctgcagctg cagattccct    1200
gaggaggagg aggggggctg tgagctgaga gtgaagttca gcagatctgc tgatgcccct    1260
gcctatcagc aagggcagaa tcagctgtac aatgagctga atctgggcag aagagaggag    1320
tatgatgtgc tggacaagag aagaggcaga gaccctgaga tggggggcaa gcctagaaga    1380 aagaacccc aagagggcct gtataatgag ctgcagaagg acaagatggc tgaggcctac    1440
tctgagattg gcatgaaggg gggagagaaga agaggcaagg gccatgatgg cctgtaccaa    1500
ggcctgagca cagccaccaa ggacacctat gatgccctac acatgcaagc tctgcctcct    1560
aga                                                                   1563
```

```
<210> SEQ ID NO 62
<211> LENGTH: 521
<212> TYPE: PRT
<213> ORGANISM: Artificial
<220> FEATURE:
<223> OTHER INFORMATION: pXL1704 CAR protein sequence

<400> SEQUENCE: 62

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Asn Tyr Ala Met Gly Trp Val Arg Gln Ala Pro Gly Lys
        50                  55                  60

Gly Leu Glu Trp Val Ser Ser Ile Thr Gly Leu Gly Gly Asn Met Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Met Tyr Tyr Ser Gln Gly Val Asn Asn
        115                 120                 125

Tyr Ser Tyr Pro Ser Thr Asp Ile Trp Gly Gln Gly Thr Leu Val Thr
    130                 135                 140

Val Ser Ser Gly Ser Thr Ser Gly Ser Gly Lys Pro Gly Ser Gly Glu
145                 150                 155                 160

Gly Ser Thr Glu Val Gln Leu Leu Glu Ser Gly Gly Gly Leu Val Gln
                165                 170                 175

Pro Gly Gly Ser Leu Arg Leu Ser Cys Ala Ala Ser Gly Phe Thr Phe
            180                 185                 190

Ser Ser Glu Ala Met Gly Trp Val Arg Gln Ala Pro Gly Lys Gly Leu
        195                 200                 205

Glu Trp Val Ser Ser Ile Asn Gly Ser Gly Arg Asn Thr Tyr Tyr Ala
    210                 215                 220

Asp Ser Val Lys Gly Arg Phe Thr Ile Ser Arg Asp Asn Ser Lys Asn
225                 230                 235                 240

Thr Leu Tyr Leu Gln Met Asn Ser Leu Arg Ala Glu Asp Thr Ala Val
                245                 250                 255

Tyr Tyr Cys Ala Arg Lys His Gly Glu Tyr Tyr Asp Ser Gly Tyr Asp
            260                 265                 270

Val Trp Gly Gln Gly Thr Leu Val Thr Val Ser Ser Phe Val Pro Val
```

```
                    275                 280                 285
Phe Leu Pro Ala Lys Pro Thr Thr Thr Pro Ala Pro Arg Pro Pro Thr
    290                 295                 300
Pro Ala Pro Thr Ile Ala Ser Gln Pro Leu Ser Leu Arg Pro Glu Ala
305                 310                 315                 320
Cys Arg Pro Ala Ala Gly Gly Ala Val His Thr Arg Gly Leu Asp Phe
                325                 330                 335
Ala Cys Asp Ile Tyr Ile Trp Ala Pro Leu Ala Gly Thr Cys Gly Val
                340                 345                 350
Leu Leu Leu Ser Leu Val Ile Thr Leu Tyr Cys Asn His Arg Asn Lys
                355                 360                 365
Arg Gly Arg Lys Lys Leu Leu Tyr Ile Phe Lys Gln Pro Phe Met Arg
        370                 375                 380
Pro Val Gln Thr Thr Gln Glu Glu Asp Gly Cys Ser Cys Arg Phe Pro
385                 390                 395                 400
Glu Glu Glu Glu Gly Gly Cys Glu Leu Arg Val Lys Phe Ser Arg Ser
                405                 410                 415
Ala Asp Ala Pro Ala Tyr Gln Gln Gly Gln Asn Gln Leu Tyr Asn Glu
                420                 425                 430
Leu Asn Leu Gly Arg Arg Glu Glu Tyr Asp Val Leu Asp Lys Arg Arg
            435                 440                 445
Gly Arg Asp Pro Glu Met Gly Gly Lys Pro Arg Arg Lys Asn Pro Gln
        450                 455                 460
Glu Gly Leu Tyr Asn Glu Leu Gln Lys Asp Lys Met Ala Glu Ala Tyr
465                 470                 475                 480
Ser Glu Ile Gly Met Lys Gly Glu Arg Arg Arg Gly Lys Gly His Asp
                485                 490                 495
Gly Leu Tyr Gln Gly Leu Ser Thr Ala Thr Lys Asp Thr Tyr Asp Ala
            500                 505                 510
Leu His Met Gln Ala Leu Pro Pro Arg
        515                 520
```

```
<210> SEQ ID NO 63
<211> LENGTH: 1554
<212> TYPE: DNA
<213> ORGANISM: Artificial
<220> FEATURE:
<223> OTHER INFORMATION: pXL1748 CAR  nucleic acid sequence

<400> SEQUENCE: 63
atggccctac ctgtgacagc cctactgtta cccctggccc tccttctgca tgctgctaga      60
cctgaggtgc aacttcttga gtctgggggg ggcttggtgc agcctggggg cagtctgaga     120
ctgagctgtg ctgcctctgg ctttaccttc aacattgatg ccatgggttg ggtaagacaa     180
gcccctggca agggtctgga gtgggtgagc agcatcagct cttctggggg cactacctac     240
tatgctgact ctgtgaaggg cagattcacc atcagcagag acaacagcaa gaacaccctg     300
tacctgcaaa tgaatagcct tagggctgag gacacagctg tatactactg tgctagaagc     360
agatactctg tgcctgatgg cagaggcagc tatgatgtgt ggggccaagg gaccttggtc     420
acagtgagct ctggcagcac ctctggctct ggcaagcctg ctctgggga gggctcaaca     480 gaggtgcagc tactggaatc tggggggggc ttagttcagc ctggtggtag ccttagatta     540
agctgtgctg catctggctt cacctttagc tctgaggcca tgggttgggt aagacaagcc     600
cctggcaagg gtctggagtg ggtgagcagc atcaatggct ctggcagaaa cacctattat     660
```

```
gctgattctg tgaagggcag attcaccatc agcagagaca acagcaagaa caccctgtac     720
ctgcagatga acagcctcag agctgaagac acagctgtgt attattgtgc tagaaaacat     780
ggggagtact atgactctgg ctatgatgtg tgggggcaag gcaccttagt gacagtgtca     840
tcttttgtgc ctgtatttct gcctgccaag cccaccacaa cacctgcccc tagaccaccc     900
acccctgccc ccaccattgc ttctcagccc cttagcttaa gacctgaagc ctgtagacct     960
gctgctgggg gggctgtgca cacaagaggc ctggactttg cctgtgacat ctacatctgg    1020
gcccccctgg ctggcacctg tggggtgctg ctgctgagcc tggtgatcac cctgtactgc    1080
aaccacagaa acaagagagg cagaaagaag ctgctgtaca tcttcaagca gcccttcatg    1140
agacctgtgc agaccaccca agaggaggat ggctgcagct gcagattccc tgaggaggag    1200
gaggggggct gtgagctgag agtgaagttc agcagatctg ctgatgcccc tgcctatcag    1260
caagggcaga atcagctgta caatgagctg aatctgggca agagagagga gtatgatgtg    1320
ctggacaaga gaagaggcag agaccctgag atggggggca gcctagaag aaagaacccc     1380 caagagggcc tgtataatga gctgcagaag gacaagatgg ctgaggccta ctctgagatt    1440
ggcatgaagg gggagagaag aagaggcaag ggccatgatg gcctgtacca aggcctgagc    1500
acagccacca aggacaccta tgatgcccta cacatgcaag ctctgcctcc taga          1554
```

```
<210> SEQ ID NO 64
<211> LENGTH: 518
<212> TYPE: PRT
<213> ORGANISM: Artificial
<220> FEATURE:
<223> OTHER INFORMATION: pXL1748 CAR protein sequence

<400> SEQUENCE: 64

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Asn Ile Asp Ala Met Gly Trp Val Arg Gln Ala Pro Gly Lys
        50                  55                  60

Gly Leu Glu Trp Val Ser Ser Ile Ser Ser Ser Gly Gly Thr Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ser Arg Tyr Ser Val Pro Asp Gly Arg
            115                 120                 125

Gly Ser Tyr Asp Val Trp Gly Gln Gly Thr Leu Val Thr Val Ser Ser
        130                 135                 140

Gly Ser Thr Ser Gly Ser Gly Lys Pro Gly Ser Gly Glu Gly Ser Thr
145                 150                 155                 160

Glu Val Gln Leu Leu Glu Ser Gly Gly Gly Leu Val Gln Pro Gly Gly
                165                 170                 175

Ser Leu Arg Leu Ser Cys Ala Ala Ser Gly Phe Thr Phe Ser Ser Glu
            180                 185                 190

Ala Met Gly Trp Val Arg Gln Ala Pro Gly Lys Gly Leu Glu Trp Val
            195                 200                 205
```

-continued

```
Ser Ser Ile Asn Gly Ser Gly Arg Asn Thr Tyr Tyr Ala Asp Ser Val
    210             215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
            245                 250                 255

Ala Arg Lys His Gly Glu Tyr Tyr Asp Ser Gly Tyr Asp Val Trp Gly
        260                 265                 270

Gln Gly Thr Leu Val Thr Val Ser Ser Phe Val Pro Val Phe Leu Pro
        275                 280                 285

Ala Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
                325                 330                 335

Ile Tyr Ile Trp Ala Pro Leu Ala Gly Thr Cys Gly Val Leu Leu Leu
            340                 345                 350

Ser Leu Val Ile Thr Leu Tyr Cys Asn His Arg Asn Lys Arg Gly Arg
        355                 360                 365

Lys Lys Leu Leu Tyr Ile Phe Lys Gln Pro Phe Met Arg Pro Val Gln
    370                 375                 380

Thr Thr Gln Glu Glu Asp Gly Cys Ser Cys Arg Phe Pro Glu Glu Glu
385                 390                 395                 400

Glu Gly Gly Cys Glu Leu Arg Val Lys Phe Ser Arg Ser Ala Asp Ala
            405                 410                 415

Pro Ala Tyr Gln Gln Gly Gln Asn Gln Leu Tyr Asn Glu Leu Asn Leu
            420                 425                 430

Gly Arg Arg Glu Glu Tyr Asp Val Leu Asp Lys Arg Arg Gly Arg Asp
        435                 440                 445

Pro Glu Met Gly Gly Lys Pro Arg Arg Lys Asn Pro Gln Glu Gly Leu
    450                 455                 460

Tyr Asn Glu Leu Gln Lys Asp Lys Met Ala Glu Ala Tyr Ser Glu Ile
465                 470                 475                 480

Gly Met Lys Gly Glu Arg Arg Arg Gly Lys Gly His Asp Gly Leu Tyr
            485                 490                 495

Gln Gly Leu Ser Thr Ala Thr Lys Asp Thr Tyr Asp Ala Leu His Met
        500                 505                 510

Gln Ala Leu Pro Pro Arg
        515
```

<210> SEQ ID NO 65
<211> LENGTH: 1554
<212> TYPE: DNA
<213> ORGANISM: Artificial
<220> FEATURE:
<223> OTHER INFORMATION: pXL1750 CAR  nucleic acid sequence

<400> SEQUENCE: 65

```
atggccctac ctgtgacagc cctactgtta cccctggccc tccttctgca tgctgctaga      60
cctgaggtgc agctactgga atctggggggg ggcttagttc agcctggtgg tagccttaga     120
ttaagctgtg ctgcatctgg cttcacctttt agctctgagg ccatgggttg ggtaagacaa     180
gcccctggca agggtctgga gtgggtgagc agcatcaatg gctctggcag aaacacctat     240
tatgctgatt ctgtgaaggg cagattcacc atcagcagag acaacagcaa gaacaccctg     300
```

-continued

```
tacctgcaga tgaacagcct cagagctgaa gacacagctg tgtattattg tgctagaaaa    360
catggggagt actatgactc tggctatgat gtgtggggggc aaggcacctt agtgacagtg    420
tcatctggca gcacctctgg ctctggcaag cctggctctg gggagggctc aacagaggtg    480
caacttcttg agtctggggg gggcttggtg cagcctgggg gcagtctgag actgagctgt    540
gctgcctctg gctttacctt caacattgat gccatgggtt gggtaagaca agcccctggc    600
aagggtctgg agtgggtgag cagcatcagc tcttctgggg gcactaccta ctatgctgac    660
tctgtgaagg gcagattcac catcagcaga gacaacagca gaacaccct gtacctgcaa      720 atgaatagcc ttagggctga ggacacagct gtatactact gtgctagaag cagatactct    780
gtgcctgatg gcagaggcag ctatgatgtg tggggccaag ggaccttggt cacagtgagc    840
tcttttgtgc ctgtatttct gcctgccaag cccaccacaa cacctgcccc tagaccaccc    900
acccctgccc ccaccattgc ttctcagccc cttagcttaa gacctgaagc ctgtagacct    960
gctgctgggg gggctgtgca cacaagaggc ctggactttg cctgtgacat ctacatctgg    1020
gcccccctgg ctggcacctg tggggtgctg ctgctgagcc tggtgatcac cctgtactgc    1080
aaccacagaa acaagagagg cagaaagaag ctgctgtaca tcttcaagca gcccttcatg    1140
agacctgtgc agaccaccca gaggaggat ggctgcagct gcagattccc tgaggaggag      1200
gaggggggct gtgagctgag agtgaagttc agcagatctg ctgatgcccc tgcctatcag    1260
caagggcaga atcagctgta caatgagctg aatctgggca gaagagagga gtatgatgtg    1320
ctggacaaga aagaggcag agaccctgag atggggggca agcctagaag aaagaacccc    1380
caagagggcc tgtataatga gctgcagaag gacaagatgg ctgaggccta ctctgagatt    1440
ggcatgaagg gggagagaag aagaggcaag ggccatgatg gcctgtacca aggcctgagc    1500
acagccacca aggacaccta tgatgcccta cacatgcaag ctctgcctcc taga           1554
```

<210> SEQ ID NO 66
<211> LENGTH: 518
<212> TYPE: PRT
<213> ORGANISM: Artificial
<220> FEATURE:
<223> OTHER INFORMATION: pXL1750 CAR protein sequence

<400> SEQUENCE: 66

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Glu Ala Met Gly Trp Val Arg Gln Ala Pro Gly Lys
    50                  55                  60

Gly Leu Glu Trp Val Ser Ser Ile Asn Gly Ser Gly Arg Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Lys His Gly Glu Tyr Tyr Asp Ser Gly
        115                 120                 125

Tyr Asp Val Trp Gly Gln Gly Thr Leu Val Thr Val Ser Ser Gly Ser
    130                 135                 140
```

```
Thr Ser Gly Ser Gly Lys Pro Gly Ser Gly Glu Gly Ser Thr Glu Val
145                 150                 155                 160

Gln Leu Leu Glu Ser Gly Gly Gly Leu Val Gln Pro Gly Gly Ser Leu
                165                 170                 175

Arg Leu Ser Cys Ala Ala Ser Gly Phe Thr Phe Asn Ile Asp Ala Met
            180                 185                 190

Gly Trp Val Arg Gln Ala Pro Gly Lys Gly Leu Glu Trp Val Ser Ser
        195                 200                 205

Ile Ser Ser Ser Gly Gly Thr Thr Tyr Tyr Ala Asp Ser Val Lys Gly
    210                 215                 220

Arg Phe Thr Ile Ser Arg Asp Asn Ser Lys Asn Thr Leu Tyr Leu Gln
225                 230                 235                 240

Met Asn Ser Leu Arg Ala Glu Asp Thr Ala Val Tyr Tyr Cys Ala Arg
                245                 250                 255

Ser Arg Tyr Ser Val Pro Asp Gly Arg Gly Ser Tyr Asp Val Trp Gly
                260                 265                 270

Gln Gly Thr Leu Val Thr Val Ser Ser Phe Val Pro Val Phe Leu Pro
            275                 280                 285

Ala Lys Pro Thr Thr Thr Pro Ala Pro Arg Pro Pro Thr Pro Ala Pro
        290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
                325                 330                 335

Ile Tyr Ile Trp Ala Pro Leu Ala Gly Thr Cys Gly Val Leu Leu Leu
            340                 345                 350

Ser Leu Val Ile Thr Leu Tyr Cys Asn His Arg Asn Lys Arg Gly Arg
            355                 360                 365

Lys Lys Leu Leu Tyr Ile Phe Lys Gln Pro Phe Met Arg Pro Val Gln
    370                 375                 380

Thr Thr Gln Glu Glu Asp Gly Cys Ser Cys Arg Phe Pro Glu Glu Glu
385                 390                 395                 400

Glu Gly Gly Cys Glu Leu Arg Val Lys Phe Ser Arg Ser Ala Asp Ala
                405                 410                 415

Pro Ala Tyr Gln Gln Gly Gln Asn Gln Leu Tyr Asn Glu Leu Asn Leu
                420                 425                 430

Gly Arg Arg Glu Glu Tyr Asp Val Leu Asp Lys Arg Arg Gly Arg Asp
        435                 440                 445

Pro Glu Met Gly Gly Lys Pro Arg Arg Lys Asn Pro Gln Glu Gly Leu
    450                 455                 460

Tyr Asn Glu Leu Gln Lys Asp Lys Met Ala Glu Ala Tyr Ser Glu Ile
465                 470                 475                 480

Gly Met Lys Gly Glu Arg Arg Arg Gly Lys Gly His Asp Gly Leu Tyr
                485                 490                 495

Gln Gly Leu Ser Thr Ala Thr Lys Asp Thr Tyr Asp Ala Leu His Met
            500                 505                 510

Gln Ala Leu Pro Pro Arg
            515
```

<210> SEQ ID NO 67
<211> LENGTH: 1569
<212> TYPE: DNA
<213> ORGANISM: Artificial
<220> FEATURE:

<223> OTHER INFORMATION: pXL1752 CAR  nucleic acid sequence

<400> SEQUENCE: 67
atggccctac ctgtgacagc cctactgtta cccctggccc tccttctgca tgctgctaga      60
cctgaggtgc aacttcttga gtctgggggg ggcttggtgc agcctggggg cagtctgaga     120
ctgagctgtg ctgcctctgg ctttaccttc aacattgatg ccatgggttg ggtaagacaa     180
gcccctggca agggtctgga gtgggtgagc agcatcagct cttctggggg cactacctac     240
tatgctgact ctgtgaaggg cagattcacc atcagcagag acaacagcaa gaacaccctg     300
tacctgcaaa tgaatagcct tagggctgag gacacagctg tatactactg tgctagaagc     360
agatactctg tgcctgatgg cagaggcagc tatgatgtgt ggggccaagg gaccttggtc     420
acagtgagct ctggcagcac ctctggctct ggcaagcctg gctctgggga gggctcaaca     480
gaggtgcagc tgctggagtc tggggggggc ttggttcaac tggggggaag cctgaggctg     540
agctgtgctg cctctggatt caccttcagc aattatgcca tggggtgggt tagacaagcc     600
cctggcaagg gcctggagtg ggtgtcaagc atcactggcc tgggggggcaa catgtattat     660 gctgactctg tgaaaggcag atttaccatc tctagagaca atagcaaaaa taccctctat     720
ctgcagatga atagcctgag agctgaggac acagctgtgt actattgtgc tagaatgtac     780
tacagccaag gggtgaacaa ctacagctac cctagtactg atatatgggg ccaaggtact     840
ctggtgaccg tctccagctt tgtgcctgta tttctgcctg ccaagcccac cacaacacct     900
gcccctagac cacccacccc tgcccccacc attgcttctc agccccttag cttaagacct     960
gaagcctgta gacctgctgc tggggggggct gtgcacacaa gaggcctgga ctttgcctgt    1020
gacatctaca tctgggcccc cctggctggc acctgtgggg tgctgctgct gagcctggtg    1080
atcaccctgt actgcaacca cagaaacaag agaggcagaa agaagctgct gtacatcttc    1140
aagcagccct tcatgagacc tgtgcagacc acccaagagg aggatggctg cagctgcaga    1200
ttccctgagg aggaggaggg gggctgtgag ctgagagtga agttcagcag atctgctgat    1260
gcccctgcct atcagcaagg gcagaatcag ctgtacaatg agctgaatct gggcagaaga    1320
gaggagtatg atgtgctgga caagagaaga ggcagagacc ctgagatggg gggcaagcct    1380
agaagaaaga accccccaaga gggcctgtat aatgagctgc agaaggacaa gatggctgag    1440
gcctactctg agattggcat gaagggggag agaagaagag gcaagggcca tgatggcctg    1500
taccaaggcc tgagcacagc caccaaggac acctatgatg ccctacacat gcaagctctg    1560
cctcctaga                                                            1569

<210> SEQ ID NO 68
<211> LENGTH: 523
<212> TYPE: PRT
<213> ORGANISM: Artificial
<220> FEATURE:
<223> OTHER INFORMATION: pXL1752 CAR protein sequence

<400> SEQUENCE: 68

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Asn Ile Asp Ala Met Gly Trp Val Arg Gln Ala Pro Gly Lys
    50                  55                  60

-continued

```
Gly Leu Glu Trp Val Ser Ser Ile Ser Ser Ser Gly Gly Thr Thr Tyr
65              70                  75                  80

Tyr Ala Asp Ser Val Lys Gly Arg Phe Thr Ile Ser Arg Asp Asn Ser
            85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ser Arg Tyr Ser Val Pro Asp Gly Arg
            115                 120                 125

Gly Ser Tyr Asp Val Trp Gly Gln Gly Thr Leu Val Thr Val Ser Ser
    130                 135                 140

Gly Ser Thr Ser Gly Ser Gly Lys Pro Gly Ser Gly Glu Gly Ser Thr
145                 150                 155                 160

Glu Val Gln Leu Leu Glu Ser Gly Gly Gly Leu Val Gln Pro Gly Gly
            165                 170                 175

Ser Leu Arg Leu Ser Cys Ala Ala Ser Gly Phe Thr Phe Ser Asn Tyr
            180                 185                 190

Ala Met Gly Trp Val Arg Gln Ala Pro Gly Lys Gly Leu Glu Trp Val
            195                 200                 205

Ser Ser Ile Thr Gly Leu Gly Gly Asn Met Tyr Tyr Ala Asp Ser Val
    210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
            245                 250                 255

Ala Arg Met Tyr Tyr Ser Gln Gly Val Asn Asn Tyr Ser Tyr Pro Ser
            260                 265                 270

Thr Asp Ile Trp Gly Gln Gly Thr Leu Val Thr Val Ser Ser Phe Val
            275                 280                 285

Pro Val Phe Leu Pro Ala Lys Pro Thr Thr Thr Pro Ala Pro Arg Pro
    290                 295                 300

Pro Thr Pro Ala Pro Thr Ile Ala Ser Gln Pro Leu Ser Leu Arg Pro
305                 310                 315                 320

Glu Ala Cys Arg Pro Ala Ala Gly Gly Ala Val His Thr Arg Gly Leu
            325                 330                 335

Asp Phe Ala Cys Asp Ile Tyr Ile Trp Ala Pro Leu Ala Gly Thr Cys
            340                 345                 350

Gly Val Leu Leu Leu Ser Leu Val Ile Thr Leu Tyr Cys Asn His Arg
            355                 360                 365

Asn Lys Arg Gly Arg Lys Lys Leu Leu Tyr Ile Phe Lys Gln Pro Phe
    370                 375                 380

Met Arg Pro Val Gln Thr Thr Gln Glu Glu Asp Gly Cys Ser Cys Arg
385                 390                 395                 400

Phe Pro Glu Glu Glu Glu Gly Gly Cys Glu Leu Arg Val Lys Phe Ser
            405                 410                 415

Arg Ser Ala Asp Ala Pro Ala Tyr Gln Gln Gly Gln Asn Gln Leu Tyr
            420                 425                 430

Asn Glu Leu Asn Leu Gly Arg Arg Glu Glu Tyr Asp Val Leu Asp Lys
            435                 440                 445

Arg Arg Gly Arg Asp Pro Glu Met Gly Gly Lys Pro Arg Arg Lys Asn
    450                 455                 460

Pro Gln Glu Gly Leu Tyr Asn Glu Leu Gln Lys Asp Lys Met Ala Glu
465                 470                 475                 480
```

-continued

```
Ala Tyr Ser Glu Ile Gly Met Lys Gly Glu Arg Arg Arg Gly Lys Gly
                485                 490                 495

His Asp Gly Leu Tyr Gln Gly Leu Ser Thr Ala Thr Lys Asp Thr Tyr
            500                 505                 510

Asp Ala Leu His Met Gln Ala Leu Pro Pro Arg
        515                 520
```

```
<210> SEQ ID NO 69
<211> LENGTH: 1569
<212> TYPE: DNA
<213> ORGANISM: Artificial
<220> FEATURE:
<223> OTHER INFORMATION: pXL1754 CAR  nucleic acid sequence

<400> SEQUENCE: 69
atggccctac ctgtgacagc cctactgtta cccctggccc tccttctgca tgctgctaga     60
cctgaggtgc agctgctgga gtctgggggg ggcttggttc aacctggggg aagcctgagg    120
ctgagctgtg ctgcctctgg attcaccttc agcaattatg ccatggggtg ggttagacaa    180
gcccctggca agggcctgga gtgggtgtca agcatcactg gcctgggggg caacatgtat    240
tatgctgact ctgtgaaagg cagatttacc atctctagag acaatagcaa aaataccctc    300
tatctgcaga tgaatagcct gagagctgag gacacagctg tgtactattg tgctagaatg    360
tactacagcc aaggggtgaa caactacagc taccctagta ctgatatatg gggccaaggt    420
actctggtga ccgtctccag cggcagcacc tctggctctg gcaagcctgg ctctggggag    480
ggctcaacag aggtgcaact tcttgagtct ggggggggct tggtgcagcc tgggggcagt    540
ctgagactga gctgtgctgc ctctggcttt accttcaaca ttgatgccat gggttgggta    600
agacaagccc ctggcaaggg tctggagtgg gtgagcagca tcagctcttc tggggggcact    660 acctactatg ctgactctgt gaagggcaga ttcaccatca gcagagacaa cagcaagaac    720
accctgtacc tgcaaatgaa tagccttagg gctgaggaca cagctgtata ctactgtgct    780
agaagcagat actctgtgcc tgatggcaga ggcagctatg atgtgtgggg ccaagggacc    840
ttggtcacag tgagctcttt tgtgcctgta tttctgcctg ccaagcccac cacaacacct    900
gcccctagac cacccacccc tgcccccacc attgcttctc agccccttag cttaagacct    960
gaagcctgta gacctgctgc tgggggggct gtgcacacaa gaggcctgga ctttgcctgt   1020
gacatctaca tctgggcccc cctggctggc acctgtgggg tgctgctgct gagcctggtg   1080
atcaccctgt actgcaacca gaaacaag agaggcagaa agaagctgct gtacatcttc   1140
aagcagccct tcatgagacc tgtgcagacc acccaagagg aggatggctg cagctgcaga   1200
ttccctgagg aggaggaggg gggctgtgag ctgagagtga agttcagcag atctgctgat   1260
gcccctgcct atcagcaagg gcagaatcag ctgtacaatg agctgaatct gggcagaaga   1320
gaggagtatg atgtgctgga caagagaaga ggcagagacc ctgagatggg gggcaagcct   1380
agaagaaaga accccaaga gggcctgtat aatgagctgc agaaggacaa gatggctgag   1440
gcctactctg agattggcat gaaggggggag agaagaagag gcaagggcca tgatggcctg   1500
taccaaggcc tgagcacagc caccaaggac acctatgatg ccctacacat gcaagctctg   1560
cctcctaga                                                          1569
```

```
<210> SEQ ID NO 70
<211> LENGTH: 523
<212> TYPE: PRT
<213> ORGANISM: Artificial
<220> FEATURE:
```

<223> OTHER INFORMATION: pXL1754 CAR protein sequence

<400> SEQUENCE: 70

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Asn Tyr Ala Met Gly Trp Val Arg Gln Ala Pro Gly Lys
    50                  55                  60

Gly Leu Glu Trp Val Ser Ser Ile Thr Gly Leu Gly Gly Asn Met Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Met Tyr Tyr Ser Gln Gly Val Asn Asn
        115                 120                 125

Tyr Ser Tyr Pro Ser Thr Asp Ile Trp Gly Gln Gly Thr Leu Val Thr
    130                 135                 140

Val Ser Ser Gly Ser Thr Ser Gly Ser Gly Lys Pro Gly Ser Gly Glu
145                 150                 155                 160

Gly Ser Thr Glu Val Gln Leu Leu Glu Ser Gly Gly Gly Leu Val Gln
                165                 170                 175

Pro Gly Gly Ser Leu Arg Leu Ser Cys Ala Ala Ser Gly Phe Thr Phe
            180                 185                 190

Asn Ile Asp Ala Met Gly Trp Val Arg Gln Ala Pro Gly Lys Gly Leu
            195                 200                 205

Glu Trp Val Ser Ser Ile Ser Ser Ser Gly Gly Thr Thr Tyr Tyr Ala
    210                 215                 220

Asp Ser Val Lys Gly Arg Phe Thr Ile Ser Arg Asp Asn Ser Lys Asn
225                 230                 235                 240

Thr Leu Tyr Leu Gln Met Asn Ser Leu Arg Ala Glu Asp Thr Ala Val
            245                 250                 255

Tyr Tyr Cys Ala Arg Ser Arg Tyr Ser Val Pro Asp Gly Arg Gly Ser
        260                 265                 270

Tyr Asp Val Trp Gly Gln Gly Thr Leu Val Thr Val Ser Ser Phe Val
    275                 280                 285

Pro Val Phe Leu Pro Ala Lys Pro Thr Thr Thr Pro Ala Pro Arg Pro
    290                 295                 300

Pro Thr Pro Ala Pro Thr Ile Ala Ser Gln Pro Leu Ser Leu Arg Pro
305                 310                 315                 320

Glu Ala Cys Arg Pro Ala Ala Gly Gly Ala Val His Thr Arg Gly Leu
            325                 330                 335

Asp Phe Ala Cys Asp Ile Tyr Ile Trp Ala Pro Leu Ala Gly Thr Cys
            340                 345                 350

Gly Val Leu Leu Leu Ser Leu Val Ile Thr Leu Tyr Cys Asn His Arg
        355                 360                 365

Asn Lys Arg Gly Arg Lys Lys Leu Leu Tyr Ile Phe Lys Gln Pro Phe
    370                 375                 380

Met Arg Pro Val Gln Thr Thr Gln Glu Glu Asp Gly Cys Ser Cys Arg
385                 390                 395                 400
```

-continued

```
Phe Pro Glu Glu Glu Glu Gly Gly Cys Glu Leu Arg Val Lys Phe Ser
            405                 410                 415

Arg Ser Ala Asp Ala Pro Ala Tyr Gln Gln Gly Gln Asn Gln Leu Tyr
        420                 425                 430

Asn Glu Leu Asn Leu Gly Arg Arg Glu Glu Tyr Asp Val Leu Asp Lys
        435                 440                 445

Arg Arg Gly Arg Asp Pro Glu Met Gly Gly Lys Pro Arg Arg Lys Asn
    450                 455                 460

Pro Gln Glu Gly Leu Tyr Asn Glu Leu Gln Lys Asp Lys Met Ala Glu
465                 470                 475                 480

Ala Tyr Ser Glu Ile Gly Met Lys Gly Glu Arg Arg Arg Gly Lys Gly
            485                 490                 495

His Asp Gly Leu Tyr Gln Gly Leu Ser Thr Ala Thr Lys Asp Thr Tyr
            500                 505                 510

Asp Ala Leu His Met Gln Ala Leu Pro Pro Arg
            515                 520

<210> SEQ ID NO 71
<211> LENGTH: 9728
<212> TYPE: DNA
<213> ORGANISM: Artificial
<220> FEATURE:
<223> OTHER INFORMATION: Nucleic acid sequence of the GoldenGate
      backbone vector containing lethal gene ccdB

<400> SEQUENCE: 71
gccgctgatc ttcagacctg gaggaggaga tatgagggac aattggagaa gtgaattata      60
taaatataaa gtagtaaaaa ttgaaccatt aggagtagca cccaccaagg caaagagaag     120
agtggtgcag agagaaaaaa gagcagtggg aataggagct tgttccttg ggttcttggg     180 agcagcagga agcactatgg gcgcagcgtc aatgacgctg acggtacagg ccagacaatt     240
attgtctggt atagtgcagc agcagaacaa tttgctgagg gctattgagg cgcaacagca     300
tctgttgcaa ctcacagtct ggggcatcaa gcagctccag gcaagaatcc tggctgtgga     360 aagatatccta aaggatcaac agctcctggg gatttggggt tgctctggaa aactcatttg     420
caccactgct gtgccttgga atgctagttg gagtaataaa tctctggaac agatttggaa     480
tcacacgacc tggatggagt gggacagaga aattaacaat tacacaagct taatacactc     540
cttaattgaa gaatcgcaaa accagcaaga aaagaatgaa caagaattat tggaattaga     600
taaatgggca gtttgtggaa ttggtttaa cataacaaat tggctgtggt atataaaatt     660
attcataatg atagtaggag gcttggtagg tttaagaata gttttttgctg tactttctat     720 agtgaataga gttaggcagg gatattcacc attatcgttt cagacccacc tcccaacccc     780
gaggggaccc gacaggcccg aaggaataga agaagaaggt ggagagagag acagagacag     840
atccattcga ttagtgaacg gatctcgacg gtatcgcctt aaaagaaaa gggggattg     900 gggggtacag tgcaggggaa agaatagtag acataatagc aacagacata caaactaaag     960
aattacaaaa acaaattaca aaaattcaaa attttcgggt ttattacagg gacagcagag    1020 atccagtttta tcgatcgtga ggctccggtg cccgtcagtg ggcagagcgc acatcgccca    1080
cagtccccga gaagttggg ggaggggtcg gcaattgaac cggtgcctag agaaggtggc    1140
gcggggtaaa ctgggaaagt gatgtcgtgt actggctccg cctttttccc gagggtgggg    1200
gagaaccgta tataagtgca gtagtcgccg tgaacgttct ttttcgcaac gggtttgccg    1260
ccagaacaca ggtaagtgcc gtgtgtggtt cccgcgggcc tggcctcttt acgggttatg    1320
```

```
gcccttgcgt gccttgaatt acttccacct ggctgcagta cgtgattctt gatcccgagc   1380
ttcgggttgg aagtgggtgg gagagttcga ggccttgcgc ttaaggagcc ccttcgcctc   1440
gtgcttgagt tgaggcctgg cctgggcgct ggggccgccg cgtgcgaatc tggtggcacc   1500
ttcgcgcctg tctcgctgct ttcgataagt ctctagccat ttaaaatttt tgatgacctg   1560
ctgcgacgct ttttttctgg caagatagtc ttgtaaatgc gggccaagat ctgcacactg   1620
gtatttcggt ttttggggcc gcgggcggcg acggggcccg tgcgtcccag cgcacatgtt   1680
cggcgaggcg gggcctgcga gcgcggccac cgagaatcgg acggggtag tctcaagctg     1740 gccggcctgc tctggtgcct ggcctcgcgc cgccgtgtat cgccccgccc tgggcggcaa   1800
ggctggcccg gtcggcacca gttgcgtgag cggaaagatg gccgcttccc ggccctgctg   1860
cagggagctc aaaatggagg acgcggcgct cgggagagcg ggcgggtgag tcacccacac   1920
aaaggaaaag ggcctttccg tcctcagccg tcgcttcatg tgactccacg gagtaccggg   1980
cgccgtccag gcacctcgat tagttctcga gcttttggag tacgtcgtct ttaggttggg   2040
gggaggggtt ttatgcgatg gagtttcccc acactgagtg ggtggagact gaagttaggc   2100
cagcttggca cttgatgtaa ttctccttgg aatttgccct ttttgagttt ggatcttggt   2160
tcattctcaa gcctcagaca gtggttcaaa gtttttttct tccatttcag gtgtcgtgag   2220
gaattagctt ggtacgaatt cctcgagact agttctagag cggccgcgga tcgccgccac   2280
catggccctg cctgtgacag ctctgctcct ccctctggcc ctgctgctcc atgccgccag   2340
acccgagacg tgagaattaa tacgactcac tatagaggga ctggtgaaat gcagttcaag   2400
gtttacacct ataaaagaga gagccgctat cgcctgtttg tggatgtaca gagtgatatt   2460
attgacacgc ccgggcgacg gatggtgatc cccctggcca gtgcacgtct gctgtcagat   2520
aaagtctccc gtgaacttta cccggtggtg catatcgggg atgaaagctg gcgcatgatg   2580
accacccaga tggtcagtgt gccggtctcc gtcatcggag aagaagtggc tgatctcagc   2640
caccgcgaaa atgacatcaa aaacgccatt aatctgatgt tctggggaat ataacgtctc   2700
ttcgtgcccg tgttcctgcc cgccaaacct actactaccc ctgcacctag gcctcccacc   2760
ccagccccaa caatcgccag ccagcctctg tctctgcggc ccgaagcctg tagacctgct   2820
gccggcggag ccgtgcacac cagaggcctg gacttcgcct gcgacatcta catctgggcc   2880
cctctggccg gcacctgtgg cgtgctgctg ctgagcctgg tgatcaccct gtactgcaac   2940
caccggaaca aacggggcag aaagaaactc ctgtatatat tcaaacaacc atttatgaga   3000
ccagtacaaa ctactcaaga ggaagatggc tgtagctgcc gatttccaga agaagaagaa   3060
ggaggatgtg aactgagagt gaagttcagc agatccgccg acgccctgc ctaccagcag    3120 ggacagaacc agctgtacaa cgagctgaac ctgggcagac gggaagagta cgacgtgctg   3180
gacaagcgga gaggccggga ccccgagatg ggcggaaagc ccagacggaa gaaccccag    3240 gaaggcctgt ataacgaact gcagaaagac aagatggccg aggcctacag cgagatcggc   3300
atgaagggcg agcggaggcg cggcaagggc cacgatggcc tgtaccaggg cctgagcacc   3360
gccaccaagg acacctacga cgccctgcac atgcaggccc tgcccccag aggatccgga    3420 gagggaaggg gcagcttatt aacatgtggc gatgtggaag agaaccccgg tcccatgctg   3480
ctgctcgtga cctctttact gttatgtgag ctgccccacc ccgcttttt actgatccct    3540 cgtaaggtgt gtaacggaat cggcattggc gagttcaagg actctttaag catcaacgcc   3600
acaaacatca agcacttcaa gaattgtacc tccatcagcg gcgatttaca cattctcccc   3660 gtggctttc gtggcgattc cttcacccac acccccctc tggacccca agagctggac      3720
```

-continued

```
attttaaaaa ccgtgaagga gatcaccggc tttctgctga tccaagcttg gcccgagaat   3780
cgtaccgacc tccacgcctt cgagaattta gagattattc gtggaaggac caagcagcac   3840
ggccagttct ctttagccgt cgtgtcttta aacattacca gcctcggttt aaggtcttta   3900
aaggagatta gcgacggcga cgtgatcatc tccggcaaca agaacctctg ctacgccaac   3960
accatcaact ggaagaagct gttcggaacc agcggccaaa agaccaagat catcagcaat   4020
cgtggagaga actcttgtaa ggccactggt caagtttgcc acgccctctg tagccccgaa   4080
ggatgttggg gccccgagcc tagggactgt gttagctgca gaaacgtgag cagaggcaga   4140
gagtgtgtgg acaaatgcaa tttactggaa ggagagccta gggagttcgt ggagaacagc   4200
gaatgtatcc agtgccaccc cgagtgttta cctcaagcca tgaacatcac ttgtaccgga   4260
aggggccccg ataactgcat ccaatgcgcc cactacatcg acggacccca ctgcgtgaaa   4320
acttgtcccg ccggagtgat gggagagaat aacactttag tgtggaagta cgccgacgct   4380
ggccacgtct gccatctgtg ccaccccaac tgtacctacg gctgcactgg tcccggttta   4440
gagggatgtc ctaccaacgg ccccaagatc ccctccatcg ccaccggaat ggtgggcgct   4500
ctgttattac tgctggtggt ggctctgggc atcggtttat tcatgtgaac gcgtctggaa   4560
caatcaacct ctggattaca aaatttgtga aagattgact ggtattctta actatgttgc   4620 tcctttacg ctatgtggat acgctgcttt aatgcctttg tatcatgcta ttgcttcccg   4680
tatggctttc attttctcct ccttgtataa atcctggttg ctgtctcttt atgaggagtt   4740
gtggcccgtt gtcaggcaac gtggcgtggt gtgcactgtg tttgctgacg caaccccac   4800 tggttggggc attgccacca cctgtcagct cctttccggg actttcgctt tcccctccc   4860 tattgccacg gcggaactca tcgccgcctg ccttgcccgc tgctggacag gggctcggct   4920
gttgggcact gacaattccg tggtgttgtc ggggaagctg acgtcctttc catggctgct   4980
cgcctgtgtt gccacctgga ttctgcgcgg gacgtccttc tgctacgtcc cttcggccct   5040
caatccagcg gaccttcctt cccgcggcct gctgccggct ctgcggcctc ttccgcgtct   5100
tcgccttcgc cctcagacga gtcggatctc cctttgggcc gcctccccgc ctggaattaa   5160
ttctgcagtc gagacctaga aaaacatgga gcaatcacaa gtagcaatac agcagctacc   5220
aatgctgatt gtgcctggct agaagcacaa gaggaggagg aggtgggttt tccagtcaca   5280
cctcaggtac ctttaagacc aatgacttac aaggcagctg tagatcttag ccactttta   5340 aaagaaaaga ggggactgga agggctaatt cactcccaac gaagacaaga tatccttgat   5400
ctgtggatct accacacaca aggctacttc cctgattagc agaactacac accagggcca   5460
ggggtcagat atccactgac ctttggatgg tgctacaagc tagtaccagt tgagccagat   5520
aaggtagaag aggccaataa aggagagaac accagcttgt tacaccctgt gagcctgcat   5580
gggatggatg acccggagag agaagtgtta gagtggaggt ttgacagccg cctagcattt   5640
catcacgtgg cccgagagct gcatccggag tacttcaaga actgctgata tcgagcttgc   5700
tacaagggac tttccgctgg ggactttcca gggaggcgtg gcctgggcgg gactggggag   5760
tggcgagccc tcagatcctg catataagca gctgcttttt gcctgtactg ggtctctctg   5820
gttagaccag atctgagcct gggagctctc tggctaacta gggaacccac tgcttaagcc   5880
tcaataaagc ttgccttgag tgcttcaagt agtgtgtgcc cgtctgttgt gtgactctgg   5940
taactagaga tccctcagac cctttttagtc agtgtggaaa atctctagca gtagtagttc   6000
atgtcatctt attattcagt atttataact tgcaaagaaa tgaatatcag agagtgagag   6060
```

```
gccttgacat tgctagcgtt taccgtcgac ctctagctag agcttggcgt aatcatggtc    6120
atagctgttt cctgtgtgaa attgttatcc gctcacaatt ccacacaaca tacgagccgg    6180
aagcataaag tgtaaagcct ggggtgccta atgagtgagc taactcacat taattgcgtt    6240
gcgctcactg cccgctttcc agtcgggaaa cctgtcgtgc cagctgcatt aatgaatcgg    6300
ccaacgcgcg gggagaggcg gtttgcgtat tgggccgctt cctcgctcac tgactcgctg    6360
cgctcggtcg ttcggctgcg gcgagcggta tcagctcact caaaggcggt aatacggtta    6420
tccacagaat caggggataa cgcaggaaag aacatgtgag caaaaggcca gcaaaaggcc    6480
aggaaccgta aaaaggccgc gttgctggcg tttttccata ggctccgccc ccctgacgag    6540
catcacaaaa atcgacgctc aagtcagagg tggcgaaacc cgacaggact ataaagatac    6600
caggcgtttc cccctggaag ctccctcgtg cgctctcctg ttccgaccct gccgcttacc    6660
ggatacctgt ccgcctttct cccttcggga agcgtggcgc tttctcatag ctcacgctgt    6720
aggtatctca gttcggtgta ggtcgttcgc tccaagctgg gctgtgtgca cgaacccccc    6780
gttcagcccg accgctgcgc cttatccggt aactatcgtc ttgagtccaa cccggtaaga    6840
cacgacttat cgccactggc agcagccact ggtaacagga ttagcagagc gaggtatgta    6900
ggcggtgcta cagagttctt gaagtggtgg cctaactacg gctacactag aagaacagta    6960
tttggtatct gcgctctgct gaagccagtt accttcggaa aaagagttgg tagctcttga    7020
tccggcaaac aaaccaccgc tggtagcggt ggtttttttg tttgcaagca gcagattacg    7080
cgcagaaaaa aaggatctca agaagatcct ttgatctttt ctacggggtc tgacgctcag    7140
tggaacgaaa actcacgtta agggattttg gtcatgagat tatcaaaaag gatcttcacc    7200
tagatccttt taaattaaaa atgaagtttt aaatcaatct aaagtatata tgagtaaact    7260
tggtctgaca gttaccaatg cttaatcagt gaggcaccta tctcagcgat ctgtctattt    7320
cgttcatcca tagttgcctg actccccgtc gtgtagataa ctacgatacg ggagggctta    7380
ccatctggcc ccagtgctgc aatgataccg cgagacccac gctcaccggc tccagattta    7440
tcagcaataa accagccagc cggaagggcc gagcgcagaa gtggtcctgc aactttatcc    7500
gcctccatcc agtctattaa ttgttgccgg gaagctagag taagtagttc gccagttaat    7560
agtttgcgca acgttgttgc cattgctaca ggcatcgtgg tgtcacgctc gtcgtttggt    7620
atggcttcat tcagctccgg ttcccaacga tcaaggcgag ttacatgatc ccccatgttg    7680
tgcaaaaaag cggttagctc cttcggtcct ccgatcgttg tcagaagtaa gttggccgca    7740
gtgttatcac tcatggttat ggcagcactg cataattctc ttactgtcat gccatccgta    7800
agatgctttt ctgtgactgg tgagtactca accaagtcat tctgagaata gtgtatgcgg    7860
cgaccgagtt gctcttgccc ggcgtcaata cgggataata ccgcgccaca tagcagaact    7920
ttaaaagtgc tcatcattgg aaaacgttct cggggcgaa aactctcaag gatcttaccg    7980
ctgttgagat ccagttcgat gtaacccact cgtgcaccca actgatcttc agcatctttt    8040
actttcacca gcgtttctgg gtgagcaaaa acaggaaggc aaaatgccgc aaaaaaggga    8100
ataagggcga cacggaaatg ttgaatactc atactcttcc tttttcaata ttattgaagc    8160
atttatcagg gttattgtct catgagcgga tacatatttg aatgtattta gaaaaataaa    8220
caaatagggg ttccgcgcac atttccccga aaagtgccac ctgacgtcga cggatcggga    8280
gatcaacttg tttattgcag cttataatgg ttacaaataa agcaatagca tcacaaattt    8340
cacaaataaa gcattttttt cactgcattc tagttgtggt ttgtccaaac tcatcaatgt    8400
atcttatcat gtctggatca actggataac tcaagctaac caaaatcatc ccaaacttcc    8460
```

-continued

```
caccccatac cctattacca ctgccaatta cctgtggttt catttactct aaacctgtga    8520
ttcctctgaa ttattttcat tttaaagaaa ttgtatttgt taaatatgta ctacaaactt    8580
agtagttgga agggctaatt cactcccaaa gaagacaaga tatccttgat ctgtggatct    8640
accacacaca aggctacttc cctgattagc agaactacac accagggcca ggggtcagat    8700
atccactgac ctttggatgg tgctacaagc tagtaccagt tgagccagat aaggtagaag    8760
aggccaataa aggagagaac accagcttgt tacaccctgt gagcctgcat gggatggatg    8820
acccggagag agaagtgtta gagtggaggt ttgacagccg cctagcattt catcacgtgg    8880
cccgagagct gcatccggag tacttcaaga actgctgata tcgagcttgc tacaagggac    8940
tttccgctgg ggactttcca gggaggcgtg gcctgggcgg gactggggag tggcgagccc    9000
tcagatcctg catataagca gctgcttttt gcctgtactg ggtctctctg gttagaccag    9060
atctgagcct gggagctctc tggctaacta gggaacccac tgcttaagcc tcaataaagc    9120
ttgccttgag tgcttcaagt agtgtgtgcc cgtctgttgt gtgactctgg taactagaga    9180
tccctcagac cctttttagtc agtgtggaaa atctctagca gtggcgcccg aacagggact    9240
tgaaagcgaa agggaaacca gaggagctct ctcgacgcag gactcggctt gctgaagcgc    9300
gcacggcaag aggcgagggg cggcgactgg tgagtacgcc aaaaattttg actagcggag    9360
gctagaagga gagagatggg tgcgagagcg tcagtattaa gcggggggaga attagatcgc    9420 gatgggaaaa aattcggtta aggccagggg gaaagaaaaa atataaatta aaacatatag    9480
tatgggcaag cagggagcta gaacgattcg cagttaatcc tggcctgtta gaaacatcag    9540
aaggctgtag acaaatactg ggacagctac aaccatccct tcagacagga tcagaagaac    9600
ttagatcatt atataataca gtagcaaccc tctattgtgt gcatcaaagg atagagataa    9660
aagacaccaa ggaagcttta gacaagatag agaaaacaaa agtaagacca ccgcacagca    9720
agcggccg                                                             9728
```

```
<210> SEQ ID NO 72
<211> LENGTH: 8
<212> TYPE: PRT
<213> ORGANISM: Artificial
<220> FEATURE:
<223> OTHER INFORMATION: amino acid sequence of HCDR1 of 06 antibody

<400> SEQUENCE: 72

Gly Gly Ser Phe Thr Asn Tyr Leu
1               5

<210> SEQ ID NO 73
<211> LENGTH: 8
<212> TYPE: PRT
<213> ORGANISM: Artificial
<220> FEATURE:
<223> OTHER INFORMATION: amino acid sequence of HCDR2 of 06 antibody

<400> SEQUENCE: 73

Ile Ile Pro Val Tyr Gly Thr Pro
1               5

<210> SEQ ID NO 74
<211> LENGTH: 14
<212> TYPE: PRT
<213> ORGANISM: Artificial
<220> FEATURE:
<223> OTHER INFORMATION: amino acid sequence of HCDR3 of 06 antibody
```

```
<400> SEQUENCE: 74

Val Arg Glu Asp Glu Gly Tyr Gly Asp Leu Tyr Leu Ala Tyr
1               5                   10

<210> SEQ ID NO 75
<211> LENGTH: 8
<212> TYPE: PRT
<213> ORGANISM: Artificial
<220> FEATURE:
<223> OTHER INFORMATION: amino acid sequence of LCDR1 of 06 antibody

<400> SEQUENCE: 75

Ser Ser Asn Ile Gly Arg Asn Thr
1               5

<210> SEQ ID NO 76
<211> LENGTH: 3
<212> TYPE: PRT
<213> ORGANISM: Artificial
<220> FEATURE:
<223> OTHER INFORMATION: amino acid sequence of LCDR2 of 06 antibody

<400> SEQUENCE: 76

Ser Asn Asp
1

<210> SEQ ID NO 77
<211> LENGTH: 11
<212> TYPE: PRT
<213> ORGANISM: Artificial
<220> FEATURE:
<223> OTHER INFORMATION: amino acid sequence of LCDR3 of 06 antibody

<400> SEQUENCE: 77

Ala Ser Trp Asp Asp Ser Leu Thr Gly Trp Val
1               5                   10

<210> SEQ ID NO 78
<211> LENGTH: 8
<212> TYPE: PRT
<213> ORGANISM: Artificial
<220> FEATURE:
<223> OTHER INFORMATION: amino acid sequence of HCDR1 of 09 antibody

<400> SEQUENCE: 78

Gly Phe Thr Phe Asn Ile Asp Ala
1               5

<210> SEQ ID NO 79
<211> LENGTH: 8
<212> TYPE: PRT
<213> ORGANISM: Artificial
<220> FEATURE:
<223> OTHER INFORMATION: amino acid sequence of HCDR2 of 09 antibody

<400> SEQUENCE: 79

Ile Ser Ser Ser Gly Gly Thr Thr
1               5

<210> SEQ ID NO 80
<211> LENGTH: 16
<212> TYPE: PRT
<213> ORGANISM: Artificial
<220> FEATURE:
<223> OTHER INFORMATION: amino acid sequence of HCDR3 of 09 antibody

<400> SEQUENCE: 80
```

-continued

```
Ala Arg Ser Arg Tyr Ser Val Pro Asp Gly Arg Gly Ser Tyr Asp Val
1               5                   10                  15

<210> SEQ ID NO 81
<211> LENGTH: 8
<212> TYPE: PRT
<213> ORGANISM: Artificial
<220> FEATURE:
<223> OTHER INFORMATION: amino acid sequence of HCDR1 of 13 antibody

<400> SEQUENCE: 81

Gly Phe Thr Phe Ser Ser Glu Ala
1               5

<210> SEQ ID NO 82
<211> LENGTH: 8
<212> TYPE: PRT
<213> ORGANISM: Artificial
<220> FEATURE:
<223> OTHER INFORMATION: amino acid sequence of HCDR2 of 13 antibody

<400> SEQUENCE: 82

Ile Asn Ala Ser Gly Arg Asn Thr
1               5

<210> SEQ ID NO 83
<211> LENGTH: 14
<212> TYPE: PRT
<213> ORGANISM: Artificial
<220> FEATURE:
<223> OTHER INFORMATION: amino acid sequence of HCDR3 of 13 antibody

<400> SEQUENCE: 83

Ala Arg Lys His Gly Glu Tyr Tyr Asp Ser Gly Tyr Asp Val
1               5                   10

<210> SEQ ID NO 84
<211> LENGTH: 8
<212> TYPE: PRT
<213> ORGANISM: Artificial
<220> FEATURE:
<223> OTHER INFORMATION: amino acid sequence of HCDR1 of 20 antibody

<400> SEQUENCE: 84

Gly Phe Thr Phe Ser Ser Tyr Ala
1               5

<210> SEQ ID NO 85
<211> LENGTH: 8
<212> TYPE: PRT
<213> ORGANISM: Artificial
<220> FEATURE:
<223> OTHER INFORMATION: amino acid sequence of HCDR2 of 20 antibody

<400> SEQUENCE: 85

Ile Ser Gly Tyr Gly Glu Glu Thr
1               5

<210> SEQ ID NO 86
<211> LENGTH: 13
<212> TYPE: PRT
<213> ORGANISM: Artificial
<220> FEATURE:
<223> OTHER INFORMATION: amino acid sequence of HCDR3 of 20 antibody

<400> SEQUENCE: 86
```

```
Ala Arg Phe Tyr Tyr Arg Tyr Trp Lys Glu Phe Asp Tyr
1               5                   10
```

<210> SEQ ID NO 87
<211> LENGTH: 8
<212> TYPE: PRT
<213> ORGANISM: Artificial
<220> FEATURE:
<223> OTHER INFORMATION: amino acid sequence of HCDR1 of 21 antibody

<400> SEQUENCE: 87

```
Gly Phe Thr Phe Ser Asn Tyr Ala
1               5
```

<210> SEQ ID NO 88
<211> LENGTH: 8
<212> TYPE: PRT
<213> ORGANISM: Artificial
<220> FEATURE:
<223> OTHER INFORMATION: amino acid sequence of HCDR2 of 21 antibody

<400> SEQUENCE: 88

```
Ile Thr Gly Leu Gly Gly Asn Met
1               5
```

<210> SEQ ID NO 89
<211> LENGTH: 19
<212> TYPE: PRT
<213> ORGANISM: Artificial
<220> FEATURE:
<223> OTHER INFORMATION: amino acid sequence of HCDR3 of 21 antibody

<400> SEQUENCE: 89

```
Ala Arg Met Tyr Tyr Ser Gln Gly Val Asn Asn Tyr Ser Tyr Pro Ser
1               5                   10                  15

Thr Asp Ile
```

<210> SEQ ID NO 90
<211> LENGTH: 20
<212> TYPE: DNA
<213> ORGANISM: Artificial
<220> FEATURE:
<223> OTHER INFORMATION: sgRNA-1

<400> SEQUENCE: 90

```
gagcagcccg aaccctcctc                                                    20
```

<210> SEQ ID NO 91
<211> LENGTH: 20
<212> TYPE: DNA
<213> ORGANISM: Artificial
<220> FEATURE:
<223> OTHER INFORMATION: sgRNA-2

<400> SEQUENCE: 91

```
ggaggagggt tcgggctgct                                                    20
```

<210> SEQ ID NO 92
<211> LENGTH: 20
<212> TYPE: DNA
<213> ORGANISM: Artificial
<220> FEATURE:
<223> OTHER INFORMATION: gRNA-3

<400> SEQUENCE: 92

```
atcaccaagc ccgcgaccaa                                                    20
```

-continued

```
<210> SEQ ID NO 93
<211> LENGTH: 20
<212> TYPE: DNA
<213> ORGANISM: Artificial
<220> FEATURE:
<223> OTHER INFORMATION: sgRNA-4

<400> SEQUENCE: 93
agcgctggat gcacaccacg                                                                  20

<210> SEQ ID NO 94
<211> LENGTH: 20
<212> TYPE: DNA
<213> ORGANISM: Artificial
<220> FEATURE:
<223> OTHER INFORMATION: sgRNA-5

<400> SEQUENCE: 94
gggcttggtg atctgcctcg                                                                  20
```

ANTIBODY AND CHIMERIC ANTIGEN RECEPTOR (CAR) BINDING TO CD70, AND APPLICATION THEREOF

CROSS-REFERENCES TO RELATED APPLICATIONS

This application is a National Stage of International Application No. PCT/CN2021/123347, filed Oct. 12, 2021, which claims priority to Chinese Application No. 202011081505.7, filed Oct. 12, 2020, the disclosures of which are incorporated herein by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is 1483-P8USPNP_Seq_List_20230412_ST25.txt. The text file is 125,000 bytes; was created on Apr. 12, 2023, contains no new matter, and is being submitted electronically via Patent Center.

FIELD OF THE INVENTION

The present application relates to the field of biomedicine, and in particular to an antibody and a chimeric antigen receptor capable of specifically binding to CD70 protein.

BACKGROUND OF THE INVENTION

Cell therapy, especially chimeric antigen receptor-modified T cells (CAR-T), has become a research hotspot in tumor immunotherapy. As of July 2020, 3 CAR-T products have been approved by the FDA for marketing. These CAR-T products all target the CD19 antigen on B cell tumors. Despite the very effective targets such as CD19 and BCMA, the continuous development of more effective targets is still one of the research directions for widening CAR-T therapy.

CD70 is a member of the tumor necrosis factor superfamily, which has the ability to regulate the activation, proliferation and differentiation of T cells and B cells, and plays an important role in regulating the immune response. In normal tissues, CD70 is only expressed on activated T and B cells and mature DC cells, but CD70 is highly expressed in a variety of tumor tissues, making it an effective target molecule in tumor immunotherapy.

A CD70-targeting chimeric antigen receptor molecule (CD70 CAR) are described herein, which can be used to treat CD70-positive tumors.

SUMMARY OF THE INVENTION

The present application provides an antibody and a chimeric antigen receptor that can specifically bind to CD70 and uses thereof.

In one aspect, the present application provides a CD70-targeting fully human antibody or a single-chain antibody or an antigen-binding fragment thereof. The fully human antibody includes a heavy chain variable region (HCVR) and/or a light chain variable region (LCVR). The heavy chain variable region includes a HCDR1, a HCDR2 and a HCDR3, and the light chain variable region includes a LCDR1, a LCDR2 and a LCDR3. The HCDR1, HCDR2, HCDR3 and/or LCDR1, LCDR2 and LCDR3 are any one selected from:

(1) the LCDR1 having an amino acid sequence of SSNIGRNT (SEQ ID NO: 75);
the LCDR2 having an amino acid sequence of SND (SEQ ID NO: 76);
the LCDR3 having an amino acid sequence of ASWDDSLTGWV (SEQ ID NO: 77);
the HCDR1 having an amino acid sequence of GGSFTNYL (SEQ ID NO: 72);
the HCDR2 having an amino acid sequence of IIPVYGTP (SEQ ID NO: 73); and
the HCDR3 having an amino acid sequence of VREDEGYGDLYLAY (SEQ ID NO: 74);
(2) the HCDR1 having an amino acid sequence of GFTFNIDA (SEQ ID NO: 78);
the HCDR2 having an amino acid sequence of ISSSGGTT (SEQ ID NO: 79); and
the HCDR3 having an amino acid sequence of ARSRYSVPDGRGSYDV (SEQ ID NO: 80);
(3) the HCDR1 having an amino acid sequence of GFTFSSEA (SEQ ID NO: 81);
the HCDR2 having an amino acid sequence of INASGRNT (SEQ ID NO: 82); and
the HCDR3 having an amino acid sequence of ARKHGEYYDSGYDV (SEQ ID NO: 83);
(4) the HCDR1 having an amino acid sequence of GFTFSSYA (SEQ ID NO: 84);
the HCDR2 having an amino acid sequence of ISGYGEET (SEQ ID NO: 85); and
the HCDR3 having an amino acid sequence of ARFYYRYWKEFDY (SEQ ID NO: 86); and
(5) the HCDR1 having an amino acid sequence of GFTFSNYA (SEQ ID NO: 87);
the HCDR2 having an amino acid sequence of ITGLGGNM (SEQ ID NO: 88); and
the HCDR3 having an amino acid sequence of ARMYYSQGVNNYSYPSTDI (SEQ ID NO: 89);
or the fully human antibody comprises a variant of the CDR sequence combination in any one of (1)-(5), wherein compared with the CDR sequences in any one of (1)-(5), the variant has at least 90% sequence identity, or comprises at least 1 and no more than 10, or no more than 5, 4, 3, 2 or 1 amino acid change in total in the CDR sequences.

In some embodiments, the amino acid sequence of the heavy chain variable region and/or the light chain variable region is selected from any one of the following:

(1) a sequence as shown in SEQ ID NO: 28 or a heavy chain variable region sequence having at least 90% sequence identity thereto, and
a sequence as shown in SEQ ID NO: 30 or a light chain variable region sequence having at least 90% sequence identity thereto;
(2) a sequence as shown in SEQ ID NO: 33 or a heavy chain variable region sequence having at least 90% sequence identity thereto;
(3) a sequence as shown in SEQ ID NO: 36 or a heavy chain variable region sequence having at least 90% sequence identity thereto;
(4) a sequence as shown in SEQ ID NO: 39 or a heavy chain variable region sequence having at least 90% sequence identity thereto; and
(5) a sequence as shown in SEQ ID NO: 42 or a heavy chain variable region sequence having at least 90% sequence identity thereto.

In some embodiments, the amino acid sequence of the heavy chain variable region and/or the light chain variable region is selected from any one of the following:

(1) a heavy chain variable region sequence as shown in SEQ ID NO: 28, and a light chain variable region sequence as shown in SEQ ID NO: 30;

(2) a heavy chain variable region sequence as shown in SEQ ID NO: 33;

(3) a heavy chain variable region sequence as shown in SEQ ID NO: 36;

(4) a heavy chain variable region sequence as shown in SEQ ID NO: 39; and (5) a heavy chain variable region sequence as shown in SEQ ID NO: 42.

In some embodiments, the fully human antibody comprises an amino acid sequence as shown in SEQ ID NO: 26.

In another aspect, the present application provides a nucleic acid molecule encoding the fully human antibody or a single-chain antibody or an antigen-binding fragment thereof.

In some embodiments, the nucleic acid molecule comprises a nucleotide sequence as shown in any one of SEQ ID NO: 25, 27, 29, 31, 32, 34, 35, 37, 38, 40 and 41, or a functional variant thereof.

In another aspect, the present application provides an expression vector comprising the aforementioned nucleic acid molecule.

In another aspect, the present application provides a host cell comprising the aforementioned expression vector.

In another aspect, the present application provides a pharmaceutical composition comprising the aforementioned fully human antibody or a single-chain antibody or antigen-binding fragment thereof, and a pharmaceutically acceptable adjuvant or diluent.

In another aspect, the present application provides a method for treating a disease or disorder. The method includes administering, to a patient in need thereof, a therapeutically effective amount of the aforementioned fully human antibody or a single-chain antibody or antigen-binding fragment thereof, the aforementioned host cell, or the aforementioned pharmaceutical composition, to eliminate, inhibit or reduce CD70 activity, thereby preventing, alleviating, improving or inhibiting the disease or disorder.

In some embodiments, the disease or disorder is selected from: a cancer or an autoimmune disease.

In some embodiments, the cancer is selected from the group consisting of renal cell carcinoma, metastatic breast cancer, brain tumor, leukemia, lymphoma and nasopharyngeal carcinoma.

In another aspect, the present application provides an antibody or an antigen-binding fragment that competes for the same epitope with the fully human antibody or a single-chain antibody or an antigen-binding fragment thereof.

In another aspect, the present application provides a kit for detecting CD70 protein in a sample comprising the aforementioned fully human antibody or a single-chain antibody or antigen-binding fragment thereof.

In another aspect, the present application provides use of the fully human antibody or a single-chain antibody or antigen-binding fragment thereof, or the host cell in the preparation of a drug for eliminating, inhibiting or reducing CD70 activity, thereby preventing, alleviating, improving or inhibiting a disease or a disorder.

In some embodiments, the disease or disorder is selected from: a cancer or an autoimmune disease.

In some embodiments, the cancer is selected from the group consisting of renal cell carcinoma, metastatic breast cancer, brain tumor, leukemia, lymphoma and nasopharyngeal carcinoma.

In another aspect, the present application comprises a chimeric antigen receptor (CAR). The CAR comprises a CD70 binding domain, a transmembrane domain, a co-stimulatory domain and an intracellular signaling domain. The CD70 binding domain comprises one or more antibodies or fragments thereof specifically binding to CD70. Each antibody comprises a heavy chain complementarity determining region 1 (HCDR1), a heavy chain complementarity determining region 2 (HCDR2) and a heavy chain complementarity determining region 3 (HCDR3). The amino acid sequences of the HCDR1, HCDR2 and HCDR3 of each antibody are independently selected from the following combinations: (1) the HCDR1 having an amino acid sequence as shown in SEQ ID NO: 72, the HCDR2 having an amino acid sequence as shown in SEQ ID NO: 73, and the HCDR3 having an amino acid sequence as shown in SEQ ID NO: 74; (2) the HCDR1 having an amino acid sequence as shown in SEQ ID NO: 78, the HCDR2 having an amino acid sequence as shown in SEQ ID NO: 79, and the HCDR3 having an the amino acid sequence as shown in NO: 80; (3) the HCDR1 having an amino acid sequence as shown in SEQ ID NO: 81, the HCDR2 having an amino acid sequence as shown in SEQ ID NO: 82, and the HCDR3 having an the amino acid sequence as shown in SEQ ID NO: 83; (4) the HCDR1 having an amino acid sequence as shown in SEQ ID NO: 84, the HCDR2 having an amino acid sequence as shown in SEQ ID NO: 85, and the HCDR3 having an amino acid sequence as shown in SEQ ID NO: 86; or (5) the HCDR1 having an amino acid sequence as shown in SEQ ID NO: 87, the HCDR2 having an amino acid sequence as shown in SEQ ID NO: 88, and the HCDR3 having an amino acid sequence as shown in SEQ ID NO: 89.

In some embodiments, the antibody further comprises a light chain complementarity determining region 1 (LCDR1), a light chain complementarity determining region 2 (LCDR2) and a light chain complementarity determining region 3 (LCDR3). The amino acid sequence of LCDR1 is as shown in SEQ ID NO: 75, the amino acid sequence of LCDR2 is as shown in SEQ ID NO: 76, and the amino acid sequence of LCDR3 is as shown in SEQ ID NO: 77.

In some embodiments, the CD70 binding domain comprises a combination of any two selected from the following antibodies or fragments thereof; (1) an antibody comprising a HCDR1 having an amino acid sequence as shown in SEQ ID NO: 78, a HCDR2 having an amino acid sequence as shown in SEQ ID NO: 79, and a HCDR3 having an amino acid sequence as shown in SEQ ID NO: 80, or a fragment thereof; (2) an antibody comprising a HCDR1 having an amino acid sequence as shown in SEQ ID NO: 81, a HCDR2 having an amino acid sequence as shown in SEQ ID NO: 82, and a HCDR3 having an amino acid sequence as shown in SEQ ID NO: 83, or a fragment thereof; (3) an antibody comprising a HCDR1 having an amino acid sequence as shown in SEQ ID NO: 84, a HCDR2 having an amino acid sequence as shown in SEQ ID NO: 85, and a HCDR3 having an amino acid sequence as shown in SEQ ID NO: 86, or a fragment thereof; or (4) an antibody comprising a HCDR1 having an amino acid sequence as shown in SEQ ID NO: 87, a HCDR2 having an amino acid sequence as shown in SEQ ID NO: 88, and a HCDR3 having an amino acid sequence as shown in SEQ ID NO: 89, or a fragment thereof.

In some embodiments, the antibody comprises a heavy chain variable region having an amino acid sequence as shown in SEQ ID NO: 28, 33, 36, 39 or 42. In some embodiments, the antibody further comprises a light chain variable region having an amino acid sequence as shown in SEQ ID NO: 30. In some embodiments, the antibody is a single-chain antibody or a single-domain antibody. In some embodiments, the CD70 binding domain comprises a plurality of single-chain antibodies or single-domain antibodies, and the plurality of single-chain antibodies or single-domain antibodies are linked via a fragment as shown in SEQ ID NO: 44.

In some embodiments, the amino acid sequence contained in the CD70 binding domain is any one selected from the following combinations: (1) an amino acid sequence as shown in SEQ ID No: 26; (2) an amino acid sequence as shown in SEQ ID No: 36 and an amino acid sequence as shown in SEQ ID No: 39, linked by a fragment as shown in SEQ ID NO: 44; (3) an amino acid sequence as shown in SEQ ID No: 33 and an amino acid sequence as shown in SEQ ID NO: 36, linked by a fragment as shown in SEQ ID NO: 44; (4) an amino acid sequence as shown in SEQ ID No: 33 and an amino acid sequence as shown in SEQ ID No: 42, linked by a fragment as shown in SEQ ID NO: 44; (5) an amino acid sequence as shown in SEQ ID No: 36 and an amino acid sequence as shown in SEQ ID No: 42, linked by a fragment as shown in SEQ ID NO: 44; or a functional variant of any combination of (1)-(5).

In some embodiments, the transmembrane domain of the CAR comprises a polypeptide from a protein selected from the group consisting of α, β or ζ chain of T cell receptors, CD28, CD3e, CD45, CD4, CD5, CD8a, CD9, CD16, CD22, CD33, CD37, CD64, CD80, CD86, CD134, CD137, and CD154. In some embodiments, the transmembrane domain comprises an amino acid sequence as shown in SEQ ID No: 9 or a functional variant thereof.

In some embodiments, the co-stimulatory domain of the CAR comprises a polypeptide selected from the group consisting of CD28, 4-1BB, OX-40, and ICOS. In some embodiments, the co-stimulatory domain comprises an amino acid sequence as shown in SEQ ID No: 12 or a functional variant thereof.

In some embodiments, the intracellular signaling domain of the CAR comprises a signaling domain from CD3z. In some embodiments, the intracellular signaling domain comprises an amino acid sequence as shown in SEQ ID No: 15 or a functional variant thereof.

In some embodiments, the CAR further comprises a hinge region linking the antibody and the transmembrane domain. In some embodiments, the hinge region comprises an amino acid sequence as shown in SEQ ID No: 6 or a functional variant thereof.

In some embodiments, the CAR is further linked with a signal peptide. In some embodiments, the signal peptide comprises an amino acid sequence as shown in SEQ ID No: 3 or a functional variant thereof.

In some embodiments, the CAR is further linked with a cleaving peptide. In some embodiments, the cleaving peptide comprises an amino acid sequence from T2A peptide. In some embodiments, the cleaving peptide comprises an amino acid sequence as shown in SEQ ID No: 18 or a functional variant thereof. In some embodiments, the cleaving peptide is linked to CSF2RA signal peptide, and the CSF2RA signal peptide comprises an amino acid sequence as shown in SEQ ID No: 21 or a functional variant thereof. In some embodiments, the CSF2RA signal peptide is linked to a tEGFR protein sequence, and the tEGFR protein sequence comprises an amino acid sequence as shown in SEQ ID No: 24 or a functional variant thereof.

In some embodiments, the CAR comprises an amino acid sequence as shown in SEQ ID No: 46, 48, 50, 52, 54, 56, 58, 60, 62, 64, 66, 68 or 70 or a functional variant thereof.

In another aspect, the present application further comprises an isolated nucleic acid molecule encoding the CAR described herein.

In another aspect, the present application further comprises a CAR encoding isolated nucleic acid molecule, which comprises a nucleic acid sequence as shown in SEQ ID No: 1, 2, 4, 5, 7, 8, 10, 11, 13, 14, 25, 27, 29, 31, 32, 34, 35, 37, 38, 40, 41, 43, 45, 47, 49, 51, 53, 55, 57, 59, 61, 63, 65, 67 or 69, or a functional variant thereof.

In another aspect, the present application further comprises a vector comprising the nucleic acid molecule according to the present application. In some embodiments, the vector is selected from the group consisting of a plasmid, a retroviral vector and a lentiviral vector.

In another aspect, the present application further comprises an immune effector cell comprising the CAR described in the present application, the nucleic acid molecule described in the present application, or the vector described in the present application. In some embodiments, the immune effector cell is selected from T lymphocyte and natural killer (NK) cell. In some embodiments, CD70 is not expressed on the immune effector cell.

In another aspect, the present application further comprises a method for preparing an immune effector cell, which comprises knocking out the CD70 gene of the immune effector cell, and introducing the vector described in the present application into the immune effector cell.

In another aspect, the present application further comprises a composition comprising the immune effector cell described in the present application.

In another aspect, the present application further comprises use of the CAR, the nucleic acid molecule, the vector, or the immune effector cells in the preparation of a drug for treating a disease or disorder related to CD70 expression. In some embodiments, the disease or disorder related to CD70 expression is a cancer or a malignant tumor.

Those skilled in the art can easily perceive other aspects and advantages of the present application from the following detailed description. In the following detailed description, only exemplary embodiments of the present application are shown and described. It will be recognized by those skilled in the art that changes can be made to the disclosed specific embodiments by those skilled in the art based on the disclosure of the present application without departing from the spirit and scope of the present application. Correspondingly, the drawings and descriptions in the specification of the present application are only exemplary rather than restrictive.

7

Figure 5:
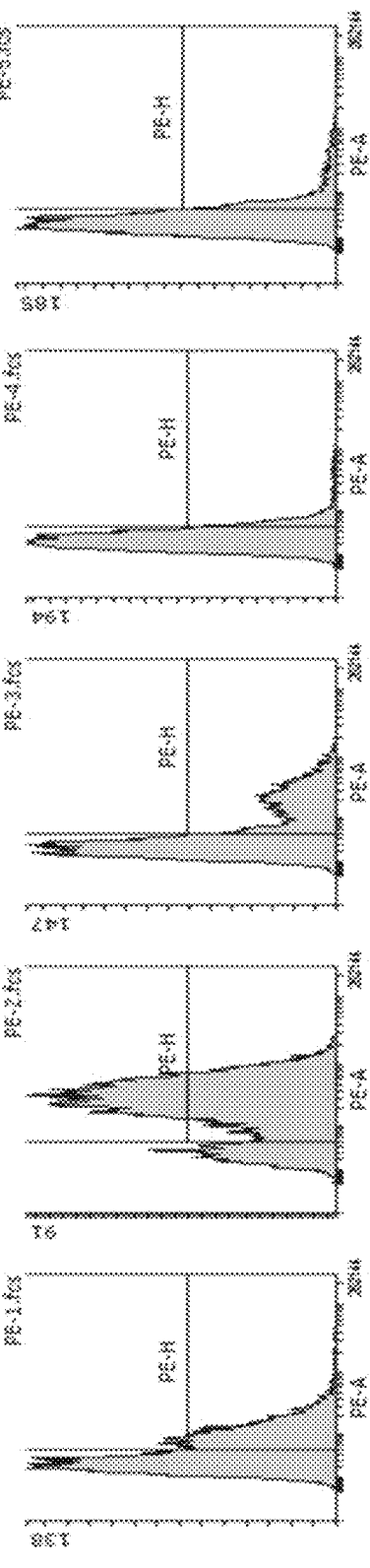

CAR molecule controls, where in PXL1323, the extracellular region of CD27 protein is used as an antigen recognizing region of the CAR molecule, and in PXL1331, the scFv composed of the variable region of cusatuzumab is used as an antigen recognizing region. The results for each CAR molecule are, from left to right, the results after co-incubation with U266, THP-1, RS4, HEL, K562, and Buffer FIG. 5 is a diagram showing CD70 protein on the surface of THP-1 cells detected by flow cytometry 7 days after electrotransduction of THP-1 cells with sgRNA and Cas9 RNPs.

FIG. 6 shows the CD107a positive rate (CD107a %) in the CD8+/CAR+ cell population 3 hrs after the co-incubation of CAR-T cells and target cells detected by flow cytometry, and the CD107a MFI ratio of CD8+/CAR+ cell population to CD8+/CAR– cell population.

Figure 7:
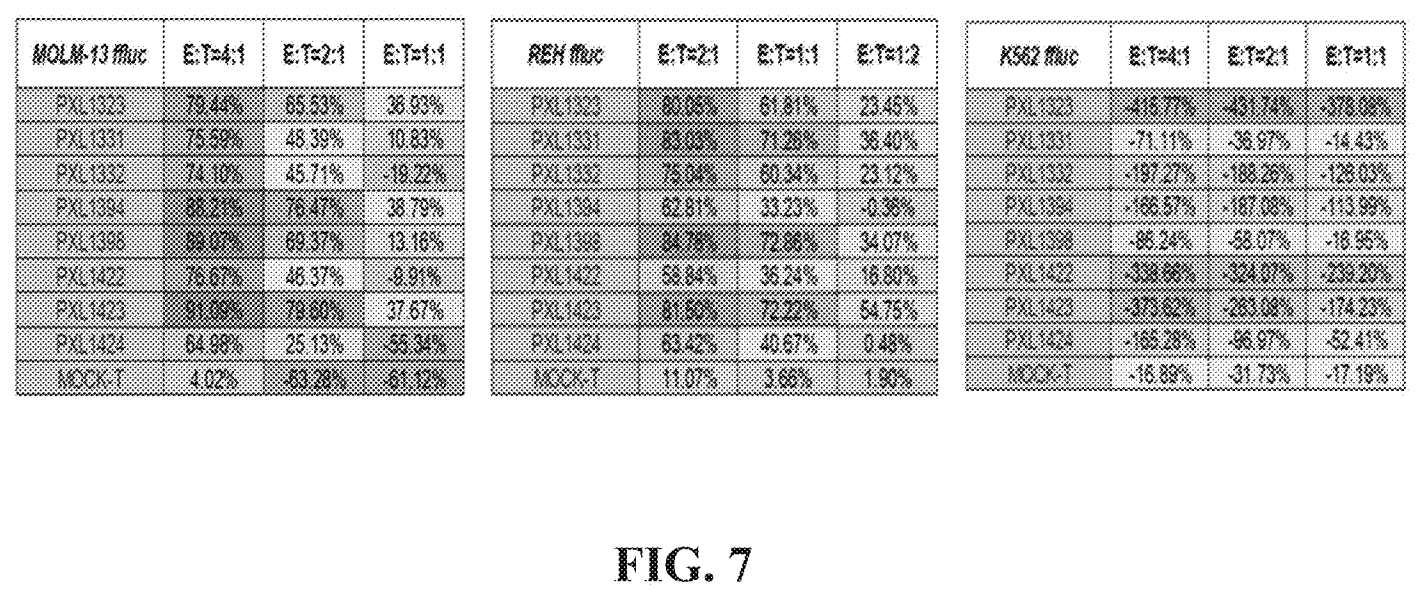

FIG. 7 shows the in-vitro killing efficiency over 24 hrs of CAR-T cells on various target cells, where the negative value indicates that the target cells are not killed, but expanded.

Figure 8:
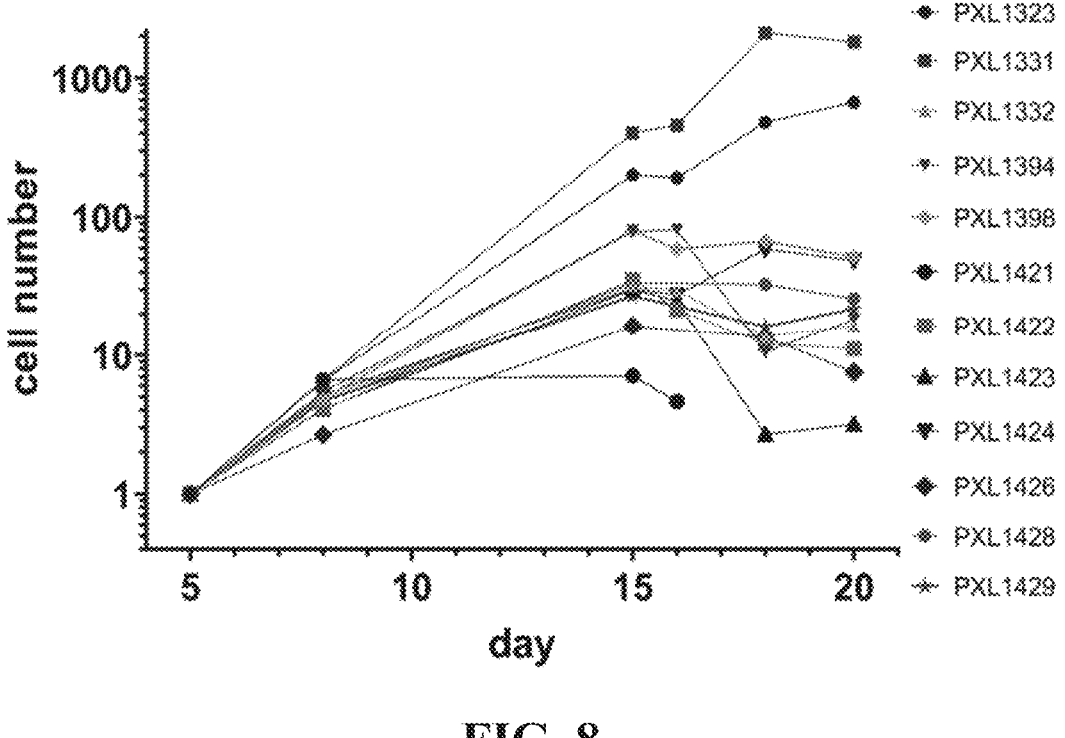

FIG. 8 shows the expansion curve in in-vitro culture of CAR-T cells.

FIG. 9 shows the CD107a positive rate (CD107a %) in the CD8+/CAR+ cell population 3 hrs after the co-incubation of 2×VHH CAR-T cells and target cells detected by flow cytometry, and the CD107a MFI ratio of CD8+/CAR+ cell population to CD8$^+$/CAR– cell population.

Figure 10:
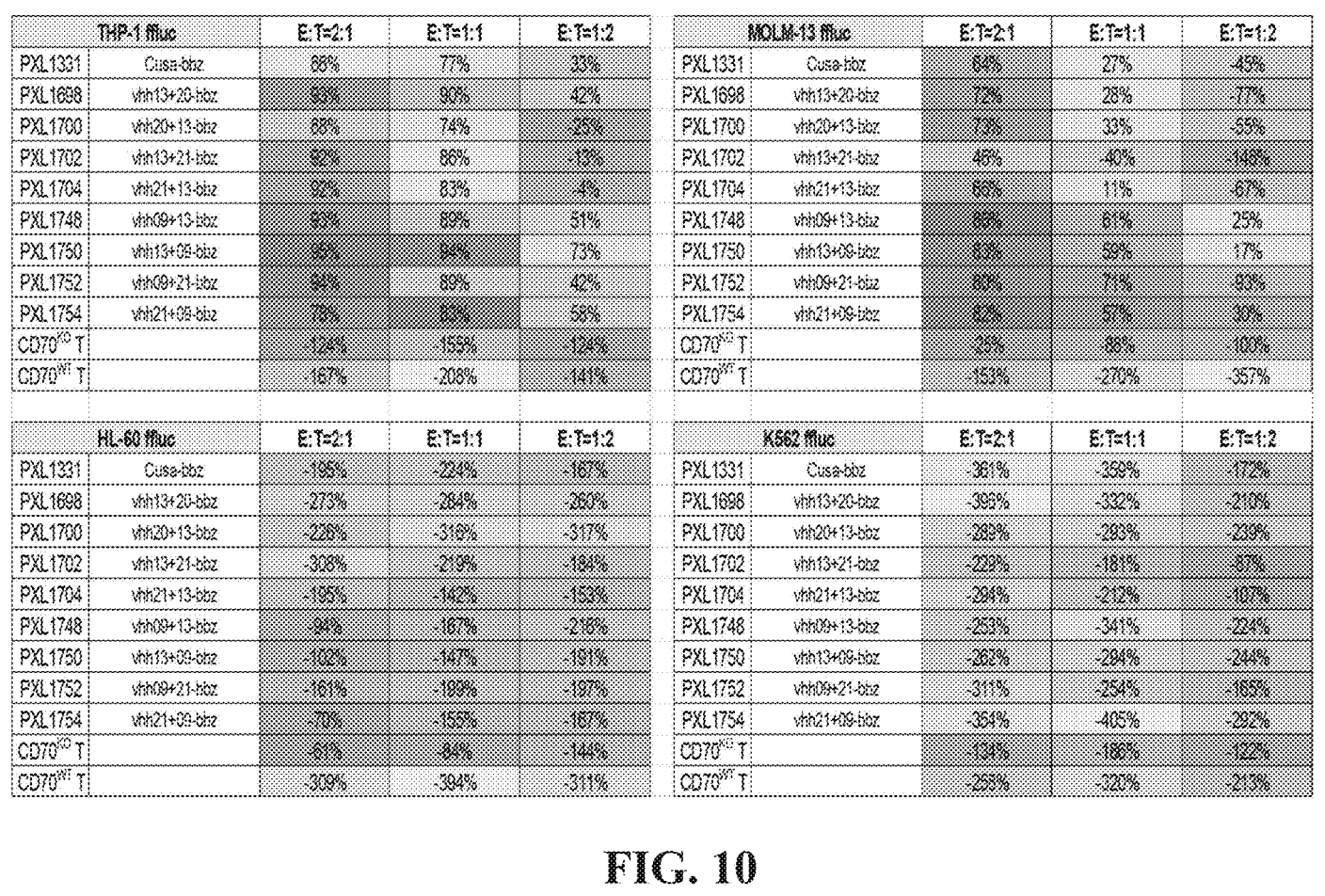

FIG. 10 shows the in-vitro killing efficiency over 24 hrs of 2×VHH CAR-T cells on various target cells, where the negative value indicates that the target cells are not killed, but expanded.

Figure 11:
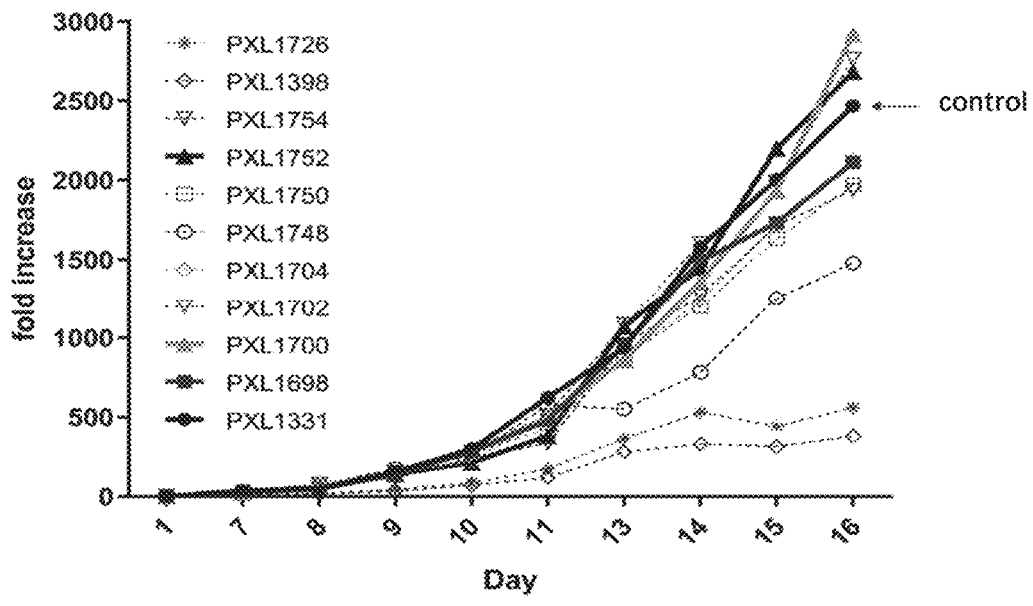

FIG. 11 shows the in-vitro expansion curve of 2×VHH CAR-T cells.

FIG. 12 shows the basic flow for screening specific antibodies targeting CD70 from a phage antibody library in the present invention.

Figure 13:
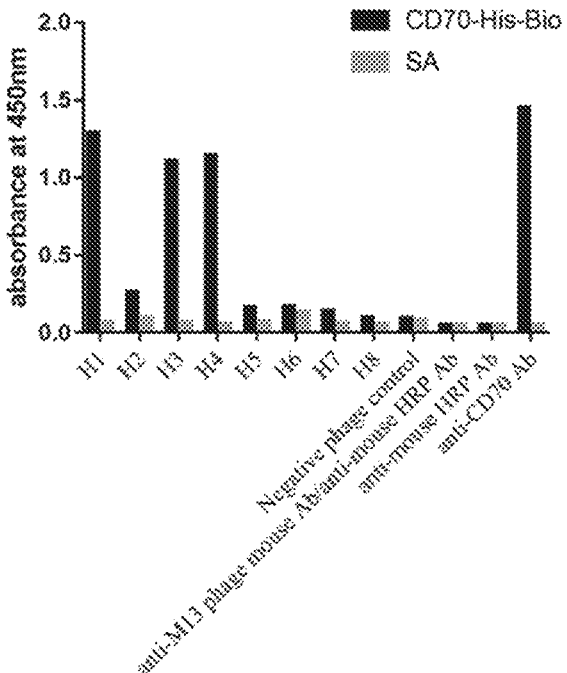

FIG. 13 shows the results of enzyme-linked immunosorbent assay (ELISA) of some of the panned phage monoclonal antibodies with the target antigen and control antigen.

Figure 14:
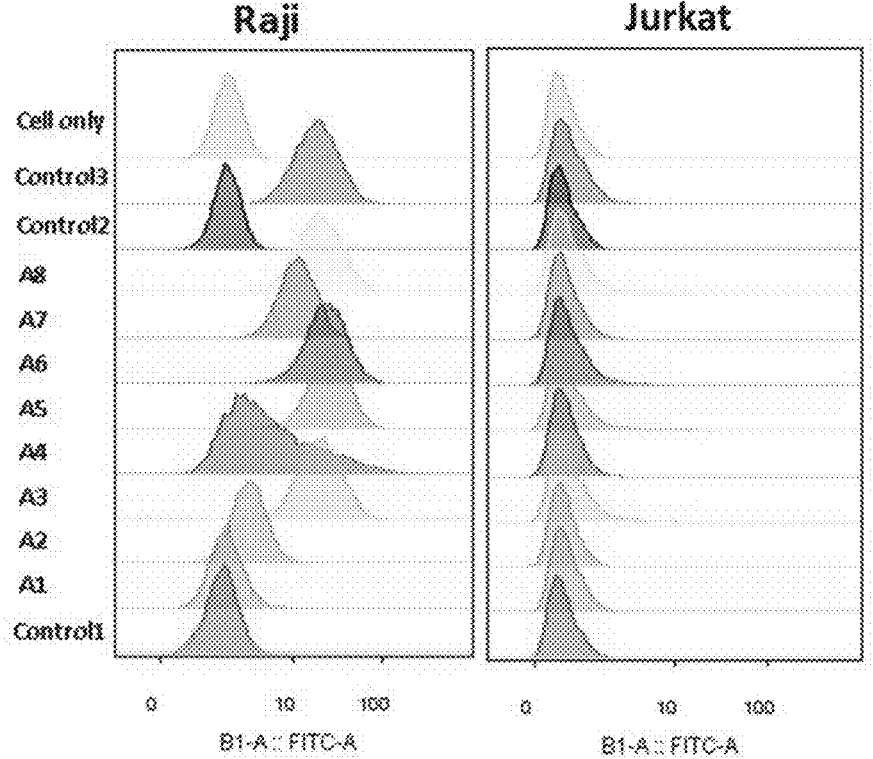
Figure 15A:
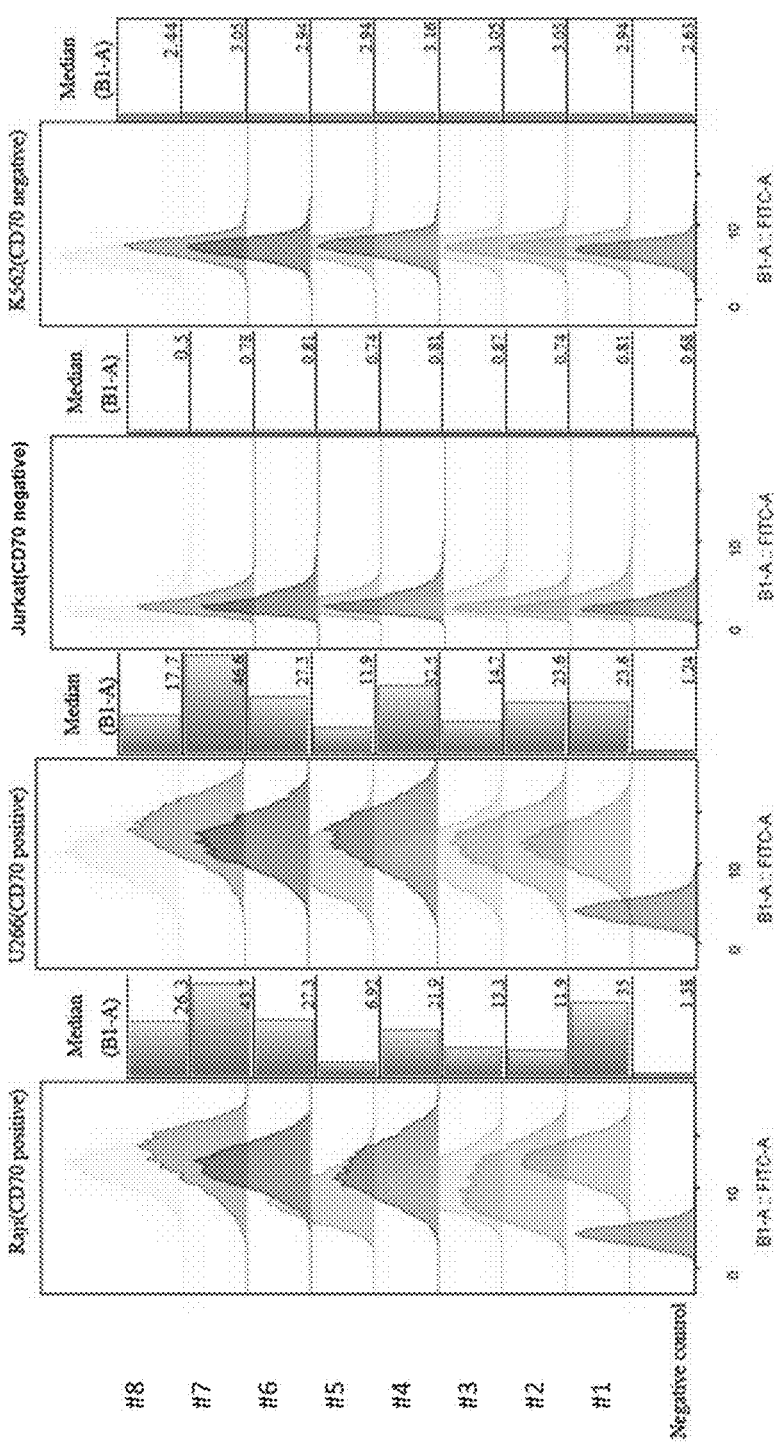
Figure 15B:
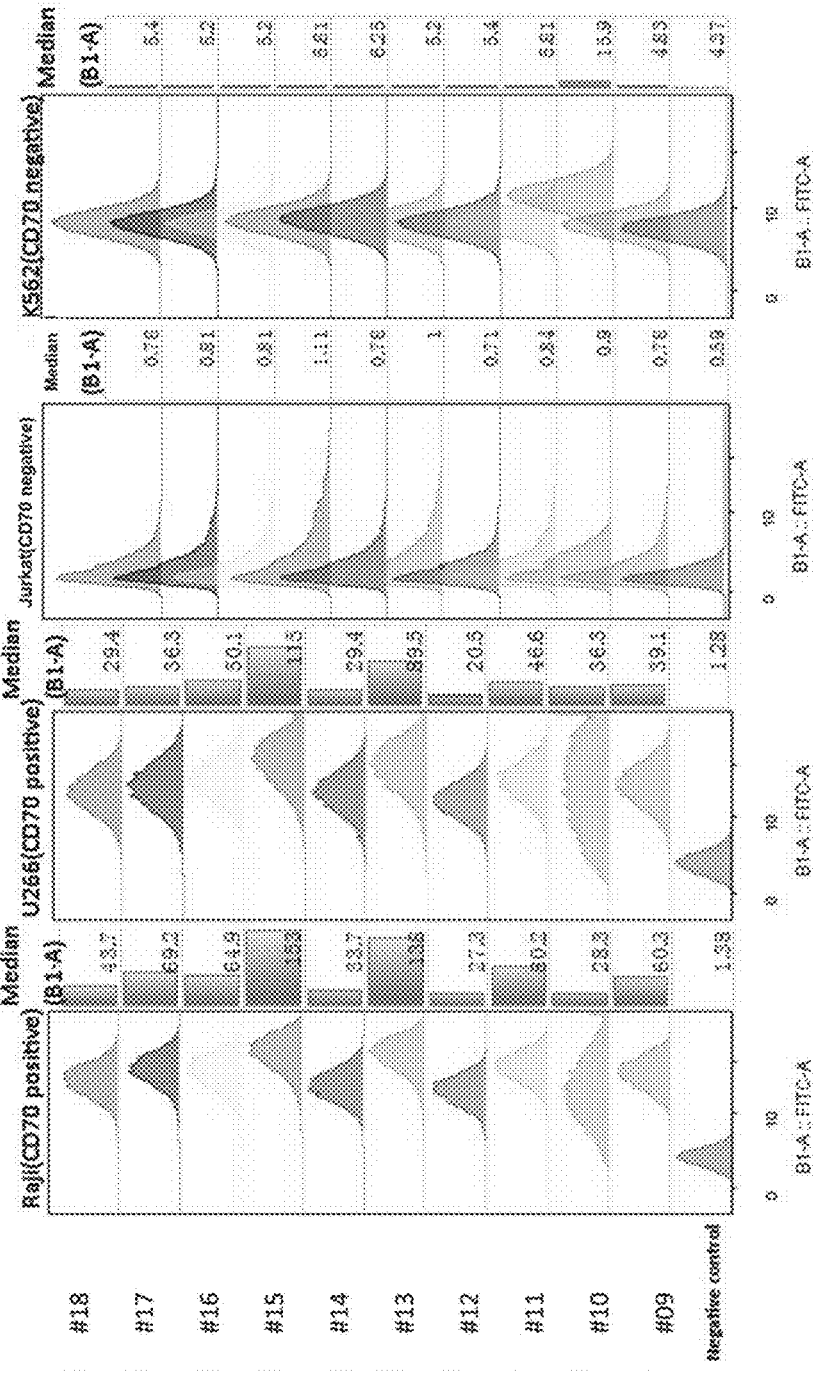
Figure 15C:
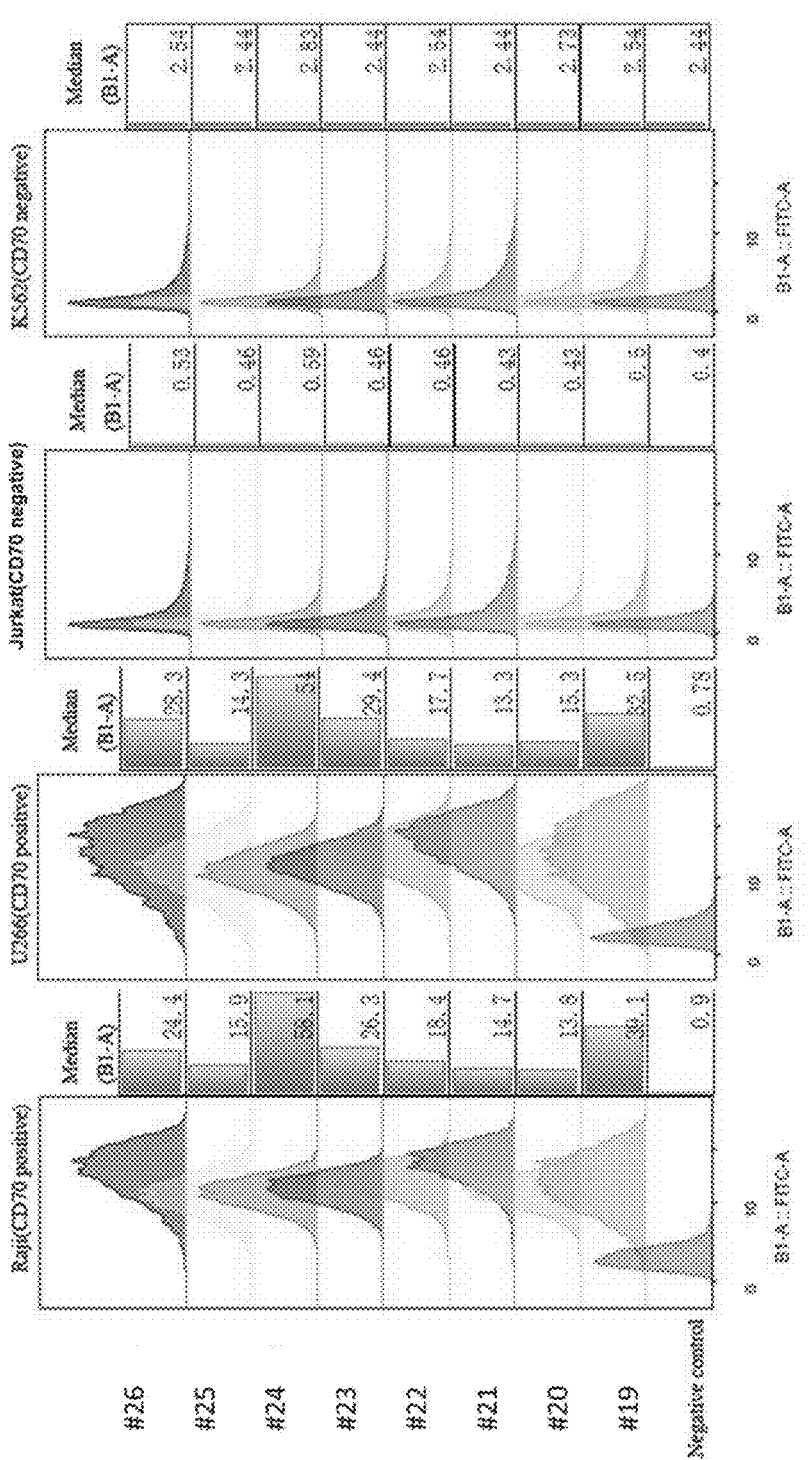
Figure 15D:
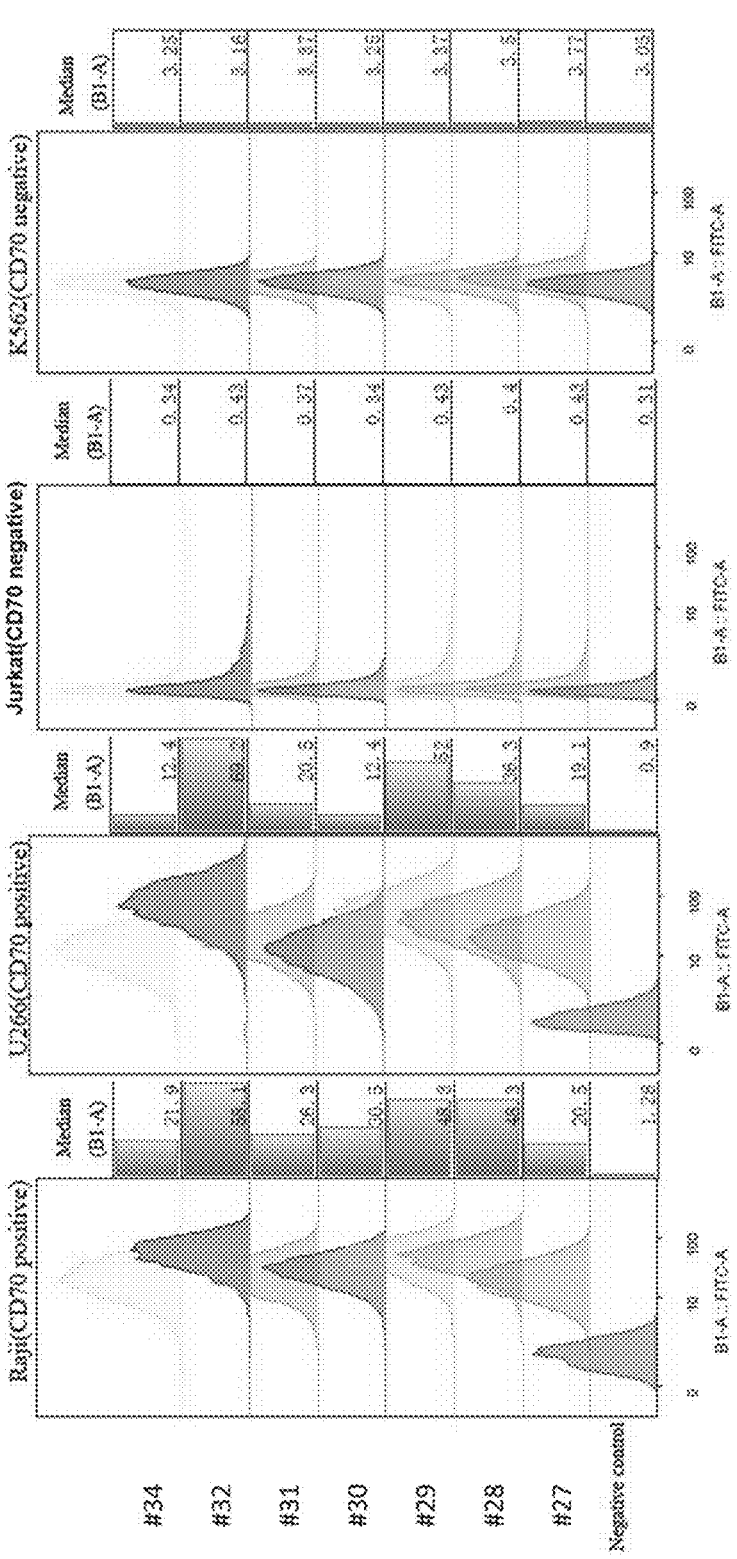
Figure 15E:
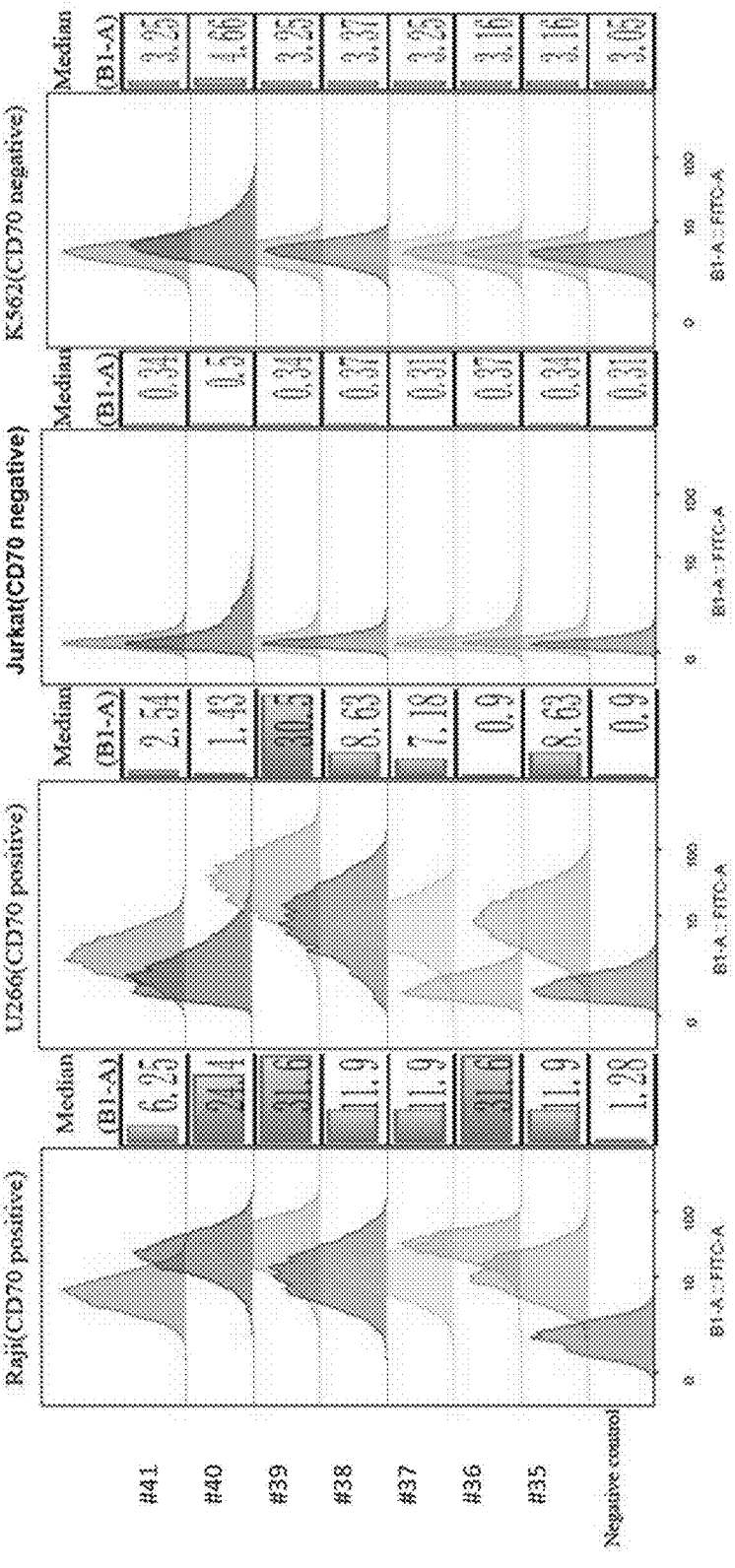

FIG. 14 shows the results of flow cytometric analysis of some phage monoclonal antibodies binding to Raji and Jurkat cells, in which Control 1 is the phage negative control, Control 2 is a negative control with only the primary antibody (Anti-M13 phage mouse Ab) and the second antibody (anti-mouse HRP Ab), and Control 3 is the CD70 antibody positive control.

FIGS. 15A-E show the results of flow cytometric analysis (peak shape and MFI value) of the screened phage monoclonal antibodies #1~32 and #34~41 binding to various CD70 positive and negative cell lines, in which Negative Control is the phage antibody clone negative control.

Figure 16A:
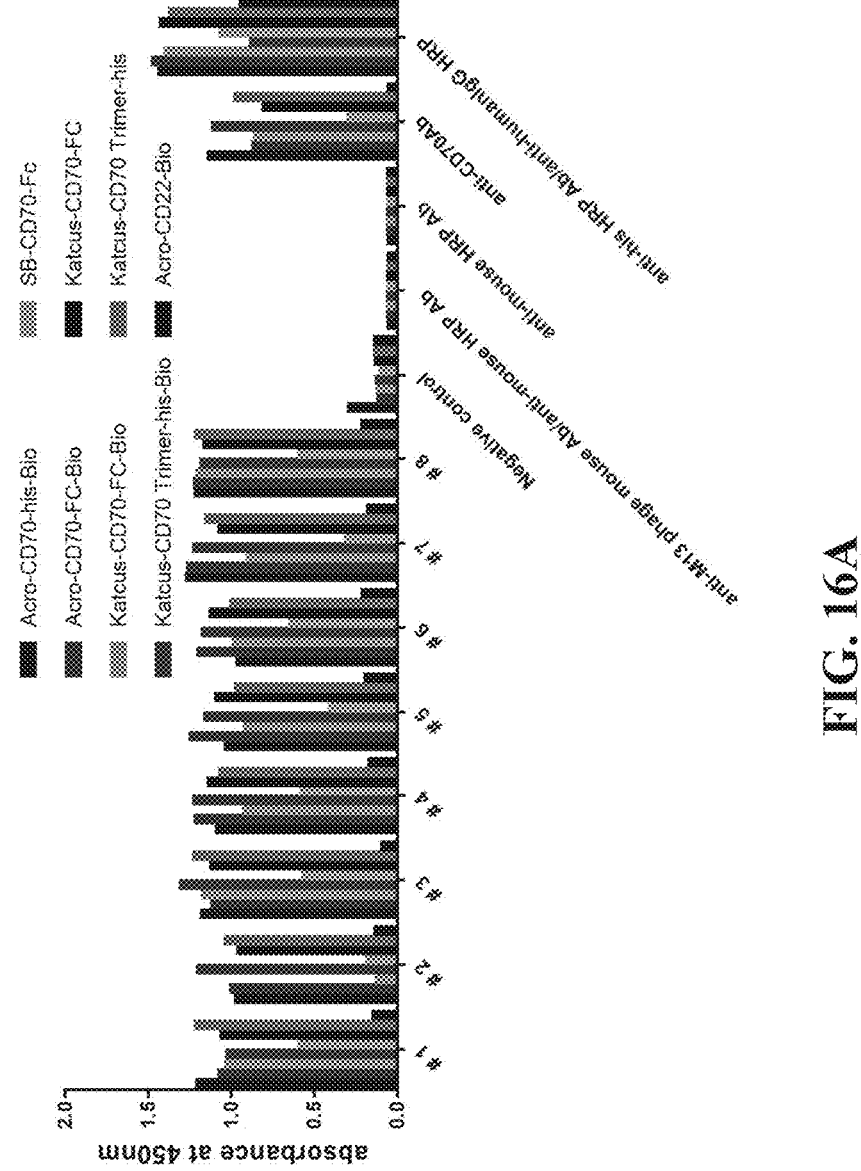
Figure 16B:
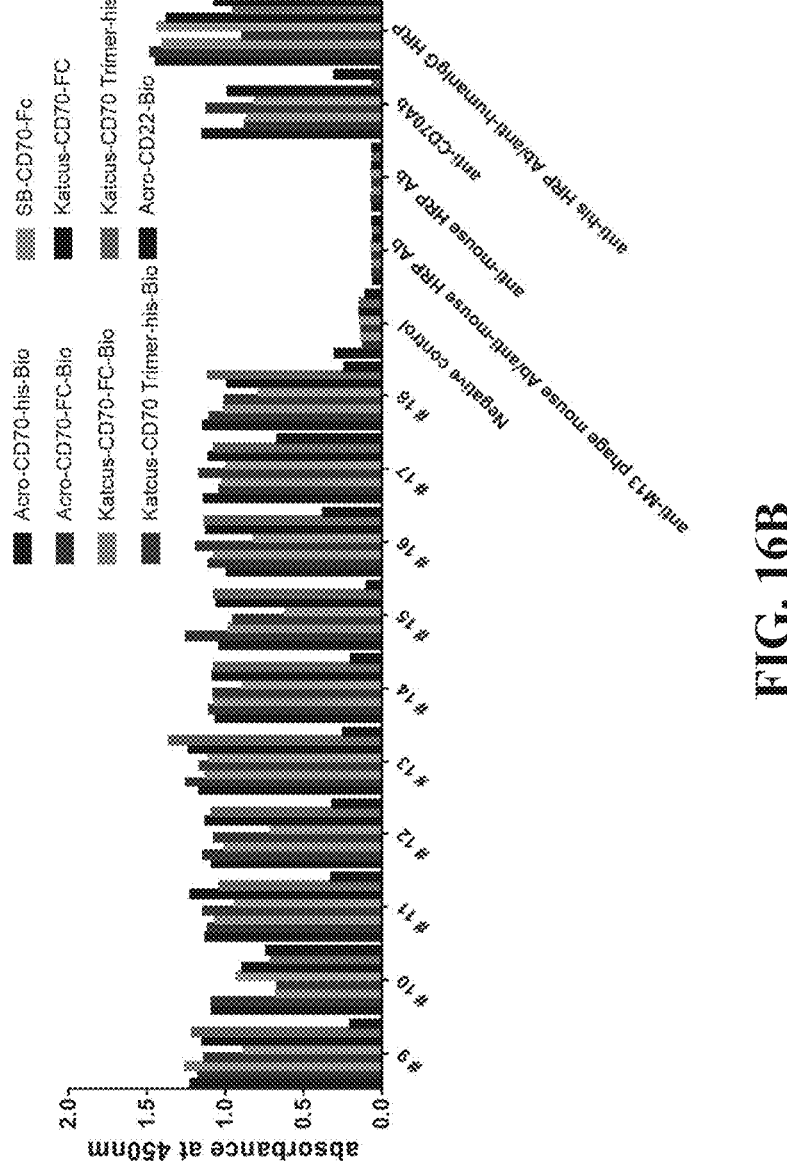
Figure 16C:
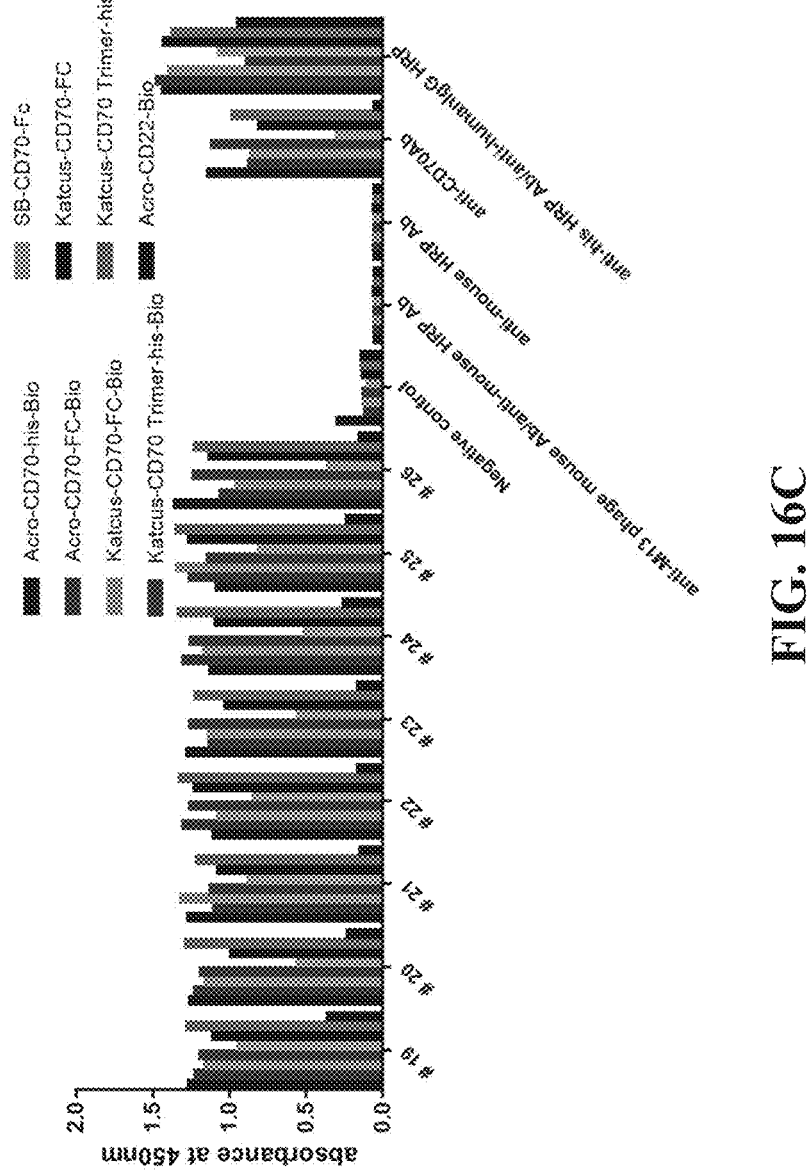
Figure 16D:
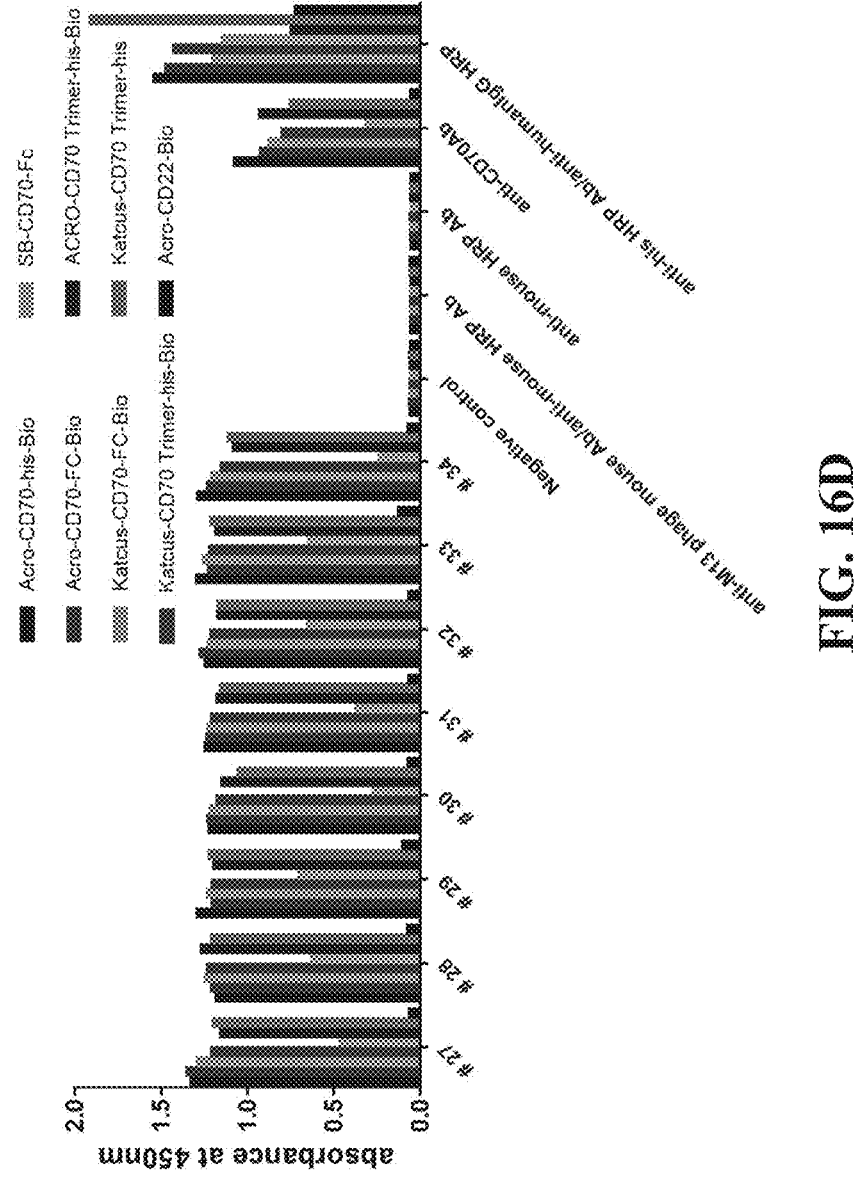
Figure 16E:
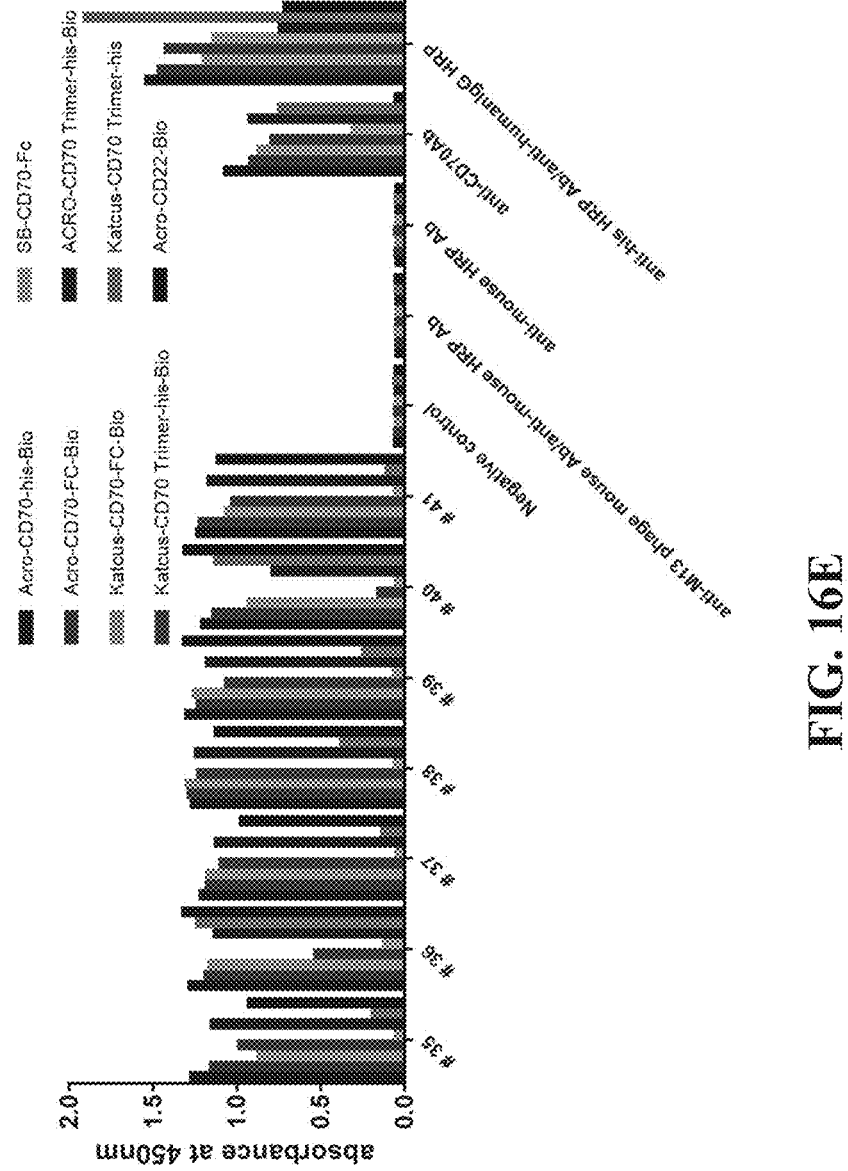

FIGS. 16A-E show the results of enzyme-linked immunosorbent assay of the screened phage monoclonal antibodies #1-32 and #34-41 with various CD70 antigen proteins from different manufacturers and irrelevant antigens, in which Negative Control is the phage antibody clone negative control, Anti-M13 phage mouse Ab/anti-mouse HRP Ab is a negative control without the phage and with only the primary antibody (Anti-M13 phage mouse Ab) and secondary antibody (anti-mouse HRP Ab); anti-mouse HRP Ab is a negative control with only the second antibody (anti-mouse HRP Ab), anti-CD70 Ab is the CD70 detection antibody positive control; and anti-his HRP/anti-human IgG HRP is the detection antigen tag antibody positive control. In FIGS. 16A-C, the histograms corresponding to each test antibody and the control group indicate, from left to right, the test results with the reagents Acro-CD70-his-Bio, Acro-CD70-Fc-Bio, Kactus-CD70-Fc-Bio, Kactus-CD70Trimer-his-Bio, SB-CD70-Fc, Kactus-CD70-Fc, Kactus-CD70Trimer-his, and Acro-CD22-Bio, and in FIGS. 16D and 16E, the histograms corresponding to each test antibody and the control group indicate, from left to right, the test results with the reagents Acro-CD70-his-Bio, Acro-CD70-Fc-Bio, Kactus-CD70-Fc-Bio, Kactus-CD70Trimer-his-Bio, SB-CD70-Fc. ACRO-CD70 Trimer-his-Bio, Kactus-CD70 Trimer-his, and Acro-CD22-Bio.

DETAILED DESCRIPTION OF THE INVENTION

The embodiment of the present application will be described by way of specific examples, and those skilled in the art can easily understand other advantages and effects of the present application from the disclosure in this specification. The CAR described in the present application can specifically bind to CD70, and the CAR-T cells prepared with the CAR can stably express the CAR, and the CAR-T cells prepared with the CAR have a higher CAR-positive rate. In addition, the CAR can promote the release of cytokines and can be used to treat diseases or conditions related to CD70 expression.

Unless expressly indicated otherwise, conventional methods of chemistry, biochemistry, organic chemistry, molecular biology, microbiology, recombinant DNA techniques, genetics, immunology and cell biology in art will be employed in the practice of the present application. Descriptions of these methods can be found, for example, in Sambrook et al., Molecular Cloning: A Laboratory Manual (3rd Ed., 2001); Sambrook et al., Molecular Cloning: A Laboratory Manual (2nd Ed., 1989); Maniatis et al., Molecular Cloning: A Laboratory Manual (1982); Ausubel et al., Current Protocols in Molecular Biology (John Wiley and Sons, updated in July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I&II (IRL Press, Oxford, 1985); Anand, Techniques for the Analysis of Complex Genomes, (Academic Press, New York, 1992); Transcription and Translation (B. Hames & S. Higgins, Eds., 1984); Perbal, A Practical Guide to Molecular Cloning (1984); Harlow and Lane, Antibodies, (Cold Spring Harbor Laboratory Press, Cold Spring Harbor, NY, 1998) Current Protocols in Immunology Q. E. Coligan, A. M. Kruisbeek, D. H. Margulies, E. M. Shevach and W. Strober, eds., 1991); Annual Review of Immunology; and journals and monographs such as Advances in Immunology.

Unless otherwise defined, all technical and scientific terms used in the present application have the same meaning as commonly understood by those of ordinary skill in the art. For the purposes of the present application, the following terms are defined below.

In the present application, the term "chimeric antigen receptor" (CAR) is a fusion protein of a variable region of a single-chain antibody and a T cell signaling molecule. It allows T cells to recognize a specific antigen in a non-MHC-restricted manner and to exert a killing effect. CAR is a core component in chimeric antigen receptor-T cells (CAR-T), which can include a tumor-associated antigen (TAA) binding region, a transmembrane domain, a co-stimulatory domain and an intracellular signaling domain. In the present application, the CAR can be a genetically engineered chimeric protein capable of redirecting the cytotoxicity of immune effector cells to B cells, which combines an antibody-based specificity for an antigen (such as CD70) with an intracellular domain for T cell receptor activation. T cells genetically modified to express CAR can specifically recognize and eliminate malignant cells expressing a target antigen. For the descriptions of CAR and CAR T cells, see, for example, Sadelain M, Brentjens R. Rivi'ere I. The basic principles of chimeric antigen receptor design. Cancer Discov. 2013; 3(4): 388-398; Turtle C J, Hudecek M, Jensen M C, Riddell S R. Engineered T cells for anti-cancer therapy. CurrOpin Immunol. 2012; 24(5): 633-639; Dotti G, Gottschalk S. Savoldo B, Brenner M K. Design and development of therapies using chimeric antigen receptor-expressing T cells. Immunol Rev. 2014; 257(1): 107-126; and WO2013154760, WO2016014789.

In the present application, the term "CD70" is a member of the tumor necrosis factor receptor (TNFR) superfamily, which has the ability to regulate the activation, proliferation and differentiation of T cells and B cells, and plays an important role in maintaining the immune response in the body. CD70 is expressed not only on normal cells, but also on many malignant cell tumors. The CD70 protein may also include a fragment of CD70, such as an extracellular domain and a fragment thereof.

In the present application, the term "CD70 binding domain" generally refers to an extracellular domain of CD70 CAR, which can specifically bind to an antigen. For example, the CD70 extracellular binding domain may comprise a chimeric antigen receptor capable of specifically binding to a CD70 polypeptide expressed on a human cell, an anti-CD70 antibody or an antigen-binding fragment thereof. The terms "binding domain", "extracellular domain", "extracellular binding domain", "antigen-specific binding domain" and "extracellular antigen-specific binding domain" are used interchangeably in the present application, and a CAR with the ability to specifically bind a target antigen of interest (e.g., CD70) is provided. The CD70 binding domain may be of natural, synthetic, semi-synthetic or recombinant origin.

In the present application, the term "antibody" generally refers to a polypeptide molecule capable of specifically recognizing and/or neutralizing a specific antigen. For example, an antibody may comprise an immunoglobulin composed of at least two heavy (H) chains and two light (L) chains inter-connected by disulfide linkages, and includes any molecule comprising an antigen-binding portion thereof. The term "antibody" includes monoclonal antibodies, antibody fragments or antibody derivatives, including, but not limited to, human antibodies, humanized antibodies, chimeric antibodies, single domain antibodies (e.g., dAb or VHH), and single chain antibodies (e.g., scFv). In the present application, a "fragment" of an antibody may refer to an antigen-binding fragment of the antibody, for example, Fab, Fab', (Fab')$_2$ fragments and the like. The term "antibody" also includes all recombinant forms of antibodies, such as antibodies expressed in prokaryotic cells, unglycosylated antibodies, and any antigen-binding antibody fragments and derivatives thereof. Each heavy chain can consist of a heavy chain variable region (VH) and a heavy chain constant region. Each light chain can consist of a light chain variable domain (VL) and a light chain constant domain CL. The VH and VL regions further include hypervariable regions called complementarity determining regions (CDRs), which are interspersed in more conserved regions called framework regions (FRs). Each VH and VL may consist of three CDR and four FR regions, which may be arranged in the following order from the amino-terminus to the carboxy-terminus: FR1, CDR1, FR2, CDR2, FR3, CDR3 and FR4. The heavy and light chain variable region contain binding domains that interact with the antigen. The constant regions of the antibodies mediate the binding of the immunoglobulin to host tissues or factors, including various cells of the immune system (e.g., effector cells) and the first component (Clq) of the classical complement system.

In the present application, the term "single-chain antibody" may also be referred to as scFv, which is an antibody of one chain formed by the heavy chain variable region and the light chain variable region connected by a linker peptide. The term "single-domain antibody" refers to an antibody formed with the heavy chain variable domain alone.

"Murine antibody" is an antibody produced by murine against a specific antigen, and generally an antibody produced by mouse B lymphocytes. In most cases, the murine antibody is a monoclonal antibody produced by hybridoma cells. The fully human antibody mentioned in the present application is screened from a human phage antibody library, which reduces the immunogenicity compared with a murine antibody, and is more conducive to the therapeutic use in human.

The "fully human antibody or a single-chain antibody or antigen-binding fragment thereof" described in the present application generally refers to any form of antigen-binding molecule capable of binding to a target antigen. For example, the antigen-binding molecule can be a protein or a polypeptide, including, for example, antibodies and antigen-binding fragments thereof, single-chain scFv antibodies, single-domain antibodies, various fusions and conjugates based on scFv, such as scFv-Fc antibodies, immunoconjugates, antibody drug conjugates (ADC), poly/bispecific antibodies, and chimeric antigen receptors (CARs).

"Epitope" refers to a portion of a molecule that is bound by an antigen-binding protein (e.g., an antibody). The epitope may comprise non-contiguous portions of the molecule (e.g., amino acid residues in a polypeptide that are not contiguous in the primary sequence of the polypeptide, but are sufficiently close to each other in the trivalent and tetravalent structure of the polypeptide to be bound by the antigen binding protein).

In the present application, the term "transmembrane domain" is generally a domain in CAR that passes through the cell membrane, which is connected to the intracellular signaling domain and serves to transmit signals.

In the present application, the term "co-stimulatory domain" is generally an intracellular domain able to provide an immune co-stimulatory molecule that is a cell surface molecule required by lymphocytes for an effective response to the antigen. The co-stimulatory domain may include the co-stimulatory domain of CD28, and may also include a costimulatory domain of the TNF receptor family, such as the costimulatory domain of OX40 and 4-1BB.

In the present application, the term "hinge region" generally refers to a linker region between the antigen-binding region and the Fc receptor (FcR) binding region of immune cells.

In the present application, the term "intracellular signaling domain" is generally an intracellular signal signaling component of CAR, which includes a signaling domain and a domain that specifically binds to the receptor component, for example, one selected from CD3ζ intracellular domain, CD28 intracellular domain, CD28 intracellular domain, 4-1BB intracellular domain and OX40 intracellular domain.

In the present application, the term "signal peptide" is generally a short (5-30 amino acids in length) peptide chain that directs the transfer of newly synthesized proteins to the secretory pathway.

In the present application, the term "cleaving peptide" refers to self-cleaving 2A peptide, which can realize the function of cleaving a protein through ribosome skipping instead of proteolytic hydrolysis, and may include T2A, F2A and P2A, etc.

In the present application, the term "marker detection signal" is generally a gene, protein or other molecules of known functions or sequences that can function as a specific marker to emit a detectable signal. The marker detection signal can be a fluorescent protein, such as: GFP, RFP, YFP and the like. The marker detection signal may be EGFRt. The term "EGFRt" refers to a gene encoding a truncated human epidermal growth factor receptor polypeptide, which lacks the distal membrane EGF-binding domain and cytoplasmic signaling tail, but retains the extracellular epitope recognizable by an anti-EGFR antibody. EGFRt can be used as a non-immunogenic selection tool and a tracking marker for the function of genetically modified cells. In the present application, it can be used as a marker molecule for CAR-T cells, and used to clear CAR-T cells in vivo if necessary, through the cetuximab mediated ADCC pathway (see U.S. Pat. No. 8,802,374B2).

In the present application, "sequence identity" generally refers to the degree to which the sequences are identical on a nucleotide-by-nucleotide or amino acid-by-amino acid basis over a comparison window. "Percent sequence identity" can be calculated by comparing two optimally aligned sequences over a comparison window, determining the number of positions at which identical nucleic acid bases (e.g., A, T, C, G, I) or identical amino acid residues (e.g., Ala, Pro, Ser, Thr, Gly, Val, Leu, Ile, Phe, Tyr, Trp, Lys, Arg, His, Asp, Glu, Asn, Gln, Cys, and Met) are present to obtain the number of matching positions, dividing the number of matching positions by the total number of positions in the comparison window (i.e., window size), and multiplying the result by 100 to yield the percent sequence identity. Optimal alignment for the purpose of determining the percent sequence identity can be achieved in various ways known in the art, for example, by using publicly available computer software such as BLAST, BLAST-2, ALIGN or Megalign (DNASTAR) software. Those skilled in the art can determine appropriate parameters for aligning the sequences, including any algorithms needed to achieve maximal alignment over the full length of the sequences being compared or over a region of the sequence of interest.

In some embodiments, the fully human antibody provided in the present application further comprises an amino acid sequence having at least 90% sequence identity (for example, at least 95%, at least 98%, at least 99% or even 100% sequence identity) to the sequence as shown in SEQ ID NO: 26, 33, 36, 39 or 42.

Those skilled in the art can understand that on the basis of specific sequences provided herein, corresponding variants of the CD70 targeting antibody provided herein can be obtained by substituting, deleting, or adding a few amino acids, and verifying or screening the resultant product for its binding ability with the corresponding antigen CD70 or its biological activity. These variants are also embraced in the scope of the present invention. For example, the fully human antibody or a single-chain antibody or antigen-binding fragment thereof according to the present application may have at least 1 and no more than 10, or no more than 5, 4, 3, 2 or 1 amino acid changes in the full length or CDR sequence.

Those skilled in the art can also understand that on the basis of the specific heavy chain variable region sequences provided herein, an antibody light chain library (such as a human phage light chain library) can be screened by using CD70 as the antigen, so as to obtain light chain variable regions matched with the heavy chain variable region and maintaining the CD70 binding ability. Anti-CD70 antibody molecules obtainable in this way are also included in the scope of the present invention.

In some embodiments, the antigen binding molecules of the present application may further comprise post-translational modifications. Examples of post-translational protein modifications include: phosphorylation, acetylation, methylation. ADP-ribosylation, ubiquitination, glycosylation, carbonylation, sumoylation, biotinylation, or addition of a polypeptide side chain or a hydrophobic group. Thus, a modified soluble polypeptide may comprise a non-amino acid component such as lipid, polysaccharide or monosaccharide, and phosphate. A preferred form of glycosylation is the modification by sialylation, where one or more sialic acid groups is/are attached to a polypeptide. The sialic acid group improves the solubility and serum half-life of the protein, and reduces the possible immune inheritance of the protein. See Raju et al. *Biochemistry.* 2001 31; 40(30): 8868-76.

The term "functional variant" with reference to an antibody refers in the present application to an antibody comprising an antibody region of interest (e.g. heavy chain variable region, light chain variable region, heavy chain CDR region or light chain CDR region) having amino acid changes by at least 1, for example, 1-30, 1-20 or 1-10, such as 1, 2, 3, 4 or 5 amino acid substitutions, deletions and/or insertions. The amino acid substitutions, deletions and/or Insertions can occur in either the heavy chain CDR region, the light chain CDR region, the heavy chain FR region, the light chain FR region, the heavy chain constant region or the light chain constant region. The variant substantially retains the biological features of the antibody molecule before the changes. In one aspect, the present application encompasses variants of any of the antibodies described in the present application. In some embodiments, the antibody variant retains at least 60%, 70%, 80%, 90%, or 100% of the biological activity (e.g., antigen binding ability) of the antibody before the changes. In some embodiments, the changes do not cause the antibody variant to lose its ability to bind to the antigen, but optionally impart properties such as increased affinity to the antigen and different effector functions. It is to be understood that the heavy chain variable region or light chain variable region of the antibody or each CDR region can be changed individually or in combination. In some embodiments, no more than 1, 2, 3, 4, 5, 6, 7, 8, 9 or 10 amino acid changes occur in one or more or all three heavy chain CDRs. In some embodiments, the amino acid changes may be amino acid substitutions, such as conservative substitutions. In some embodiments, the functional variant of the antibody has at least 80%, 85%, 90%, 95% or 99% or more amino acid identity to the parent antibody over the sequence region of the antibody of interest. Similarly, a "functional variant" of a nucleic acid molecule in the present application refers to a nucleic acid molecule that encodes the same amino acid sequence with the parent nucleic acid molecule.

In the present application, the term "isolated" generally means that the antibody is one that has been separated from components existing in its naturally occurring environment. In some embodiments, the antibody is purified to have a purity of 95% or 99% or higher, by for example, electrophoresis (e.g., SDS-PAGE, isoelectric focusing (IEF), and capillary electrophoresis) or chromatography (e.g., ion exchange or reversed-phase HPLC). A review of methods for assessing the antibody purity can be found in Flatman, S. et al., J. Chrom. B 848 (2007) 79-87.

In the present application, the term "nucleic acid molecule" generally refers to an isolated nucleotide, deoxyribonucleotide, ribonucleotide or an analog thereof of any length separated from its naturally occurring environment or artificially synthesized. The nucleic acid molecule described herein can be isolated. For example, it can be produced or synthesized by (i) in-vitro amplification, such as polymerase chain reaction (PCR) amplification; (ii) cloning and recombination; (iii) purification, for example, by enzymatic cleavage and fractional separation by gel electrophoresis; and (iv) synthesis, for example, chemical synthesis. In some embodiments, the isolated nucleic acid is a nucleic acid molecule prepared by recombinant DNA techniques. In the present application, a nucleic acid encoding the antibody or an antigen-binding fragment thereof can be prepared by various methods known in the art, including, but not limited to, manipulations using restriction fragments or overlap extension PCR using synthetic oligonucleotides. Specific operations can refer to Sambrook et al., Molecular Cloning, A Laboratory Manual, Cold Spring Harbor Laboratory Press, Cold Spring Harbor, NY, 1989; and Ausube et al. Current Protocols in Molecular Biology, Greene Publishing and Wiley-Interscience, New York NY, 1993.

In the present application, the term "vector" generally refers to a nucleic acid molecule capable of self-replication in a suitable host for transferring the inserted nucleic acid molecule into and/or between host cells. The vector may include a vector mainly used for inserting DNA or RNA into cells, a vector mainly used for replicating DNA or RNA, and an expression vector mainly used for the transcription and/or translation of DNA or RNA. The vector also includes a vector having various functions as described above. The vector may be a polynucleotide capable of being transcribed and translated into a polypeptide w % ben introduced into a suitable host cell. Generally, the vector can produce a desired expression product by culturing an appropriate host cell containing the vector. In the present application, one or more nucleic acid molecules may be included in the vector. In addition, other genes may be further included in the vector, such as a marker gene that allows the selection of the vector in an appropriate host cell under appropriate conditions. In addition, the vector may further contain an expression control element that permits proper expression of a coding region in an appropriate host. Such a control element is well known to those skilled in the art, and may include, for example, a promoter, a ribosome binding site, an enhancer, and other control elements that regulate the gene transcription or mRNA translation, and the like. In some embodiments, the expression control sequence is a regulatory element. The specific structure of the expression control sequence may vary depending on the function of the species or cell type, but generally includes a 5' non-transcribed sequence and 5' and 3' non-translated sequences involved in the initiation of transcription and translation, respectively, such as TATA box, capping sequence, and CAAT sequence, etc. For example, the 5' non-transcribed expression control sequence may comprise a promoter region which may comprise a promoter sequence for transcriptional control of the functionally linked nucleic acid. The vector described in the present application may be selected from plasmids, retroviral vectors and lentiviral vectors. The plasmids, retrovirus vectors and lentivirus vectors described in the present application can contain the CAR.

In the present application, the term "plasmid" generally refers to DNA molecules other than chromosomes or nucleoids in organisms such as bacteria and yeasts, which exist in the cytoplasm and have the ability of self-replication, enabling them to maintain constant copies in daughter cells and express the genetic information carried. Plasmids are used as vectors of genes in genetic engineering research.

In the present application, the term "retroviral vector" generally refers to a type of RNA virus having genetic information stored on ribonucleic acid, and such viruses largely have reverse transcriptases. Retroviruses contain at least three genes: gag, comprising the gene of protein forming the center and structure of the virus; pol, comprising the gene of the reverse transcriptase enzyme; and env, comprising the gene of protein forming the virus coat. Through retroviral transfection, the retroviral vector can randomly and stably integrate its own genome and foreign genes carried into the host cell genome, for example, by which the CAR molecule can be integrated into the host cell.

In the present application, the term "lentiviral vector" generally refers to a diploid RNA viral vector belonging to retroviruses. The lentiviral vector is based on the genome of lentivirus, where multiple sequence structures related to viral activity are removed to make it biologically safe, and then a vector prepared with the sequence of a target gene required for the experiment and an expression construct is introduced into the genome backbone. Compared with other retroviruses, lentiviral vectors are applicable to a wider range of hosts, and have the ability to infect both dividing and non-dividing cells. For some cells that are difficult to transfect, such as primary cells, stem cells, and undifferentiated cells, etc., the lentiviral vectors can greatly improve the transduction efficiency of the target gene (see Chen Chen and Wan Haisu, "Lentiviral vectors and their research progress, Chinese Journal of Lung Cancer 17.12 (2014): 870-876. PMCs). Through lentiviral transfection, the retroviral vector can randomly and stably integrate its own genome and foreign genes carried into the host cell genome, for example, by which the CAR molecule can be integrated into the host cell.

In the present application, the term "transposon" generally refers to a discrete segment of DNA containing a transposase gene, flanked by terminal inverted repeats (TIRs) containing a transposase binding site. Transposases can bind to TIR and transfer the transposon to a new site. The transposon described in the present application is a two-component system consisting of a plasmid carrying a CAR (transposon) and another plasmid carrying a transposase. The transposon can be introduced into target cells by means of electrotransduction. For example, the two components are electroporated into peripheral blood mononuclear cells (PBMCs), and the expressed transposase acts on the terminal inverted repeats (TIRs) at both sides of the CAR, to cleave the CAR (transposon), which is subsequently integrated into the TA dinucleotide sequence in the genome of the target cell (e.g. T cell). After the transposition and stable genomic integration, the CAR protein can be expressed on the surface of the target cell (see Cheng Zhang, Jun Liu, Jiang F Zhong, et al. Engineering CAR-T cells. Biomarker Research. 2017, 5:22).

In the present application, the term "gene editing" generally refers to the technology of site-directed modification of the genome, which may include technologies based on zinc finger nucleases (ZFNs), transcription activator like effector nucleases (TALENs), clustered regularly interspaced short palindromic repeats/CRISPR-associated (Cas9), CRISPR/Cas9, and so on. It enables highly efficient targeted modification of the genome by adding, removing or changing the genetic material at specific locations in the genome. The gene editing described in the present application may include introducing a CAR molecule into the genome of recipient cells through gene editing techniques (such as CRISPR-Cas9).

In the present application, the term "immune effector cells" generally refers to immune cells involved in clearing foreign antigens and performing effector functions in an immune response. Examples include plasma cells, cytotoxic T cells, NK cells, APSC pluripotent cells, and mast cells, etc.

In the present application, the term "pharmaceutically acceptable adjuvant" generally refers to a pharmaceutically acceptable carrier, solution or additive that enhances the properties of the formulation. Such additives are well known to those skilled in the art.

In the present application, the term "cancer" generally refers to or describes the physiological condition in mammals that is typically characterized by dysregulation of cell proliferation or survival. In the present application, hyperproliferative diseases referred to as cancers include, but are not limited to, solid tumors such as those occurring in the breast, respiratory tract, brain, reproductive organs, digestive tract, urinary tract, eye, liver, skin, head and neck, thyroid, parathyroid glandular carcinomas, and their distant metastases. Such diseases also include lymphomas, sarcomas, and leukemias. Examples of breast cancer include, but are not limited to, invasive ductal carcinoma, invasive lobular carcinoma, primary ductal carcinoma in situ, and lobular carcinoma in situ. Examples of cancers of the respiratory tract include, but are not limited to, small cell lung cancer and non-small cell lung cancer, as well as bronchial adenoma and pleuropulmonary blastoma. Examples of brain cancers include, but are not limited to, brainstem and hypothalamic keratomas, cerebellar and cerebral astrocytomas, medulloblastomas, ependymomas, and neuroectodermal and pineal tumors. Tumors of the male genitalia include, but are not limited to, prostate and testicular cancers. Tumors of the female genitalia include, but are not limited to, endometrial carcinoma, cervical cancer, ovarian cancer, vaginal cancer, vulvar cancer, and hysteromyoma. Gastrointestinal tumors include, but are not limited to, cancers of the anus, colon, colorectum, esophagus, gallbladder, stomach, pancreas, rectum, small intestine, and salivary glands. Tumors of the urethra include, but are not limited to, cancers of the bladder, penis, kidney, renal pelvis, ureter, and urethra. Eye cancers include, but are not limited to, intraocular melanoma and retinoblastoma. Examples of liver cancer include, but are not limited to, hepatocellular carcinoma (hepatocellular carcinoma with or without the fibrolamellar variant), cholangiocarcinoma (carcinoma of the bile ducts within the liver), and mixed hepatocellular cholangiocarcinoma. Skin cancers include, but are not limited to, squamous cell carcinoma, Kaposi's sarcoma, malignant melanoma, Merkel cell skin cancer, and non-melanoma skin cancer. Head and neck cancers include, but are not limited to, cancers of the larynx, hypopharynx, nasopharynx, oropharynx, and lips and mouth. Lymphoma include, but are not limited to, AIDS-related lymphoma, non-Hodgkin's lymphoma, cutaneous T-cell lymphoma, Hodgkin's disease, and central nervous system lymphoma. Sarcomas include, but are not limited to, soft tissue sarcomas, osteosarcomas, malignant fibrous histiocytomas, lymphosarcomas, and rhabdomyosarcomas. Leukemias include, but are not limited to, acute myeloid leukemia, acute lymphocytic leukemia, chronic lymphocytic leukemia, chronic myeloid leukemia, and hairy cell leukemia.

A "therapeutically effective amount" refers to an amount of an active compound sufficient to elicit a biological or medical response in a subject desired by a clinician. The "therapeutically effective amount" of the antibody of the present application can be determined by those skilled in the art according to the administration route, the body weight, age, and condition of the subject, and other factors. For example, a typical daily dose may range from 0.01 mg to 100 mg of active ingredient per kg of body weight. The administration mode of the antibody of the present application includes, but is not limited to, injection, such as intravenous, intramuscular, intrarterial, subcutaneous, intraperitoneal injection and others.

The term "and/or" should be understood as including any one of the options or both of the options.

As used in the present application, the term "comprising" or "including" is intended to include the stated elements, integers or steps, but not exclude any other elements, integers or steps. In the present application, when the term "comprising" or "including" is used, the situation consisting of the mentioned elements, integers or steps is also covered, unless otherwise specified. For example, when referring to an antibody variable region that "comprises" a particular sequence, it is also intended to encompass an antibody variable region that consists of that particular sequence.

In the present application, the term "about" generally refers to a variation with the range of 0.5%-10% higher or lower than a specified value, such as a variation with the range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% higher or lower than a specified value.

CD70 Antibody

In the present invention, the fully human phages are used for screening CD70 antibodies to directly obtain fully human monoclonal antibodies. Compared with the traditional hybridoma technology, it saves the difficult step of humanizing the mouse antibodies, and the fully human antibodies have lower immunogenicity than humanized mouse antibodies, and thus have good application potential in the development of antibody drugs (monoclonal antibodies, dual antibodies, and antibody-drug conjugates (ADC), etc.) and cell therapy drugs (including CAR-T, and CAR-NK, etc.). In addition, the high-affinity specific antibody provided in the present invention can also be used in the development of detection reagents.

In the process of screening the antibody, it is found that the antibody clones screened directly using the recombinantly expressed CD70 protein cannot bind to the cell line Raji, which highly expresses CD70. This may be due to the great difference in conformation and accessible antigenic epitope between the recombinantly expressed CD70 protein antigen and the naturally occurring CD70 on the cell membrane surface. To overcome this problem, the method of protein/cell line alternate panning is used to enrich the phage antibodies that can simultaneously bind to recombinantly expressed CD70 protein and Raji cells, from which monoclonal antibodies that can specifically bind to the CD70 antigen on the cell membrane surface are screened.

Specifically, a large phage antibody library is used to screen fully human CD70-specific antibodies, and the specificity of these antibodies at the phage level is evaluated through ELISA and FACS assays. Finally, several fully human antibody clones with good specificity are obtained.

Different antibody libraries are used. After recombinant CD70 protein panning and protein/cell alternate panning, a total of 828 monoclonal antibodies were selected for primary screening by enzyme-linked immunosorbent assay (ELISA) and flow cytometry (FACS). Among them, 344 clones specifically bind to CD70-his-Bio protein and CD70-expression positive cells Raji, but do not bind to the control protein Streptavidin (SA) and CD70-expression negative cells Jurkat (protein panning, protein/cell alternate panning, and primary screening by ELISA and FACS). After sequencing, 41 different monoclonal sequences are obtained. Subsequently, the 41 antibodies are identified by flow cytometric analysis (FACS) for binding with various CD70positive (Raji, U266) and negative cell lines (Jurkat, K562), and for binding with CD70 proteins as different polymers from different manufacturers (Acro-CD70-His-Bio, Acro-CD70-Fc-Bio, Acro-CD70 Trimer-His-Bio, Katcus-CD70-Fc-Bio, Katcus-CD70 Trimer-His-Bio, SB-CD70-Fc, and Kactus-CD70-Fc, Kactus-CD70 Trimer-his), and irrelevant protein (CD22-Fc-Bio) by enzyme-linked immunosorbent assay (ELISA). 40 clones show good binding affinity and specificity for multiple cell lines and multiple protein antigens. The acquisition of these clones provides the foundation for the subsequent development of fully human CD70 CAR-T products or antibody drugs. The overall process of antibody screening is shown in FIG. 12.

The present application provides a kit, which comprises one or more containers containing a large amount of gene construct encoding the polypeptide of the present application, and a pharmaceutically acceptable excipient. The kit may also contain instructions for use. The kit may also have a notice in a form prescribed by a governmental agency regulating the manufacture, use or sale of pharmaceuticals or biological products, which indicates that it has been licensed by the institution for the manufacture, use or sale of pharmaceuticals for humans.

Chimeric Antigen Receptor

In the present application, the CAR may comprise an extracellular domain specifically binding to CD70, a transmembrane domain, an intracellular co-stimulatory signaling domain, and an intracellular signaling domain. In the present application, the extracellular domain of the CAR can be composed of a single-domain antibody (VHH), a single-chain antibody (scFv), two or more tandem single-chain antibodies (2×scFv) or two or more tandem single domain antibodies (2×VHH). For example, the extracellular domain may be linked to the transmembrane domain via a hinge region, such as the CD8 hinge. In the present application, the CAR can be used to electrotransduct the immune effector cells (such as T cells) and expressed on the cell surface. Therefore, the present application can also provide T cells expressing the chimeric antigen receptor, and the use of the T cells and/or the CAR in the preparation of drugs for treating diseases related to CD70 expression.

In the present application, the chimeric antigen receptor (CAR) may comprise a CD70 binding domain, a transmembrane domain, a co-stimulatory domain and an intracellular signaling domain. In the present application, the CD70 binding domain may comprise one or more antibodies or fragments thereof that specifically bind to CD70. The antibody may comprise a heavy chain complementarity determining region 1 (HCDR1), a heavy chain complementarity determining region 2 (HCDR2) and a heavy chain complementarity determining region 3 (HCDR3). The amino acid sequences of the HCDRs 1-3 are as shown in SEQ ID NOs: 72-74, 78-80, 81-83, 84-86, and 87-89. The antibody may comprise a light chain complementarity determining region 1 (LCDR1), a light chain complementarity determining region 2 (LCDR2) and a light chain complementarity determining region 3 (LCDR3), and the amino acid sequences of LCDRs 1-3 are as shown in SEQ ID Nos: 75-77. In the present application, the CD70 binding domain may comprise a pairwise combination of the following antibodies or fragments thereof: (1) an antibody comprising HCDRs 1-3 as shown in SEQ ID NOs: 78-80, or a fragment thereof; (2) an antibody comprising HCDRs 1-3 as shown in SEQ ID NOs: 81-83, or a fragment thereof; (3) an antibody comprising HCDRs 1-3 as shown in SEQ ID NOs: 84-86, or a fragment thereof; and (4) an antibody comprising HCDR 1-3 as shown in SEQ ID NO: 87-89, or a fragment thereof.

In the present application, the antibody may comprise a heavy chain variable region having an amino acid sequence as shown in SEQ ID Nos: 28, 33, 36, 39, or 42. In the present application, the antibody may comprise a light chain variable region having an amino acid sequence as shown in SEQ ID No: 30.

In the present application, the antibody may be a single-chain antibody. In some embodiments, the antibody may comprise an amino acid sequence as shown in SEQ ID No: 26 or a functional variant thereof. For example, the single-chain antibody described in the present application may be scFv 06, having a sequence as shown in SEQ ID No: 26. The amino acid sequences of LCDRs 1-3 of the single-chain antibody scFv06 are as shown in SEQ ID Nos: 75-77 respectively; the amino acid sequence of VL is as shown in SEQ ID No: 30; the amino acid sequences of HCDRs 1-3 are as shown in SEQ ID Nos: 72-74 respectively; and the amino acid sequence of VH is as shown in SEQ ID No: 28.

In the present application, the antibody may be a single-domain antibody. In some embodiments, the CD70 binding domain comprises two single domain antibodies and a linker fragment therefor. For example, the single-domain antibody described in the present application is VHH 09, VHH13, VHH20, VHH21 or a functional variant thereof, where the amino acid sequences of HCDRs 1-3 of the single-domain antibody are respectively as shown in SEQ ID Nos: 78-80, 81-83, 84-86, or 87-89 respectively, and the amino acid sequence of the heavy chain variable region is as shown in SEQ ID No: 33, 36, 39, and 42, respectively. The linker fragment described in the present application is as shown in SEQ ID NO: 44.

The CAR described in the present application may comprise a transmembrane domain comprising a polypeptide derived from a protein selected from α, β or ζ chain of T cell receptors, CD28, CD3e, CD45, CD4, CD5, CD8a, CD9, CD16, CD22, CD33, CD37, CD64, CD80, CD86, CD134, CD137, and CD154. In the present application, the transmembrane domain comprises an amino acid sequence as shown in SEQ ID No: 9 or a functional variant thereof. For example, the transmembrane domain of the present application may include CD8a having a sequence as shown in SEQ ID No: 9.

In the present application, the co-stimulatory domain may comprise a polypeptide derived from a protein selected from CD28, 4-1BB, OX40 and ICOS. In the present application, the co-stimulatory domain comprises an amino acid sequence as shown in SEQ ID No: 12 or a functional variant thereof.

The CAR described in the present application may include an intracellular signaling domain comprising a signaling domain derived from CD3ζ. In the present application, the intracellular signaling domain comprises an amino acid sequence as shown in SEQ ID No: 15 or a functional variant thereof.

The CAR described in the present application may include a hinge region linking the antibody and the transmembrane domain. In the present application, the hinge region comprises an amino acid sequence as shown in SEQ ID No: 6 or a functional variant thereof.

The CAR described in the present application may include a signal peptide comprising an amino acid sequence as shown in SEQ ID No: 3 or a functional variant thereof. For example, the signal peptide may be a CD8a signal peptide having a sequence as shown in SEQ ID No: 3.

In the present application, the CAR may comprise an amino acid sequence as shown in SEQ ID No: 46, 48, 50, 52, 54, 56, 58, 60, 62, 64, 66, 68 or 70 or a functional variant thereof. For example, the CAR can be selected from pXL1416 CAR having a sequence as shown in SEQ ID No: 46; pXL1698CAR having a sequence as shown in SEQ ID No: 56; pXL1700CAR having a sequence as shown in SEQ ID No: 58; pXL1702 CAR having a sequence as shown in SEQ ID No: 60; pXL1704 CAR having a sequence as shown in SEQ ID No: 62; pXL1748 CAR having a sequence as shown in SEQ ID No: 64; pXL1750 CAR having a sequence as shown in SEQ ID No: 66; pXL1752 CAR having a sequence as shown in SEQ ID No: 68; pXL1754 CAR having a sequence as shown in SEQ ID No: 70.

Nucleic Acid, Vector, Cell, Preparation Method and Composition

In another aspect, the present application provides an isolated nucleic acid molecule encoding the CAR as described in the present application. The isolated nucleic acid molecule encoding the CAR as described in the present application may comprise a nucleic acid sequence as shown in SEQ ID No: 1, 2, 4, 5, 7, 8, 10, 11, 13, 14, 25, 27, 29, 31, 32, 34, 35, 37, 38, 40, 41, 43, 45, 47, 49, 51, 53, 55, 57, 59, 61, 63, 65, 67 or 69, or a functional variant thereof. In the present application, for a CAR having a CD70 binding domain that is a single-chain antibody or single-domain antibody and a linker fragment therefor, the nucleic acid sequence is as shown in 1, 4, 7, 10, 13, 16, 19, 22, 31, 34, 37, or 40; and for a CAR having a CD70 binding domain that is two single-domain antibodies in tandem and a linker fragment therefor, the nucleic acid sequence may include a nucleic acid sequence as shown in 2, 5, 8, 11, 14, 17, 20, 23, 32, 35, 38, or 41.

The nucleic acid molecule described herein can be isolated. For example, it can be produced or synthesized by (i) in-vitro amplification, such as polymerase chain reaction (PCR) amplification; (ii) cloning and recombination; (iii) purification, for example, by enzymatic cleavage and fractional separation by gel electrophoresis; and (iv) synthesis, for example, chemical synthesis. In some embodiments, the isolated nucleic acid is a nucleic acid molecule prepared by recombinant DNA techniques.

In another aspect, the present application provides a vector comprising the nucleic acid molecule. In the present application, the vector is one or more selected from plasmids, retroviral vectors and lentiviral vectors. The lentiviral vector described in the present application can contain the CAR. For example, the lentiviral vector as described in the present application may comprise a nucleic acid sequence as shown in SEQ ID No: 1, 2, 4, 5, 7, 8, 10, 11, 13, 14, 25, 27, 29, 31, 32, 34, 35, 37, 38, 40, 41, 43, 45, 47, 49, 51, 53, 55, 57, 59, 61, 63, 65, 67 or 69, or a functional variant thereof. In addition, other genes may be included in the vector, such as marker genes that allow selection of the vector in appropriate host cells and under appropriate conditions. In addition, the vector may further contain an expression control element that permits proper expression of a coding region in an appropriate host. Such a control element is well known to those skilled in the art, and may include, for example, a promoter, a ribosome binding site, an enhancer, and other control elements that regulate the gene transcription or mRNA translation, and the like. In some embodiments, the expression control sequence is a regulatory element. The specific structure of the expression control sequence may vary depending on the function of the species or cell type, but generally includes a 5' non-transcribed sequence and 5' and 3' non-translated sequences involved in the initiation of transcription and translation, respectively, such as TATA box, capping sequence, and CAAT sequence, etc. For example, the 5' non-transcribed expression control sequence may comprise a promoter region which may comprise a promoter sequence for transcriptional control of the functionally linked nucleic acid. One or more nucleic acid molecules described in the present application can be operably linked to the expression control element. Such vectors may include, for example, plasmids, cosmids, viruses, phages, or other vectors commonly used in, for example, genetic engineering. For example, the vector is an expression vector, including vector scFv plasmid, VHH plasmid and/or CAR plasmid.

In another aspect, the present application provides an immune effector cell comprising the CAR, the nucleic acid molecule or the vector described in the present application. In the present application, the immune effector cells may be mammalian cells. In the present application, the immune effector cells may be selected from T lymphocytes and natural killer (NK) cells.

In another aspect, the present application provides a method for preparing an immune effector cell, which comprises knocking out the CD70 gene of the immune effector cell, and introducing the vector described in the present application into the immune effector cell. For example, the vectors described in the present application can be introduced into the immune effector cells, such as T lymphocytes or natural killer (NK) cells. In some embodiments, each type of cells or each cell may comprise one or more of the vectors described in the present application. In some embodiments, each type of cells or each cell may contain multiple (e.g., 2 or more) or multiple types (e.g., 2 or more) of vectors described herein. In the present application, the vector can be introduced into immune effector cells. The vector described in the present application can be introduced into the cells by methods known in the art. For example, a retroviral vector can be used to transfect immune effector cells, to integrate the viral genome carrying the CAR molecule into the host genome, so as to ensure long-term and stable expression of the target gene. For another example, a transposon can be used to introduce a CAR (transposon)-carrying plasmid and a transposase-carrying plasmid into the target cells. For another example, the CAR molecule can be added to the genome through gene editing (such as CRISPR, Cas9). In the present application, the vector carrying the CAR molecule described in the present application can be introduced into the cells by methods known in the art, such as electroporation, liposome transfection (lipofectamine2000, Invitrogen) and the like.

In another aspect, the present application provides a composition, which may comprise the immune effector cells and a pharmaceutically acceptable adjuvant. The pharmaceutically acceptable adjuvant may include buffers, antioxidants, preservatives, low molecular weight polypeptides, proteins, hydrophilic polymers, amino acids, sugars, chelating agents, counterions, metal complexes, and/or non-ionic surfactants etc. In the present application, the pharmaceutical composition can be formulated for oral administration, intravenous administration (e.g., intravenous injection, IV), intramuscular administration (e.g., intramuscular injection, IM), in-situ administration at the site of the tumor, inhalation, rectal, vaginal or transdermal administration or administration via a subcutaneous depot.

Pharmaceutical Use

In another aspect, the present application provides use of the antibody, the CAR, the nucleic acid molecule, the vector or the immune effector cell, in the preparation of drugs for treating diseases or disorders related to CD70 expression. In the present application, the diseases or disorders related to CD70 expression are cancers or malignant tumors.

In another aspect, the present application provides the antibody, the CAR, the nucleic acid molecule, the vector or the immune effector cells for treating diseases or disorders related to CD70 expression.

In another aspect, the present application provides a method for treating diseases or disorders related to CD70 expression, which comprises administering, to a patient, the antibody, the CAR, the nucleic acid molecule, the vector or the immune effector cells.

Without being bound by any theory, the following examples are merely provided for illustrating the working patterns of the antibodies, chimeric antigen receptors, vectors, cells, and compositions of the present application, and not intended to limit the scope of the present application.

Example 1. Enrichment of Specific Antibody Clones Targeting CD70 Protein from Phage Antibody Library by Affinity Panning Appropriate negative panning and positive panning strategies were used to enrich specific antibody clones desired from the phage antibody library.

Construction of Phage Antibody Library

The phage antibody library constructed is a fully human antibody library, including a natural library, a semi-synthetic library and a single domain library. The semi-synthetic phage antibody library, used together with the natural library, solves the problem that the natural library may lack CD70 high-affinity antibody clones. The single-domain phage antibody library is an antibody library composed exclusively of the variable region amino acids of heavy chain antibodies having a molecular weight of only 12-15 kDa, but similar or higher specificity and affinity than traditional antibodies. In addition, single domain antibodies have attracted much attention because of their stable physical and chemical properties, high affinity, easy recombinant expression and preparation, and easy combination with other target or epitope antibodies. CD70 is an antigen expressed by normal cells in the human body. For this type of antigen, cells that can express CD70 antibodies are inactivated in the body by the mechanism of clonal screening during development, resulting in the lack of high-affinity antibody for this type of antigen in normal human body. Clonal screening is a normal self-identification and self-protection mechanism of the body. However, the most commonly used form of phage antibody library is the natural library, which is constructed by direct cloning of antibody genes in healthy human lymphocytes, and likely lacks antibody clones targeting antigens normally present in humans such as CD70. For this consideration, both a natural library and a semi-synthetic antibody library are constructed when the antibody library is constructed. The semi-synthetic antibody library consists of light chains heavy chains FR1-FR3 from natural antibody sequences and artificially designed heavy chain CDR3, which can greatly increase the diversity of antibodies and increase the chance of screening high-affinity antibodies against antigens that normally exist in the body.

CD70 Protein Panning

Multiple rounds of panning were performed using CD70-His as a positive panning protein to obtain a phage pool with enriched target antibody clones. The experimental steps were briefly described as follows:

1) SA magnetic beads were blocked with a blocking solution for 2 hrs, and then the target antigen (CD70-His) were bound to the blocked SA magnetic beads.

2) A phage library (containing $5 \times 10^{12}$ phage particles) was added and incubated with a portion of clean SA magnetic beads to subtract phage antibody clones that do not specifically bind to SA magnetic beads.

3) After incubation, the supernatant was transferred to SA magnetic beads bound with the target antigen, and incubated continuously to allow the phage to bind to the target antigen.

4) The magnetic beads were washed with a washing solution to wash away the unbound phage.

5) The positive phage was eluted off from the target antigen with an eluent, and neutralized by adding a neutralizing solution.

6) The host strain XL1-blue was infected with the eluted phage, and the recovered phage was amplified. A small amount of sample was diluted over gradients. The host strain was infected, and plated on an Amp-coated plate. The recovered phage was counted.

7) Steps 1) to 6) were repeated, and usually 3 to 4 rounds of panning were needed until a significant increase in the recovery rate of the phage (counts of eluted phage/counts of fed phage) was observed.

The enriched phage pool can be used for subsequent selection of monoclonal antibodies and screening by ELISA/FACS.

Raji/Jurkat Cell Panning

Multiple rounds of panning were performed with Jurkat cells negative for CD70 expression as a negative panning cell and Raji cells positive for CD70 expression as a positive panning cell to obtain a phage pool enriched with target antibody clones.

The experimental steps were briefly as follows:

1) The phage pool (containing $5 \times 10^{11}$ phage particles) enriched with specific clones after protein panning was mixed with $1 \times 10^7$ negative panning Jurkat cells, and incubated on a rotary mixer for 2 hrs at room temperature. The antibody clones binding to the negative panning cell line were allowed to fully bind to these cells.

2) The cells were pelleted by centrifugation at 1500 rpm for 5 min. The supernatant was transferred to a new tube, mixed with $1 \times 10^7$ Raji cells (CD70 positive cells), and bound on a rotary mixer for 2 hrs at room temperature.

3) The cells were washed 6 times with PBS, where the supernatant was discarded each time, and the cells were re-suspended and centrifuged at 1500 rpm for 5 min to remove unbound phage.

4) The positive phage was eluted off from the target antigen with an eluent, and neutralized by adding a neutralizing solution.

5) The host cells were infected with the eluted phage, and the recovered phage was amplified. A small amount of sample was diluted over gradients. The host strain was infected, and plated on an Amp-coated plate. The recovered phage was counted.

6) Steps 1) to 5) were repeated, and 2-3 rounds of panning were usually needed, until the recovery rate of phage (counts of eluted phage/counts of fed phage) was obviously increased.

The enriched phage pool can be further used for selection of monoclonal antibodies and screening by ELISA/FACS.

Main Materials and Reagents:

Fully human phage antibody library, including a natural library, a semi-synthetic library and a single-domain library;

Helper phage KO7, Thermo/Invitrogen, 18311019;

Biotinylated Human CD27 Ligand, HIS, Avitag, ACRO biosystem, CDL-H82Q9;

BeaverBeads™ Streptavidin, Beaver Bio, 22307-10;

High binding ELISA plate, Costar, #3590

Blocking solution: PBS+3% BSA

Rinse solution: PBS+0.1% Tween20

Eluent: 0.2M Glycine, pH2.2

Neutralizing solution: 1 M Tris, pH 9.1

Experimental Results 3 rounds of protein panning are performed using different antibody libraries, and a significant increase in the recovery rate is observed after each panning (Table 1), proving that antibody clones are effectively enriched.

TABLE 1

| Protein panning experiment results | | | |
| Antibody library | Round | Recovery rate | Enrichment factor |
| --- | --- | --- | --- |
| XL-SD-1 | 1st | 1.74E−05 | / |
| | 2nd | 2.58E−05 | 1.48 |
| | 3rd | 1.80E−03 | 64.8 |
| XL-NVH | 1st | 3.14E−05 | / |
| | 2nd | 3.52E−05 | 1.12 |
| | 3rd | 1.30E−03 | 36.9 |
| XL-V1 | 1st | 2.14E−05 | / |
| | 2nd | 4.00E−06 | 0.19 |
| | 3rd | 2.20E−03 | 550 |
| XL-V2 | 1st | 1.80E−05 | / |
| | 2nd | 9.40E−06 | 0.52 |
| | 3rd | 8.20E−04 | 87.2 |

It can be seen that after three rounds of panning, different antibody libraries are enriched (the recovery rate of the third round is significantly higher than that of the previous rounds). However, in subsequent FACS experiment, none of the clones selected from these phage pools can bind to the Raji cell line that highly expresses the CD70 antigen, that is, they cannot recognize the natural CD70 antigen on the cell surface. Therefore, in subsequent experiment, the method of protein and cell alternate panning was used to enrich specific antibody clones that can bind to both the CD70 protein and the natural CD70 on the cell surface from the phage antibody library. Table 2 shows the results of co-panning using recombinant CD70 protein and Raji/Jurkat cell line. As shown by the recovery rate, enrichment is achieved in all 4 panning processes and monoclonal antibodies can be selected in the next step.

TABLE 2

| Protein/cell panning experiment results | | | | |
| Antibody library | Round | Panning method | Recovery rate | Enrichment factor |
| --- | --- | --- | --- | --- |
| XL-SD-1 | 1st | Protein | 1.74E−05 | / |
| | 2nd | Protein | 2.58E−05 | 1.48 |
| | 3rd | Cell | 1.46E−06 | 0.06 |
| | 4th | Cell | 4.80E−05 | 32.78 |
| XL-NVH | 1st | Protein | 3.14E−05 | / |
| | 2nd | Protein | 3.52E−05 | 1.12 |
| | 3rd | Cell | 6.08E−06 | 0.17 |
| | 4th | Cell | 1.30E−05 | 2.14 |
| XL-V1 | 1st | Protein | 2.14E−05 | / |
| | 2nd | Protein | 4.00E−06 | 0.19 |
| | 3rd | Cell | 3.65E−06 | 0.91 |
| | 4th | Cell | 2.52E−05 | 6.9 |
| XL-V2 | 1st | Protein | 1.80E−05 | / |
| | 2nd | Protein | 9.40E−06 | 0.52 |
| | 3rd | Cell | 2.88E−06 | 0.31 |
| | 4th | Cell | 1.16E−05 | 4.03 |

Example 2. Screening of Specific Clones from Enriched Phage Pools by Enzyme-Linked Immunosorbent Assay (ELISA) and Flow Cytometry (FACS)

Objective and principle: The phage pool enriched by the affinity panning step contains phage antibodies of various properties, including: specific clones, non-specific clones, and negative clones. In order to obtain specific clones, monoclonal antibodies needed to be isolated, and packaged into monoclonal phages, and preliminary screening was performed on a large number of monoclonal antibodies by enzyme-linked immunoassay (ELISA) and flow cytometry (FACS), to screen monoclonal antibodies specifically binding to both CD70 protein and CD70 positive cell line Raji. The specific monoclonal antibodies were further determined by DNA sequencing to determine the unique antibody sequence contained therein.

In the primary screening by ELISA, through the binding to Streptavidin and Biotin, the biotinylated target protein (CD70-his-Bio) was closer to the natural antigen conformation in the reaction solution. Clones that only bind to CD70-his-Bio but not Streptavidin were identified as specific clones. The primary screening by FACS was carried out using the positive cell line Raji with high expression of CD70 and the Jurkat cell line negative for CD70 expression, and clones that only bind to Raji cells but not to Jurkat cells were identified as specific clones. Through two primary screening processes by ELISA and FACS, candidate antibodies that can not only bind to recombinantly expressed CD70 protein, but also recognize the natural CD70 molecule on the cell surface were obtained, for subsequent further screening.

Brief Steps of ELISA:

1) Monoclonal phages were incubated and packaged in a deep-well 96-well plate.

2) Strepavidin was diluted to 2 μg/mL with PBS, added in an amount of 100 μL/well to a high-binding microtiter plate, and allowed to bind at room temperature for 2 hrs.

3) The coating solution was discarded, 250 μL of a blocking solution was added to each well, for blocking overnight at 4° C.

4) The plate was washed twice with 250 μL rinse solution.

5) The biotin-labeled target protein was diluted to 2 μg/mL with PBS, added in an amount of 100 μg/well to the microtiter plate pre-coated with Strepavidin, and allowed to bind for 1 hr at room temperature.

6) The plate was rinsed twice with 250 μL rinse solution.

7) 100 μL of the phage supernatant cultured in step 1) to the wells coated with the target antigen, and allowed to bind at room temperature for 2 hrs.

8) The plate was rinsed four times with 250 μL rinse solution.

9) 1:2000 diluted primary antibody mouse anti M13 was added in an amount of 100 μL/well, and incubated at room temperature for 45 min.

10) The plate was rinsed four times with 250 μL rinse solution.

11) 1:2000 diluted HRP Donkey anti-mouse IgG was added in an amount of 100 μL/well, and incubated at room temperature for 45 min.

12) The plate was rinsed six times with 250 μL rinse solution.

13) 100 μL of a TMB developing substrate was added, and developed for 5 to 10 min.

14) 100 μL of 2M $H_2SO_4$ was added to terminate the reaction, and the result was read on a microplate reader.

Brief Steps of Primary Screening by FACS:

1) Monoclonal phages were incubated and packaged in a deep-well 96-well plate.

2) Raji and Jurkat cells were washed twice with PBS, re-suspended in PBS to a concentration of $1 \times 10^7$/mL, and dispensed in an amount of 50 μL into a 96-well deep-well plate.

3) 50 μL of packaged monoclonal phages was added to each well, mixed well, and allowed to bind at 4° C. for 2 hrs.

4) The system was washed twice with 200 μL PBS.

5) 1:2000 diluted primary antibody mouse anti M13 was added in an amount of 100 μL/well, mixed uniformly by pipetting, and incubated at room temperature for 45 min.

6) The system was washed twice with 200 μL PBS.

7) 1:300 diluted FITC horse anti mouse-IgG (H+L) was added in an amount of 100 μL/well, mixed uniformly by pipetting, and incubated at room temperature for 45 min.

8) The cells were washed twice with 200 μL PBS; and finally re-suspended in 200 μL PBS.

9) The fluorescence intensity of the sample in the FITC channel was detected on a flow cytometer, and the results were analyzed.

Main Materials and Reagents:

Helper phage KO7, Thermo/Invitrogen, 18311019

Streptavidin, Pierce, 21125

Biotinylated Human CD27 Ligand, HIS, Avitag, ACRO biosystem, CDL-H82Q9;

High binding ELISA plate, Costar, #3590

Corning 96 Well Clear Round Bottom TC-Treated Micro-plate, Costar, #3799

Blocking solution: PBS+3% BSA

Rinse solution: PBS+0.1% Tween20

Soluble one-component TMB substrate solution, Tiangen, PA-107-02

Anti-M13 Bacteriophage Coat Protein g8p antibody, abcam, ab9225

HRP Goat anti-mouse IgG (minimal x-reactivity) Anti-body, Biolegend, 405306

FITC horse anti mouse-IgG(H+L), Vector, FI2000

Experimental Results

Monoclonal phages were randomly picked from the enriched phage antibody pool, and packaged into phages.

The binding of monoclonal phages to CD70-his-Bio protein and SA protein was detected by ELISA to find CD70-specific phage antibody clones. The ELISA results of some clones are shown in FIG. 13. It can be seen from FIG. 13 that clones H1, H3, and H4 bind well to the target antigen CD70 (CD70-his-Bio), and do not bind to the control antigen Streptavidin, showing good specificity. Clones H2, H5, H7 and H8 do not bind to the target antigen CD70 (CD70-His-Bio) and Streptavidin, and are negative clones. Clone H6 can bind to the target antigen CD70 (CD70-His-Bio), but can also bind to the control antigen SA, which is thus a non-specific clone.

The results of primary screening by FACS of some clones are shown in FIG. 14. Control 1 is a phage negative control, Control 2 is a negative control with only the primary antibody (Anti-M13 Bacteriophage Coat Protein g8p anti-body) and the secondary antibody (HRP Goat anti-mouse IgG (minimal x-reactivity) Antibody), and Control 3 is a CD70 antibody positive control. Clones A2, A3, A5, A6, A7 and A8 do not bind to Jurkat cells, but to Raji cells, and thus are specific clones. Other clones are non-specific (binding to both cells) or negative clones (not binding to both cells).

Through detection by ELISA and primary screening by FACS, a total of 344 specific clones are obtained.

Example 3. Identification of Specificity of Monoclonal Antibodies by FACS Using Multiple Cell Lines Experimental objective and principle: The antibody used for treatment needs to have very good target specificity, and binds only to the target antigen and not to any irrelevant antigens. Moreover, since the same antigen on different cell lines has different amino acid sequences (isomers or mutants) or binds to different ligands, whether the antibody can bind to various target antigen-positive cells also needs to be investigated. To further analyze the specificity and universality of these monoclonal antibodies and find the best candidate clones, the specificity of the primarily screened clones was further evaluated by flow cytometry. In this experiment, a variety of CD70-positive cell lines and a variety of CD70-negative cell lines were used to react with these monoclonal phage antibodies, and whether these clones could bind to the CD70 antigen on different cell lines and whether they non-specifically bind to other cell lines not expressing CD70 were analyzed. Through this experiment, several clones with excellent specificity were obtained.

Experimental method: the same as that in the primary screening by FACS;

Main Samples and Reagents:

Raji cell line, CD70 positive cell line;

Jurkat cell line, CD70 negative cell line;

U266, CD70 positive cell line;

K562, CD70 negative cell line; and rest of the reagents, the same as those in the primary screening by FACS.

Experimental Results

The antibody used for treatment needs to have very good target specificity. To further analyze the specificity of these monoclonal antibodies, the specific clones obtained in Example 2 were identified on more antigens and cell lines by using ELISA and flow cytometry. The results are shown in FIGS. 15A-E, in which Negative Control is the phage antibody clone negative control. Clones #1-32, #34-35, #37-39, and #41 bind to two CD70-positive cell lines Raji, with an either strong or weak median fluorescence intensity (MFI); and do not bind to the CD70-negative cell lines, with a low MFI, so the specificity is good. Clones #36 and #40 do not bind to the CD70-positive cell line U266. Clone #40 clone has tailing when binds to the CD70-negative cell lines Jurkat and K562, indicating that the conformation of the CD70 antigen it bound to is different or CD70 expressed on different cells has different isomers.

Example 4. Identification of Monoclonal Specificity by ELISA Using Antigens from Different Manufacturers Experimental objective and principle: The antibody used for treatment needs to have very good target specificity, and binds only to the target antigen and not to any irrelevant antigens. Moreover, since the amino acid sequence of the same antigen produced by different manufacturers will be different (isomers or mutants), whether the antibody can bind to the target proteins produced by different manufacturers also needs to be investigated. To further analyze the specificity and universality of these monoclonal antibodies and find the best candidate clones, the specificity of the primarily screened clones was further evaluated by enzyme-linked immunosorbent assay (ELISA). In this experiment, CD70 antigens purchased from different manufacturers and a variety of CD70 irrelevant antigens were used to react with these monoclonal phage antibodies, and whether these clones can bind to different CD70 antigens and whether they non-specifically bind to other CD70 irrelevant antigens were analyzed. Through this experiment, several clones with excellent specificity were obtained.

Experimental method: The same as the primary screening by ELISA.
Main Samples and Reagents:

| Abbreviation | Name | Manufacturer | Item No. |
|---|---|---|---|
| Acro-CD70-his-Bio | Biotinylated Human CD27 Ligand, HIS, Avitag | ACRO biosystem | CDL-H82Q9 |
| Acro-CD70-Fc-Bio | Biotinylated Human CD27 Ligand, Avitag, human Fc Tag | ACRO biosystem | TN7-H82F4 |
| Kactus-CD70-Fc-Bio | Human CD70/CD27 Ligand Protein (human FC Tag)-Biotin | Kactus | CD7-HM270 |
| Kactus-CD70Trimer-his-Bio | Human CD70/CD27 Ligand Protein-his-Trimer-Biotin | Kactus | CD7-HM271 |
| SB-CD70-Fc | CD70 Protein, Human, Recombinant (human FC Tag) | Sino Biological | 10780-H01H |

-continued

| Abbreviation | Name | Manufacturer | Item No. |
|---|---|---|---|
| Kactus-CD70-Fc | Human CD70/CD27 Ligand Protein(human FC Tag) | Kactus | CD7-HM270 |
| Kactus-CD70 Trimer-his | Human CD70/CD27 Ligand Protein-his-Trimer | Kactus | CD7-HM271-1 |
| ACRO-CD70 Trimer-his-Bio | Biotinylated Human CD27 Ligand/CD70 Protein, His, Avitag ™, Flag Tag (active trimer) | ACRO biosystem | CDL-H82D7 |
| Acro-CD22-Bio | Biotinylated Human Siglec-2/CD22 Protein, human Fc, Avitag ™ | ACRO biosystem | SI2-H82F8 |
| anti-CD70 Ab | Mouse monoclonal [BU69] to CD70 | Abcam | ab77868 |

The other reagents were the same as those in primary screening by ELISA.
Experimental Results The antibody used for treatment needs to have very good target specificity. To further analyze the specificity of these monoclonal antibodies, multiple clones obtained in Example 2 were identified on multiple antigens by ELISA. The results are shown in FIGS. 16A-E, in which Negative Control is the phage antibody clone negative control, Anti-M13 phage mouse Ab/anti-mouse HRP Ab is a negative control without the phage and with only the primary antibody (Anti-M13 phage mouse Ab) and secondary antibody (anti-mouse HRP Ab); anti-mouse HRP Ab is a negative control with only the second antibody (anti-mouse HRP Ab), anti-CD70 Ab is the CD70 detection antibody positive control; and anti-his HRP/anti-human IgG HRP is the detection antigen tag positive control antibody. Clones #1-32, #34-35, #37-39, and #41 all bind to 7 CD70 antigens, where the binding to SB-CD70 antigen is either weak or strong, and they do not bind to the irrelevant antigen Acro-CD22-Bio, indicating that they can bind CD70 antigens with different conformations with good specificity. Compared with other clones, Clones #36 and #40 have the strongest binding to SB-CD70 antigen, and does not bind to the irrelevant antigen Acro-CD22-Bio, indicating that it may bind to a different epitope compared with other clones.

The table below lists the amino acid and nucleic acid sequence numbers corresponding to the heavy chain variable region (HCVR), light chain variable region (LCVR), ScFv and CDR sequences of some of the selected anti-CD70 antibodies:

| Antibody number | Amino acid sequence SEQ ID NO: | | | | | | | | | DNA sequence SEQ ID NO: | | |
|---|---|---|---|---|---|---|---|---|---|---|---|---|
| | HCDR1 | HCDR2 | HCDR3 | HCVR | LCDR1 | LCDR2 | LCDR3 | LCVR | ScFv | HCVR | LCVR | ScFv |
| #6 | 72 | 73 | 74 | 28 | 75 | 76 | 77 | 30 | 26 | 27 | 29 | 25 |
| #9 | 78 | 79 | 80 | 33 | — | — | — | — | — | 31, 32 | | |
| #13 | 81 | 82 | 83 | 36 | | | | | | 34, 35 | | |
| #20 | 84 | 85 | 86 | 39 | | | | | | 37, 38 | | |
| #21 | 87 | 88 | 89 | 42 | | | | | | 40, 41 | | |

Example 5. Construction of Vector of CD70 CAR Molecule

On the basis of the CD70 antigen-binding fragments screened in the previous stage, 136 new CD70 CAR molecular structures were constructed for further screening.
Brief Description of the CAR Construction Process:

A GoldenGate backbone vector containing the lethal gene ccdB was synthesized (the nucleic acid sequence of the backbone plasmid is: SEQ ID NO: 17). After the backbone plasmid was digested with BsmBI, the large fragment of the two fragments had no BsmBI recognition site. Then, using BsmBI as an ITS-type endonuclease having the property of seamless ligation, insert gene fragments such as scFv, VHH, or VHH-Linker-VHH with BsmBI recognition site and cleavage site at the 5' and 3' ends were amplified:
NNCGTCTCagaccc+insert gene fragment+ttcgtGGA-GACGNN A fragment obtained after the fragment was digested with BsmBI had no BsmBI recognition site, but the nicks at both ends of the fragment were complementary to the nicks of the above-mentioned GoldenGate backbone vector, so that the target vector could be constructed by ligation by T4 DNA ligase. Because the lethal gene ccdB had a "lethal" effect in stbl3 competent cells, a BsmBI+T4 reaction system and reaction conditions were designed and optimized. BsmBI digestion and T4 ligation were carried out at the same time, to achieve high positive-rate and high-throughput build.
BsmBI+T4 Reaction System:

| | |
| --- | --- |
| 10 × T4 DNA Ligase Buffer | 1 ul |
| GoldenGate backbone plasmid | 0.015 pmol |
| Fragment | 0.045 pmol |
| BsmBI (10 U, ul) | 0.25 ul |
| T4 DNA Ligase (350 U, ul) | 0.25 ul |
| dH2O | Up to 10 ul |
| 37° C. | 5 min 10× |
| 25° C. | 5 min |
| 4° C. | Hold |

Figure 1:
FIG. 1 is a schematic diagram showing the molecular structure of CD70 CAR.

Reaction Conditions:

As shown in FIG. 1, the antigen recognition portion of the CD70 CAR molecule consists of a single-domain antibody (VHH), or a single-chain antibody (scFv), or two tandem single-domain antibodies (2×VHH). In the screening process of candidate drugs, CD70 CAR molecules mainly assume the second-generation or third-generation CAR structure. The antigen recognition portions corresponding to the exemplary CAR molecules are shown in Table 3 below, and the antibody numbers (06, 09, 13, 20, and 21) listed do not include all antibodies used in the screening studies.

TABLE 3

Exemplary CAR molecules and antigen recognition portions thereof

| Serial number | Antigen recognition portion | CAR number |
| --- | --- | --- |
| 1 | Scfv06 | pXL1416 |
| 2 | VHH 09 | pXL1394 |
| 3 | VHH 13 | pXL1398 |
| 4 | VHH 20 | pXL1423 |
| 5 | VHH 21 | pXL1424 |
| 6 | VHH 13-Whitlow Linker-VHH 20 | pXL1698 |
| 7 | VHH20-Whitlow Linker-VHH13 | pXL1700 |
| 8 | VHH13-Whitlow Linker-VHH 21 | pXL1702 |
| 9 | VHH21-Whitlow Linker-VHH13 | pXL1704 |
| 10 | VHH09-Whitlow Linker-VHH13 | pXL1748 |
| 11 | VHH13-Whitlow Linker-VHH09 | pXL1750 |

TABLE 3-continued

Exemplary CAR molecules and antigen recognition portions thereof

| Serial number | Antigen recognition portion | CAR number |
| --- | --- | --- |
| 12 | VHH09-Whitlow Linker-VHH 21 | pXL1752 |
| 13 | VHH21-Whitlow Linker-VHH09 | pXL1754 |
| Positive control | Cusatuzumab scFv | pXL1331 |
| Positive control | Vorsetuzumab scFv | pXL1332 |
| Positive control | Extracellular domain of CD27 protein | pXL1323 |

Example 6. Detection of the Activity of CAR Molecules in Activating NFAT Transcription Factor by Reporter Gene Method (1) Objective and Principle of the Experiment The activation of CAR-T cells is achieved by CD3z and costimulatory factors in the intracellular region of CAR molecules, where CD3z can activate the NFAT signaling pathway in the cells, which is a necessary condition for CAR-T cell activation. Therefore, CAR molecules with the function of activating the NFAT signaling pathway can be screened out by the NFAT reporter gene method.

Figure 2:
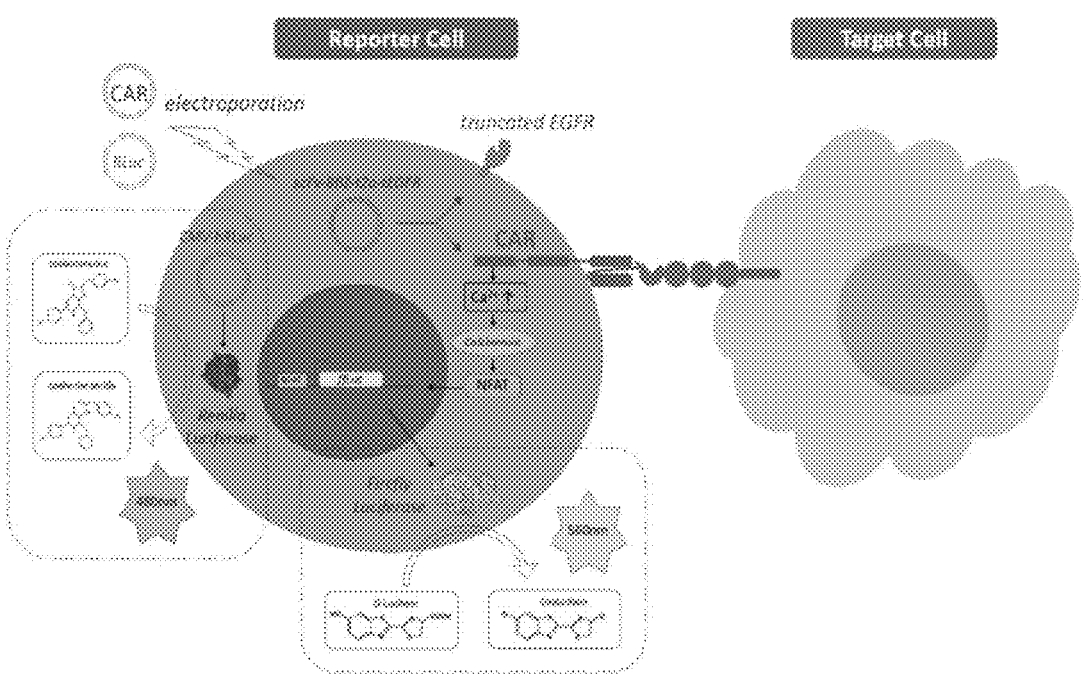
FIG. 2 is a schematic diagram showing the working principle of a reporter gene method.

In the process of primary screening, Jurkat cells integrated with the NFAT-RE-ffLuc reporter gene were used as reporter cells (Reporter Cell as shown in FIG. 2, and designated as JLuc307). The CAR molecules were transiently expressed on the surface of reporter cells by electroporation of the plasmid. When the reporter cell expressing the CAR molecule and a target cell were co-incubated, the surface antigen on the target cell can specifically activate the CAR molecule, thereby activating the expression of the reporter gene (ffLuc, firefly luciferase). Then, by detecting the activity of luciferase, the ability of the CAR molecule to activate the NFAT signaling pathway was evaluated. In addition, since different CAR molecules have different electroporation efficiencies, an internal reference plasmid (CMV-hRLuc, Renilla luciferase) mixed with CAR molecules could be used to calibrate the electroporation efficiency.

(2) Operation Steps i. The CAR plasmid to be tested and the internal reference plasmid were mixed according to a fixed ratio, and then the reporter cells was transfected by electroporation.

ii. 48 hrs after transfection, some cells were taken, stained with PE-anti human EGFR antibody and detected by flow cytometry to evaluate the transient expression of CAR plasmid.

iii. 72 hrs after transfection, the reporter cells and target cells were mixed at a ratio of 1:1, and then plated in a U-bottom 96-well plate and incubated for 24 hrs. $3 \times 10^4$ reporter cells were added to each well, and 3 duplicate wells are set for each type of target cells.

iv. After incubation, the system was centrifuged at 1000 g for 5 min at 4° C. The culture supernatant was removed, and 100 ul of a lysis buffer was added to each well to lyse the cells. 20 ul of the cell lysate was taken for dual-luciferase activity detection.

(3) Screening Criteria

The CD70-positive target cells (for example, U266, THP-1, and RS4:11 etc.) can effectively activate the CD70 CAR molecule, and a fluorescent signal is generated by the NFAT-RE reporter gene. In the absence of stimulation by target cells or with stimulation by CD70-negative target cells (for example, HEL, and K562 etc.), the fluorescent signal resulting from background (tonic effects) or non-specific activation is low.

Example 7. Screening of sgRNA for Knocking CD70 Out (1) Objective and Principle of the Experiment Since CD70 antigen is also expressed on highly activated T cells, CD70 CAR-T will have the problem of fratricide. In order to solve the problem of fratricide of CD70 CAR-T cells, the CD70 gene can be knocked out by using the CRISPR method.

(2) Operation Steps i. 5 sgRNAs targeting exon 1 region of CD70 gene were synthesized (GenScript Inc.).

```
>sgRNA-1
                          (SEQ ID NO: 90)
GAGCAGCCCGAACCCTCTCTC

>sgRNA-2
                          (SEQ ID NO: 91)
GGAGGAGGGTTCGGGCTGCT

>gRNA-3
                          (SEQ ID NO: 92)
ATCACCAAGCCCGCGACCAA

>sgRNA-4
                          (SEQ ID NO: 93)
AGCGCTGGATGCACACCACG

>sgRNA-5
                          (SEQ ID NO: 94)
GGGCTTGGTGATCTGCCTCG
``` ii. After mixing the sgRNA and Cas9 protein at an appropriate ratio, they were transformed into CD70-positive THP-1 cells by electrotransduction to knock out the CD70 gene.

iii. After 72 hrs of electrotransduction, the expression of CD70 on the surface of THP-1 cells was detected by flow cytometry, and the editing efficiency of CD70 gene was evaluated by sequencing.

(3) Screening Criteria

The sgRNA with the highest CD70 gene editing efficiency was selected for knocking out CD70 gene in T cells.

Example 8. In-Vitro Function Evaluation of CD70 CAR-T Cells

The in-vitro function of CD70 CAR-T cells was mainly evaluated by CD107a degranulation assay and in vitro cell killing experiment Preparation of CD70 Knockout CAR-T Cells The preparation process of CD70 knockout CAR-T cells (CD70ko CAR-T) was as follows:

i. PBMCs from healthy human were purchased from Milestone® Biotechnologies. PBMCs were thawed, and sorted using CD3 MicroBeads to obtain T cells. CD3 and CD28 dynabeads were added to T cells for activation and culture for 24 hrs.

ii. Cas9 protein and sgRNA were co-incubated in advance to form a RNP complex. After removing CD3 and CD28 dynabeads in T cells, RNP was mixed with and electroporated into T cells. The T cells after electroporation were continued to be cultured.

iii. About 16 hrs after electroporation, the T cells were electrotransduted with lentiviral vector to obtain CD70ko CAR-T cells.

CD107a Degranulation Assay (1) Objective and Principle of the Experiment

CD107a is a marker of intracellular microvesicles, and CD107a on the cell membrane increases after granzyme-loaded microvesicles are fused with the cell membrane. When its recovery is blocked by monesin (purchased from BioLegend), the degree of microvesicle release can be quantitatively reflected. Therefore, when CAR-T cells are stimulated by surface antigens on the target cells to undergo degranulation, the CD107a positive rate on the surface of CAR-T cells can be detected by flow cytometry to determine the activation of CAT-T cells.

(2) Operation Steps iv. Different target cells were separately centrifuged at room temperature and 300 g for 5 min. The supernatant was discarded, and the cells were re-suspended in T cell culture medium to $2 \times 10^5$ cells/mL.

v. According to the CAR positive rate and E:T value (usually 0.3:1) of the CAR-T cells to be tested, the CAR-T cells were re-suspended to an appropriate density, and monensin and PE/Cy7 mouse anti-human CD107a antibody were added.

vi. In a U-bottom 96-well plate, 100 ul/well CAR-T cells to be tested and 100 ul/well target cells were added individually, mixed well, and then incubated in an incubator ($37^\circ$ C., 5% $CO_2$) for 3 hrs.

vii. After incubation, the system was centrifuged at $4^\circ$ C. and 600 g for 5 min, the supernatant was discarded, and the cells were washed twice with 200 ul/well DPBS+ 1% HSA.

viii. The cells were re-suspended in 20 ul/well DPBS+1% HSA, and APC mouse anti-human CD8 antibody and Alexa Fluor 488 anti-human EGFR antibody were added, mixed well and incubated on ice in the dark for 20 min.

ix. After completion of incubation, wash the cells 3 times with 200 ul/well DPBS+1% HSA, and then re-suspend the cells with 200 ul/well DPBS+1% HSA for flow cytometry.

(3) Screening Criteria

CD70 CAR can specifically recognize CD70 positive target cells and effectively activate CAR-T cells (in the CD8+/CAR+ cell population, the proportion of CD107a positive cells is high). CD70 CAR is not activated by CD70-negative target cells, and the CD107a-positive rate is low in the CD8+/CAR+ cell population.

In Vitro Cell Killing Experiment (1) Objective and Principle of the Experiment

In the evaluation of the antigen-specific killing ability of CAR-T cells, CD70 positive cells (for example, THP-1, and Molm-13) were used as the target cells. Cell lines stably expressing firefly luciferase were obtained from these target cells by lentiviral electrotransduction.

In the in-vitro cell killing assay, the CAR-T cells and target cells were co-incubated according to different effector-target ratios (E:T) separately. When the target cells were killed by CAR-T cells, luciferase was released and quickly inactivated (where the firefly luciferase has a half-life of about 0.5 h). If the target cells are not killed or inhibited by CAR-T cells, more luciferases will be produced as the target cells proliferate and continue to express luciferase. Therefore, the killing of target cells by CAR-T can be detected by the activity of luciferase.

(2) Operation Steps i. The target cells were centrifuged at room temperature and 300 g for 5 min separately. The supernatant was discarded, and then the cells were re-suspended in T cell complete medium to $2 \times 10^5$ cells/ml. 100 ul/well target cells were added to a 96-well plate with clear bottom separately.

ii. According to the CAR positive rate and E:T value (usually 2:1, 1:1, and 0.5:1) of the CAR-T cells to be tested, 100 ul/well CAR-T cells were added to the 96-well plate separately, mixed well with the target cells, and incubated in an incubator (37° C., 5% $CO_2$) for 24 hrs.

iii. After incubation, the system was centrifuged at room temperature and 800 g for 5 min, 100 ul/well supernatant was collected and used as a reserved sample for cytokine detection (stored at −80° C.);

iv. The luciferase activity of the remaining cells in each well after sample reservation was detected using a luciferase detection kit.

(3) Screening Criteria

CD70 CAR-T cells can effectively kill CD70-positive target cells, but not CD70-negative target cells.

Results and Analysis

1. Detection of CD70 Protein Expression on Cell Lines

Figure 3:
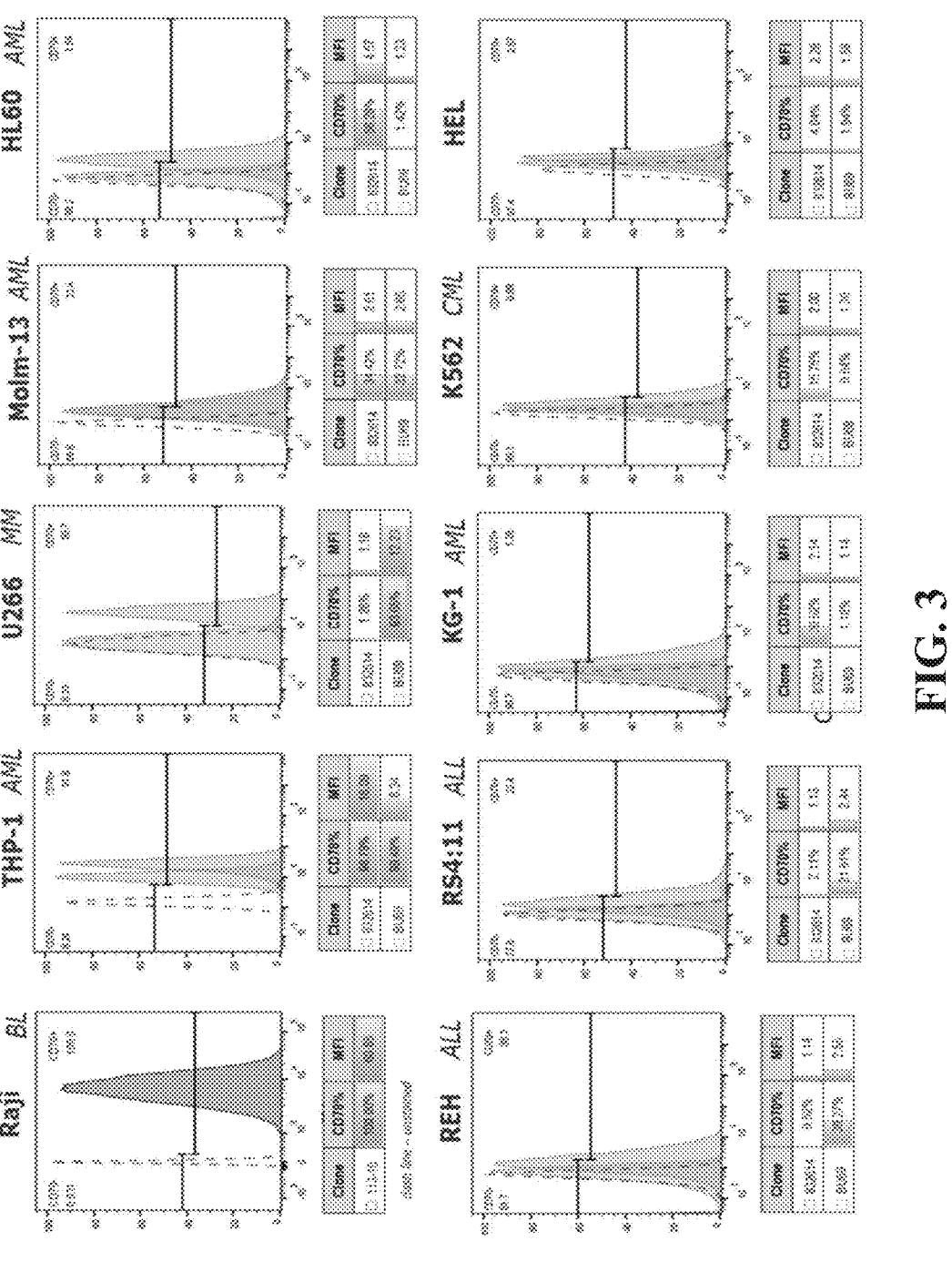
FIG. 3 shows the expression of CD70 protein on various cell lines detected by flow cytometry antibodies of two clone numbers (Clone BU69, Thermo, Cat. No. MA5-17727 and clone 832614, R&D Systems, Cat. No. FAB27381G), in which Raji cells are detected using clone 113-16 (Biolegend, Cat. No. 355103) antibody.

As shown in FIG. 3, the staining results of antibodies with different clone numbers on some cell lines are different, which may be due to the existence of multiple splicing isomers of CD70. Combining the antibody staining results of two different clone numbers, Raji, THP-1, U266 and other cell lines are cells with high expression of CD70, cells such as Molm-13, RS4:11, REH, and HL-60 have low expression of CD70, KG-1, K562, HEL and other cells do not express CD70.

2. Preliminary Screening of CD70 CAR Molecule by Reporter Gene Method

Figure 4:
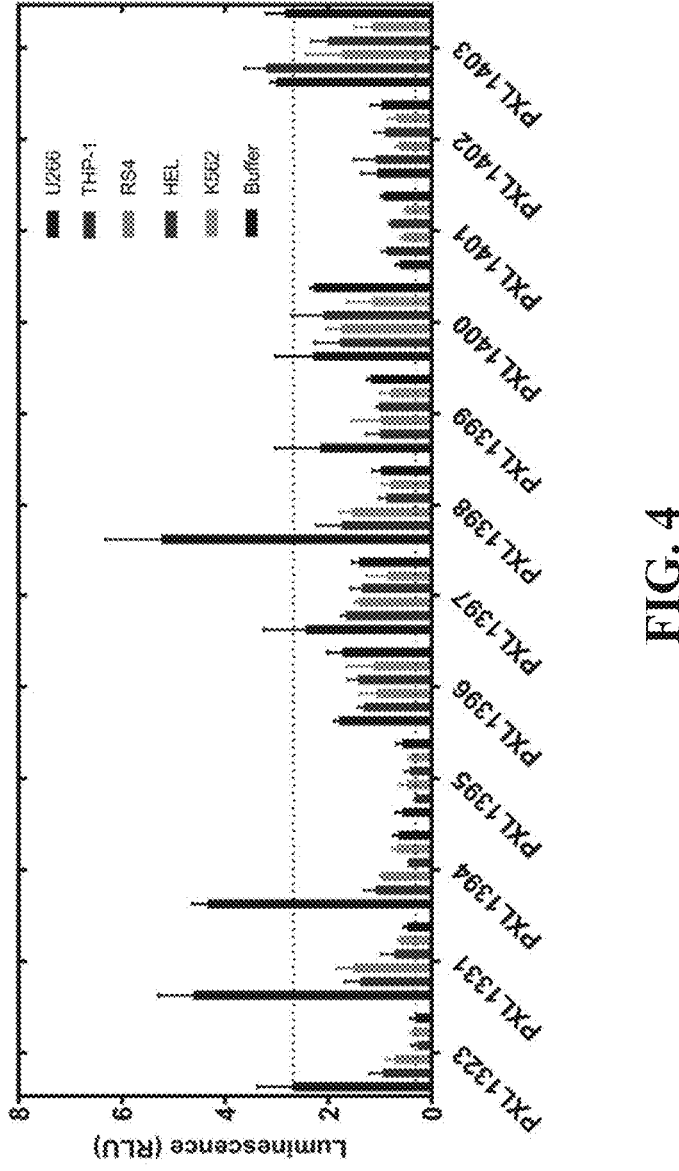
FIG. 4 shows Relative readout of chemiluminescence obtained by screening CD70 CAR molecules by a reporter gene method, in which PXL1323 and PXL1331 are positive

As shown in FIG. 4, three cell lines U266, THP-1, and RS4:11 were used as CD70-positive target cells during the primary screening process by the reporter gene method, and HEL and K562 were used as CD70-negative target cells.

PXL1323 and PXL1331 were used as positive control CAR molecules. After the transfected JLuc307 cells were co-incubated with positive target cells for 24 hrs, high chemiluminescent signals were generated, where the signal intensity was positively correlated with the expression level of CD70 on target cells. When they were incubated alone (buffer group) or with negative target cells for 24 hrs, the chemiluminescent signals produced were relatively weak. Considering the results of the control CAR molecule, PXL1394 and PXL1398 can be selected from PXL1394 to PXL1403 and used as candidate drugs obtained after primary screening (FIG. 4).

Similarly, after multiple batches of preliminary screening by reporter gene method, a group of candidate CAR molecules can also be obtained for the next step of in-vitro functional evaluation (results not shown).

3. Screening of sgRNAs for Knocking CD70 Out

Since the activated T cells also express CD70 at a low level, the problem of fratricide of CD70 CAR-T cells is caused. Therefore, using THP-1 as a model cell, the sgRNA sequence that can be used to knock out the CD70 gene was screened. After THP-1 cells were electrotranducted using RNPs, the knockout efficiency of CD70 gene was detected by flow cytometry and sequencing respectively, as shown in FIG. 5 and Table 4. sgRNA-4 has the highest efficiency in knocking out CD70 gene.

TABLE 4

| | Knockout efficiency of CD70 gene in THP-1 cells detected by flow cytometry and sequencing. | | |
| --- | --- | --- | --- |
| Sample | CD70 positive rate (%) by flow cytometry | Knockout efficiency (%) detected by flow cytometry | Knockout efficiency (%) detected by sequencing |
| Blank | 0.60 | / | / |
| Control | 98.41 | / | / |
| sgRNA-1 | 42.33 | 57.67 | 48 |
| sgRNA-2 | 82.03 | 17.97 | 8 |
| sgRNA-3 | 37.22 | 62.78 | 52 |
| sgRNA-4 | 13.03 | 86.97 | 87 |
| sgRNA-5 | 19.52 | 80.48 | 61 |

4. CD107a Degranulation Function of CD70 CAR-T

As shown in FIG. 6, for CAR-T cells of PXL1323 and PXL1331 used as positive controls, CD107a positive rate is high in the CD8+/CAR+ cell population under the stimulation of CD70-positive target cells (U266, Raji, THP-1, REH, RS4:11, and Molm-13 etc.); however, under the stimulation of CD70-negative target cells (such as HEL, and K562, etc.), non-specific activation will not occur, and the CD107a positive rate in the CD8+/CAR+ cell population is low. Similar to the control, the CAR-T cells used for test can also be stimulated by CD70-positive target cells to produce CD107a, and some clones can also maintain a low CD107a-positive rate under the stimulation of CD70-negative target cells.

5. In-Vitro Cell Killing Function of CD70 CAR-T

As shown in FIG. 7, all CAR-Ts used in the test can kill CD70-positive target cells (Molm-13 and RHE) to different degrees, but not CD70-negative target cells (K562).

6. In-Vitro Expansion Ability of CD70 CAR-T

As shown in FIG. 8, although the CAR-T cells used for test can be expanded normally during in-vitro culture. However, compared with the control CAR-T (PXL1323 and PXL1331), the amplification factor is significantly lower, and some CAR-T clones show the stop of expansion and cell exhaustion after 15 days of culture.

In Vitro Function Evaluation of 2×VHH CAR-T

As shown by the previous data, although the CAR-T cells used in the test have CD107a degranulation activity and in-vitro cell killing function comparable to the control CAR-T cells, the expansion ability of these CAR-T cells in vitro is not as good as that of the control CAR-T cells. Therefore, the antigen recognition portion of these CAR-T cells corresponding to the CAR molecule was changed from a single VHH to a structure of two VHHs in tandem (2×VHH CAR). By increasing the antigen binding ability, the in-vitro function of the CAR molecule was improved.

As shown in FIG. 9, 2×VHH CAR-T cells have CD107a degranulation function similar to that of control CAR-T cells (PXL1331). As shown in FIG. 10, some 2×VHH CAR-T cells have a stronger killing function on CD70-positive target cells than the control CAR-T cells (PXL1331). As shown in FIG. 11, the in-vitro expansion curves of some 2×VHH CAR-T cells were similar to that of control CAR-T cells, and significantly better than that of single VHH CAR-T cells.

The foregoing detailed description is provided for the purpose of explanation and exemplification, and is not intended to limit the scope of the appended claims. Variations of the embodiments recited in the present application will be apparent to those of ordinary skill in the art and are embraced in the scope of the appended claims and their equivalents.

REFERENCES

1. Goodwin R G, Alderson M R, Smith C A, et al Molecular and biological characterization of a ligand for CD27 defines a new family of cytokines with homology to tumor necrosis factor. Cell. 1993; 73(3):447-456. doi: 10.1016/0092-8674(93)90133-b.
2. Hintzen R Q, Lens S M, Beckmann M P, Goodwin R G, Lynch D, van Lier R A. Characterization of the human CD27 ligand, a novel member of the TNF gene family. J Immunol. 1994; 152(4):1762-1773.
3. Junker K, Hindermann W, von Eggeling F, Diegmann J, Haessler K, Schubert J. CD70: a new tumor specific biomarker for renal cell carcinoma. J Urol. 2005; 173(6): 2150-2153. doi:10.1097/01.ju.0000158121.49085.ba.
4. Sloan D D, Nicholson B, Urquidi V, Goodison S. Detection of differentially expressed genes in an isogenic breast metastasis model using RNA arbitrarily primed-polymerase chain reaction coupled with array hybridization (RAP-array). Am J Pathol. 2004; 164(1):315-323. doi: 10.1016/S0002-9440(10)63121-5
5. Held-Feindt J, Mentlein R. CD70/CD27 ligand, a member of the TNF family, is expressed in human brain tumors. Int J Cancer. 2002; 98(3):352-356. doi:10.1002/ijc.10207
6. Hishima T, Fukayama M, Hayashi Y, et al. CD70 expression in thymic carcinoma. Am J Surg Pathol. 2000; 24(5):742-746. doi:10.1097/00000478-200005000-00014.

7. Lens S M, Drillenburg P, den Drijver B F, et al. Aberrant expression and reverse signalling of CD70 on malignant B cells. Br J Haematol. 1999; 106(2):491-503. doi: 10.1046/j.1365-2141.1999.01573.x.
8. Nakajima A, Oshima H, Nohara C, et al. Involvement of CD70-CD27 interactions in the induction of experimental autoimmune encephalomyelitis. J Neuroimmunol. 2000; 109(2):188-196. doi:10.1016/s0165-5728(00)00324-6.
9. Bowman M R, Crimmins M A, Yetz-Aldape J, Kriz R, Kelleher K, Herrmann S. The cloning of CD70 and its identification as the ligand for CD27. J Immunol. 1994; 152(4):1756-1761.
10. Oshima H, Nakano H, Nohara C, et al. Characterization of murine CD70 by molecular cloning and mAb. Int Immunol. 1998; 10(4):517-526. doi:10.1093/intimm/10.4.517.
11. Phage display-methods and protocols, ISSN 1064-3745 ISSN 1940-6029 (electronic) Methods in Molecular Biology ISBN 978-1-4939-7446-7 ISBN 978-1-4939-7447-4 (eBook), DOI 10.1007/978-1-4939-7447-4.
12. Wang, Q. J., et al., Preclinical Evaluation of Chimeric Antigen Receptors Targeting CD70-Expressing Cancers. Clin Cancer Res, 2017. 23(9): p. 2267-2276.
13. Silence, K., et al., ARGX-110, a highly potent antibody targeting CD70, eliminates tumors via both enhanced ADCC and immune checkpoint blockade. MAbs, 2014. 6(2): p. 523-32.

Some amino acid and nucleic acid sequences described herein and in the accompanying drawings are listed below:

```
CD8asignalnucleic acid sequence
                                              (SEQ ID NO: 1)
ATGGCCCTGCCTGTGACAGCTCTGCTCCTCCCTCTGGCCCTGCTGCTCCATGCCGC CAGACCC
or CD8asignal nucleic acid sequence
                                              (SEQ ID NO: 2)
ATGGCCCTACCTGTGACAGCCCTACTGTTACCCCTGGCCCCTCCTTCTGCATGCTG

CTAGACCT

CD8asignalprotein sequence
                                              (SEQ ID NO: 3)
MALPVTALLLPLALLLHAARP CD8a hinge nucleic acid sequence
                                              (SEQ ID NO: 4)
TTCGTGCCCGTGTTCCTGCCCGCCAAACCTACTACTACCCCTGCACCTAGGCCTCC

CACCCCAGCCCCAACAATCGCCAGCCAGCCTCTGTCTCTGCGGCCCGAAGCCTGTAG

ACCTGCTGCCGGCGGAGCCGTGCACACCAGAGGCCTGGACTTCGCCTGCGAC
or

CD8a hinge nucleic acid sequence
                                              (SEQ ID NO: 5)
TTTGTGCCTGTATTTCTGCCTGCCAAGCCCCACCACAACACCTGCCCCTAGACCA

CCCACCCCTGCCCCCACCATTGCTTCTCAGCCCCTTAGCTTAAGACCTGAAGCCTGTA

GACCTGCTGCTGGGGGGGCTGTGCACACAAGAGGCCTGGACTTTGCCTGTGAC

CD8a hinge protein sequence
                                              (SEQ ID NO: 6)
FVPVFLPAKPTTTPAPRPPTPAPTIASQPLSLRPEACRPAAGGAVHTRGLDFACD CD8a TM nucleic acid sequence
                                              (SEQ ID NO: 7)
ATCTACATCTGGGCCCCTCTGGCCGGCACCTGTGGCGTGCTGCTGCTGAGCCTGG TGATCACCCTGTACTGCAACCACCGGAAC
or
```

-continued

CD8a TM nucleic acid sequence
                                         (SEQ ID NO: 8)
ATCTACATCTGGGCCCCCCTGGCTGGCACCTGTGGGGTGCTGCTGCTGAGCCTGG

TGATCACCCCTGTACTGCAACCACAGAAAC

CD8a TM protein sequence
                                         (SEQ ID NO: 9)
IYIWAPLAGTCGVLLLSLVITLYCNHRN 4-1BB intracellular domain nucleic acid sequence
                                         (SEQ ID NO: 10)
AAACGGGGCAGAAAGAAACTCCTGTATATATTCAAACAACCATTTATGAGACCA

GTACAAACTACTCAAGAGGAAGATGGCTGTAGCTGCCGATTTCCAGAAGAAGAAGA

AGGAGGATGTGAACTG
or 4-1BB intracellular domain nucleic acid sequence
                                         (SEQ ID NO: 11)
AAGAGAGGCAGAAAGAAGCTGCTGTACATCTTCAAGCAGCCCTTCATGAGACCT

GTGCAGACCACCCAAGAGGAGGATGGCTGCAGCTGCAGATTCCCTGAGGAGGAGGA

GGGGGGCTGTGAGCTG 4-1BB intracellular domain protein sequence
                                         (SEQ ID NO: 12)
KRGRKKLLYIFKQPFMRPVQTTQEEDGCSCRFPEEEEGGCEL CD3z intracellular signaling domain nucleic acid sequence
                                         (SEQ ID NO: 13)
AGAGTGAAGTTCAGCAGATCCGCCGACGCCCCTGCCTACCAGCAGGGACAGAAC

CAGCTGTACAACGAGCTGAACCTGGGCAGACGGGAAGAGTACGACGTGCTGGACAA

GCGGAGAGGCCGGGACCCCGAGATGGGCGGAAAGCCCAGACGGAAGAACCCCCAG

GAAGGCCTGTATAACGAACTGCAGAAAGACAAGATGGCCGAGGCCTACAGCGAGAT

CGGCATGAAGGGCGAGCGGAGGCGCGGCAAGGGCCACGATGGCCTGTACCAGGGC

CTGAGCACCGCCACCAAGGACACCTACGACGCCCTGCACATGCAGGCCCTGCCCCCC

AGA
or

CD3z intracellular signaling domain nucleic acid sequence
                                         (SEQ ID NO: 14)
AGAGTGAAGTTCAGCAGATCTGCTGATGCCCCTGCCTATCAGCAAGGGCAGAAT

CAGCTGTACAATGAGCTGAATCTGGGCAGAAGAGAGGAGTATGATGTGCTGGACAA

GAGAAGAGGCAGAGACCCTGAGATGGGGGGCAAGCCTAGAAGAAAGAACCCCCAA

GAGGGCCTGTATAATGAGCTGCAGAAGGACAAGATGGCTGAGGCCTACTCTGAGAT

TGGCATGAAGGGGGAGAGAAGAAGAGGCAAGGGCCATGATGGCCTGTACCAAGGC

CTGAGCACAGCCACCAAGGACACCTATGATGCCCTACACATGCAAGCTCTGCCTCCT

AGA

CD3z intracellular signaling domain protein sequence
                                         (SEQ ID NO: 15)
RVKFSRSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALPPR

Cleaving peptide T2A nucleic acid sequence
                                         (SEQ ID NO: 16)
GAGGGAAGGGGCAGCTTATTAACATGTGGCGATGTGGAAGAGAACCCCGGTCCC
or cleaving peptide T2A nucleic acid sequence
                                         (SEQ ID NO: 17)
GAAGGAAGGGGCAGCCTACTGACCTGTGGGGATGTGGAGGAGAACCCTGGCCCC -continued Cleaving peptide T2A protein sequence
(SEQ ID NO: 18)
EGRGSLLTCGDVEENPGP CSF2RA signal nucleic acid sequence
(SEQ ID NO: 19)
ATGCTGCTGCTCGTGACCTCTTACTGTTATGTGAGCTGCCCCACCCCGCTTTTTTA CTGATCCCT
or CSF2RA signal nucleic acid sequence
(SEQ ID NO: 20)
ATGTTGCTATTAGTAACCAGCCTGCTGCTGTGTGAGCTGCCCCACCCTGCCTTCCT

GTTAATCCCA

CSF2RA signal protein sequence
(SEQ ID NO: 21)
MLLLVTSLLLCELPHPAFLLIP tEGFR nucleic acid sequence
(SEQ ID NO: 22)
CGTAAGGTGTGTAACGGAATCGGCATTGGCGAGTTCAAGGACTCTTTAAGCATCA

ACGCCACAAACATCAAGCACTTCAAGAATTGTACCTCCATCAGCGGCGATTTACACA

TTCTCCCCGTGGCTTTTCGTGGCGATTCCTTCACCCACACCCCCCCTCTGGACCCCCA

AGAGCTGGACATTTTAAAAACCGTGAAGGAGATCACCGGCTTTCTGCTGATCCAAGC

TTGGCCCGAGAATCGTACCGACCTCCACGCCTTCGAGAATTTAGAGATTATTCGTGG

AAGGACCAAGCAGCACGGCCAGTTCTCTTTAGCCGTCGTGTCTTTAAACATTACCAG

CCTCGGTTTAAGGTCTTTAAAGGAGATTAGCGACGGCGACGTGATCATCTCCGGCAA

CAAGAACCTCTGCTACGCCAACACCATCAACTGGAAGAAGCTGTTCGGAACCAGCG

GCCAAAAGACCAAGATCATCAGCAATCGTGGAGAGAACTCTTGTAAGGCCACTGGT

CAAGTTTGCCACGCCCTCTGTAGCCCCGAAGGATGTTGGGGCCCCGAGCCTAGGGAC

TGTGTTAGCTGCAGAAACGTGAGCAGAGGCAGAGAGTGTGTGGACAAATGCAATTT

ACTGGAAGGAGAGCCTAGGGAGTTCGTGGAGAACAGCGAATGTATCCAGTGCCACC

CCGAGTGTTTACCTCAAGCCATGAACATCACTTGTACCGGAAGGGGCCCCGATAACT

GCATCCAATGCGCCCACTACATCGACGGACCCCACTGCGTGAAAACTTGTCCCGCCG

GAGTGATGGGAGAGAATAACACTTTAGTGTGGAAGTACGCCGACGCTGGCCACGTC

TGCCATCTGTGCCACCCCAACTGTACCTACGGCTGCACTGGTCCCGGTTTAGAGGGA

TGTCCTACCAACGGCCCCAAGATCCCCTCCATCGCCACCGGAATGGTGGGCGCTCTG

TTATTACTGCTGGTGGTGGCTCTGGGCATCGGTTTATTCATG
or tEGFR nucleic acid sequence
(SEQ ID NO: 23)
CGAAAGGTATGTAATGGCATTGGCATTGGGGAGTTTAAGGACAGCCTGAGCATC

AATGCCACCAACATCAAGCACTTCAAGAACTGCACAAGCATCAGTGGGGACTTGCA

CATCCTGCCTGTGGCCTTCAGAGGGGACAGCTTCACCCACACCCCCCCCCCTGGACCC

CCAAGAGCTGGACATCCTGAAGACAGTGAAGGAGATCACTGGCTTCTTGCTGATCCA

AGCCTGGCCTGAGAACAGAACAGACCTGCATGCCTTTGAGAACCTGGAGATCATCA

GAGGCAGAACCAAGCAGCATGGGCAGTTCAGCCTGGCTGTGGTGAGCCTGAACATC

ACAAGCCTGGGCCTGAGAAGCTTAAAGGAGATCTCTGATGGGGATGTGATCATCTCT

GGCAACAAGAACCTGTGCTATGCCAACACCATCAACTGGAAGAAGCTGTTTGGCAC

CTCTGGGCAGAAGACCAAGATCATCAGCAACAGAGGGGAGAACTCCTGTAAGGCCA

-continued

CTGGCCAAGTGTGTCATGCCCTATGCAGCCCTGAGGGGTGCTGGGGCCCTGAGCCTA

GAGACTGTGTGAGCTGCAGAAATGTGAGCAGAGGCAGAGAGTGTGTGGACAAGTGC

AACCTGCTGGAGGGGGAGCCTAGAGAGTTTGTGGAGAACTCTGAGTGTATTCAGTGT

CATCCTGAGTGCCTGCCCCAAGCCATGAACATCACCTGCACTGGCAGAGGCCCTGAC

AACTGCATTCAGTGTGCCCACTACATTGATGGCCCCCACTGTGTGAAGACCTGCCCT

GCTGGGGTGATGGGGGAGAACAACACCCTGGTGTGGAAGTATGCTGATGCTGGCCA

TGTGTGTCACCTGTGCCATCCCAACTGCACCTATGGCTGCACTGGCCCTGGCCTGGA

GGGCTGCCCCACCAATGGTCCCAAGATTCCTAGCATTGCCACTGGCATGGTGGGGGC

CCTGCTCCTACTTCTGGTGGTTGCCCTGGGCATTGGCCTGTTCATG tEGFR protein sequence (SEQ ID NO: 24)

RKVCNGIGIGEFKDSLSINATNIKHFKNCTSISGDLHILPVAFRGDSFTHTPPLDPQELD

ILKTVKEITGFLLIQAWPENRTDLHAFENLEIIRGRTKQHGQFSLAVVSLNITSLGLRSLKE

ISDGDVIISGNKNLCYANTINWKKLFGTSGQKTKIISNRGENSCKATGQVCHALCSPEGC

WGPEPRDCVSCRNVSRGRECVDKCNLLEGEPREFVENSECIQCHPECLPQAMNITCTGR

GPDNCIQCAHYIDGPHCVKTCPAGVMGENNTLVWKYADAGHVCHLCHPNCTYGCTGP

GLEGCPTNGPKIPSIATGMVGALLLLLVVALGIGLFM

Scfv 06 nucleic acid sequence (SEQ ID NO: 25)

CAGGCTGTGCTGACTCAGCCACCCTCAGCGTCTGCGACCCCCGGGCAGAGGGTCT

CCATCTCCTGTTCGGGGAGCAGCTCCAACATCGGAAGGAATACTGTTAATTGGTACC

AGCACCTCCCTGGAACGGCCCCCAAACTCCTCATTTATAGTAATGATCATCGGCCCT

CAGGGGTCCCTGACCGATTCTCTGGCTCCCAGTCTGGCACCTCAGCCTCCCTGGCCA

TCAGTGGGCTCCAGTCTGAGGATGAGGCTGATTATTACTGTGCATCATGGGATGACA

GCCTGACTGGATGGGTGTTCGGCGGAGGGACCAAGGTCACCGTCCTAGGTTCTAGAG

GTGGTGGTGGTAGCGGCGGCGGCGGCTCTGGTGGTGGTGGATCCCTCGAGATGGCCC

AGGTGCAGCTGGTGCAGTCTGGGGCTGAGGTGAAGAAGGCTGGGTCCTCGCTGAAG

GTCTCGTGCAAGGCTAATGGAGGCAGTTTCACCAACTATCTTATCAACTGGGTGCGC

CAGGCCCCTGGACAGGGGCTTGAGTGGATGGGAGGGATCATCCCTGTCTATGGAAC

ACCAATCTACTCACAGAAATTCCAGGGCAGAGTCACATTTACCGCGGACGAGCCCA

CGAGGACAGCCTACATGGAACTGAGCAGCCTGACATTTGAGGACACGGCCGTGTAT

TATTGTGTGAGAGAAGACGAAGGCTACGGTGACCTTTATCTCGCCTACTGGGGACAG

GGGACCCTGGTCACCGTCTCCTCA

Scfv 06 protein sequence (SEQ ID NO: 26)

QAVLTQPPSASATPGQRVSISCSGSSSNIGRNTVNWYQHLPGTAPKLLIYSNDHRPSG

VPDRFSGSQSGTSASLAISGLQSEDEADYYCASWDDSLTGWVFGGGTKVTVLGSRGGG

GSGGGGSGGGGSLEMAQVQLVQSGAEVKKAGSSLKVSCKANGGSFTNYLINWVRQAP

GQGLEWMGGIIPVYGTPIYSQKFQGRVTFTADEPTRTAYMELSSLTFEDTAVYYCVRED

EGYGDLYLAYWGQGTLVTVSS

VH06 nucleic acid sequence (SEQ ID NO: 27)

ATGGCCCAGGTGCAGCTGGTGCAGTCTGGGGCTGAGGTGAAGAAGGCTGGGTCC

TCGCTGAAGGTCTCGTGCAAGGCTAATGGAGGCAGTTTCACCAACTATCTTATCAAC

TGGGTGCGCCAGGCCCCTGGACAGGGGCTTGAGTGGATGGGAGGGATCATCCCTGT

-continued

```
CTATGGAACACCAATCTACTCACAGAAATTCCAGGGCAGAGTCACATTTACCGCGGA

CGAGCCCACGAGGACAGCCTACATGGAACTGAGCAGCCTGACATTTGAGGACACGG

CCGTGTATTATTGTGTGAGAGAAGACGAAGGCTACGGTGACCTTTATCTCGCCTACT

GGGGACAGGGGACCCTGGTCACCGTCTCCTCA
```

VH06 protein sequence
                                              (SEQ ID NO: 28)
```
MAQVQLVQSGAEVKKAGSSLKVSCKANGGSFTNYLINWVRQAPGQGLEWMGGIIP

VYGTPIYSQKFQGRVTFTADEPTRTAYMELSSLTFEDTAVYYCVREDEGYGDLYLAYW

GQGTLVTVSS
```

VL06 nucleic acid sequence
                                              (SEQ ID NO: 29)
```
CAGGCTGTGCTGACTCAGCCACCCTCAGCGTCTGCGACCCCCGGGCAGAGGGTCT

CCATCTCCTGTTCGGGGAGCAGCTCCAACATCGGAAGGAATACTGTTAATTGGTACC

AGCACCTCCCTGGAACGGCCCCCAAACTCCTCATTTATAGTAATGATCATCGGCCCT

CAGGGGTCCCTGACCGATTCTCTGGCTCCCAGTCTGGCACCTCAGCCTCCCTGGCCA

TCAGTGGGCTCCAGTCTGAGGATGAGGCTGATTATTACTGTGCATCATGGGATGACA

GCCTGACTGGATGGGTGTTCGGCGGAGGGACCAAGGTCACCGTCCTAGGT
```

VL06 protein sequence
                                              (SEQ ID NO: 30)
```
QAVLTQPPSASATPGQRVSISCSGSSSNIGRNTVNWYQHLPGTAPKLLIYSNDHRPSG

VPDRFSGSQSGTSASLAISGLQSEDEADYYCASWDDSLTGWVFGGGTKVTVLG
```

VHH 09 nucleic acid sequence
                                              (SEQ ID NO: 31)
```
GAAGTTCAGCTGCTGGAAAGCGGTGGTGGTCTGGTTCAGCCTGGTGGTAGCCTGC

GTCTGAGCTGTGCAGCAAGCGGTTTTACCTTTAACATCGATGCCATGGGTTGGGTTC

GTCAGGCACCTGGTAAAGGTCTGGAATGGGTTAGCAGCATCAGCAGCAGCGGCGGC

ACCACCTATTATGCAGATAGCGTTAAAGGTCGTTTTTACCATTAGCCGTGATAACAGC

AAAAATACCCTGTACCTGCAGATGAATAGTCTGCGTGCAGAGGATACCGCAGTGTAT

TATTGTGCGCGCTCTCGTTACTCTGTTCCGGACGGTCGTGGTTCTTACGATGTTTGGG

GTCAAGGTACTCTGGTGACCGTCTCCTCA
```
or

VHH 09 nucleic acid sequence
                                              (SEQ ID NO: 32)
```
GAGGTGCAACTTCTTGAGTCTGGGGGGGGCTTGGTGCAGCCTGGGGGCAGTCTG

AGACTGAGCTGTGCTGCCTCTGGCTTTACCTTCAACATTGATGCCATGGGTTGGGTA

AGACAAGCCCCTGGCAAGGGTCTGGAGTGGGTGAGCAGCATCAGCTCTTCTGGGGG

CACTACCTACTATGCTGACTCTGTGAAGGGCAGATTCACCATCAGCAGAGACAACAG

CAAGAACACCCTGTACCTGCAAATGAATAGCCTTAGGGCTGAGGACACAGCTGTAT

ACTACTGTGCTAGAAGCAGATACTCTGTGCCTGATGGCAGAGGCAGCTATGATGTGT

GGGGCCAAGGGACCTTGGTCACAGTGAGCTCT
```

VHH 09 protein sequence
                                              (SEQ ID NO: 33)
```
EVQLLESGGGLVQPGGSLRLSCAASGFTFNIDAMGWVRQAPGKGLEWVSSISSSGGT

TYYADSVKGRFTISRDNSKNTLYLQMNSLRAEDTAVYYCARSRYSVPDGRGSYDVWG

QGTLVTVSS
```

-continued

VHH13 nucleic acid sequence (SEQ ID NO: 34)

GAAGTTCAGCTGCTGGAAAGCGGTGGTGGTCTGGTTCAGCCTGGTGGTAGCCTGC

GTCTGAGCTGTGCAGCAAGCGGTTTTACCTTTAGCAGCGAAGCCATGGGTTGGGTTC

GTCAGGCACCTGGTAAAGGTCTGGAATGGGTTAGCAGCATCAACGGCAGCGGCCGC

AACACCTATTATGCAGATAGCGTTAAAGGTCGTTTTACCATTAGCCGTGATAACAGC

AAAAATACCCTGTACCTGCAGATGAATAGTCTGCGTGCAGAGGATACCGCAGTGTAT

TACTGTGCGCGCAAACATGGTGAATACTACGACTCTGGTTACGATGTTTGGGGTCAA

GGTACTCTGGTGACCGTCTCCTCA
or

VHH13 nucleic acid sequence (SEQ ID NO: 35)

GAGGTGCAGCTACTGGAATCTGGGGGGGGGCTTAGTTCAGCCTGGTGGTAGCCTTA

GATTAAGCTGTGCTGCATCTGGCTTCACCTTTAGCTCTGAGGCCATGGGTTGGGTAA

GACAAGCCCCTGGCAAGGGTCTGGAGTGGGTGAGCAGCATCAATGGCTCTGGCAGA

AACACCTATTATGCTGATTCTGTGAAGGGCAGATTCACCATCAGCAGAGACAACAGC

AAGAACACCCTGTACCTGCAGATGAACAGCCTCAGAGCTGAAGACACAGCTGTGTA

TTATTGTGCTAGAAAACATGGGGAGTACTATGACTCTGGCTATGATGTGTGGGGGCA

AGGCACCTTAGTGACAGTGTCATCT

VHH13 protein sequence (SEQ ID NO: 36)

EVQLLESGGGLVQPGGSLRLSCAASGFTFSSEAMGWVRQAPGKGLEWVSSINGSGR

NTYYADSVKGRFTISRDNSKNTLYLQMNSLRAEDTAVYYCARKHGEYYDSGYDVWGQ

GTLVTVSS

VHH 20 nucleic acid sequence (SEQ ID NO: 37)

GAAGTTCAGCTGCTGGAAAGCGGTGGTGGTCTGGTTCAGCCTGGTGGTAGCCTGC

GTCTGAGCTGTGCAGCAAGCGGTTTTACCTTTAGCAGCTATGCCATGGGTTGGGTTC

GTCAGGCACCTGGTAAAGGTCTGGAATGGGTTAGCAGCATCAGCGGCTATGGCGAA

GAAACCTATTATGCAGATAGCGTTAAAGGTCGTTTTACCATTAGCCGTGATAACAGC

AAAAATACCCTGTACCTGCAGATGAATAGTCTGCGTGCAGAGGATACCGCAGTGTAT

TATTGTGCGCGCTTCTACTACCGTTACTGGAAAGAATTCGATTACTGGGGTCAAGGT

ACTCTGGTGACCGTCTCCTCA
or

VHH 20 nucleic acid sequence (SEQ ID NO: 38)

GAGGTTCAGCTCCTGGAATCTGGGGGGGGGCTGGTTCAACCTGGGGGCTCACTG

AGGCTGAGCTGTGCTGCCTCTGGATTTACCTTTAGCAGCTATGCCATGGGTTGGGTTC

GTCAGGCCCCTGGCAAGGGCCTGGAATGGGTTAGCAGCATTAGTGGTTATGGGGAG

GAGACCTATTATGCTGACTCTGTGAAAGGCAGATTTACCATCAGCAGAGATAATAGC

AAAAATACCCTGTACCTACAAATGAACAGCCTGAGAGCTGAGGACACAGCTGTGTA

CTACTGTGCTAGATTCTACTACCGTTACTGGAAAGAGTTTGACTACTGGGGCCAAGG

CACCCTGGTGACAGTGTCATCC

VHH20 protein sequence (SEQ ID NO: 39)

EVQLLESGGGLVQPGGSLRLSCAASGFTFSSYAMGWVRQAPGKGLEWVSSISGYGE

ETYYADSVKGRFTISRDNSKNTLYLQMNSLRAEDTAVYYCARFYYRYWKEFDYWGQG

TLVTVSS

VHH21 nucleic acid sequence (SEQ ID NO: 40)

GAAGTTCAGCTGCTGGAAAGCGGTGGTGGTCTGGTTCAGCCTGGTGGTAGCCTGC

GTCTGAGCTGTGCAGCAAGCGGTTTTACCTTTAGCAACTATGCCATGGGTTGGGTTC

GTCAGGCACCTGGTAAAGGTCTGGAATGGGTTAGCAGCATCACCGGCCTGGGGGC

AACATGTATTATGCAGATAGCGTTAAAGGTCGTTTTACCATTAGCCGTGATAACAGC

AAAAATACCCTGTACCTGCAGATGAATAGTCTGCGTGCAGAGGATACCGCAGTGTAT

TATTGTGCGCGCATGTACTACTCTCAGGGTGTTAACAACTACTCTTACCCGTCTACTG

ATATCTGGGGTCAAGGTACTCTGGTGACCGTCTCCTCA
or

VHH21 nucleic acid sequence (SEQ ID NO: 41)

GAGGTGCAGCTGCTGGAGTCTGGGGGGGGCTTGGTTCAACCTGGGGGAAGCCTG

AGGCTGAGCTGTGCTGCCTCTGGATTCACCTTCAGCAATTATGCCATGGGGTGGGTT

AGACAAGCCCCTGGCAAGGGCCTGGAGTGGGTGTCAAGCATCACTGGCCTGGGGGG

CAACATGTATTATGCTGACTCTGTGAAAGGCAGATTTACCATCTCTAGAGACAATAG

CAAAAATACCCTCTATCTGCAGATGAATAGCCTGAGAGCTGAGGACACAGCTGTGTA

CTATTGTGCTAGAATGTACTACAGCCAAGGGGTGAACAACTACAGCTACCCTAGTAC

TGATATATGGGGCCAAGGTACTCTGGTGACCGTCTCCAGC

VHH21 protein sequence (SEQ ID NO: 42)

EVQLLESGGGLVQPGGSLRLSCAASGFTFSNYAMGWVRQAPGKGLEWVSSITGLGG

NMYYADSVKGRFTISRDNSKNTLYLQMNSLRAEDTAVYYCARMYYSQGVNNYSYPST

DIWGQGTLVTVSS

Whitlow Linkernucleic acid sequence (SEQ ID NO: 43)

GGCAGCACCTCTGGCTCTGGCAAGCCTGGCTCTGGGGAGGGCTCAACA

Whitlow Linkerprotein sequence (SEQ ID NO: 44)

GSTSGSGKPGSGEGST pXL1416 CAR nucleic acid sequence (SEQ ID NO: 45)

ATGGCCCTGCCTGTGACAGCTCTGCTCCTCCCTCTGGCCCTGCTGCTCCATGCCGC

CAGACCCCAGGCTGTGCTGACTCAGCCACCCTCAGCGTCTGCGACCCCCGGGCAGAG

GGTCTCCATCTCCTGTTCGGGGAGCAGCTCCAACATCGGAAGGAATACTGTTAATTG

GTACCAGCACCTCCCTGGAACGGCCCCCAAACTCCTCATTTATAGTAATGATCATCG

GCCCTCAGGGGTCCCTGACCGATTCTCTGGCTCCCAGTCTGGCACCTCAGCCTCCCTG

GCCATCAGTGGGCTCCAGTCTGAGGATGAGGCTGATTATTACTGTGCATCATGGGAT

GACAGCCTGACTGGATGGGTGTTCGGCGGAGGGACCAAGGTCACCGTCCTAGGTTCT

AGAGGTGGTGGTGGTAGCGGCGGCGGCGGCTCTGGTGGTGGTGGATCCCTCGAGAT

GGCCCAGGTGCAGCTGGTGCAGTCTGGGGCTGAGGTGAAGAAGGCTGGGTCCTCGC

TGAAGGTCTCGTGCAAGGCTAATGGAGGCAGTTTCACCAACTATCTTATCAACTGGG

TGCGCCAGGCCCCTGGACAGGGGCTTGAGTGGATGGGAGGGATCATCCCTGTCTATG

-continued

```
GAACACCAATCTACTCACAGAAATTCCAGGGCAGAGTCACATTTACCGCGGACGAG

CCCACGAGGACAGCCTACATGGAACTGAGCAGCCTGACATTTGAGGACACGGCCGT

GTATTATTGTGTGAGAGAAGACGAAGGCTACGGTGACCTTTATCTCGCCTACTGGGG

ACAGGGGACCCTGGTCACCGTCTCCTCATTCGTGCCCGTGTTCCTGCCCGCCAAACC

TACTACTACCCCTGCACCTAGGCCTCCCACCCCAGCCCCAACAATCGCCAGCCAGCC

TCTGTCTCTGCGGCCCGAAGCCTGTAGACCTGCTGCCGGCGGAGCCGTGCACACCAG

AGGCCTGGACTTCGCCTGCGACATCTACATCTGGGCCCCTCTGGCCGGCACCTGTGG

CGTGCTGCTGCTGAGCCTGGTGATCACCCTGTACTGCAACCACCGGAACAAACGGGG

CAGAAAGAAACTCCTGTATATATTCAAACAACCATTTATGAGACCAGTACAAACTAC

TCAAGAGGAAGATGGCTGTAGCTGCCGATTTCCAGAAGAAGAAGAAGGAGGATGTG

AACTGAGAGTGAAGTTCAGCAGATCCGCCGACGCCCCTGCCTACCAGCAGGGACAG

AACCAGCTGTACAACGAGCTGAACCTGGGCAGACGGGAAGAGTACGACGTGCTGGA

CAAGCGGAGAGGCCGGGACCCCGAGATGGGCGGAAAGCCCAGACGGAAGAACCCC

CAGGAAGGCCTGTATAACGAACTGCAGAAAGACAAGATGGCCGAGGCCTACAGCGA

GATCGGCATGAAGGGCGAGCGGAGGCGCGGCAAGGGCCACGATGGCCTGTACCAGG

GCCTGAGCACCGCCACCAAGGACACCTACGACGCCCTGCACATGCAGGCCCTGCCC

CCCAGA
``` pXL1416 CAR protein sequence (SEQ ID NO: 46)

```
MALPVTALLLPLALLLHAARPQAVLTQPPSASATPGQRVSISCSGSSSNIGRNTVNWY

QHLPGTAPKLLIYSNDHRPSGVPDRFSGSQSGTSASLAISGLQSEDEADYYCASWDDSLT

GWVFGGGTKVTVLGSRGGGGSGGGGSGGGGSLEMAQVQLVQSGAEVKKAGSSLKVSC

KANGGSFTNYLINWVRQAPGQGLEWMGGIIPVYGTPIYSQKFQGRVTFTADEPTRTAYM

ELSSLTFEDTAVYYCVREDEGYGDLYLAYWGQGTLVTVSSFVPVFLPAKPTTTPAPRPPT

PAPTIASQPLSLRPEACRPAAGGAVHTRGLDFACDIYIWAPLAGTCGVLLLSLVITLYCNH

RNKRGRKKLLYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKDKMAEAYS

EIGMKGERRRGKGHDGLYQGLSTATKDTYDALHMQALPPR
``` pXL1394 CAR nucleic acid sequence (SEQ ID NO: 47)

```
ATGGCCCTGCCTGTGACAGCTCTGCTCCTCCCTCTGGCCCTGCTGCTCCATGCCGC

CAGACCCGAAGTTCAGCTGCTGGAAAGCGGTGGTGGTCTGGTTCAGCCTGGTGGTAG

CCTGCGTCTGAGCTGTGCAGCAAGCGGTTTTACCTTTAACATCGATGCCATGGGTTG

GGTTCGTCAGGCACCTGGTAAAGGTCTGGAATGGGTTAGCAGCATCAGCAGCAGCG

GCGGCACCACCTATTATGCAGATAGCGTTAAAGGTCGTTTTACCATTAGCCGTGATA

ACAGCAAAAATACCCTGTACCTGCAGATGAATAGTCTGCGTGCAGAGGATACCGCA

GTGTATTATTGTGCGCGCTCTCGTTACTCTGTTCCGGACGGTCGTGGTTCTTACGATG

TTTGGGGTCAAGGTACTCTGGTGACCGTCTCCTCATTCGTGCCCGTGTTCCTGCCCGC

CAAACCTACTACTACCCCTGCACCTAGGCCTCCCACCCCAGCCCCAACAATCGCCAG

CCAGCCTCTGTCTCTGCGGCCCGAAGCCTGTAGACCTGCTGCCGGCGGAGCCGTGCA

CACCAGAGGCCTGGACTTCGCCTGCGACATCTACATCTGGGCCCCTCTGGCCGGCAC

CTGTGGCGTGCTGCTGCTGAGCCTGGTGATCACCCTGTACTGCAACCACCGGAACAA
```

-continued

```
ACGGGGCAGAAAGAAACTCCTGTATATATTCAAACAACCATTTATGAGACCAGTAC

AAACTACTCAAGAGGAAGATGGCTGTAGCTGCCGATTTCCAGAAGAAGAAGAAGGA

GGATGTGAACTGAGAGTGAAGTTCAGCAGATCCGCCGACGCCCCTGCCTACCAGCA

GGGACAGAACCAGCTGTACAACGAGCTGAACCTGGGCAGACGGGAAGAGTACGAC

GTGCTGGACAAGCGGAGAGGCCGGGACCCCGAGATGGGCGGAAAGCCCAGACGGA

AGAACCCCCAGGAAGGCCTGTATAACGAACTGCAGAAAGACAAGATGGCCGAGGCC

TACAGCGAGATCGGCATGAAGGGCGAGCGGAGGCGCGGCAAGGGCCACGATGGCCT

GTACCAGGGCCTGAGCACCGCCACCAAGGACACCTACGACGCCCTGCACATGCAGG

CCCTGCCCCCCAGA
``` pXL1394 CAR protein sequence
(SEQ ID NO: 48)
```
MALPVTALLLPLALLLHAARPEVQLLESGGGLVQPGGSLRLSCAASGFTFNIDAMGW

VRQAPGKGLEWVSSISSSGGTTYYADSVKGRFTISRDNSKNTLYLQMNSLRAEDTAVYY

CARSRYSVPDGRGSYDVWGQGTLVTVSSFVPVFLPAKPTTTPAPRPPTPAPTIASQPLSLR

PEACRPAAGGAVHTRGLDFACDIYIWAPLAGTCGVLLLSLVITLYCNHRNKRGRKKLLY

IFKQPFMRPVQTTQEEDGCSCRFPEEEEGGCELRVKFSRSADAPAYQQGQNQLYNELNL

GRREEYDVLDKRRGRDPEMGGKPRRKNPQEGLYNELQKDKMAEAYSEIGMKGERRRG

KGHDGLYQGLSTATKDTYDALHMQALPPR
``` pXL1398 CAR nucleic acid sequence
(SEQ ID NO: 49)
```
ATGGCCCTGCCTGTGACAGCTCTGCTCCTCCCTCTGGCCCTGCTGCTCCATGCCGC

CAGACCCGAAGTTCAGCTGCTGGAAAGCGGTGGTGGTCTGGTTCAGCCTGGTGGTAG

CCTGCGTCTGAGCTGTGCAGCAAGCGGTTTTACCTTTAGCAGCGAAGCCATGGGTTG

GGTTCGTCAGGCACCTGGTAAAGGTCTGGAATGGGTTAGCAGCATCAACGGCAGCG

GCCGCAACACCTATTATGCAGATAGCGTTAAAGGTCGTTTTACCATTAGCCGTGATA

ACAGCAAAAATACCCTGTACCTGCAGATGAATAGTCTGCGTGCAGAGGATACCGCA

GTGTATTACTGTGCGCGCAAACATGGTGAATACTACGACTCTGGTTACGATGTTTGG

GGTCAAGGTACTCTGGTGACCGTCTCCTCATTCGTGCCCGTGTTCCTGCCCGCCAAAC

CTACTACTACCCCTGCACCTAGGCCTCCCACCCCAGCCCCAACAATCGCCAGCCAGC

CTCTGTCTCTGCGGCCCGAAGCCTGTAGACCTGCTGCCGGCGGAGCCGTGCACACCA

GAGGCCTGGACTTCGCCTGCGACATCTACATCTGGGCCCCTCTGGCCGGCACCTGTG

GCGTGCTGCTGCTGAGCCTGGTGATCACCCTGTACTGCAACCACCGGAACAAACGGG

GCAGAAAGAAACTCCTGTATATATTCAAACAACCATTTATGAGACCAGTACAAACTA

CTCAAGAGGAAGATGGCTGTAGCTGCCGATTTCCAGAAGAAGAAGAAGGAGGATGT

GAACTGAGAGTGAAGTTCAGCAGATCCGCCGACGCCCCTGCCTACCAGCAGGGACA

GAACCAGCTGTACAACGAGCTGAACCTGGGCAGACGGGAAGAGTACGACGTGCTGG

ACAAGCGGAGAGGCCGGGACCCCGAGATGGGCGGAAAGCCCAGACGGAAGAACCC

CCAGGAAGGCCTGTATAACGAACTGCAGAAAGACAAGATGGCCGAGGCCTACAGCG

AGATCGGCATGAAGGGCGAGCGGAGGCGCGGCAAGGGCCACGATGGCCTGTACCAG

GGCCTGAGCACCGCCACCAAGGACACCTACGACGCCCTGCACATGCAGGCCCTGCC

CCCCAGA
```

-continued pXL1398 CAR protein sequence (SEQ ID NO: 50)

MALPVTALLLPLALLLHAARPEVQLLESGGGLVQPGGSLRLSCAASGFTFSSEAMGW

VRQAPGKGLEWVSSINGSGRNTYYADSVKGRFTISRDNSKNTLYLQMNSLRAEDTAVY

YCARKHGEYYDSGYDVWGQGTLVTVSSFVPVFLPAKPTTTPAPRPPTPAPTIASQPLSLR

PEACRPAAGGAVHTRGLDFACDIYIWAPLAGTCGVLLLSLVITLYCNHRNKRGRKKLLY

IFKQPFMRPVQTTQEEDGCSCRFPEEEEGGCELRVKFSRSADAPAYQQGQNQLYNELNL

GRREEYDVLDKRRGRDPEMGGKPRRKNPQEGLYNELQKDKMAEAYSEIGMKGERRRG

KGHDGLYQGLSTATKDTYDALHMQALPPR pXL1423 CAR nucleic acid sequence (SEQ ID NO: 51)

ATGGCCCTGCCTGTGACAGCTCTGCTCCTCCCTCTGGCCCTGCTGCTCCATGCCGC

CAGACCCGAAGTTCAGCTGCTGGAAAGCGGTGGTGGTCTGGTTCAGCCTGGTGGTAG

CCTGCGTCTGAGCTGTGCAGCAAGCGGTTTTACCTTTAGCAGCTATGCCATGGGTTG

GGTTCGTCAGGCACCTGGTAAAGGTCTGGAATGGGTTAGCAGCATCAGCGGCTATGG

CGAAGAAACCTATTATGCAGATAGCGTTAAAGGTCGTTTTACCATTAGCCGTGATAA

CAGCAAAAATACCCTGTACCTGCAGATGAATAGTCTGCGTGCAGAGGATACCGCAG

TGTATTATTGTGCGCGCTTCTACTACCGTTACTGGAAAGAATTCGATTACTGGGGTCA

AGGTACTCTGGTGACCGTCTCCTCATTCGTGCCCGTGTTCCTGCCCGCCAAACCTACT

ACTACCCCTGCACCTAGGCCTCCCACCCCAGCCCCAACAATCGCCAGCCAGCCTCTG

TCTCTGCGGCCCGAAGCCTGTAGACCTGCTGCCGGCGGAGCCGTGCACACCAGAGG

CCTGGACTTCGCCTGCGACATCTACATCTGGGCCCCTCTGGCCGGCACCTGTGGCGT

GCTGCTGCTGAGCCTGGTGATCACCCTGTACTGCAACCACCGGAACAAACGGGGCA

GAAAGAAACTCCTGTATATATTCAAACAACCATTTATGAGACCAGTACAAACTACTC

AAGAGGAAGATGGCTGTAGCTGCCGATTTCCAGAAGAAGAAGAAGGAGGATGTGAA

CTGAGAGTGAAGTTCAGCAGATCCGCCGACGCCCCTGCCTACCAGCAGGGACAGAA

CCAGCTGTACAACGAGCTGAACCTGGGCAGACGGGAAGAGTACGACGTGCTGGACA

AGCGGAGAGGCCGGGACCCCGAGATGGGCGGAAAGCCCAGACGGAAGAACCCCCA

GGAAGGCCTGTATAACGAACTGCAGAAAGACAAGATGGCCGAGGCCTACAGCGAGA

TCGGCATGAAGGGCGAGCGGAGGCGCGGCAAGGGCCACGATGGCCTGTACCAGGGC

CTGAGCACCGCCACCAAGGACACCTACGACGCCCTGCACATGCAGGCCCTGCCCCCC

AGA pXL1423 CAR protein sequence (SEQ ID NO: 52)

MALPVTALLLPLALLLHAARPEVQLLESGGGLVQPGGSLRLSCAASGFTFSSYAMG

WVRQAPGKGLEWVSSISGYGEETYYADSVKGRFTISRDNSKNTLYLQMNSLRAEDTAV

YYCARFYYRYWKEFDYWGQGTLVTVSSFVPVFLPAKPTTTPAPRPPTPAPTIASQPLSLR

PEACRPAAGGAVHTRGLDFACDIYIWAPLAGTCGVLLLSLVITLYCNHRNKRGRKKLLY

IFKQPFMRPVQTTQEEDGCSCRFPEEEEGGCELRVKFSRSADAPAYQQGQNQLYNELNL

GRREEYDVLDKRRGRDPEMGGKPRRKNPQEGLYNELQKDKMAEAYSEIGMKGERRRG

KGHDGLYQGLSTATKDTYDALHMQALPPR

-continued pXL1424 CAR nucleic acid sequence (SEQ ID NO: 53)

ATGGCCCTGCCTGTGACAGCTCTGCTCCTCCCTCTGGCCCTGCTGCTCCATGCCGC

CAGACCCGAAGTTCAGCTGCTGGAAAGCGGTGGTGGTCTGGTTCAGCCTGGTGGTAG

CCTGCGTCTGAGCTGTGCAGCAAGCGGTTTTACCTTTAGCAACTATGCCATGGGTTG

GGTTCGTCAGGCACCTGGTAAAGGTCTGGAATGGGTTAGCAGCATCACCGGCCTGGG

CGGCAACATGTATTATGCAGATAGCGTTAAAGGTCGTTTTACCATTAGCCGTGATAA

CAGCAAAAATACCCTGTACCTGCAGATGAATAGTCTGCGTGCAGAGGATACCGCAG

TGTATTATTGTGCGCGCATGTACTACTCTCAGGGTGTTAACAACTACTCTTACCCGTC

TACTGATATCTGGGGTCAAGGTACTCTGGTGACCGTCTCCTCATTCGTGCCCGTGTTC

CTGCCCGCCAAACCTACTACTACCCCTGCACCTAGGCCTCCCACCCCAGCCCCAACA

ATCGCCAGCCAGCCTCTGTCTCTGCGGCCCGAAGCCTGTAGACCTGCTGCCGGCGGA

GCCGTGCACACCAGAGGCCTGGACTTCGCCTGCGACATCTACATCTGGGCCCCTCTG

GCCGGCACCTGTGGCGTGCTGCTGCTGAGCCTGGTGATCACCCTGTACTGCAACCAC

CGGAACAAACGGGGCAGAAAGAAACTCCTGTATATATTCAAACAACCATTTATGAG

ACCAGTACAAACTACTCAAGAGGAAGATGGCTGTAGCTGCCGATTTCCAGAAGAAG

AAGAAGGAGGATGTGAACTGAGAGTGAAGTTCAGCAGATCCGCCGACGCCCCTGCC

TACCAGCAGGGACAGAACCAGCTGTACAACGAGCTGAACCTGGGCAGACGGGAAGA

GTACGACGTGCTGGACAAGCGGAGAGGCCGGGACCCCGAGATGGGCGGAAAGCCC

AGACGGAAGAACCCCCAGGAAGGCCTGTATAACGAACTGCAGAAAGACAAGATGG

CCGAGGCCTACAGCGAGATCGGCATGAAGGGCGAGCGGAGGCGCGGCAAGGGCCA

CGATGGCCTGTACCAGGGCCTGAGCACCGCCACCAAGGACACCTACGACGCCCTGC

ACATGCAGGCCCTGCCCCCCAGA pXL1424 CAR protein sequence (SEQ ID NO: 54)

MALPVTALLLPLALLLHAARPEVQLLESGGGLVQPGGSLRLSCAASGFTFSNYAMG

WVRQAPGKGLEWVSSITGLGGNMYYADSVKGRFTISRDNSKNTLYLQMNSLRAEDTAV

YYCARMYYSQGVNNYSYPSTDIWGQGTLVTVSSFVPVFLPAKPTTTPAPRPPTPAPTIAS

QPLSLRPEACRPAAGGAVHTRGLDFACDIYIWAPLAGTCGVLLLSLVITLYCNHRNKRG

RKKLLYIFKQPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEAYSEIGMK

GERRRGKGHDGLYQGLSTATKDTYDALHMQALPPR pXL1698 CAR nucleic acid sequence (SEQ ID NO: 55)

ATGGCCCTACCTGTGACAGCCCTACTGTTACCCCTGGCCCTCCTTCTGCATGCTGC

TAGACCTGAGGTGCAGCTACTGGAATCTGGGGGGGGCTTAGTTCAGCCTGGTGGTAG

CCTTAGATTAAGCTGTGCTGCATCTGGCTTCACCTTTAGCTCTGAGGCCATGGGTTGG

GTAAGACAAGCCCCTGGCAAGGGTCTGGAGTGGGTGAGCAGCATCAATGGCTCTGG

CAGAAACACCTATTATGCTGATTCTGTGAAGGGCAGATTCACCATCAGCAGAGACAA

CAGCAAGAACACCCTGTACCTGCAGATGAACAGCCTCAGAGCTGAAGACACAGCTG

TGTATTATTGTGCTAGAAAACATGGGGAGTACTATGACTCTGGCTATGATGTGTGGG

GGCAAGGCACCTTAGTGACAGTGTCATCTGGCAGCACCTCTGGCTCTGGCAAGCCTG

GCTCTGGGGAGGGCTCAACAGAGGTTCAGCTCCTGGAATCTGGGGGGGGGCTGGTT

-continued

```
CAACCTGGGGGCTCACTGAGGCTGAGCTGTGCTGCCTCTGGATTTACCTTTAGCAGC

TATGCCATGGGTTGGGTTCGTCAGGCCCCTGGCAAGGGCCTGGAATGGGTTAGCAGC

ATTAGTGGTTATGGGGAGGAGACCTATTATGCTGACTCTGTGAAAGGCAGATTTACC

ATCAGCAGAGATAATAGCAAAAATACCCTGTACCTACAAATGAACAGCCTGAGAGC

TGAGGACACAGCTGTGTACTACTGTGCTAGATTCTACTACCGTTACTGGAAAGAGTT

TGACTACTGGGGCCAAGGCACCCTGGTGACAGTGTCATCCTTTGTGCCTGTATTTCTG

CCTGCCAAGCCCACCACAACACCTGCCCCTAGACCACCCACCCCTGCCCCCACCATT

GCTTCTCAGCCCCCTTAGCTTAAGACCTGAAGCCTGTAGACCTGCTGCTGGGGGGGCT

GTGCACACAAGAGGCCTGGACTTTGCCTGTGACATCTACATCTGGGCCCCCCTGGCT

GGCACCTGTGGGGTGCTGCTGCTGAGCCTGGTGATCACCCTGTACTGCAACCACAGA

AACAAGAGAGGCAGAAAGAAGCTGCTGTACATCTTCAAGCAGCCCTTCATGAGACC

TGTGCAGACCACCCAAGAGGAGGATGGCTGCAGCTGCAGATTCCCTGAGGAGGAGG

AGGGGGGCTGTGAGCTGAGAGTGAAGTTCAGCAGATCTGCTGATGCCCCTGCCTATC

AGCAAGGGCAGAATCAGCTGTACAATGAGCTGAATCTGGGCAGAAGAGAGGAGTAT

GATGTGCTGGACAAGAGAAGAGGCAGAGACCCTGAGATGGGGGGCAAGCCTAGAA

GAAAGAACCCCCAAGAGGGCCTGTATAATGAGCTGCAGAAGGACAAGATGGCTGAG

GCCTACTCTGAGATTGGCATGAAGGGGGAGAGAAGAAGAGGCAAGGGCCATGATGG

CCTGTACCAAGGCCTGAGCACAGCCACCAAGGACACCTATGATGCCCTACACATGC

AAGCTCTGCCTCCTAGA
``` pXL1698 CAR protein sequence (SEQ ID NO: 56)

```
MEFGLSWLFLVAILKGVQCEVQLLESGGGLVQPGGSLRLSCAASGFTFSSEAMGWV

RQAPGKGLEWVSSINGSGRNTYYADSVKGRFTISRDNSKNTLYLQMNSLRAEDTAVYY

CARKHGEYYDSGYDVWGQGTLVTVSSGSTSGSGKPGSGEGSTEVQLLESGGGLVQPGG

SLRLSCAASGFTFSSYAMGWVRQAPGKGLEWVSSISGYGEETYYADSVKGRFTISRDNS

KNTLYLQMNSLRAEDTAVYYCARFYYRYWKEFDYWGQGTLVTVSSFVPVFLPAKPTTT

PAPRPPTPAPTIASQPLSLRPEACRPAAGGAVHTRGLDFACDIYIWAPLAGTCGVLLLSLV

ITLYCNHRNKRGRKKLLYIFKQPFMRPVQTTQEEDGCSCRFPEEEEGGCELRVKFSRSAD

APAYQQGQNQLYNELNLGRREEYDVLDKRRGRDPEMGGKPRRKNPQEGLYNELQKDK

MAEAYSEIGMKGERRRGKGHDGLYQGLSTATKDTYDALHMQALPPR
``` pXL1700 CAR nucleic acid sequence (SEQ ID NO: 57)

```
ATGGCCCTACCTGTGACAGCCCTACTGTTACCCCTGGCCCTCCTTCTGCATGCTGC

TAGACCTGAGGTTCAGCTCCTGGAATCTGGGGGGGGGGCTGGTTCAACCTGGGGGCTC

ACTGAGGCTGAGCTGTGCTGCCTCTGGATTTACCTTTAGCAGCTATGCCATGGGTTG

GGTTCGTCAGGCCCCTGGCAAGGGCCTGGAATGGGTTAGCAGCATTAGTGGTTATGG

GGAGGAGACCTATTATGCTGACTCTGTGAAAGGCAGATTTACCATCAGCAGAGATA

ATAGCAAAAATACCCTGTACCTACAAATGAACAGCCTGAGAGCTGAGGACACAGCT

GTGTACTACTGTGCTAGATTCTACTACCGTTACTGGAAAGAGTTTGACTACTGGGGC

CAAGGCACCCTGGTGACAGTGTCATCCGGCAGCACCTCTGGCTCTGGCAAGCCTGGC

TCTGGGGAGGGCTCAACAGAGGTGCAGCTACTGGAATCTGGGGGGGGGCTTAGTTCA

GCCTGGTGGTAGCCTTAGATTAAGCTGTGCTGCATCTGGCTTCACCTTTAGCTCTGAG

GCCATGGGTTGGGTAAGACAAGCCCCTGGCAAGGGTCTGGAGTGGGTGAGCAGCAT
```

-continued

```
CAATGGCTCTGGCAGAAACACCTATTATGCTGATTCTGTGAAGGGCAGATTCACCAT

CAGCAGAGACAACAGCAAGAACACCCTGTACCTGCAGATGAACAGCCTCAGAGCTG

AAGACACAGCTGTGTATTATTGTGCTAGAAAACATGGGGAGTACTATGACTCTGGCT

ATGATGTGTGGGGGCAAGGCACCTTAGTGACAGTGTCATCTTTTGTGCCTGTATTTCT

GCCTGCCAAGCCCACCACAACACCTGCCCCTAGACCACCCACCCCTGCCCCCACCAT

TGCTTCTCAGCCCCTTAGCTTAAGACCTGAAGCCTGTAGACCTGCTGCTGGGGGGGC

TGTGCACACAAGAGGCCTGGACTTTGCCTGTGACATCTACATCTGGGCCCCCCTGGC

TGGCACCTGTGGGGTGCTGCTGCTGAGCCTGGTGATCACCCTGTACTGCAACCACAG

AAACAAGAGAGGCAGAAAGAAGCTGCTGTACATCTTCAAGCAGCCCTTCATGAGAC

CTGTGCAGACCACCCAAGAGGAGGATGGCTGCAGCTGCAGATTCCCTGAGGAGGAG

GAGGGGGGCTGTGAGCTGAGAGTGAAGTTCAGCAGATCTGCTGATGCCCCTGCCTAT

CAGCAAGGGCAGAATCAGCTGTACAATGAGCTGAATCTGGGCAGAAGAGAGGAGTA

TGATGTGCTGGACAAGAGAAGAGGCAGAGACCCTGAGATGGGGGGCAAGCCTAGA

AGAAAGAACCCCCAAGAGGGCCTGTATAATGAGCTGCAGAAGGACAAGATGGCTGA

GGCCTACTCTGAGATTGGCATGAAGGGGGGAGAGAAGAAGAGGCAAGGGCCATGATG

GCCTGTACCAAGGCCTGAGCACAGCCACCAAGGACACCTATGATGCCCTACACATG

CAAGCTCTGCCTCCTAGA
``` pXL1700 CAR protein sequence
                                        (SEQ ID NO: 58)

```
MALPVTALLLPLALLLHAARPEVQLLESGGGLVQPGGSLRLSCAASGFTFSSYAMG

WVRQAPGKGLEWVSSISGYGEETYYADSVKGRFTISRDNSKNTLYLQMNSLRAEDTAV

YYCARFYYRYWKEFDYWGQGTLVTVSSGSTSGSGKPGSGEGSTEVQLLESGGGLVQPG

GSLRLSCAASGFTFSSEAMGWVRQAPGKGLEWVSSINGSGRNTYYADSVKGRFTISRDN

SKNTLYLQMNSLRAEDTAVYYCARKHGEYYDSGYDVWGQGTLVTVSSFVPVFLPAKP

TTTPAPRPPTPAPTIASQPLSLRPEACRPAAGGAVHTRGLDFACDIYIWAPLAGTCGVLLL

SLVITLYCNHRNKRGRKKLLYIFKQPFMRPVQTTQEEDGCSCRFPEEEEGGCELRVKFSR

SADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR
``` pXL1702 CAR nucleic acid sequence
                                        (SEQ ID NO: 59)

```
ATGGCCCTACCTGTGACAGCCCTACTGTTACCCCTGGCCCTCCTTCTGCATGCTGC

TAGACCTGAGGTGCAGCTACTGGAATCTGGGGGGGGCTTAGTTCAGCCTGGTGGTAG

CCTTAGATTAAGCTGTGCTGCATCTGGCTTCACCTTTAGCTCTGAGGCCATGGGTTGG

GTAAGACAAGCCCCTGGCAAGGGTCTGGAGTGGGTGAGCAGCATCAATGGCTCTGG

CAGAAACACCTATTATGCTGATTCTGTGAAGGGCAGATTCACCATCAGCAGAGACAA

CAGCAAGAACACCCTGTACCTGCAGATGAACAGCCTCAGAGCTGAAGACACAGCTG

TGTATTATTGTGCTAGAAAACATGGGGAGTACTATGACTCTGGCTATGATGTGTGGG

GGCAAGGCACCTTAGTGACAGTGTCATCTGGCAGCACCTCTGGCTCTGGCAAGCCTG

GCTCTGGGGAGGGCTCAACAGAGGTGCAGCTGCTGGAGTCTGGGGGGGGCTTGGTT

CAACCTGGGGGAAGCCTGAGGCTGAGCTGTGCTGCCTCTGGATTCACCTTCAGCAAT

TATGCCATGGGGTGGGTTAGACAAGCCCCTGGCAAGGGCCTGGAGTGGGTGTCAAG

CATCACTGGCCTGGGGGGCAACATGTATTATGCTGACTCTGTGAAAGGCAGATTTAC
```

CATCTCTAGAGACAATAGCAAAAATACCCTCTATCTGCAGATGAATAGCCTGAGAGC

TGAGGACACAGCTGTGTACTATTGTGCTAGAATGTACTACAGCCAAGGGGTGAACA

ACTACAGCTACCCTAGTACTGATATATGGGGCCAAGGTACTCTGGTGACCGTCTCCA

GCTTTGTGCCTGTATTTCTGCCTGCCAAGCCCACCACAACACCTGCCCCTAGACCACC

CACCCCTGCCCCCACCATTGCTTCTCAGCCCCTTAGCTTAAGACCTGAAGCCTGTAG

ACCTGCTGCTGGGGGGGCTGTGCACACAAGAGGCCTGGACTTTGCCTGTGACATCTA

CATCTGGGCCCCCCTGGCTGGCACCTGTGGGGTGCTGCTGCTGAGCCTGGTGATCAC

CCTGTACTGCAACCACAGAAACAAGAGAGGCAGAAAGAAGCTGCTGTACATCTTCA

AGCAGCCCTTCATGAGACCTGTGCAGACCACCCAAGAGGAGGATGGCTGCAGCTGC

AGATTCCCTGAGGAGGAGGAGGGGGGCTGTGAGCTGAGAGTGAAGTTCAGCAGATC

TGCTGATGCCCCTGCCTATCAGCAAGGGCAGAATCAGCTGTACAATGAGCTGAATCT

GGGCAGAAGAGAGGAGTATGATGTGCTGGACAAGAGAAGAGGCAGAGACCCTGAG

ATGGGGGGCAAGCCTAGAAGAAAGAACCCCCAAGAGGGCCTGTATAATGAGCTGCA

GAAGGACAAGATGGCTGAGGCCTACTCTGAGATTGGCATGAAGGGGGAGAGAAGA

AGAGGCAAGGGCCATGATGGCCTGTACCAAGGCCTGAGCACAGCCACCAAGGACAC

CTATGATGCCCTACACATGCAAGCTCTGCCTCCTAGA pXL1702 CAR protein sequence (SEQ ID NO: 60)

MALPVTALLLPLALLLHAARPEVQLLESGGGLVQPGGSLRLSCAASGFTFSSEAMGW

VRQAPGKGLEWVSSINGSGRNTYYADSVKGRFTISRDNSKNTLYLQMNSLRAEDTAVY

YCARKHGEYYDSGYDVWGQGTLVTVSSGSTSGSGKPGSGEGSTEVQLLESGGGLVQPG

GSLRLSCAASGFTFSNYAMGWVRQAPGKGLEWVSSITGLGGNMYYADSVKGRFTISRD

NSKNTLYLQMNSLRAEDTAVYYCARMYYSQGVNNYSYPSTDIWGQGTLVTVSSFVPVF

LPAKPTTTPAPRPPTPAPTIASQPLSLRPEACRPAAGGAVHTRGLDFACDIYIWAPLAGTC

GVLLLSLVITLYCNHRNKRGRKKLLYIFKQPFMRPVQTTQEEDGCSCRFPEEEEGGCELR

VKFSRSADAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR pXL1704 CAR nucleic acid sequence (SEQ ID NO: 61)

ATGGCCCTACCTGTGACAGCCCTACTGTTACCCCTGGCCCTCCTTCTGCATGCTGC

TAGACCTGAGGTGCAGCTGCTGGAGTCTGGGGGGGGCTTGGTTCAACCTGGGGGAA

GCCTGAGGCTGAGCTGTGCTGCCTCTGGATTCACCTTCAGCAATTATGCCATGGGGT

GGGTTAGACAAGCCCCTGGCAAGGGCCTGGAGTGGGTGTCAAGCATCACTGGCCTG

GGGGGCAACATGTATTATGCTGACTCTGTGAAAGGCAGATTTACCATCTCTAGAGAC

AATAGCAAAAATACCCTCTATCTGCAGATGAATAGCCTGAGAGCTGAGGACACAGC

TGTGTACTATTGTGCTAGAATGTACTACAGCCAAGGGGTGAACAACTACAGCTACCC

TAGTACTGATATATGGGGCCAAGGTACTCTGGTGACCGTCTCCAGCGGCAGCACCTC

TGGCTCTGGCAAGCCTGGCTCTGGGGAGGGCTCAACAGAGGTGCAGCTACTGGAAT

CTGGGGGGGGCTTAGTTCAGCCTGGTGGTAGCCTTAGATTAAGCTGTGCTGCATCTG

GCTTCACCTTTAGCTCTGAGGCCATGGGTTGGGTAAGACAAGCCCCTGGCAAGGGTC

TGGAGTGGGTGAGCAGCATCAATGGCTCTGGCAGAAACACCTATTATGCTGATTCTG

TGAAGGGCAGATTCACCATCAGCAGAGACAACAGCAAGAACACCCTGTACCTGCAG

ATGAACAGCCTCAGAGCTGAAGACACAGCTGTGTATTATTGTGCTAGAAAACATGG

-continued

GGAGTACTATGACTCTGGCTATGATGTGTGGGGGGCAAGGCACCTTAGTGACAGTGTC

ATCTTTTGTGCCTGTATTTCTGCCTGCCAAGCCCACCACAACACCTGCCCCTAGACCA

CCCACCCCTGCCCCCACCATTGCTTCTCAGCCCCTTAGCTTAAGACCTGAAGCCTGTA

GACCTGCTGCTGGGGGGGCTGTGCACACAAGAGGCCTGGACTTTGCCTGTGACATCT

ACATCTGGGCCCCCCTGGCTGGCACCTGTGGGGTGCTGCTGCTGAGCCTGGTGATCA

CCCTGTACTGCAACCACAGAAACAAGAGAGGCAGAAAGAAGCTGCTGTACATCTTC

AAGCAGCCCTTCATGAGACCTGTGCAGACCACCCAAGAGGAGGATGGCTGCAGCTG

CAGATTCCCTGAGGAGGAGGAGGGGGGCTGTGAGCTGAGAGTGAAGTTCAGCAGAT

CTGCTGATGCCCCTGCCTATCAGCAAGGGCAGAATCAGCTGTACAATGAGCTGAATC

TGGGCAGAAGAGAGGAGTATGATGTGCTGGACAAGAGAAGAGGCAGAGACCCTGA

GATGGGGGGCAAGCCTAGAAGAAAGAACCCCCAAGAGGGCCTGTATAATGAGCTGC

AGAAGGACAAGATGGCTGAGGCCTACTCTGAGATTGGCATGAAGGGGGAGAGAAG

AAGAGGCAAGGGCCATGATGGCCTGTACCAAGGCCTGAGCACAGCCACCAAGGACA

CCTATGATGCCCTACACATGCAAGCTCTGCCTCCTAGA pXL1704 CAR protein sequence (SEQ ID NO: 62)
MALPVTALLLPLALLLHAARPEVQLLESGGGLVQPGGSLRLSCAASGFTFSNYAMG

WVRQAPGKGLEWVSSITGLGGNMYYADSVKGRFTISRDNSKNTLYLQMNSLRAEDTAV

YYCARMYYSQGVNNYSYPSTDIWGQGTLVTVSSGSTSGSGKPGSGEGSTEVQLLESGG

GLVQPGGSLRLSCAASGFTFSSEAMGWVRQAPGKGLEWVSSINGSGRNTYYADSVKGR

FTISRDNSKNTLYLQMNSLRAEDTAVYYCARKHGEYYDSGYDVWGQGTLVTVSSFVPV

FLPAKPTTTPAPRPPTPAPTIASQPLSLRPEACRPAAGGAVHTRGLDFACDIYIWAPLAGT

CGVLLLSLVITLYCNHRNKRGRKKLLYIFKQPFMRPVQTTQEEDGCSCRFPEEEEGGCEL

RVKFSRSADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQALPPR pXL1748 CAR nucleic acid sequence (SEQ ID NO: 63)
ATGGCCCTACCTGTGACAGCCCTACTGTTACCCCTGGCCCTCCTTCTGCATGCTGC

TAGACCTGAGGTGCAACTTCTTGAGTCTGGGGGGGGCTTGGTGCAGCCTGGGGGCAG

TCTGAGACTGAGCTGTGCTGCCTCTGGCTTTACCTTCAACATTGATGCCATGGGTTGG

GTAAGACAAGCCCCTGGCAAGGGTCTGGAGTGGGTGAGCAGCATCAGCTCTTCTGG

GGGCACTACCTACTATGCTGACTCTGTGAAGGGCAGATTCACCATCAGCAGAGACAA

CAGCAAGAACACCCTGTACCTGCAAATGAATAGCCTTAGGGCTGAGGACACAGCTG

TATACTACTGTGCTAGAAGCAGATACTCTGTGCCTGATGGCAGAGGCAGCTATGATG

TGTGGGGCCAAGGGACCTTGGTCACAGTGAGCTCTGGCAGCACCTCTGGCTCTGGCA

AGCCTGGCTCTGGGGAGGGCTCAACAGAGGTGCAGCTACTGGAATCTGGGGGGGGC

TTAGTTCAGCCTGGTGGTAGCCTTAGATTAAGCTGTGCTGCATCTGGCTTCACCTTTA

GCTCTGAGGCCATGGGTTGGGTAAGACAAGCCCCTGGCAAGGGTCTGGAGTGGGTG

AGCAGCATCAATGGCTCTGGCAGAAACACCTATTATGCTGATTCTGTGAAGGGCAGA

TTCACCATCAGCAGAGACAACAGCAAGAACACCCTGTACCTGCAGATGAACAGCCT

CAGAGCTGAAGACACAGCTGTGTATTATTGTGCTAGAAAACATGGGGAGTACTATG

ACTCTGGCTATGATGTGTGGGGGCAAGGCACCTTAGTGACAGTGTCATCTTTTGTGC

-continued

CTGTATTTCTGCCTGCCAAGCCCACCACAACACCTGCCCCTAGACCACCCACCCCTG

CCCCCACCATTGCTTCTCAGCCCCTTAGCTTAAGACCTGAAGCCTGTAGACCTGCTGC

TGGGGGGGCTGTGCACACAAGAGGCCTGGACTTTGCCTGTGACATCTACATCTGGGC

CCCCCTGGCTGGCACCTGTGGGGTGCTGCTGCTGAGCCTGGTGATCACCCTGTACTG

CAACCACAGAAACAAGAGAGGCAGAAAGAAGCTGCTGTACATCTTCAAGCAGCCCT

TCATGAGACCTGTGCAGACCACCCAAGAGGAGGATGGCTGCAGCTGCAGATTCCCT

GAGGAGGAGGAGGGGGGCTGTGAGCTGAGAGTGAAGTTCAGCAGATCTGCTGATGC

CCCTGCCTATCAGCAAGGGCAGAATCAGCTGTACAATGAGCTGAATCTGGGCAGAA

GAGAGGAGTATGATGTGCTGGACAAGAGAAGAGGCAGAGACCCTGAGATGGGGGG

CAAGCCTAGAAGAAAGAACCCCCAAGAGGGCCTGTATAATGAGCTGCAGAAGGACA

AGATGGCTGAGGCCTACTCTGAGATTGGCATGAAGGGGGGAGAGAAGAAGAGGCAA

GGGCCATGATGGCCTGTACCAAGGCCTGAGCACAGCCACCAAGGACACCTATGATG

CCCTACACATGCAAGCTCTGCCTCCTAGA pXL1748 CAR protein sequence
                                        (SEQ ID NO: 64)
MALPVTALLLPLALLLHAARPEVQLLESGGGLVQPGGSLRLSCAASGFTFNIDAMGW

VRQAPGKGLEWVSSISSSGGTTYYADSVKGRFTISRDNSKNTLYLQMNSLRAEDTAVYY

CARSRYSVPDGRGSYDVWGQGTLVTVSSGSTSGSGKPGSGEGSTEVQLLESGGGLVQPG

GSLRLSCAASGFTFSSEAMGWVRQAPGKGLEWVSSINGSGRNTYYADSVKGRFTISRDN

SKNTLYLQMNSLRAEDTAVYYCARKHGEYYDSGYDVWGQGTLVTVSSFVPVFLPAKP

TTTPAPRPPTPAPTIASQPLSLRPEACRPAAGGAVHTRGLDFACDIYIWAPLAGTCGVLLL

SLVITLYCNHRNKRGRKKLLYIFKQPFMRPVQTTQEEDGCSCRFPEEEEGGCELRVKFSR

SADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR pXL1750 CAR nucleic acid sequence
                                        (SEQ ID NO: 65)
ATGGCCCTACCTGTGACAGCCCTACTGTTACCCCTGGCCCTCCTTCTGCATGCTGC

TAGACCTGAGGTGCAGCTACTGGAATCTGGGGGGGGCTTAGTTCAGCCTGGTGGTAG

CCTTAGATTAAGCTGTGCTGCATCTGGCTTCACCTTTAGCTCTGAGGCCATGGGTTGG

GTAAGACAAGCCCCTGGCAAGGGTCTGGAGTGGGTGAGCAGCATCAATGGCTCTGG

CAGAAACACCTATTATGCTGATTCTGTGAAGGGCAGATTCACCATCAGCAGAGACAA

CAGCAAGAACACCCTGTACCTGCAGATGAACAGCCTCAGAGCTGAAGACACAGCTG

TGTATTATTGTGCTAGAAAACATGGGGAGTACTATGACTCTGGCTATGATGTGTGGG

GGCAAGGCACCTTAGTGACAGTGTCATCTGGCAGCACCTCTGGCTCTGGCAAGCCTG

GCTCTGGGGAGGGCTCAACAGAGGTGCAACTTCTTGAGTCTGGGGGGGGCTTGGTGC

AGCCTGGGGGCAGTCTGAGACTGAGCTGTGCTGCCTCTGGCTTTACCTTCAACATTG

ATGCCATGGGTTGGGTAAGACAAGCCCCTGGCAAGGGTCTGGAGTGGGTGAGCAGC

ATCAGCTCTTCTGGGGGCACTACCTACTATGCTGACTCTGTGAAGGGCAGATTCACC

ATCAGCAGAGACAACAGCAAGAACACCCTGTACCTGCAAATGAATAGCCTTAGGGC

TGAGGACACAGCTGTATACTACTGTGCTAGAAGCAGATACTCTGTGCCTGATGGCAG

AGGCAGCTATGATGTGTGGGGCCAAGGGACCTTGGTCACAGTGAGCTCTTTTGTGCC

TGTATTTCTGCCTGCCAAGCCCACCACAACACCTGCCCCTAGACCACCCACCCCTGC

CCCCACCATTGCTTCTCAGCCCCTTAGCTTAAGACCTGAAGCCTGTAGACCTGCTGCT

```
GGGGGGGCTGTGCACACAAGAGGCCTGGACTTTGCCTGTGACATCTACATCTGGGCC

CCCCTGGCTGGCACCTGTGGGGTGCTGCTGCTGAGCCTGGTGATCACCCTGTACTGC

AACCACAGAAACAAGAGAGGCAGAAAGAAGCTGCTGTACATCTTCAAGCAGCCCTT

CATGAGACCTGTGCAGACCACCCAAGAGGAGGATGGCTGCAGCTGCAGATTCCCTG

AGGAGGAGGAGGGGGGCTGTGAGCTGAGAGTGAAGTTCAGCAGATCTGCTGATGCC

CCTGCCTATCAGCAAGGGCAGAATCAGCTGTACAATGAGCTGAATCTGGGCAGAAG

AGAGGAGTATGATGTGCTGGACAAGAGAAGAGGCAGAGACCCTGAGATGGGGGGC

AAGCCTAGAAGAAAGAACCCCCAAGAGGGCCTGTATAATGAGCTGCAGAAGGACAA

GATGGCTGAGGCCTACTCTGAGATTGGCATGAAGGGGGAGAGAAGAAGAGGCAAG

GGCCATGATGGCCTGTACCAAGGCCTGAGCACAGCCACCAAGGACACCTATGATGC

CCTACACATGCAAGCTCTGCCTCCTAGA
``` pXL1750 CAR protein sequence (SEQ ID NO: 66)

```
MALPVTALLLPLALLLHAARPEVQLLESGGGLVQPGGSLRLSCAASGFTFSSEAMGW

VRQAPGKGLEWVSSINGSGRNTYYADSVKGRFTISRDNSKNTLYLQMNSLRAEDTAVY

YCARKHGEYYDSGYDVWGQGTLVTVSSGSTSGSGKPGSGEGSTEVQLLESGGGLVQPG

GSLRLSCAASGFTFNIDAMGWVRQAPGKGLEWVSSISSSGGTTYYADSVKGRFTISRDN

SKNTLYLQMNSLRAEDTAVYYCARSRYSVPDGRGSYDVWGQGTLVTVSSFVPVFLPAK

PTTTPAPRPPTPAPTIASQPLSLRPEACRPAAGGAVHTRGLDFACDIYIWAPLAGTCGVLL

LSLVITLYCNHRNKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR
``` pXL1752 CAR nucleic acid sequence (SEQ ID NO: 67)

```
ATGGCCCTACCTGTGACAGCCCTACTGTTACCCCTGGCCCTCCTTCTGCATGCTGC

TAGACCTGAGGTGCAACTTCTTGAGTCTGGGGGGGGCTTGGTGCAGCCTGGGGGCAG

TCTGAGACTGAGCTGTGCTGCCTCTGGCTTTACCTTCAACATTGATGCCATGGGTTGG

GTAAGACAAGCCCCTGGCAAGGGTCTGGAGTGGGTGAGCAGCATCAGCTCTTCTGG

GGGCACTACCTACTATGCTGACTCTGTGAAGGGCAGATTCACCATCAGCAGAGACAA

CAGCAAGAACACCCTGTACCTGCAAATGAATAGCCTTAGGGCTGAGGACACAGCTG

TATACTACTGTGCTAGAAGCAGATACTCTGTGCCTGATGGCAGAGGCAGCTATGATG

TGTGGGGCCAAGGGACCTTGGTCACAGTGAGCTCTGGCAGCACCTCTGGCTCTGGCA

AGCCTGGCTCTGGGGAGGGCTCAACAGAGGTGCAGCTGCTGGAGTCTGGGGGGGGC

TTGGTTCAACCTGGGGGAAGCCTGAGGCTGAGCTGTGCTGCCTCTGGATTCACCTTC

AGCAATTATGCCATGGGGTGGGTTAGACAAGCCCCTGGCAAGGGCCTGGAGTGGGT

GTCAAGCATCACTGGCCTGGGGGGGCAACATGTATTATGCTGACTCTGTGAAAGGCAG

ATTTACCATCTCTAGAGACAATAGCAAAAATACCCTCTATCTGCAGATGAATAGCCT

GAGAGCTGAGGACACAGCTGTGTACTATTGTGCTAGAATGTACTACAGCCAAGGGG

TGAACAACTACAGCTACCCTAGTACTGATATATGGGGCCAAGGTACTCTGGTGACCG

TCTCCAGCTTTGTGCCTGTATTTCTGCCTGCCAAGCCCACCACAACACCTGCCCCTAG

ACCACCCACCCCTGCCCCCACCATTGCTTCTCAGCCCCCTTAGCTTAAGACCTGAAGC

CTGTAGACCTGCTGCTGGGGGGGCTGTGCACACAAGAGGCCTGGACTTTGCCTGTGA
```

-continued

```
CATCTACATCTGGGCCCCCCTGGCTGGCACCTGTGGGGTGCTGCTGCTGAGCCTGGT

GATCACCCTGTACTGCAACCACAGAAACAAGAGAGGCAGAAAGAAGCTGCTGTACA

TCTTCAAGCAGCCCTTCATGAGACCTGTGCAGACCACCCAAGAGGAGGATGGCTGCA

GCTGCAGATTCCCTGAGGAGGAGGAGGGGGGCTGTGAGCTGAGAGTGAAGTTCAGC

AGATCTGCTGATGCCCCTGCCTATCAGCAAGGGCAGAATCAGCTGTACAATGAGCTG

AATCTGGGCAGAAGAGAGGAGTATGATGTGCTGGACAAGAGAAGAGGCAGAGACC

CTGAGATGGGGGGGCAAGCCTAGAAGAAAGAACCCCCAAGAGGGCCTGTATAATGAG

CTGCAGAAGGACAAGATGGCTGAGGCCTACTCTGAGATTGGCATGAAGGGGGAGAG

AAGAAGAGGCAAGGGCCATGATGGCCTGTACCAAGGCCTGAGCACAGCCACCAAGG

ACACCTATGATGCCCTACACATGCAAGCTCTGCCTCCTAGA
``` pXL1752 CAR protein sequence (SEQ ID NO: 68)

```
MALPVTALLLPLALLLHAARPEVQLLESGGGLVQPGGSLRLSCAASGFTFNIDAMGW

VRQAPGKGLEWVSSISSSGGTTYYADSVKGRFTISRDNSKNTLYLQMNSLRAEDTAVYY

CARSRYSVPDGRGSYDVWGQGTLVTVSSGSTSGSGKPGSGEGSTEVQLLESGGGLVQPG

GSLRLSCAASGFTFSNYAMGWVRQAPGKGLEWVSSITGLGGNMYYADSVKGRFTISRD

NSKNTLYLQMNSLRAEDTAVYYCARMYYSQGVNNYSYPSTDIWGQGTLVTVSSFVPVF

LPAKPTTTPAPRPPTPAPTIASQPLSLRPEACRPAAGGAVHTRGLDFACDIYIWAPLAGTC

GVLLLSLVITLYCNHRNKRGRKKLLYIFKQPFMRPVQTTQEEDGCSCRFPEEEEGGCELR

VKFSRSADAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR
``` pXL1754 CAR nucleic acid sequence (SEQ ID NO: 69)

```
ATGGCCCTACCTGTGACAGCCCTACTGTTACCCCTGGCCCTCCTTCTGCATGCTGC

TAGACCTGAGGTGCAGCTGCTGGAGTCTGGGGGGGGCTTGGTTCAACCTGGGGGAA

GCCTGAGGCTGAGCTGTGCTGCCTCTGGATTCACCTTCAGCAATTATGCCATGGGGT

GGGTTAGACAAGCCCCTGGCAAGGGCCTGGAGTGGGTGTCAAGCATCACTGGCCTG

GGGGGCAACATGTATTATGCTGACTCTGTGAAAGGCAGATTTACCATCTCTAGAGAC

AATAGCAAAAATACCCTCTATCTGCAGATGAATAGCCTGAGAGCTGAGGACACAGC

TGTGTACTATTGTGCTAGAATGTACTACAGCCAAGGGGTGAACAACTACAGCTACCC

TAGTACTGATATATGGGGCCAAGGTACTCTGGTGACCGTCTCCAGCGGCAGCACCTC

TGGCTCTGGCAAGCCTGGCTCTGGGGAGGGCTCAACAGAGGTGCAACTTCTTGAGTC

TGGGGGGGGCTTGGTGCAGCCTGGGGGCAGTCTGAGACTGAGCTGTGCTGCCTCTGG

CTTTACCTTCAACATTGATGCCATGGGTTGGGTAAGACAAGCCCCTGGCAAGGGTCT

GGAGTGGGTGAGCAGCATCAGCTCTTCTGGGGGCACTACCTACTATGCTGACTCTGT

GAAGGGCAGATTCACCATCAGCAGAGACAACAGCAAGAACACCCTGTACCTGCAAA

TGAATAGCCTTAGGGCTGAGGACACAGCTGTATACTACTGTGCTAGAAGCAGATACT

CTGTGCCTGATGGCAGAGGCAGCTATGATGTGTGGGGCCAAGGGACCTTGGTCACA

GTGAGCTCTTTTGTGCCTGTATTTCTGCCTGCCAAGCCCACCACAACACCTGCCCCTA

GACCACCCACCCCTGCCCCCACCATTGCTTCTCAGCCCCTTAGCTTAAGACCTGAAG

CCTGTAGACCTGCTGCTGGGGGGGGCTGTGCACACAAGAGGCCTGGACTTTGCCTGTG

ACATCTACATCTGGGCCCCCCTGGCTGGCACCTGTGGGGTGCTGCTGCTGAGCCTGG

TGATCACCCTGTACTGCAACCACAGAAACAAGAGAGGCAGAAAGAAGCTGCTGTAC
```

-continued

```
ATCTTCAAGCAGCCCTTCATGAGACCTGTGCAGACCACCCAAGAGGAGGATGGCTGC

AGCTGCAGATTCCCTGAGGAGGAGGAGGGGGGCTGTGAGCTGAGAGTGAAGTTCAG

CAGATCTGCTGATGCCCCTGCCTATCAGCAAGGGCAGAATCAGCTGTACAATGAGCT

GAATCTGGGCAGAAGAGAGGAGTATGATGTGCTGGACAAGAGAAGAGGCAGAGAC

CCTGAGATGGGGGGCAAGCCTAGAAGAAAGAACCCCCAAGAGGGCCTGTATAATGA

GCTGCAGAAGGACAAGATGGCTGAGGCCTACTCTGAGATTGGCATGAAGGGGGAGA

GAAGAAGAGGCAAGGGCCATGATGGCCTGTACCAAGGCCTGAGCACAGCCACCAAG

GACACCTATGATGCCCTACACATGCAAGCTCTGCCTCCTAGA
``` pXL1754 CAR protein sequence (SEQ ID NO: 70)
```
MALPVTALLLPLALLLHAARPEVQLLESGGGLVQPGGSLRLSCAASGFTFSNYAMG

WVRQAPGKGLEWVSSITGLGGNMYYADSVKGRFTISRDNSKNTLYLQMNSLRAEDTAV

YYCARMYYSQGVNNYSYPSTDIWGQGTLVTVSSGSTSGSGKPGSGEGSTEVQLLESGG

GLVQPGGSLRLSCAASGFTFNIDAMGWVRQAPGKGLEWVSSISSSGGTTYYADSVKGRF

TISRDNSKNTLYLQMNSLRAEDTAVYYCARSRYSVPDGRGSYDVWGQGTLVTVSSFVP

VFLPAKPTTTPAPRPPTPAPTIASQPLSLRPEACRPAAGGAVHTRGLDFACDIYIWAPLAG

TCGVLLLSLVITLYCNHRNKRGRKKLLYIFKQPFMRPVQTTQEEDGCSCRFPEEEEGGCE

LRVKFSRSADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHMQALPPR
```

Nucleic acid sequence of the GoldenGate backbone vector containing
lethal gene ccdB (SEQ ID NO: 71)
```
GCCGCTGATCTTCAGACCTGGAGGAGGAGATATGAGGGACAATTGGAGAAGTGA

ATTATATAAATATAAAGTAGTAAAAATTGAACCATTAGGAGTAGCACCCACCAAGG

CAAAGAGAAGAGTGGTGCAGAGAGAAAAAAGAGCAGTGGGAATAGGAGCTTTGTT

CCTTGGGTTCTTGGGAGCAGCAGGAAGCACTATGGGCGCAGCGTCAATGACGCTGA

CGGTACAGGCCAGACAATTATTGTCTGGTATAGTGCAGCAGCAGAACAATTTGCTGA

GGGCTATTGAGGCGCAACAGCATCTGTTGCAACTCACAGTCTGGGGCATCAAGCAGC

TCCAGGCAAGAATCCTGGCTGTGGAAAGATACCTAAAGGATCAACAGCTCCTGGGG

ATTTGGGGTTGCTCTGGAAAACTCATTTGCACCACTGCTGTGCCTTGGAATGCTAGTT

GGAGTAATAAATCTCTGGAACAGATTTGGAATCACACGACCTGGATGGAGTGGGAC

AGAGAAATTAACAATTACACAAGCTTAATACACTCCTTAATTGAAGAATCGCAAAAC

CAGCAAGAAAAGAATGAACAAGAATTATTGGAATTAGATAAATGGGCAAGTTTGTG

GAATTGGTTTAACATAACAAATTGGCTGTGGTATATAAAATTATTCATAATGATAGT

AGGAGGCTTGGTAGGTTTAAGAATAGTTTTTGCTGTACTTTCTATAGTGAATAGAGTT

AGGCAGGGATATTCACCATTATCGTTTCAGACCCACCTCCCAACCCCGAGGGGACCC

GACAGGCCCGAAGGAATAGAAGAAGAAGGTGGAGAGAGAGACAGAGACAGATCCA

TTCGATTAGTGAACGGATCTCGACGGTATCGCCTTTAAAAGAAAAGGGGGGATTGG

GGGGTACAGTGCAGGGGAAAGAATAGTAGACATAATAGCAACAGACATACAAACTA

AAGAATTACAAAAACAAATTACAAAAATTCAAAATTTTCGGGTTTATTACAGGGACA

GCAGAGATCCAGTTTATCGATCGTGAGGCTCCGGTGCCCGTCAGTGGGCAGAGCGCA

CATCGCCCACAGTCCCCGAGAAGTTGGGGGGGAGGGGTCGGCAATTGAACCGGTGCC

TAGAGAAGGTGGCGCGGGGTAAACTGGGAAAGTGATGTCGTGTACTGGCTCCGCCT
```

-continued

```
TTTTCCCGAGGGTGGGGGAGAACCGTATATAAGTGCAGTAGTCGCCGTGAACGTTCT

TTTTCGCAACGGGTTTGCCGCCAGAACACAGGTAAGTGCCGTGTGTGGTTCCCGCGG

GCCTGGCCTCTTTACGGGTTATGGCCCTTGCGTGCCTTGAATTACTTCCACCTGGCTG

CAGTACGTGATTCTTGATCCCGAGCTTCGGGTTGGAAGTGGGTGGGAGAGTTCGAGG

CCTTGCGCTTAAGGAGCCCCTTCGCCTCGTGCTTGAGTTGAGGCCTGGCCTGGGCGC

TGGGGCCGCCGCGTGCGAATCTGGTGGCACCTTCGCGCCTGTCTCGCTGCTTTCGAT

AAGTCTCTAGCCATTTAAAATTTTTGATGACCTGCTGCGACGCTTTTTTTCTGGCAAG

ATAGTCTTGTAAATGCGGGCCAAGATCTGCACACTGGTATTTCGGTTTTTGGGGCCG

CGGGCGGCGACGGGGCCCGTGCGTCCCAGCGCACATGTTCGGCGAGGCGGGGCCTG

CGAGCGCGGCCACCGAGAATCGGACGGGGGTAGTCTCAAGCTGGCCGGCCTGCTCT

GGTGCCTGGCCTCGCGCCGCCGTGTATCGCCCCGCCCTGGGCGGCAAGGCTGGCCCG

GTCGGCACCAGTTGCGTGAGCGGAAAGATGGCCGCTTCCCGGCCCTGCTGCAGGGA

GCTCAAAATGGAGGACGCGGCGCTCGGGAGAGCGGGCGGGTGAGTCACCCACACAA

AGGAAAAGGGCCTTTCCGTCCTCAGCCGTCGCTTCATGTGACTCCACGGAGTACCGG

GCGCCGTCCAGGCACCTCGATTAGTTCTCGAGCTTTTGGAGTACGTCGTCTTTAGGTT

GGGGGGAGGGGTTTTATGCGATGGAGTTTCCCCACACTGAGTGGGTGGAGACTGAA

GTTAGGCCAGCTTGGCACTTGATGTAATTCTCCTTGGAATTTGCCCTTTTTGAGTTTG

GATCTTGGTTCATTCTCAAGCCTCAGACAGTGGTTCAAAGTTTTTTTCTTCCATTTCA

GGTGTCGTGAGGAATTAGCTTGGTACGAATTCCTCGAGACTAGTTCTAGAGCGGCCG

CGGATCGCCGCCACCATGGCCCTGCCTGTGACAGCTCTGCTCCTCCCTCTGGCCCTGC

TGCTCCATGCCGCCAGACCCGAGACGTGAgAATTAATACGACTCACTATAGAGGGAC

TGGTGAAATGCAGTTCAAGGTTTACACCTATAAAAGAGAGAGCCGCTATCGCCTGTT

TGTGGATGTACAGAGTGATATTATTGACACGCCCGGGCGACGGATGGTGATCCCCCT

GGCCAGTGCACGTCTGCTGTCAGATAAAGTCTCCCGTGAACTTTACCCGGTGGTGCA

TATCGGGGATGAAAGCTGGCGCATGATGACCACCCAGATGGTCAGTGTGCCGGTCTC

CGTCATCGGAGAAGAAGTGGCTGATCTCAGCCACCGCGAAAATGACATCAAAAACG

CCATTAATCTGATGTTCTGGGGAATATAACGTCTCTTCGTGCCCGTGTTCCTGCCCGC

CAAACCTACTACTACCCCTGCACCTAGGCCTCCCACCCCAGCCCCAACAATCGCCAG

CCAGCCTCTGTCTCTGCGGCCCGAAGCCTGTAGACCTGCTGCCGGCGGAGCCGTGCA

CACCAGAGGCCTGGACTTCGCCTGCGACATCTACATCTGGGCCCCTCTGGCCGGCAC

CTGTGGCGTGCTGCTGCTGAGCCTGGTGATCACCCTGTACTGCAACCACCGGAACAA

ACGGGGCAGAAAGAAACTCCTGTATATATTCAAACAACCATTTATGAGACCAGTAC

AAACTACTCAAGAGGAAGATGGCTGTAGCTGCCGATTTCCAGAAGAAGAAGAAGGA

GGATGTGAACTGAGAGTGAAGTTCAGCAGATCCGCCGACGCCCCTGCCTACCAGCA

GGGACAGAACCAGCTGTACAACGAGCTGAACCTGGGCAGACGGGAAGAGTACGAC

GTGCTGGACAAGCGGAGAGGCCGGGACCCCGAGATGGGCGGAAAGCCCAGACGGA

AGAACCCCCAGGAAGGCCTGTATAACGAACTGCAGAAAGACAAGATGGCCGAGGCC

TACAGCGAGATCGGCATGAAGGGCGAGCGGAGGCGCGGCAAGGGCCACGATGGCCT

GTACCAGGGCCTGAGCACCGCCACCAAGGACACCTACGACGCCCTGCACATGCAGG

CCCTGCCCCCCAGAGGATCCGGAGAGGGAAGGGGCAGCTTATTAACATGTGGCGAT
```

-continued

```
GTGGAAGAGAACCCCGGTCCCATGCTGCTGCTCGTGACCTCTTTACTGTTATGTGAG

CTGCCCCACCCCGCTTTTTTACTGATCCCTCGTAAGGTGTGTAACGGAATCGGCATTG

GCGAGTTCAAGGACTCTTTAAGCATCAACGCCACAAACATCAAGCACTTCAAGAATT

GTACCTCCATCAGCGGCGATTTACACATTCTCCCCGTGGCTTTTCGTGGCGATTCCTT

CACCCACACCCCCCCTCTGGACCCCCAAGAGCTGGACATTTTAAAAACCGTGAAGGA

GATCACCGGCTTTCTGCTGATCCAAGCTTGGCCCGAGAATCGTACCGACCTCCACGC

CTTCGAGAATTTAGAGATTATTCGTGGAAGGACCAAGCAGCACGGCCAGTTCTCTTT

AGCCGTCGTGTCTTTAAACATTACCAGCCTCGGTTTAAGGTCTTTAAAGGAGATTAG

CGACGGCGACGTGATCATCTCCGGCAACAAGAACCTCTGCTACGCCAACACCATCA

ACTGGAAGAAGCTGTTCGGAACCAGCGGCCAAAAGACCAAGATCATCAGCAATCGT

GGAGAGAACTCTTGTAAGGCCACTGGTCAAGTTTGCCACGCCCTCTGTAGCCCCGAA

GGATGTTGGGGCCCCGAGCCTAGGGACTGTGTTAGCTGCAGAAACGTGAGCAGAGG

CAGAGAGTGTGTGGACAAATGCAATTTACTGGAAGGAGAGCCTAGGGAGTTCGTGG

AGAACAGCGAATGTATCCAGTGCCACCCCGAGTGTTTACCTCAAGCCATGAACATCA

CTTGTACCGGAAGGGGCCCCGATAACTGCATCCAATGCGCCCACTACATCGACGGAC

CCCACTGCGTGAAAACTTGTCCCGCCGGAGTGATGGGAGAGAATAACACTTTAGTGT

GGAAGTACGCCGACGCTGGCCACGTCTGCCATCTGTGCCACCCCAACTGTACCTACG

GCTGCACTGGTCCCGGTTTAGAGGGATGTCCTACCAACGGCCCCAAGATCCCCTCCA

TCGCCACCGGAATGGTGGGCGCTCTGTTATTACTGCTGGTGGTGGCTCTGGGCATCG

GTTTATTCATGTGAACGCGTCTGGAACAATCAACCTCTGGATTACAAAATTTGTGAA

AGATTGACTGGTATTCTTAACTATGTTGCTCCTTTTACGCTATGTGGATACGCTGCTT

TAATGCCTTTGTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGCAACGTGGC

GTGGTGTGCACTGTGTTTGCTGACGCAACCCCCACTGGTTGGGGCATTGCCACCACC

TGTCAGCTCCTTTCCGGGACTTTCGCTTTCCCCCTCCCTATTGCCACGGCGGAACTCA

TCGCCGCCTGCCTTGCCCGCTGCTGGACAGGGGCTCGGCTGTTGGGCACTGACAATT

CCGTGGTGTTGTCGGGGAAGCTGACGTCCTTTCCATGGCTGCTCGCCTGTGTTGCCAC

CTGGATTCTGCGCGGGACGTCCTTCTGCTACGTCCCTTCGGCCCTCAATCCAGCGGA

CCTTCCTTCCCGCGGCCTGCTGCCGGCTCTGCGGCCTCTTCCGCGTCTTCGCCTTCGC

CCTCAGACGAGTCGGATCTCCCTTTGGGCCGCCTCCCCGCCTGGAATTAATTCTGCA

GTCGAGACCTAGAAAAACATGGAGCAATCACAAGTAGCAATACAGCAGCTACCAAT

GCTGATTGTGCCTGGCTAGAAGCACAAGAGGAGGAGGAGGTGGGTTTTCCAGTCAC

ACCTCAGGTACCTTTAAGACCAATGACTTACAAGGCAGCTGTAGATCTTAGCCACTT

TTTAAAAGAAAAGAGGGGACTGGAAGGGCTAATTCACTCCCAACGAAGACAAGATA

TCCTTGATCTGTGGATCTACCACACACAAGGCTACTTCCCTGATTAGCAGAACTACA

CACCAGGGCCAGGGGTCAGATATCCACTGACCTTTGGATGGTGCTACAAGCTAGTAC

CAGTTGAGCCAGATAAGGTAGAAGAGGCCAATAAAGGAGAGAACACCAGCTTGTTA

CACCCTGTGAGCCTGCATGGGATGGATGACCCGGAGAGAGAAGTGTTAGAGTGGAG

GTTTGACAGCCGCCTAGCATTTCATCACGTGGCCCGAGAGCTGCATCCGGAGTACTT

CAAGAACTGCTGATATCGAGCTTGCTACAAGGGACTTTCCGCTGGGGACTTTCCAGG

GAGGCGTGGCCTGGGCGGGACTGGGGAGTGGCGAGCCCTCAGATCCTGCATATAAG
```

-continued

CAGCTGCTTTTTGCCTGTACTGGGTCTCTCTGGTTAGACCAGATCTGAGCCTGGGAGC

TCTCTGGCTAACTAGGGAACCCACTGCTTAAGCCTCAATAAAGCTTGCCTTGAGTGC

TTCAAGTAGTGTGTGCCCGTCTGTTGTGTGACTCTGGTAACTAGAGATCCCTCAGACC

CTTTTAGTCAGTGTGGAAAATCTCTAGCAGTAGTAGTTCATGTCATCTTATTATTCAG

TATTTATAACTTGCAAAGAAATGAATATCAGAGAGTGAGAGGCCTTGACATTGCTAG

CGTTTACCGTCGACCTCTAGCTAGAGCTTGGCGTAATCATGGTCATAGCTGTTTCCTG

TGTGAAATTGTTATCCGCTCACAATTCCACACAACATACGAGCCGGAAGCATAAAGT

GTAAAGCCTGGGGTGCCTAATGAGTGAGCTAACTCACATTAATTGCGTTGCGCTCAC

TGCCCGCTTTCCAGTCGGGAAACCTGTCGTGCCAGCTGCATTAATGAATCGGCCAAC

GCGCGGGGAGAGGCGGTTTGCGTATTGGGCCGCTTCCTCGCTCACTGACTCGCTGCG

CTCGGTCGTTCGGCTGCGGCGAGCGGTATCAGCTCACTCAAAGGCGGTAATACGGTT

ATCCACAGAATCAGGGGATAACGCAGGAAAGAACATGTGAGCAAAAGGCCAGCAA

AAGGCCAGGAACCGTAAAAAGGCCGCGTTGCTGGCGTTTTTCCATAGGCTCCGCCCC

CCTGACGAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCGCTTT

CTCATAGCTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGG

CCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGT

AGCGGTGGTTTTTTTGTTTGCAAGCAGCAGATTACGCGCAGAAAAAAAGGATCTCAA

GAAGATCCTTTGATCTTTTCTACGGGGTCTGACGCTCAGTGGAACGAAAACTCACGT

TAAGGGATTTTGGTCATGAGATTATCAAAAAGGATCTTCACCTAGATCCTTTTAAATT

AAAAATGAAGTTTTAAATCAATCTAAAGTATATATGAGTAAACTTGGTCTGACAGTT

ACCAATGCTTAATCAGTGAGGCACCTATCTCAGCGATCTGTCTATTTCGTTCATCCAT

AGTTGCCTGACTCCCCGTCGTGTAGATAACTACGATACGGGAGGGCTTACCATCTGG

CCCCAGTGCTGCAATGATACCGCGAGACCCACGCTCACCGGCTCCAGATTTATCAGC

AATAAACCAGCCAGCCGGAAGGGCCGAGCGCAGAAGTGGTCCTGCAACTTTATCCG

CCTCCATCCAGTCTATTAATTGTTGCCGGGAAGCTAGAGTAAGTAGTTCGCCAGTTA

ATAGTTTGCGCAACGTTGTTGCCATTGCTACAGGCATCGTGGTGTCACGCTCGTCGTT

TGGTATGGCTTCATTCAGCTCCGGTTCCCAACGATCAAGGCGAGTTACATGATCCCC

CATGTTGTGCAAAAAAGCGGTTAGCTCCTTCGGTCCTCCGATCGTTGTCAGAAGTAA

GTTGGCCGCAGTGTTATCACTCATGGTTATGGCAGCACTGCATAATTCTCTTACTGTC

ATGCCATCCGTAAGATGCTTTTCTGTGACTGGTGAGTACTCAACCAAGTCATTCTGA

GAATAGTGTATGCGGCGACCGAGTTGCTCTTGCCCGGCGTCAATACGGGATAATACC

GCGCCACATAGCAGAACTTTAAAAGTGCTCATCATTGGAAAACGTTCTTCGGGGCGA

AAACTCTCAAGGATCTTACCGCTGTTGAGATCCAGTTCGATGTAACCCACTCGTGCA

CCCAACTGATCTTCAGCATCTTTTACTTTCACCAGCGTTTCTGGGTGAGCAAAAACAG

-continued

```
GAAGGCAAAATGCCGCAAAAAAGGGAATAAGGGCGACACGGAAATGTTGAATACT

CATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTT

CCCCGAAAAGTGCCACCTGACGTCGACGGATCGGGAGATCAACTTGTTTATTGCAGC

TTATAATGGTTACAAATAAAGCAATAGCATCACAAATTTCACAAATAAAGCATTTTT

TTCACTGCATTCTAGTTGTGGTTTGTCCAAACTCATCAATGTATCTTATCATGTCTGG

ATCAACTGGATAACTCAAGCTAACCAAAATCATCCCAAACTTCCCACCCCATACCCT

ATTACCACTGCCAATTACCTGTGGTTTCATTTACTCTAAACCTGTGATTCCTCTGAAT

TATTTTCATTTTAAAGAAATTGTATTTGTTAAATATGTACTACAAACTTAGTAGTTGG

AAGGGCTAATTCACTCCCAAAGAAGACAAGATATCCTTGATCTGTGGATCTACCACA

CACAAGGCTACTTCCCTGATTAGCAGAACTACACACCAGGGCCAGGGGTCAGATATC

CACTGACCTTTGGATGGTGCTACAAGCTAGTACCAGTTGAGCCAGATAAGGTAGAAG

AGGCCAATAAAGGAGAGAACACCAGCTTGTTACACCCTGTGAGCCTGCATGGGATG

GATGACCCGGAGAGAGAAGTGTTAGAGTGGAGGTTTGACAGCCGCCTAGCATTTCA

TCACGTGGCCCGAGAGCTGCATCCGGAGTACTTCAAGAACTGCTGATATCGAGCTTG

CTACAAGGGACTTTCCGCTGGGGACTTTCCAGGGAGGCGTGGCCTGGGCGGGACTG

GGGAGTGGCGAGCCCTCAGATCCTGCATATAAGCAGCTGCTTTTTGCCTGTACTGGG

TCTCTCTGGTTAGACCAGATCTGAGCCTGGGAGCTCTCTGGCTAACTAGGGAACCCA

CTGCTTAAGCCTCAATAAAGCTTGCCTTGAGTGCTTCAAGTAGTGTGTGCCCGTCTGT

TGTGTGACTCTGGTAACTAGAGATCCCTCAGACCCTTTTAGTCAGTGTGGAAAATCT

CTAGCAGTGGCGCCCGAACAGGGACTTGAAAGCGAAAGGGAAACCAGAGGAGCTCT

CTCGACGCAGGACTCGGCTTGCTGAAGCGCGCACGGCAAGAGGCGAGGGGCGGCGA

CTGGTGAGTACGCCAAAAATTTTGACTAGCGGAGGCTAGAAGGAGAGAGATGGGTG

CGAGAGCGTCAGTATTAAGCGGGGGAGAATTAGATCGCGATGGGAAAAAATTCGGT

TAAGGCCAGGGGGAAAGAAAAAATATAAATTAAAACATATAGTATGGGCAAGCAG

GGAGCTAGAACGATTCGCAGTTAATCCTGGCCTGTTAGAAACATCAGAAGGCTGTAG

ACAAATACTGGGACAGCTACAACCATCCCTTCAGACAGGATCAGAAGAACTTAGAT

CATTATATAATACAGTAGCAACCCTCTATTGTGTGCATCAAAGGATAGAGATAAAAG

ACACCAAGGAAGCTTTAGACAAGATAGAGAAACAAAAGTAAGACCACCGCACAG

CAAGCGGCCG
```

CDRs of 06 antibody (SEQ ID NO: 72)
the amino acid sequence of HCDR1 is GGSFTNYL;

(SEQ ID NO: 73)
the amino acid sequence of HCDR2 is IIPVYGTP;

(SEQ ID NO: 74)
the amino acid sequence of HCDR3 is VREDEGYGDLYLAY;

(SEQ ID NO: 75)
the amino acid sequence of LCDR1 is SSNIGRNT;

(SEQ ID NO: 76)
the amino acid sequence of LCDR2 is SND;

(SEQ ID NO: 77)
the amino acid sequence of LCDR3 is ASWDDSLTGWV

-continued

CDRs of 09 antibody (SEQ ID NO: 78)

the amino acid sequence of HCDR1 is GFTFNIDA;

(SEQ ID NO: 79)

the amino acid sequence of HCDR2 is ISSSGGTT;

(SEQ ID NO: 80)

the amino acid sequence of HCDR3 is ARSRYSVPDGRGSYDV

CDRs of 13 antibody (SEQ ID NO: 81)

the amino acid sequence of HCDR1 is GFTFSSEA;

(SEQ ID NO: 82)

the amino acid sequence of HCDR2 is INASGRNT;

(SEQ ID NO: 83)

the amino acid sequence of HCDR3 is ARKHGEYYDSGYDV

CDRs of 20 antibody (SEQ ID NO: 84)

the amino acid sequence of HCDR1 is GFTFSSYA;

(SEQ ID NO: 85)

the amino acid sequence of HCDR2 is ISGYGEET;

(SEQ ID NO: 86)

the amino acid sequence of HCDR3 is ARFYYRYWKEFDY

CDRs of 21 antibody (SEQ ID NO: 87)

the amino acid sequence of HCDR1 is GFTFSNYA;

(SEQ ID NO: 88)

the amino acid sequence of HCDR2 is ITGLGGNM;

(SEQ ID NO: 89)

the amino acid sequence of HCDR3 is ARMYYSQGVNNYSYPSTDI

---

The invention claimed is:

1. A chimeric antigen receptor (CAR), comprising a CD70 binding domain, a transmembrane domain, a costimulatory domain and an intracellular signaling domain, wherein the CD70 binding domain comprises one or more antibodies or fragments thereof specifically binding to CD70, wherein each antibody is independently selected from the following:

(1) an antibody comprising a HCDR1 having an amino acid sequence as shown in SEQ ID NO: 72, a HCDR2 having an amino acid sequence as shown in SEQ ID NO: 73, a HCDR3 having an amino acid sequence as shown in SEQ ID NO: 74, a LCDR1 having an amino acid sequence as shown in SEQ ID NO: 75, a LCDR2 having an amino acid sequence as shown in SEQ ID NO: 76, and a LCDR3 having an amino acid sequence as shown in SEQ ID NO: 77;

(2) an antibody comprising a HCDR1 having an amino acid sequence as shown in SEQ ID NO: 78, a HCDR2 having an amino acid sequence as shown in SEQ ID NO: 79, and a HCDR3 having an amino acid sequence as shown in SEQ ID NO: 80;

(3) an antibody comprising a HCDR1 having an amino acid sequence as shown in SEQ ID NO: 81, a HCDR2 having an amino acid sequence as shown in SEQ ID NO: 82, and a HCDR3 having an amino acid sequence as shown in SEQ ID NO: 83;

(4) an antibody comprising a HCDR1 having an amino acid sequence as shown in SEQ ID NO: 84, a HCDR2 having an amino acid sequence as shown in SEQ ID NO: 85, and a HCDR3 having an amino acid sequence as shown in SEQ ID NO: 86; or (5) an antibody comprising a HCDR1 having an amino acid sequence as shown in SEQ ID NO: 87, a HCDR2 having an amino acid sequence as shown in SEQ ID NO: 88, and a HCDR3 having an amino acid sequence as shown in SEQ ID NO: 89.

2. The CAR according to claim 1, wherein the CD70 binding domain comprises a pairwise combination of any two selected from the following antibodies or fragments thereof:

(1) an antibody comprising a HCDR1 having an amino acid sequence as shown in SEQ ID NO: 78, a HCDR2 having an amino acid sequence as shown in SEQ ID NO: 79, and a HCDR3 having an amino acid sequence as shown in SEQ ID NO: 80, or a fragment thereof;

(2) an antibody comprising a HCDR1 having an amino acid sequence as shown in SEQ ID NO: 81, a HCDR2 having an amino acid sequence as shown in SEQ ID NO: 82, and a HCDR3 having an amino acid sequence as shown in SEQ ID NO: 83, or a fragment thereof;

(3) an antibody comprising a HCDR1 having an amino acid sequence as shown in SEQ ID NO: 84, a HCDR2 having an amino acid sequence as shown in SEQ ID NO: 85, and a HCDR3 having an amino acid sequence as shown in SEQ ID NO: 86, or a fragment thereof; or (4) an antibody comprising a HCDR1 having an amino acid sequence as shown in SEQ ID NO: 87, a HCDR2 having an amino acid sequence as shown in SEQ ID NO: 88, and a HCDR3 having an amino acid sequence as shown in SEQ ID NO: 89, or a fragment thereof.

3. The CAR according to claim 1, wherein the antibody comprises:

(1) a heavy chain variable region having an amino acid sequence as shown in SEQ ID NO: 28 and a light chain variable region having an amino acid sequence as shown in SEQ ID NO: 30; or (2) a heavy chain variable region having an amino acid sequence as shown in SEQ ID NOs: 33, 36, 39 or 42.

4. The CAR according to claim 1, wherein the antibody is a single chain antibody or a single-domain antibody.

5. The CAR according to claim 1, wherein the CD70 binding domain comprises any one selected from the following:

(1) an amino acid sequence as shown in SEQ ID NO: 26;

(2) an amino acid sequence as shown in SEQ ID NO: 36 and an amino acid sequence as shown in SEQ ID NO: 39, linked by a fragment as shown in SEQ ID NO: 44;

(3) an amino acid sequence as shown in SEQ ID NO: 33 and an amino acid sequence as shown in SEQ ID NO: 36, linked by a fragment as shown in SEQ ID NO: 44;

(4) an amino acid sequence as shown in SEQ ID NO: 33 and an amino acid sequence as shown in SEQ ID NO: 42, linked by a fragment as shown in SEQ ID NO: 44; and (5) an amino acid sequence as shown in SEQ ID NO: 36 and an amino acid sequence as shown in SEO ID NO: 42, linked by a fragment as shown in SEO ID NO: 44.

6. The CAR according to claim 1, comprising an amino acid sequence as shown in SEQ ID NO: 46, 48, 50, 52, 54, 56, 58, 60, 62, 64, 66, 68 or 70.

7. An isolated nucleic acid molecule encoding the CAR according to claim 1.

8. A vector, comprising the nucleic acid molecule according to claim 7.

9. An immune effector cell, comprising the CAR according to claim 1.

10. The immune effector cell according to claim 9, wherein the immune effector cell is selected from a T lymphocyte and a natural killer (NK) cell.

11. The immune effector cell according to claim 9, wherein CD70 is not expressed on the immune effector cell.

12. A composition, comprising the immune effector cell according to claim 9.

13. A CD70-targeting fully human antibody or a single-chain antibody or an antigen-binding fragment thereof, wherein the fully human antibody comprises a heavy chain variable region (HC VR) and/or a light chain variable region (LCVR), and the heavy chain variable region comprises a HCDR1, a HCDR2 and a HCDR3, the light chain variable region comprises a LCDR1, a LCDR2 and a LCDR3, and the HCDR1, HCDR2, HCDR3 and/or LCDR1, LCDR2 and LCDR3 are any one selected from:

(1) the LCDR1 having an amino acid sequence of SSNI-GRNT (SEQ ID NO: 75); the LCDR2 having an amino acit sequence of SND (SEQ ID NO: 76); the LCDR3 having an amino acid sequence of ASWDDSLTGWYV (SEQ ID NO: 77); the HCDR1 having an amino acid sequence of GGSFTNYL (SEQ ID NO: 72); the HCDR2 having an amino acid sequence of IIPVYGTP (SEQ ID NO: 73); and the HCDR3 having an amino acid sequence of VREDEGYGDLYLAY (SEQ ID NO: 74);

(2) the HCDR1 having an amino acid sequence of GFTFNIDA (SEQ ID NO: 78); the HCDR2 having an amino acid sequence of ISSSGGTT (SEQ ID NO: 79); and the HCDR3 having an amino acid sequence of ARSRYSVPDGRGSYDV (SEQ ID NO: 80);

(3) the HCDR1 having an amino acid sequence of GFTFSSEA (SEQ ID NO: 80); the HCDR2 having an amino acid sequence of INASGRNT (SEQ ID NO: 82);

the HCDR3 having an amino acid sequence of ARKHGEY YDSGYDV (SEQ ID NO: 83);

(4) the HCDR1 having an amino acid sequence of GFTFSSYA (SEQ ID NO: 84); the HCDR2 having an amino acid sequence of ISGYGEET (SEQ ID NO: 85); and the HCDR3 having an amino acid sequence of ARFYYRYWKEFDY (SEQ ID NO: 86); and (5) the HCDR1 having an amino acid sequence of GFTFSNYA (SEQ ID NO: 87); the HCDR2 having an amino acid sequence of ITGLGGNM (SEQ ID NO: 88); and the LCDR3 having an amino acid sequence of ARMYYSQGVNNYSYPSTDI (SEQ ID NO: 89).

14. The fully human antibody or a single-chain antibody or antigen-binding fragment thereof according to claim 13, wherein the amino acid sequence(s) of the heavy chain variable region and/or the light chain variable region is/are any one selected from:

(1) a heavy chain variable region sequence as shown in SEQ ID NO: 28, and a light chain variable region sequence as shown in SEQ ID NO: 30;

(2) a heavy chain variable region sequence as shown in SEQ ID NO: 33;

(3) a heavy chain variable region sequence as shown in SEQ ID NO: 36;

(4) a heavy chain variable region sequence as shown in SEQ ID NO: 39; and (5) a heavy chain variable region sequence as shown in SEQ ID NO: 42.

15. The fully human antibody or a single-chain antibody or antigen-binding fragment thereof according to claim 13, wherein the fully human antibody comprises an amino acid sequence as shown in SEQ ID NO: 26.

16. A pharmaceutical composition, comprising the fully human antibody or a single-chain antibody or antigen-binding fragment thereof according to claim 13, and a pharmaceutically acceptable adjuvant or diluent.

17. A method for eliminating, inhibiting or reducing CD70 activity, the method comprising administering, to a patient in need thereof, a therapeutically effective amount of the pharmaceutical composition according to claim 16.

18. A kit for detecting CD70 protein in a sample, comprising the fully human antibody or a single-chain antibody or antigen-binding fragment thereof according to claim 13.

* * * * *